US012678628B2

(12) United States Patent
Buddha et al.

(10) Patent No.: US 12,678,628 B2
(45) Date of Patent: Jul. 14, 2026

(54) STIMULATION APPARATUS

(71) Applicant: Nalu Medical, Inc., Carlsbad, CA (US)

(72) Inventors: Rushidev Buddha, San Marcos, CA (US); Charlotte Fitzgerald, Oceanside, CA (US); Paul Freer, Irvine, CA (US); Lee Fason Hartley, Carlsbad, CA (US); Manohar Diwakar Joshi, Pune (IN); Xinting Lan, Carlsbad, CA (US); Christopher Linden, Vista, CA (US); James Makous, Carlsbad, CA (US); J. Christopher Flaherty, Auburndale, FL (US); Lakshmi Narayan Mishra, Carlsbad, CA (US); Casey James Oconnell, San Marcos, CA (US); Logan Palmer, Santa Monica, CA (US); Ayesha Patel, Vista, CA (US); Daniel Pivonka, Del Mar, CA (US); Brijesh Sirpatil, San Marcos, CA (US); Sameer Tendulkar, Santa Clarita, CA (US); Allen Curtis, San Clemente, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 558 days.

(21) Appl. No.: 17/384,020

(22) Filed: Jul. 23, 2021

(65) Prior Publication Data

US 2022/0118251 A1 Apr. 21, 2022

Related U.S. Application Data

(63) Continuation of application No. PCT/US2020/054150, filed on Oct. 2, 2020.
(Continued)

(51) Int. Cl.
*A61N 1/36* (2006.01)
*A61N 1/372* (2006.01)

(52) U.S. Cl.
CPC ....... *A61N 1/3615* (2013.01); *A61N 1/36071* (2013.01); *A61N 1/36132* (2013.01);
(Continued)

(58) Field of Classification Search
CPC .............. A61N 1/3615; A61N 1/36071; A61N 1/36132; A61N 1/36157; A61N 1/36171;
(Continued)

(56) References Cited

U.S. PATENT DOCUMENTS

| | | |
|---|---|---|
| 3,835,833 A | 9/1974 | Limoge |
| 3,902,501 A | 9/1975 | Citron et al. |

(Continued)

FOREIGN PATENT DOCUMENTS

| | | |
|---|---|---|
| AU | 2014233252 A1 | 11/2015 |
| EP | 1609501 A1 | 12/2005 |

(Continued)

OTHER PUBLICATIONS

D. Wheatley and T. Lehmann, "Electrically evoked compound action potential (ECAP) stimulus-artefact (SA) blanking low-power low-noise CMOS amplifier," 2007 50th Midwest Symposium on Circuits and Systems, Montreal, QC, Canada, 2007, pp. 41-44. ( Year: 2007).*
(Continued)

*Primary Examiner* — Jennifer Pitrak McDonald
*Assistant Examiner* — Christopher J Mutchler
(74) *Attorney, Agent, or Firm* — Nelson Mullins Riley & Scarborough LLP

(57) ABSTRACT

A medical apparatus for a patient comprises an external system and an implantable system. The external system is configured to transmit one or more transmission signals,
(Continued)

each transmission signal comprising at least power or data. The implantable system is configured to receive the one or more transmission signals from the external system, and to deliver stimulation energy to the patient. Methods of delivering stimulation energy are also provided.

27 Claims, 54 Drawing Sheets

Related U.S. Application Data

(60) Provisional application No. 62/988,281, filed on Mar. 11, 2020, provisional application No. 62/977,901, filed on Feb. 18, 2020, provisional application No. 62/933,184, filed on Nov. 8, 2019, provisional application No. 62/910,685, filed on Oct. 4, 2019.

(52) U.S. Cl.
CPC ..... *A61N 1/36157* (2013.01); *A61N 1/36171* (2013.01); *A61N 1/37247* (2013.01)

(58) Field of Classification Search
CPC ............ A61N 1/37247; A61N 1/36182; A61N 1/0551; A61N 1/36125; A61N 1/36135; A61N 1/36164; A61N 1/36178; A61N 1/37211; A61N 1/37276; A61N 1/3787; A61N 5/0601; A61N 2005/0626; A61N 5/0622; A61N 2/008; A61B 2017/00172
See application file for complete search history.

(56) References Cited

U.S. PATENT DOCUMENTS

| 3,939,843 A | 2/1976 | Smyth et al. |
|---|---|---|
| 4,033,357 A | 7/1977 | Helland et al. |
| 4,071,033 A | 1/1978 | Nawracaj et al. |
| 4,140,133 A | 2/1979 | Kastrubin et al. |
| 4,236,529 A | 12/1980 | Little |
| 4,262,678 A | 4/1981 | Stokes |
| 4,269,198 A | 5/1981 | Stokes |
| 4,301,815 A | 11/1981 | Doring |
| 4,324,251 A | 4/1982 | Mann |
| 4,407,303 A | 10/1983 | Akerstroem |
| 4,409,994 A | 10/1983 | Doring |
| 4,469,104 A | 9/1984 | Peers-Trevarton |
| 4,506,679 A | 3/1985 | Mann |
| 4,582,069 A | 4/1986 | Mcarthur |
| 4,592,356 A | 6/1986 | Gutierrez |
| 4,627,438 A | 12/1986 | Liss et al. |
| 4,658,835 A | 4/1987 | Pohndorf |
| 4,716,888 A | 1/1988 | Wesner |
| 4,721,118 A | 1/1988 | Harris |
| 4,735,204 A | 4/1988 | Sussman et al. |
| 4,796,643 A | 1/1989 | Nakazawa et al. |
| 4,841,971 A | 6/1989 | Hess |
| 4,883,070 A | 11/1989 | Hanson |
| 4,898,173 A | 2/1990 | Daglow et al. |
| 4,922,908 A | 5/1990 | Morawetz et al. |
| 4,945,922 A | 8/1990 | Van |
| 4,957,118 A | 9/1990 | Erlebacher |
| 5,031,618 A | 7/1991 | Mullett |
| 5,131,389 A | 7/1992 | Giordani |
| 5,193,539 A | 3/1993 | Schulman et al. |
| 5,201,312 A | 4/1993 | Schenck et al. |
| 5,257,634 A | 11/1993 | Kroll |
| 5,282,845 A | 2/1994 | Bush et al. |
| 5,300,107 A | 4/1994 | Stokes et al. |
| 5,395,328 A | 3/1995 | Ockuly et al. |
| 5,540,736 A | 7/1996 | Haimovich et al. |
| 5,545,206 A | 8/1996 | Carson |
| 5,662,697 A | 9/1997 | Li et al. |
| 5,735,887 A | 4/1998 | Barreras, Sr. et al. |
| 5,814,089 A | 9/1998 | Stokes et al. |
| 5,833,603 A | 11/1998 | Kovacs et al. |
| 5,868,741 A | 2/1999 | Chia et al. |
| 5,908,433 A | 6/1999 | Eager et al. |
| 5,957,965 A | 9/1999 | Moumane et al. |
| 6,021,354 A | 2/2000 | Warman et al. |
| 6,058,331 A | 5/2000 | King |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,275,737 B1 | 8/2001 | Mann |
| 6,304,786 B1 | 10/2001 | Heil, Jr. et al. |
| 6,324,434 B2 | 11/2001 | Coe et al. |
| 6,405,091 B1 | 6/2002 | Vachon et al. |
| 6,482,152 B2 | 11/2002 | Kim |
| 6,510,347 B2 | 1/2003 | Borkan |
| 6,522,926 B1 | 2/2003 | Kieval et al. |
| 6,561,975 B1 | 5/2003 | Pool et al. |
| 6,884,122 B2 | 4/2005 | Robinson et al. |
| 6,895,280 B2 | 5/2005 | Meadows et al. |
| 6,904,322 B2 | 6/2005 | Katsnelson |
| 6,909,917 B2 | 6/2005 | Woods et al. |
| 6,950,706 B2 | 9/2005 | Rodriguez et al. |
| 6,999,819 B2 | 2/2006 | Swoyer et al. |
| 7,092,763 B1 | 8/2006 | Griffith et al. |
| 7,096,070 B1 | 8/2006 | Jenkins et al. |
| 7,239,921 B2 | 7/2007 | Canfield et al. |
| 7,346,391 B1 | 3/2008 | Osorio et al. |
| 7,711,419 B2 | 5/2010 | Armstrong et al. |
| 7,717,848 B2 | 5/2010 | Heruth et al. |
| 7,734,340 B2 | 6/2010 | De |
| 7,734,354 B1 | 6/2010 | Cox |
| 7,742,818 B2 | 6/2010 | Dinsmoor et al. |
| 7,801,615 B2 | 9/2010 | Meadows et al. |
| 7,899,550 B1 | 3/2011 | Doan et al. |
| 7,912,555 B2 | 3/2011 | Swoyer et al. |
| 7,925,357 B2 | 4/2011 | Phillips et al. |
| 7,991,479 B2 | 8/2011 | Phillips et al. |
| 8,000,805 B2 | 8/2011 | Swoyer et al. |
| 8,036,756 B2 | 10/2011 | Swoyer et al. |
| 8,224,453 B2 | 7/2012 | De |
| 8,280,517 B2 | 10/2012 | Skelton et al. |
| 8,314,594 B2 | 11/2012 | Scott et al. |
| 8,334,677 B2 | 12/2012 | Single |
| 8,364,273 B2 | 1/2013 | De |
| 8,388,555 B2 | 3/2013 | Panken et al. |
| 8,401,655 B2 | 3/2013 | De |
| 8,401,666 B2 | 3/2013 | Skelton et al. |
| 8,423,147 B2 | 4/2013 | Alataris et al. |
| 8,437,853 B2 | 5/2013 | Inman et al. |
| 8,452,421 B2 | 5/2013 | Thenuwara et al. |
| 8,504,138 B1 | 8/2013 | Pivonka et al. |
| 8,504,150 B2 | 8/2013 | Skelton |
| 8,538,541 B2 | 9/2013 | Milojevic et al. |
| 8,579,834 B2 | 11/2013 | Davis et al. |
| 8,612,015 B2 | 12/2013 | Knifong, Sr. |
| 8,620,435 B2 | 12/2013 | Rooney et al. |
| 8,626,297 B2 | 1/2014 | Jaax et al. |
| 8,626,314 B2 | 1/2014 | Swoyer et al. |
| 8,634,928 B1 | 1/2014 | O'Driscoll et al. |
| 8,655,451 B2 | 2/2014 | Klosterman et al. |
| 8,706,240 B2 | 4/2014 | Bradley et al. |
| 8,718,781 B2 | 5/2014 | Alataris et al. |
| 8,758,274 B2 | 6/2014 | Sahasrabudhe et al. |
| 8,774,927 B2 | 7/2014 | Deridder |
| 8,798,773 B2 | 8/2014 | Mashiach |
| 8,834,392 B2 | 9/2014 | Panken et al. |
| 8,874,217 B2 | 10/2014 | Alataris et al. |
| 8,880,177 B2 | 11/2014 | Alataris et al. |
| 8,886,327 B2 | 11/2014 | Alataris et al. |
| 8,886,328 B2 | 11/2014 | Alataris et al. |
| 8,897,870 B2 | 11/2014 | De |
| 8,903,502 B2 | 12/2014 | Perryman et al. |
| 8,934,981 B2 | 1/2015 | De |
| 8,954,165 B2 | 2/2015 | Sharma et al. |
| 8,972,502 B2 | 3/2015 | Beslic et al. |
| 9,020,590 B1 | 4/2015 | Honeycutt et al. |
| 9,031,664 B2 | 5/2015 | Trier |
| 9,044,612 B2 | 6/2015 | Mashiach et al. |

(56) References Cited

U.S. PATENT DOCUMENTS

| | | |
|---|---|---|
| 9,061,151 B2 | 6/2015 | Mashiach et al. |
| 9,106,203 B2 | 8/2015 | Kesler et al. |
| 9,138,582 B2 | 9/2015 | Doan et al. |
| 9,144,681 B2 | 9/2015 | Decre et al. |
| 9,149,210 B2 | 10/2015 | Sahasrabudhe et al. |
| 9,173,811 B2 | 11/2015 | Greiner et al. |
| 9,220,897 B2 | 12/2015 | Perryman et al. |
| 9,254,393 B2 | 2/2016 | Perryman et al. |
| 9,272,081 B2 | 3/2016 | Cameron et al. |
| 9,339,655 B2 | 5/2016 | Carbunaru |
| 9,393,420 B2 | 7/2016 | Almendinger et al. |
| 9,403,020 B2 | 8/2016 | Wingeier |
| 9,433,750 B2 | 9/2016 | Pivonka et al. |
| 9,440,084 B2 | 9/2016 | Davis et al. |
| 9,452,288 B2 | 9/2016 | Whitehurst et al. |
| 9,462,398 B2 | 10/2016 | DeRidder |
| 9,463,318 B2 | 10/2016 | Mashiach et al. |
| 9,533,155 B2 | 1/2017 | Jiang et al. |
| 9,555,248 B2 | 1/2017 | De |
| 9,555,257 B2 | 1/2017 | Mashiach et al. |
| 9,585,642 B2 | 3/2017 | Dinsmoor et al. |
| 9,622,700 B2 | 4/2017 | Sahasrabudhe et al. |
| 9,623,245 B2 | 4/2017 | King et al. |
| 9,623,253 B2 | 4/2017 | Perryman et al. |
| 9,643,010 B2 | 5/2017 | Ranu |
| 9,656,077 B2 | 5/2017 | De |
| 9,656,085 B2 | 5/2017 | Moffitt et al. |
| 9,656,089 B2 | 5/2017 | Yip et al. |
| 9,707,406 B1 | 7/2017 | Dellamano et al. |
| 9,717,921 B2 | 8/2017 | Perryman et al. |
| 9,731,140 B1 | 8/2017 | Perryman et al. |
| 9,764,135 B2 | 9/2017 | De |
| 9,770,592 B2 | 9/2017 | Lin et al. |
| 9,789,314 B2 | 10/2017 | Perryman et al. |
| 9,789,321 B2 | 10/2017 | Dixit et al. |
| 9,826,963 B2 | 11/2017 | Scott et al. |
| 9,833,629 B2 | 12/2017 | Dellamano et al. |
| 9,913,975 B2 | 3/2018 | Carbunaru et al. |
| 9,919,159 B2 | 3/2018 | Skelton et al. |
| 9,993,646 B2 | 6/2018 | Parramon et al. |
| 10,004,635 B2 | 6/2018 | Kahook |
| 10,016,603 B2 | 7/2018 | Sachs et al. |
| 10,016,608 B2 | 7/2018 | Peterson et al. |
| 10,016,615 B2 | 7/2018 | Simon et al. |
| 10,016,627 B2 | 7/2018 | Viitala et al. |
| 10,022,549 B2 | 7/2018 | Dellamano et al. |
| 10,022,552 B2 | 7/2018 | Stahler et al. |
| 10,035,017 B2 | 7/2018 | Thakkar et al. |
| 10,035,020 B2 | 7/2018 | Wang et al. |
| 10,052,481 B2 | 8/2018 | McClure et al. |
| 10,076,668 B2 | 9/2018 | De Ridder |
| 10,086,201 B2 | 10/2018 | Chang et al. |
| 10,092,758 B2 | 10/2018 | De Ridder |
| 10,149,976 B1 | 12/2018 | Andresen et al. |
| 10,207,118 B2 | 2/2019 | Skelton |
| 10,238,872 B2 | 3/2019 | Pivonka et al. |
| 10,238,874 B2 | 3/2019 | Perryman et al. |
| 10,245,436 B2 | 4/2019 | Perryman et al. |
| 10,272,239 B1 | 4/2019 | Andresen et al. |
| 10,315,039 B2 | 6/2019 | Perryman et al. |
| 10,320,232 B2 | 6/2019 | Pivonka et al. |
| 10,328,265 B2 | 6/2019 | Moffitt et al. |
| 10,335,596 B2 | 7/2019 | Yakovlev et al. |
| 10,335,599 B2 | 7/2019 | Zottola |
| 10,411,760 B2 | 9/2019 | Yakovlev et al. |
| 10,420,947 B2 | 9/2019 | Perryman et al. |
| 10,471,262 B2 | 11/2019 | Perryman et al. |
| 10,644,539 B2 | 5/2020 | Pivonka et al. |
| 10,682,521 B2 | 6/2020 | Jiang et al. |
| 10,849,643 B2 | 12/2020 | Castillo et al. |
| 10,898,719 B2 | 1/2021 | Pivonka et al. |
| 10,967,183 B2 | 4/2021 | Yakovlev et al. |
| 11,018,721 B2 | 5/2021 | Yakovlev et al. |
| 11,090,491 B2 | 8/2021 | Mishra et al. |
| 11,097,096 B2 | 8/2021 | Linden et al. |
| 11,133,709 B2 | 9/2021 | Pivonka et al. |
| 11,160,980 B2 | 11/2021 | Mishra et al. |
| 11,260,236 B2 | 3/2022 | Mathur et al. |
| 11,318,315 B2 | 5/2022 | Hartley et al. |
| 11,331,493 B2 | 5/2022 | Pivonka et al. |
| 11,451,265 B2 | 9/2022 | Yakovlev et al. |
| 11,511,121 B2 | 11/2022 | Sit et al. |
| 11,633,151 B2 | 4/2023 | Pivonka et al. |
| 11,766,561 B2 | 9/2023 | Mishra et al. |
| 11,826,569 B2 | 11/2023 | Mishra et al. |
| 11,938,327 B2 | 3/2024 | Hartley et al. |
| 12,186,563 B2 | 1/2025 | Yakovlev et al. |
| 12,201,829 B2 | 1/2025 | Linden et al. |
| 12,390,650 B2 | 8/2025 | Sit et al. |
| 12,502,543 B2 | 12/2025 | Pivonka et al. |
| 12,533,517 B2 | 1/2026 | Mishra et al. |
| 2002/0014039 A1 | 2/2002 | Merlet |
| 2002/0140399 A1 | 10/2002 | Echarri et al. |
| 2004/0059392 A1 | 3/2004 | Parramon et al. |
| 2004/0093039 A1 | 5/2004 | Schumert |
| 2004/0215287 A1 | 10/2004 | Swoyer et al. |
| 2004/0215306 A1 | 10/2004 | Heil et al. |
| 2005/0075696 A1 | 4/2005 | Forsberg et al. |
| 2005/0151696 A1 | 7/2005 | Govari et al. |
| 2005/0278000 A1 | 12/2005 | Strother et al. |
| 2006/0095078 A1 | 5/2006 | Tronnes |
| 2006/0122653 A1 | 6/2006 | Bradley et al. |
| 2006/0217782 A1 | 9/2006 | Boveja et al. |
| 2007/0021802 A1 | 1/2007 | Heruth et al. |
| 2007/0032734 A1 | 2/2007 | Najafi et al. |
| 2007/0100411 A1 | 5/2007 | Bonde |
| 2007/0123952 A1 | 5/2007 | Strother et al. |
| 2007/0142874 A1 | 6/2007 | John |
| 2007/0156205 A1 | 7/2007 | Larson et al. |
| 2007/0270928 A1 | 11/2007 | Erlebacher |
| 2008/0269591 A1 | 10/2008 | Halperin et al. |
| 2008/0300654 A1 | 12/2008 | Lambert et al. |
| 2008/0300656 A1 | 12/2008 | Donders et al. |
| 2008/0300660 A1 | 12/2008 | John |
| 2008/0319492 A1 | 12/2008 | Katsnelson |
| 2009/0082829 A1* | 3/2009 | Panken .............. A61N 1/36139 607/45 |
| 2009/0082835 A1 | 3/2009 | Jaax et al. |
| 2009/0224361 A1 | 9/2009 | Liu et al. |
| 2010/0010383 A1 | 1/2010 | Skelton et al. |
| 2010/0010392 A1 | 1/2010 | Skelton et al. |
| 2010/0069996 A1 | 3/2010 | Strahl |
| 2010/0076525 A1 | 3/2010 | Skelton et al. |
| 2010/0082087 A1 | 4/2010 | Silipo et al. |
| 2010/0125312 A1 | 5/2010 | Stevenson et al. |
| 2010/0201368 A1 | 8/2010 | Doerr et al. |
| 2010/0274314 A1 | 10/2010 | Alataris et al. |
| 2010/0305663 A1 | 12/2010 | Aghassian |
| 2010/0331925 A1 | 12/2010 | Peterson |
| 2011/0034886 A1 | 2/2011 | Elbe et al. |
| 2011/0046697 A1 | 2/2011 | Gerber et al. |
| 2011/0054583 A1 | 3/2011 | Litt et al. |
| 2011/0172562 A1 | 7/2011 | Sahasrabudhe et al. |
| 2011/0172743 A1 | 7/2011 | Davis et al. |
| 2012/0004709 A1 | 1/2012 | Chen et al. |
| 2012/0012630 A1 | 1/2012 | Lui et al. |
| 2012/0016439 A1 | 1/2012 | Alataris et al. |
| 2012/0029597 A1 | 2/2012 | Keacher |
| 2012/0179071 A1 | 7/2012 | Skelton |
| 2012/0283800 A1 | 11/2012 | Perryman et al. |
| 2012/0296271 A1 | 11/2012 | Yomtov et al. |
| 2012/0296444 A1 | 11/2012 | Greenberg et al. |
| 2013/0053767 A1 | 2/2013 | Pivonka et al. |
| 2013/0096642 A1 | 4/2013 | Wingeier |
| 2013/0096650 A1 | 4/2013 | Aghassian |
| 2013/0110194 A1 | 5/2013 | Wei |
| 2013/0204321 A1 | 8/2013 | Alataris et al. |
| 2013/0215979 A1 | 8/2013 | Yakovlev et al. |
| 2013/0310706 A1 | 11/2013 | Stone et al. |
| 2013/0310901 A1 | 11/2013 | Perryman et al. |
| 2013/0331638 A1 | 12/2013 | Cameron et al. |
| 2014/0018788 A1 | 1/2014 | Engelman et al. |
| 2014/0025140 A1 | 1/2014 | Lui et al. |
| 2014/0058467 A1 | 2/2014 | Hamann et al. |

(56) References Cited

U.S. PATENT DOCUMENTS

| | | | |
|---|---|---|---|
| 2014/0094876 A1 | 4/2014 | Wingeier et al. | |
| 2014/0100636 A1 | 4/2014 | Mashiach et al. | |
| 2014/0107709 A1 | 4/2014 | Schmitz et al. | |
| 2014/0107752 A1 | 4/2014 | Parramon et al. | |
| 2014/0163580 A1 | 6/2014 | Tischendorf et al. | |
| 2014/0163638 A1 | 6/2014 | Marnfeldt et al. | |
| 2014/0163645 A1 | 6/2014 | Dinsmoor et al. | |
| 2014/0163646 A1 | 6/2014 | Tischendorf et al. | |
| 2014/0172047 A1 | 6/2014 | Spitaels et al. | |
| 2014/0180365 A1 | 6/2014 | Perryman et al. | |
| 2014/0194771 A1* | 7/2014 | Parker | A61B 5/24 |
| | | | 600/554 |
| 2014/0257428 A1 | 9/2014 | Zhu | |
| 2014/0275847 A1 | 9/2014 | Perryman et al. | |
| 2014/0277281 A1 | 9/2014 | Grandhe | |
| 2014/0277282 A1 | 9/2014 | Jaax | |
| 2014/0304773 A1 | 10/2014 | Woods et al. | |
| 2014/0336727 A1 | 11/2014 | Perryman et al. | |
| 2014/0346078 A1 | 11/2014 | Chang | |
| 2014/0358197 A1 | 12/2014 | Mashiach et al. | |
| 2014/0364919 A1 | 12/2014 | Doan | |
| 2014/0371515 A1 | 12/2014 | John | |
| 2015/0012057 A1 | 1/2015 | Carlson et al. | |
| 2015/0018699 A1 | 1/2015 | Zeng et al. | |
| 2015/0080982 A1 | 3/2015 | Van Funderburk | |
| 2015/0100109 A1 | 4/2015 | Feldman et al. | |
| 2015/0321000 A1 | 11/2015 | Rosenbluth et al. | |
| 2015/0321002 A1 | 11/2015 | Khalil et al. | |
| 2015/0335285 A1 | 11/2015 | Poon et al. | |
| 2015/0380972 A1 | 12/2015 | Fort | |
| 2016/0015980 A1 | 1/2016 | Biele et al. | |
| 2016/0023022 A1 | 1/2016 | Zarins et al. | |
| 2016/0030666 A1 | 2/2016 | Lozano et al. | |
| 2016/0036261 A1 | 2/2016 | Lenive | |
| 2016/0045746 A1 | 2/2016 | Jiang et al. | |
| 2016/0106994 A1 | 4/2016 | Crosby et al. | |
| 2016/0113671 A1 | 4/2016 | Berger | |
| 2016/0121124 A1 | 5/2016 | Johanek et al. | |
| 2016/0136438 A1 | 5/2016 | Perryman et al. | |
| 2016/0136443 A1 | 5/2016 | Grandhe et al. | |
| 2016/0144184 A1 | 5/2016 | Marnfeldt | |
| 2016/0157769 A1 | 6/2016 | Min et al. | |
| 2016/0199657 A1 | 7/2016 | Jiang et al. | |
| 2016/0199658 A1 | 7/2016 | Nassif et al. | |
| 2016/0218433 A1 | 7/2016 | Nghiem et al. | |
| 2016/0331956 A1 | 11/2016 | Yakovlev et al. | |
| 2016/0361545 A1 | 12/2016 | Kaula et al. | |
| 2016/0375237 A1 | 12/2016 | Hahn et al. | |
| 2017/0001003 A1 | 1/2017 | Pivonka et al. | |
| 2017/0050021 A1 | 2/2017 | Cosman, Sr. | |
| 2017/0054324 A1 | 2/2017 | Pivonka et al. | |
| 2017/0054332 A1 | 2/2017 | Pivonka et al. | |
| 2017/0087353 A1 | 3/2017 | Thota et al. | |
| 2017/0095667 A1 | 4/2017 | Yakovlev et al. | |
| 2017/0113046 A1 | 4/2017 | Fried et al. | |
| 2017/0165491 A9 | 6/2017 | De | |
| 2017/0189683 A1 | 7/2017 | Perryman et al. | |
| 2017/0197082 A1 | 7/2017 | Pang et al. | |
| 2017/0239483 A1 | 8/2017 | Mathur et al. | |
| 2017/0319855 A1 | 11/2017 | Kramer et al. | |
| 2018/0028824 A1 | 2/2018 | Pivonka et al. | |
| 2018/0064944 A1 | 3/2018 | Grill et al. | |
| 2018/0070841 A1 | 3/2018 | Honore et al. | |
| 2018/0071512 A1 | 3/2018 | Feldman et al. | |
| 2018/0071536 A1 | 3/2018 | Skelton et al. | |
| 2018/0083668 A1 | 3/2018 | Yakovlev et al. | |
| 2018/0085593 A1 | 3/2018 | Fayram et al. | |
| 2018/0140843 A1 | 5/2018 | Kent et al. | |
| 2018/0169423 A1 | 6/2018 | Perryman et al. | |
| 2018/0193651 A1 | 7/2018 | Annoni et al. | |
| 2018/0200520 A1* | 7/2018 | Tranchina | A61N 1/36139 |
| 2018/0214699 A1 | 8/2018 | Kothandaraman et al. | |
| 2018/0214700 A1 | 8/2018 | Vansickle et al. | |
| 2018/0236237 A1 | 8/2018 | Kent et al. | |
| 2018/0243563 A1 | 8/2018 | Vallejo et al. | |
| 2018/0256906 A1 | 9/2018 | Pivonka et al. | |
| 2018/0289965 A1* | 10/2018 | Nelson | A61N 1/36175 |
| 2018/0296834 A1 | 10/2018 | John et al. | |
| 2018/0326220 A1* | 11/2018 | Kaula | A61N 1/37235 |
| 2018/0333578 A1 | 11/2018 | Mock et al. | |
| 2018/0345019 A1 | 12/2018 | Greenberg et al. | |
| 2018/0368875 A1 | 12/2018 | Castillo et al. | |
| 2018/0369573 A1 | 12/2018 | Cholette et al. | |
| 2019/0001139 A1 | 1/2019 | Mishra et al. | |
| 2019/0008556 A1 | 1/2019 | Perryman et al. | |
| 2019/0009097 A1 | 1/2019 | Hartley et al. | |
| 2019/0030339 A1* | 1/2019 | Baru | A61N 1/3605 |
| 2019/0143124 A1 | 5/2019 | Perryman et al. | |
| 2019/0151659 A1 | 5/2019 | Mishra et al. | |
| 2019/0209844 A1 | 7/2019 | Esteller et al. | |
| 2019/0247198 A1 | 8/2019 | Zellmer et al. | |
| 2019/0262610 A1 | 8/2019 | Kent et al. | |
| 2019/0269913 A1 | 9/2019 | Pivonka et al. | |
| 2019/0366094 A1* | 12/2019 | Esteller | A61B 5/24 |
| 2019/0374776 A1 | 12/2019 | Mishra et al. | |
| 2019/0388692 A1* | 12/2019 | Dinsmoor | A61N 1/36071 |
| 2020/0038660 A1 | 2/2020 | Torgerson | |
| 2020/0101291 A1 | 4/2020 | Yakovlev et al. | |
| 2020/0132434 A1 | 4/2020 | Riahi et al. | |
| 2020/0139138 A1 | 5/2020 | Sit et al. | |
| 2020/0147388 A1 | 5/2020 | Huertas Fernandez et al. | |
| 2020/0204209 A1 | 6/2020 | Yakovlev et al. | |
| 2020/0206511 A1 | 7/2020 | Goedeke et al. | |
| 2020/0222000 A1 | 7/2020 | Poon et al. | |
| 2020/0305745 A1 | 10/2020 | Wagenbach et al. | |
| 2020/0306528 A1 | 10/2020 | Linden et al. | |
| 2020/0398058 A1 | 12/2020 | Pivonka et al. | |
| 2021/0099015 A1 | 4/2021 | Pivonka et al. | |
| 2021/0187300 A1 | 6/2021 | Dinsmoor et al. | |
| 2021/0196957 A1 | 7/2021 | Yakolev et al. | |
| 2021/0330981 A1 | 10/2021 | Mishra et al. | |
| 2021/0399765 A1 | 12/2021 | Yakovlev et al. | |
| 2022/0016103 A1 | 1/2022 | Baltcheva et al. | |
| 2022/0016430 A1 | 1/2022 | Hartley et al. | |
| 2022/0072300 A1 | 3/2022 | Yakovlev et al. | |
| 2022/0080189 A1 | 3/2022 | Mishra et al. | |
| 2022/0126103 A1 | 4/2022 | Pivonka et al. | |
| 2022/0134108 A1 | 5/2022 | Dinsmoor et al. | |
| 2022/0176108 A1 | 6/2022 | Linden et al. | |
| 2022/0176120 A1 | 6/2022 | Kulkarni et al. | |
| 2022/0176133 A1 | 6/2022 | Buddha et al. | |
| 2022/0218994 A1 | 7/2022 | Mishra et al. | |
| 2022/0263346 A1 | 8/2022 | Pivonka et al. | |
| 2023/0029600 A1 | 2/2023 | Pivonka et al. | |
| 2023/0129373 A1 | 4/2023 | Sit et al. | |
| 2023/0146724 A1 | 5/2023 | Debock et al. | |
| 2024/0041399 A1 | 2/2024 | Pivonka | |
| 2024/0050747 A1 | 2/2024 | Mishra et al. | |
| 2024/0050758 A1 | 2/2024 | Castillo et al. | |
| 2024/0139517 A1 | 5/2024 | Mishra | |
| 2024/0226548 A1 | 7/2024 | Mishra et al. | |
| 2024/0278022 A1 | 8/2024 | Mishra et al. | |
| 2024/0307687 A1 | 9/2024 | Mishra et al. | |
| 2025/0158657 A1 | 5/2025 | Yakovlev et al. | |
| 2025/0213872 A1 | 7/2025 | Pivonka et al. | |
| 2025/0325812 A1 | 10/2025 | Yakovlev et al. | |
| 2025/0332408 A1 | 10/2025 | Linden et al. | |

FOREIGN PATENT DOCUMENTS

| | | |
|---|---|---|
| WO | WO-9500203 A1 | 1/1995 |
| WO | WO-2005105201 A2 | 11/2005 |
| WO | WO-2007051146 A1 | 5/2007 |
| WO | WO-2010051062 A1 | 5/2010 |
| WO | WO-2010062517 A1 | 6/2010 |
| WO | WO-2014071079 A1 | 5/2014 |
| WO | WO-2014089299 A2 | 6/2014 |
| WO | WO-2014153124 A1 | 9/2014 |
| WO | WO-2014153228 A1 | 9/2014 |
| WO | WO-2014205129 A1 | 12/2014 |
| WO | WO-2015139053 A1 | 9/2015 |
| WO | WO-2015196164 | 12/2015 |
| WO | WO-2015196164 A3 | 2/2016 |
| WO | WO-2016028608 A1 | 2/2016 |

(56)               References Cited

FOREIGN PATENT DOCUMENTS

| WO | WO-2016113832 A1 | 7/2016 | | |
|----|------------------|--------|---|---|
| WO | WO-2016127130 A1 | 8/2016 | | |
| WO | WO-2017044904 A1 | 3/2017 | | |
| WO | WO-2017142948 A1 | 8/2017 | | |
| WO | WO-2017165410 A1 | 9/2017 | | |
| WO | WO-2017205675 A1 | 11/2017 | | |
| WO | WO-2018017463 A1 | 1/2018 | | |
| WO | WO-2018023057 A1 | 2/2018 | | |
| WO | WO-2018126062 A1 | 7/2018 | | |
| WO | WO-2018144631 A1 | 8/2018 | | |
| WO | WO-2018156953 A1 | 8/2018 | | |
| WO | WO-2018170141 A1 | 9/2018 | | |
| WO | WO-2018208992 A1 | 11/2018 | | |
| WO | WO-2019226557 A1 | 11/2019 | | |
| WO | WO-2019226568 A1 | 11/2019 | | |
| WO | WO-2020070492 A1 * | 4/2020 | ........... | A61N 1/3606 |
| WO | WO-2021003439 | 1/2021 | | |
| WO | WO-2021067873 | 4/2021 | | |
| WO | WO-2021/133947 | 7/2021 | | |
| WO | WO-2021262762 A1 | 12/2021 | | |
| WO | WO-2022047077 A1 | 3/2022 | | |
| WO | WO-2022103774 A1 | 5/2022 | | |
| WO | WO-2022197748 A1 | 9/2022 | | |
| WO | WO-2025158408 A1 | 7/2025 | | |

OTHER PUBLICATIONS

He Shuman, Teagle Holly F. B., Buchman Craig A.; "The Electrically Evoked Compound Action Potential: From Laboratory to Clinic;" Frontiers in Neuroscience, vol. 11, Jun. 23, 2017. (Year: 2017).*
electronics.stackexchange.com, "Can the saturation of an OPA influence its input?" https://electronics.stackexchange.com/questions/174179/can-the-saturation-of-an-opa-influence-its-input, Jun. 6, 2015, accessed Jul. 15, 2025 (Year: 2015).*
Wikipedia, "Negative-feedback amplifier," https://en.wikipedia.org/wiki/Negative-feedback_amplifier, accessed Jul. 24, 2025 (Year: 2025).*
Crosby, et al. Burst and Tonic Spinal Cord Stimulation Differentially Activate GABAergic Mechanisms to Attenuate Pain in a Rat Model of Cervical Radiculopathy. IEEE Transactions on Biomedical Engineering, 2015 62(6), 1604-1613. doi: 10.1109/tbme.2015.2399374.
PCT/US2020/054150 International Search Report and Written Opinion dated Jan. 6, 2021.
U.S. Appl. No. 63/042,293, inventors Mishra; Lakshmi Narayan et al., filed on Jun. 22, 2020.
U.S. Appl. No. 63/082,856, inventors Mishra; Lakshmi Narayan et al., filed on Sep. 24, 2020.
Buhlmann, J. et al., "Modeling of a segmented electrode for desynchronizing deep brain stimulation" Frontiers in Neuroengineering (2011) vol. 4, Article 15, pp. 1-8.
Butson, C. et al., "Current steering to Control the Volume of Tissue Activated During Deep Brain Stimulation" Brain Stimul. (2008) (1): 7-15.
EP14813206 Examination Report dated Apr. 23, 2020. 2 pages.
EP15809379.9 European Search Report dated Mar. 9, 2018. 7 pages.
European Search Report and Written Opinion in EP Application No. 16845235.7, mailed Apr. 24, 2019, 8 pages.
European Search Report and Written Opinion in EP Application No. 17770982.1, mailed Sep. 26, 2019, 7 pages.
European Search Report and Written Opinion in EP Application No. 17831624.6, mailed Feb. 20, 2020, 9 pages.
European Search Report and Written Opinion in EP Application No. 18797777.2, mailed Jan. 14, 2021, 7 pages.
Extended European Search Report for European Application No. EP21827905.7 dated Jun. 18, 2024, 5 pages.
Extended European Search Report mailed on Jan. 3, 2024, for EP Application No. 20871125.9, 15 pages.
Extended European Search Report mailed on Jan. 5, 2024, for EP Application No. 23186171.7, 7 pages.
Extended European Search Report mailed on Jun. 27, 2024, for EP Application No. 24157465.6, 7 pages.
Final Office Action for U.S. Appl. No. 16/111,868 mailed on Mar. 11, 2021, 24 pages.
Final Office Action for U.S. Appl. No. 17/379,928 dated Jul. 17, 2023, 13 pages.
Final Office Action for U.S. Appl. No. 16/222,959 mailed on Nov. 21, 2022, 21 pages.
Final Office Action mailed on Nov. 1, 2023, for U.S. Appl. No. 17/726,378, filed Apr. 21, 2022, 15 pages.
International Search Report and Written Opinion for International Application No. PCT/US2017/034553 mailed Oct. 10, 2017, 10 pages.
International Search Report and Written Opinion for PCT/US2016/051177, Nov. 10, 2016, 18 pages.
International Search Report and Written Opinion for PCT/US2017/023400, May 23, 2017, 8 pages.
International Search Report and Written Opinion for PCT/US2017/042351, Sep. 26, 2017, 9 pages.
International Search Report and Written Opinion for PCT/US2018/031904, Jul. 26, 2018, 10 pages.
International Search Report and Written Opinion for PCT/US2020/066901, Mar. 15, 2021, 7 pages.
International Search Report and Written Opinion for PCT/US2021/038545, mailed on Oct. 19, 2021, 7 pages.
International Search Report and Written Opinion mailed on Jan. 31, 2022 for PCT/US2021/058673, 8 pages.
International Search Report and Written Opinion mailed on May 18, 2022, for PCT Application No. PCT/US2022/020452, filed Mar. 15, 2022, 8 pages.
Non-Final Office Action for U.S. Appl. No. 16/111,868 mailed on Jul. 8, 2021, 30 pages.
Non-Final Office Action for U.S. Appl. No. 17/726,378 dated Apr. 14, 2023, 15 pages.
Non-Final Office Action mailed on Jan. 29, 2024, for U.S. Appl. No. 17/379,928, filed Jul. 19, 2021, 16 pages.
Non-Final Office Action mailed on Mar. 22, 2023, for U.S. Appl. No. 17/489,580, filed Sep. 29, 2021, 16 pages.
Non-Final Office Action mailed on May 20, 2024, for U.S. Appl. No. 17/726,378, filed Apr. 21, 2022, 11 pages.
Notice of Allowance for U.S. Appl. No. 16/222,959 dated May 22, 2023, 11 pages.
Notice of Allowance mailed on Nov. 22, 2023, for U.S. Appl. No. 17/489,580, filed Sep. 29, 2021, 9 pages.
Office Action dated Oct. 20, 2017 for U.S. Appl. No. 15/264,864, 14 pages.
Partial Supplementary European Search Report mailed on Sep. 18, 2023, for EP Application No. 20871125.9, 14 pages.
U.S. Appl. No. 16/672,921 Notice of Allowance dated Apr. 23, 2021, 7 pages.
U.S. Appl. No. 16/672,921 Office Action dated Feb. 16, 2021, 10 pages.
U.S. Appl. No. 16/672,921 Office Action dated Mar. 22, 2021, 11 pages.
Yakovlev, Anatoly et al., "Implantable Biomedical Devices: Wireless powering and communication," IEEE Communications Magazine, IEEE Service Center, vol. 50, No. 4, Apr. 1, 2012, pp. 152-159.
Extended European Search Report for European Application No. 21892687.1 mailed Sep. 18, 2024, 6 pages.
Extended European Search Report for European Application No. 22772095.0 mailed Dec. 23, 2024, 9 pages.
Final Office Action for U.S. Appl. No. 17/726,378 mailed Dec. 16, 2024, 15 pages.
Non-Final Office Action for U.S. Appl. No. 17/383,972 mailed Dec. 3, 2024, 23 pages.
Non-Final Office Action for U.S. Appl. No. 17/383,985 mailed Dec. 27, 2024, 14 pages.
Notice of Allowance for U.S. Appl. No. 17/379,928 mailed Sep. 18, 2024, 7 pages.
EP Application No. 21862769.3, Extended European Search Report mailed Jul. 25, 2024; Applicant Nalu Medical, Inc.; 6 pages.

(56) References Cited

OTHER PUBLICATIONS

EP Application No. 25170468.0, Extended European Search Report mailed Aug. 21, 2025; Applicant Nalu Medical, Inc.; 7 pages.

U.S. Appl. No. 18/314,624, Non-Final Office Action mailed Jul. 1, 2025, Inventor Mishra, Lakshmi Narayan et al.; 9 pages.

U.S. Appl. No. 17/726,378, Ex Parte Quayle Action mailed May 29, 2025; Inventor Pivonka, Daniel et al.; 5 pages.

U.S. Appl. No. 17/726,378, Notice of Allowance mailed Aug. 26, 2025; Inventor Pivonka, Daniel et al.; 7 pages.

U.S. Appl. No. 18/174,557, Non-Final Office Action mailed Sep. 10, 2025; Inventor Mishra, Lakshmi Narayan et al.; 9 pages.

U.S. Appl. No. 18/453,154, Non-Final Office Action mailed Oct. 16, 2025; Inventor Mishra, Lakshmi Narayan et al.; 9 pages.

U.S. Appl. No. 18/463,225, Non-Final Office Action mailed Aug. 20, 2025; Inventor Mishra, Lakshmi Narayan et al.; 9 pages.

U.S. Appl. No. 19/399,426, filed Nov. 24, 2025; Inventor Pivonka, Daniel et al.

* cited by examiner

Connecting to the lead(s) 265

Lead 265 Ancohor 221 at incision site

External Device 500 in sterile bag

Trace outline of the External Device 500

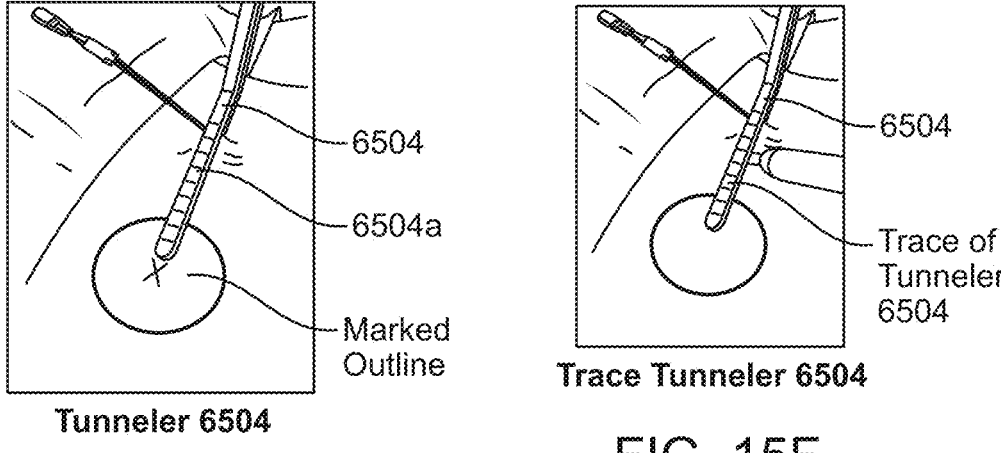
6504
6504a
Marked Outline
Tunneler 6504
FIG. 15E
6504
Trace of Tunneler 6504
Trace Tunneler 6504
FIG. 15F
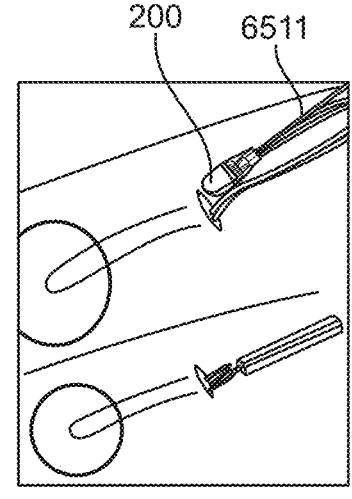
200     6511
*Using the Implantable Pulse Generator Insertion tool to advance the Implantable Pulse Generator*
FIG. 15G

*Image of leads passing through the
Tearaway Introducer*

*Stylets loaded into integrated
implanted Pulse Generator*

*Lead Alignment*

*Cross-sectional image of spine with
Tearaway Introducer and lead deployed*

*Splitting tearaway
sheaths*

HUB
TAB

Connecting to the lead(s) 265

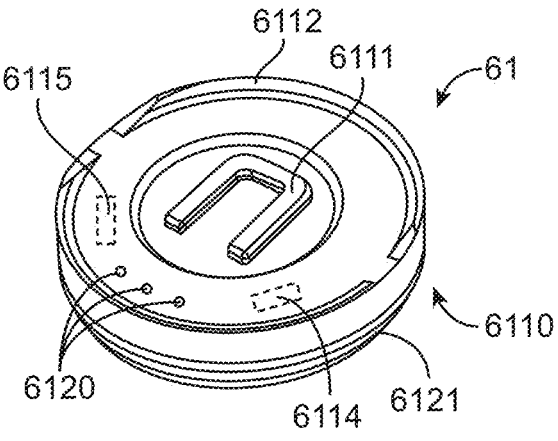
FIG. 17A
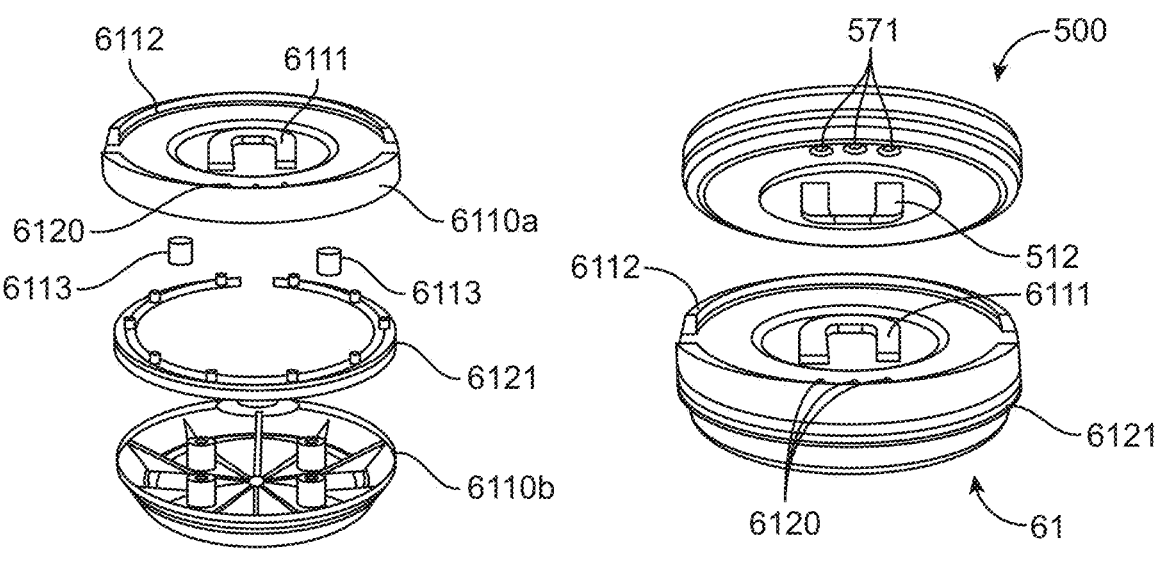
FIG. 17B          FIG. 17C

Stimulation Control Table (SCT) Block Diagram

*ETM FPGA and Surrounding System Block Diagram*

255b
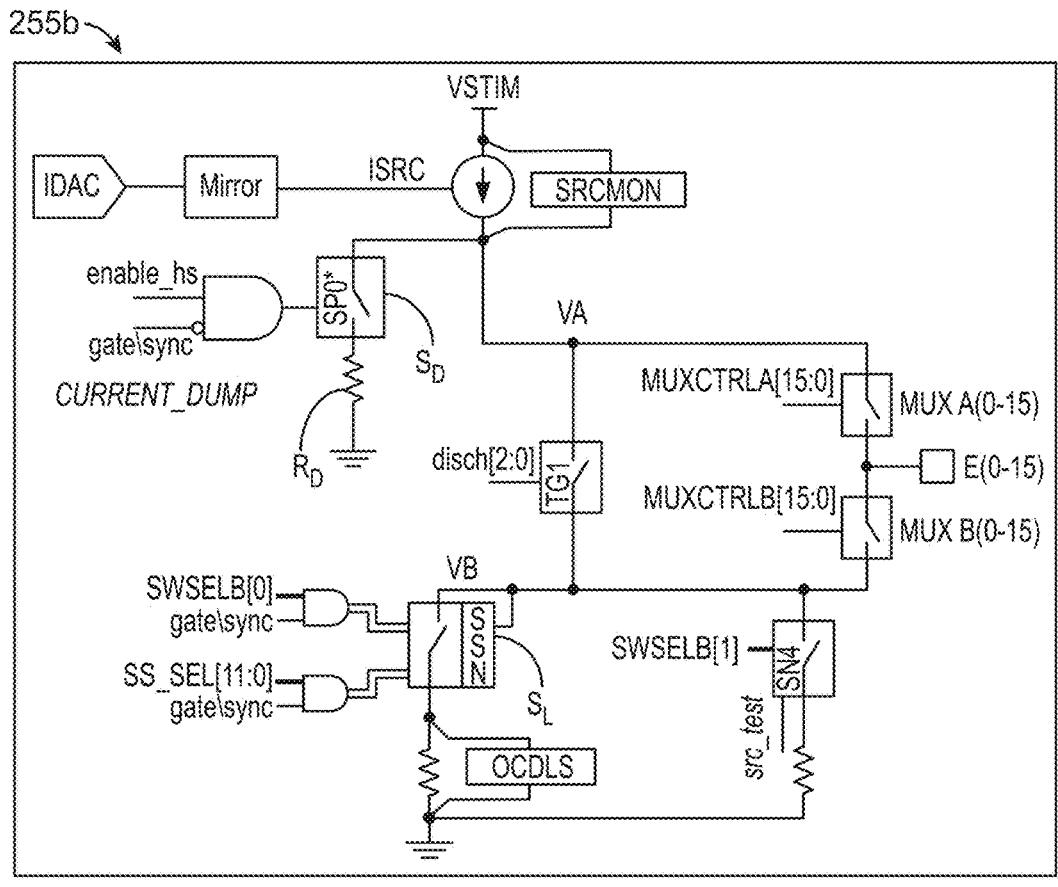
FIG. 25A
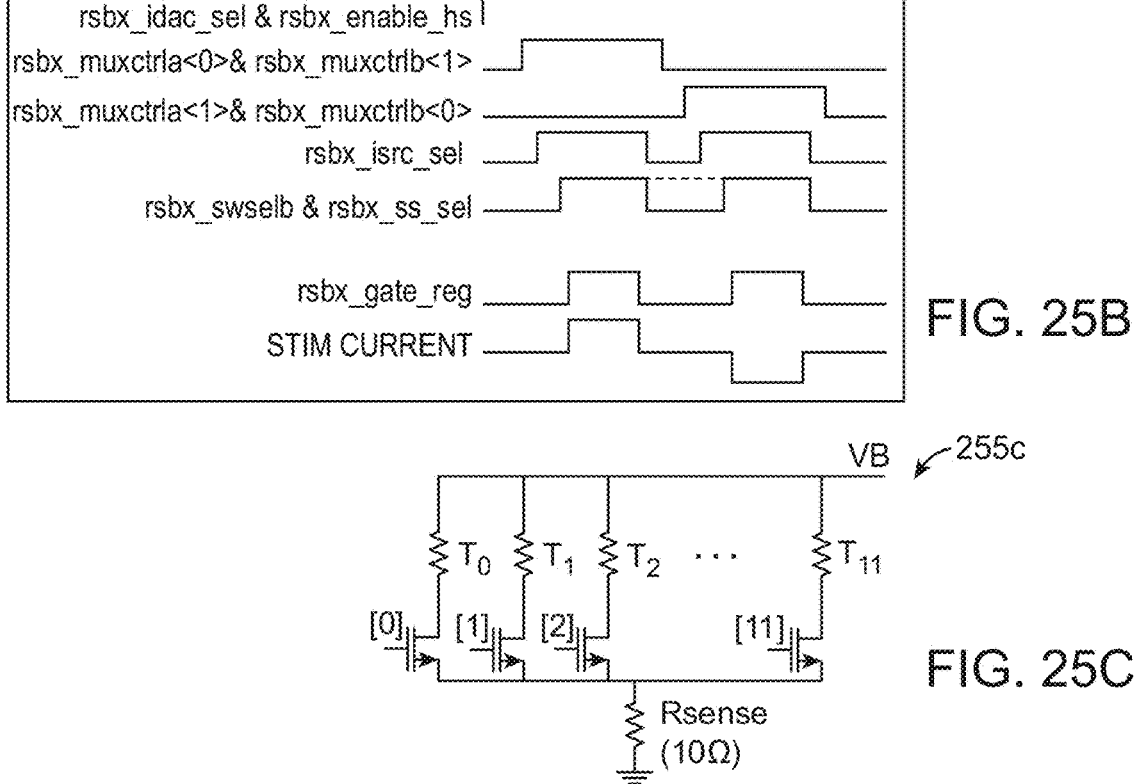
FIG. 25B
FIG. 25C

T8 – 11% of responders

T9 – 74% of responders
(100% of anatomic placements)

T10 – 16% of responders

Responders (leg or back)

STIMULATION APPARATUS

CROSS-REFERENCE

This application is a continuation of PCT Application No. PCT/US20/54150, filed Oct. 2, 2020; which claims priority to U.S. Provisional Application No. 62/910,685, filed Oct. 4, 2019; U.S. Provisional Application No. 62/933,184, filed Nov. 8, 2019; U.S. Provisional Application No. 62/977,901, filed Feb. 18, 2020; and U.S. Provisional Application No. 62/988,281, filed Mar. 11, 2020; the contents of which are incorporated herein by reference in their entirety for all purposes.

RELATED APPLICATIONS

This application is related to: U.S. patent application Ser. No. 14/975,358, titled "Method and Apparatus for Minimally Invasive Implantable Modulators", filed Dec. 18, 2015; U.S. patent application Ser. No. 15/664,231, titled "Medical Apparatus Including an Implantable System and an External System", filed Jul. 31, 2017; U.S. patent application Ser. No. 16/104,829, titled "Apparatus with Enhanced Stimulation Waveforms", filed Aug. 17, 2018; U.S. patent application Ser. No. 16/111,868, titled "Devices and Methods for Positioning External Devices in Relation to Implanted Devices", filed Aug. 24, 2018; U.S. patent application Ser. No. 16/120,139, titled "Methods and Systems for Insertion and Fixation of Implantable Devices", filed Aug. 31, 2018; U.S. patent application Ser. No. 16/222,959, titled "Methods and Systems for Treating Pelvic Disorders and Pain Conditions", filed Dec. 17, 2018; U.S. patent application Ser. No. 16/266,822, titled "Method and Apparatus for Versatile Minimally Invasive Neuromodulators", filed Feb. 4, 2019; U.S. patent application Ser. No. 16/408,989, titled "Method and Apparatus for Neuromodulation Treatments of Pain and Other Conditions", filed May 10, 2019; U.S. patent application Ser. No. 16/453,917, titled "Stimulation Apparatus", filed Jun. 26, 2019; U.S. patent application Ser. No. 16/505,425, titled "Wireless Implantable Sensing Devices", filed Jul. 8, 2019; U.S. patent application Ser. No. 16/539, 977, titled "Apparatus with Sequentially Implanted Stimulators", filed Aug. 13, 2019; U.S. patent application Ser. No. 16/672,921, titled "Stimulation Apparatus", filed Nov. 4, 2019; U.S. Provisional Application Ser. No. 62/952,717, titled "System with Implanted Conduit Tracking", filed Dec. 23, 2019; U.S. Provisional Application Ser. No. 63/042,293, titled "Systems with Implanted Conduit Tracking", filed Jun. 22, 2020; U.S. Provisional Application Ser. No. 63/082,856, titled "Stimulation Energy Systems with Current Steering", filed Sep. 24, 2020; the content of each of which is incorporated herein by reference in its entirety for all purposes.

BACKGROUND OF THE INVENTION

Field of the Invention

The present invention relates generally to medical apparatus for a patient, and in particular, apparatus that deliver enhanced stimulation to effectively deliver a therapy while avoiding undesired effects.

Background

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g. to treat pain). Most implants are relatively large devices with batteries and long conduits, such as implantable leads configured to deliver electrical energy or implantable tubes (i.e. catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices and methods that provide one or more implantable devices and are designed to provide enhanced treatment of pain and other enhanced benefits.

SUMMARY

According to an aspect of the present inventive concepts, a medical apparatus for a patient comprises: an external system and an implantable system. The external system is configured to transmit one or more transmission signals, each transmission signal comprising at least power or data. The implantable system is configured to receive the one or more transmission signals from the external system. The external system comprises a first external device comprising: at least one external antenna configured to transmit a first transmission signal to the implantable system, the first transmission signal comprising at least power or data; an external transmitter configured to drive the at least one external antenna; an external power supply configured to provide power to at least the external transmitter; and an external controller configured to control the external transmitter. The implantable system comprises a first implantable device comprising: at least one implantable antenna configured to receive the first transmission signal from the first external device; an implantable receiver configured to receive the first transmission signal from the at least one implantable antenna; at least one implantable stimulation element configured to deliver stimulation energy to the patient; an implantable controller configured to control the stimulation energy delivered to the at least one implantable stimulation element; an implantable energy storage assembly configured to provide power to an element selected from the group consisting of: the at least one implantable stimulation element; the implantable controller; the implantable receiver; and combinations thereof; and an implantable housing surrounding at least the implantable controller and the implantable receiver.

In some embodiments, the stimulation energy delivered to the patient by the at least one implantable stimulation element comprises a tonic stimulation waveform that is provided at a high amplitude for a first time period, and the tonic stimulation waveform is provided at a decreased amplitude during a subsequent second time period. The decreased amplitude can comprise a sub-threshold amplitude or zero amplitude. The apparatus can be configured to deliver the decreased amplitude in an adaptive manner. The apparatus can be configured to deliver the decreased amplitude based on patient feedback regarding pain relief. The decreased amplitude can be delivered over a pre-defined duration.

In some embodiments, the stimulation energy delivered by the at least one implantable stimulation element comprises a high frequency tonic stimulation waveform combined with a low frequency tonic stimulation waveform.

In some embodiments, the apparatus is configured to steer current, and the apparatus is further configured to perform the current steering in a deterministic or random manner. The current steering can be configured to increase an anatomical area receiving the stimulation energy. The current steering can be configured to accommodate for patient movement and/or to compensate for neural fatigue. The apparatus can comprise a user interface configured to provide an image of an anatomical area, and the user interface can be further configured to allow an operator to select a portion of the anatomical area, and the apparatus can be configured to steer current into the selected portion. The apparatus can be configured to collect and/or process posture data, and the apparatus can be further configured to automatically steer the current based on the posture data.

In some embodiments, the apparatus is configured to produce a stimulation waveform, and the stimulation waveform comprises an artifact, and the apparatus is configured to record the artifact and to apply an inverted signal to remove the artifact from the delivered stimulation energy. The apparatus can be configured to apply scale and offset factors to the applied inverted signal.

In some embodiments, the stimulation energy delivered to the patient by the at least one implantable stimulation element comprises a first set of pulses comprising multiple small duration pulses that are separated by a small inter-pulse gap (e.g. an inter-pulse gap between each pair of small duration pulses), and the first set of pulses creates a similar physiologic effect as a single pulse with a duration similar to the duration of the first set of pulses. The apparatus can comprise a user interface configured to allow an operator to enter a pulse density percentage, and the stimulation energy can be delivered based on the entered pulse density percentage. The apparatus can be configured to calculate the pulse width and inter-pulse gap of the first set of pulses based on the pulse density percentage entered and a single pulse to stimulate. The apparatus can comprise a user interface configured to allow an operator to enter two or more parameters selected from the group consisting of: pulse width; inter-pulse gap; and/or pulse density, and the apparatus can be configured to deliver the first set of pulses based on the entered two or more parameters. The apparatus can comprise a user interface configured to allow an operator to enter a single parameter from the group consisting of: pulse width; inter-pulse gap; or pulse density, and the apparatus can be configured to deliver the first set of pulses based on the entered single parameter and a default value for at least one of the non-entered parameters. The apparatus can comprise a user interface configured to allow an operator to enter a single parameter from the group consisting of: pulse width; inter-pulse gap; or pulse density, and the apparatus can be configured to deliver the first set of pulses based on the entered single parameter and to calculate a value for at least one of the non-entered parameters. The apparatus can be configured to calculate the value for the at least one non-entered parameters using a heuristic and/or machine learning approach.

In some embodiments, the at least one stimulation element comprises a set of stimulation elements that are configured to deliver the stimulation energy to multiple anatomical areas. The multiple anatomical areas can comprise at least four anatomical areas. The set of stimulation elements can comprise electrodes configured as anodes and cathodes that can be inverted to produce alternating polarities, and the stimulation waveform delivered simulates biphasic stimulation energy delivery. The stimulation energy can be delivered without passive charge recovery. The stimulation energy delivered can comprise a repeated series of multiple monophasic pulses followed by an intermittent pulse of opposite polarity. The stimulation energy can be delivered without passive charge recovery.

In some embodiments, the apparatus further comprises a programmer configured to provide multiple available stimulation waveforms for stimulation energy delivery. The apparatus can be configured to sequence through the available stimulation waveforms and deliver stimulation energy based on each stimulation waveform such that pain relief and/or presence of paresthesia can be determined for each of the stimulation waveforms. The at least one stimulation element can comprise multiple stimulation elements, and the apparatus can further comprise one or more leads comprising the multiple stimulation elements, and the apparatus can be configured to automatically determine the location of the one or more leads. The apparatus can comprise an image processing algorithm configured to determine the location of the one or more leads.

In some embodiments, the apparatus is configured to deliver stimulation energy comprising multiple stimulation waveforms without overlapping stimulation pulses and while controlling repetition of multiple stimulation waveforms. The apparatus can be configured to deliver stimulation pulses for each of the multiple stimulation waveforms at equal time periods, and the apparatus can be further configured to skip one or more pulses of one or more of the stimulation waveforms in order to maintain a desired pulse rate. The apparatus can be configured to determine a time interval of stimulation pulses to be delivered based on a stimulation waveform of the multiple stimulation waveforms that has the highest rate. The apparatus can be configured to determine a time interval of stimulation pulses to be delivered based on a desired accuracy of the stimulation pulse delivery. The apparatus can be configured to divide stimulation energy delivery into time segments, and the apparatus can be further configured to deliver or skip one or more pulses from each stimulation waveform of the multiple stimulation waveforms during each time segment. The apparatus can be configured to determine a maximum pulse rate and/or an accuracy of pulse rate delivery based on the length of each time segment and the total number of time segments.

In some embodiments, the apparatus is configured to deliver stimulation energy comprising a stimulation waveform modulated by an envelope signal. The envelope signal can comprise a sine wave. The stimulation waveform can comprise one or more trains and/or one or more bursts. The envelope signal can comprise a frequency that can be not a whole integer ratio of the frequency of the train and/or burst. The stimulation waveform can comprise one or more trains, and the envelope signal can comprise a frequency that can be between 0.01 and 100 times the frequency of the train frequency.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

6

Figures 13A, 13B:
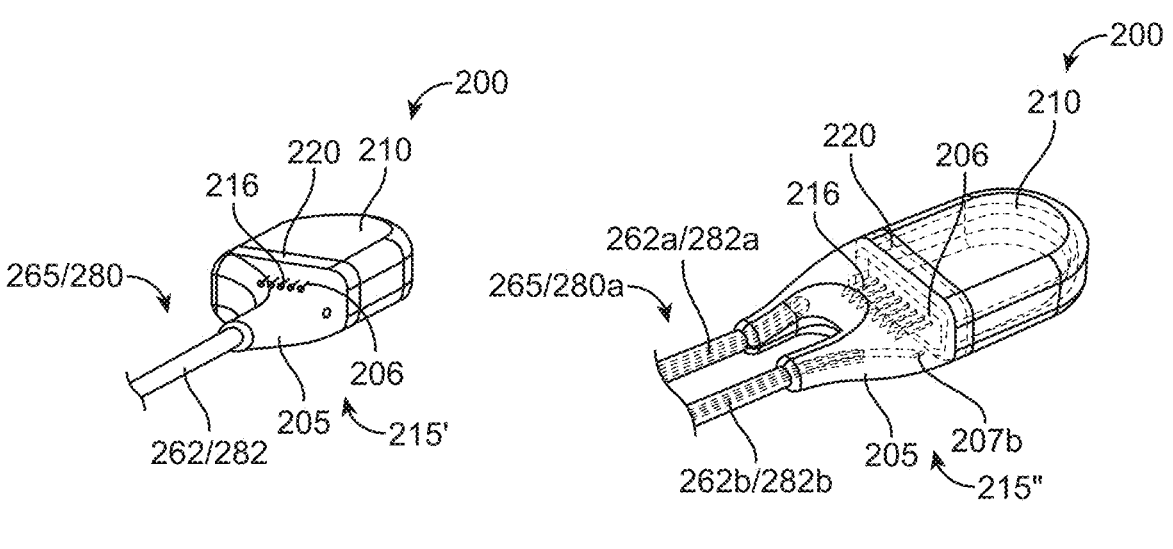

FIGS. 13A-B are perspective views and a top view, respectively, of an implantable device with a single lead, and an implantable device with dual leads, respectively, consistent with the present inventive concepts.

Figure 13C:
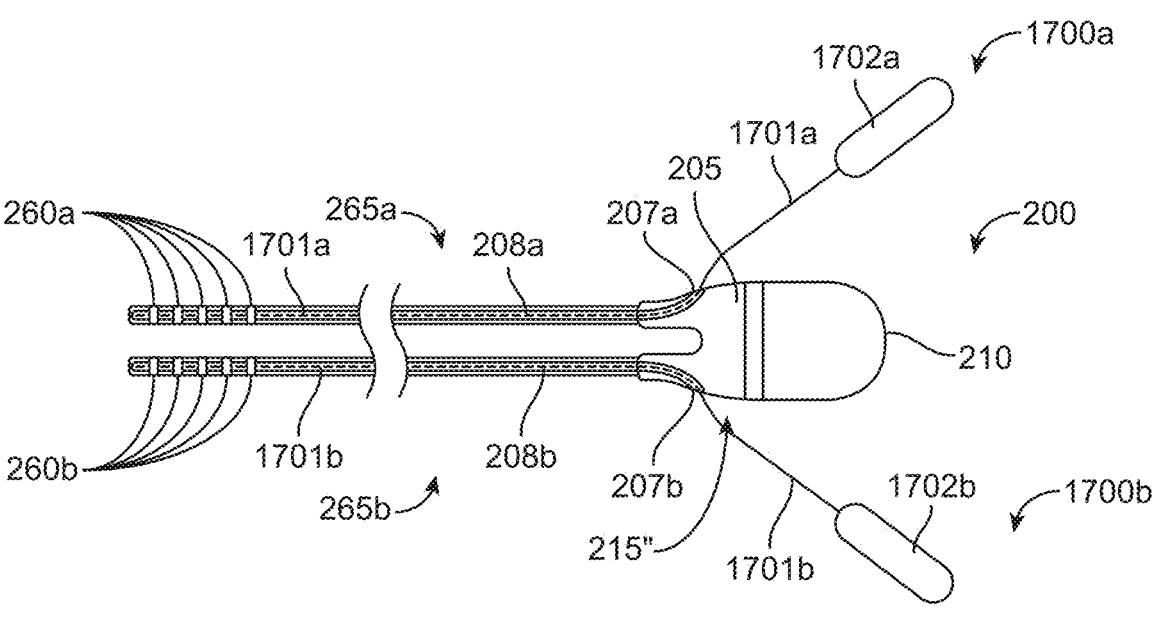

FIG. 13C is a top view of an implantable device with dual leads and separate implantation tools inserted into each lead, consistent with the present inventive concepts.

Figure 14A:
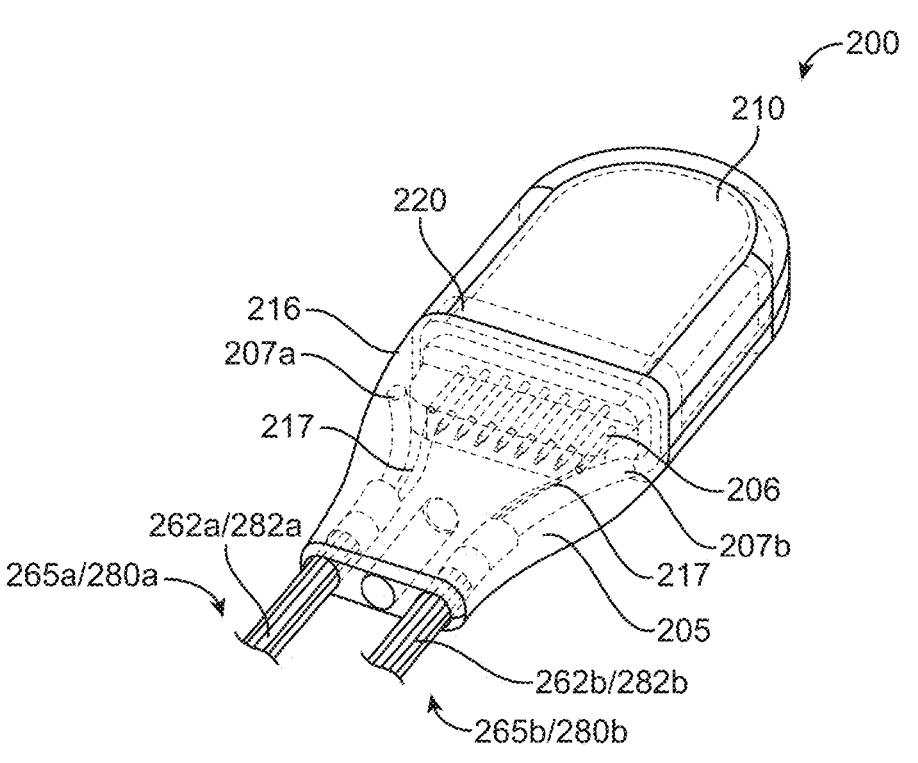
Figure 14B:
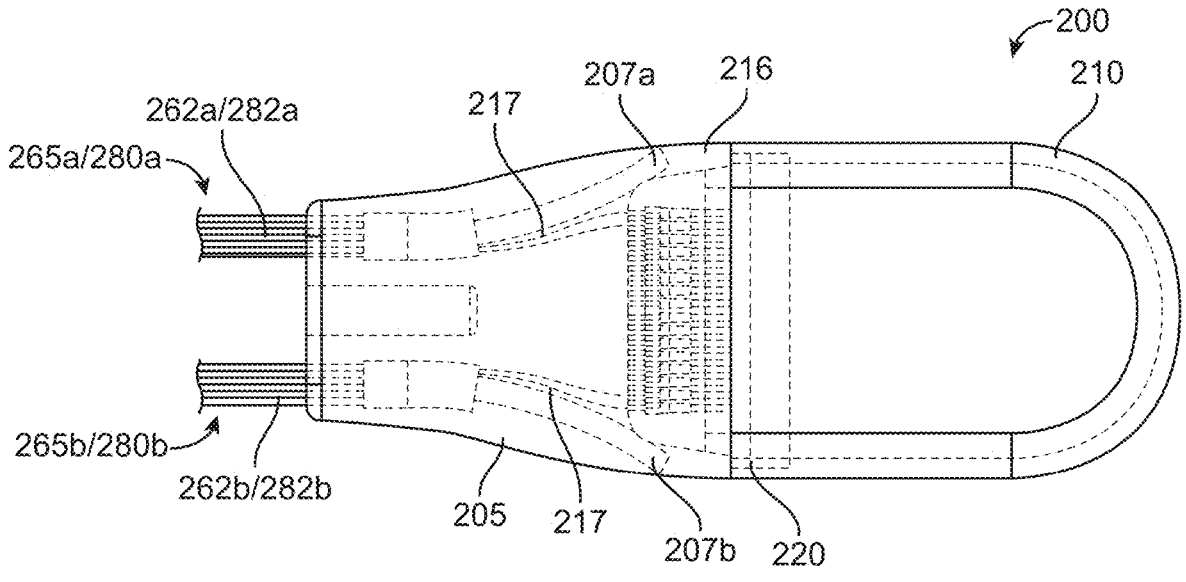

FIGS. 14A-B are a perspective view and a top view, respectively, of the proximal portion of an implantable device with dual leads, consistent with the present inventive concepts.

FIGS. 15A-M are a series of views of various implantation procedures for an implantable device, consistent with the present inventive concepts.

Figure 16A:
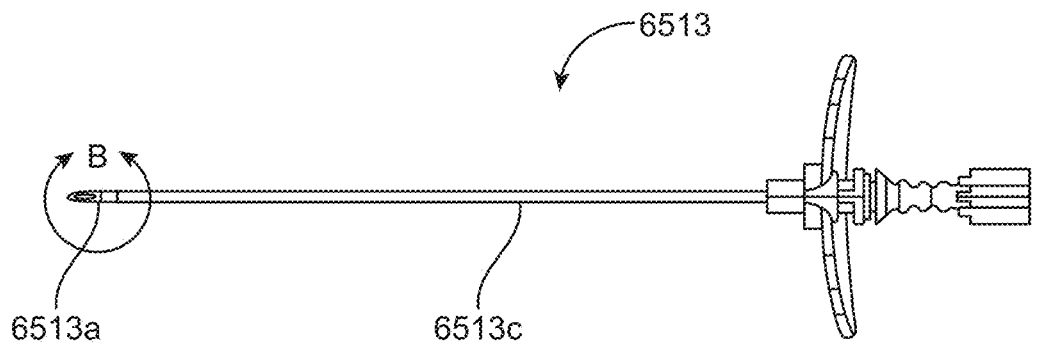
Figure 16B:
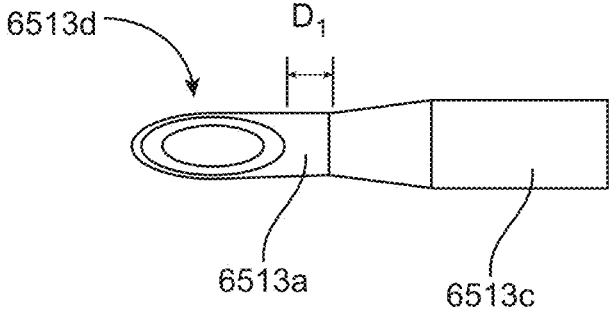

FIGS. 16A-B are a side view of an introducer tool, and a magnified view of the distal portion of the introducer tool, respectively, consistent with the present inventive concepts.

FIGS. 17A-C are various views of an external device and a charging device, consistent with the present inventive concepts.

Figure 17D:
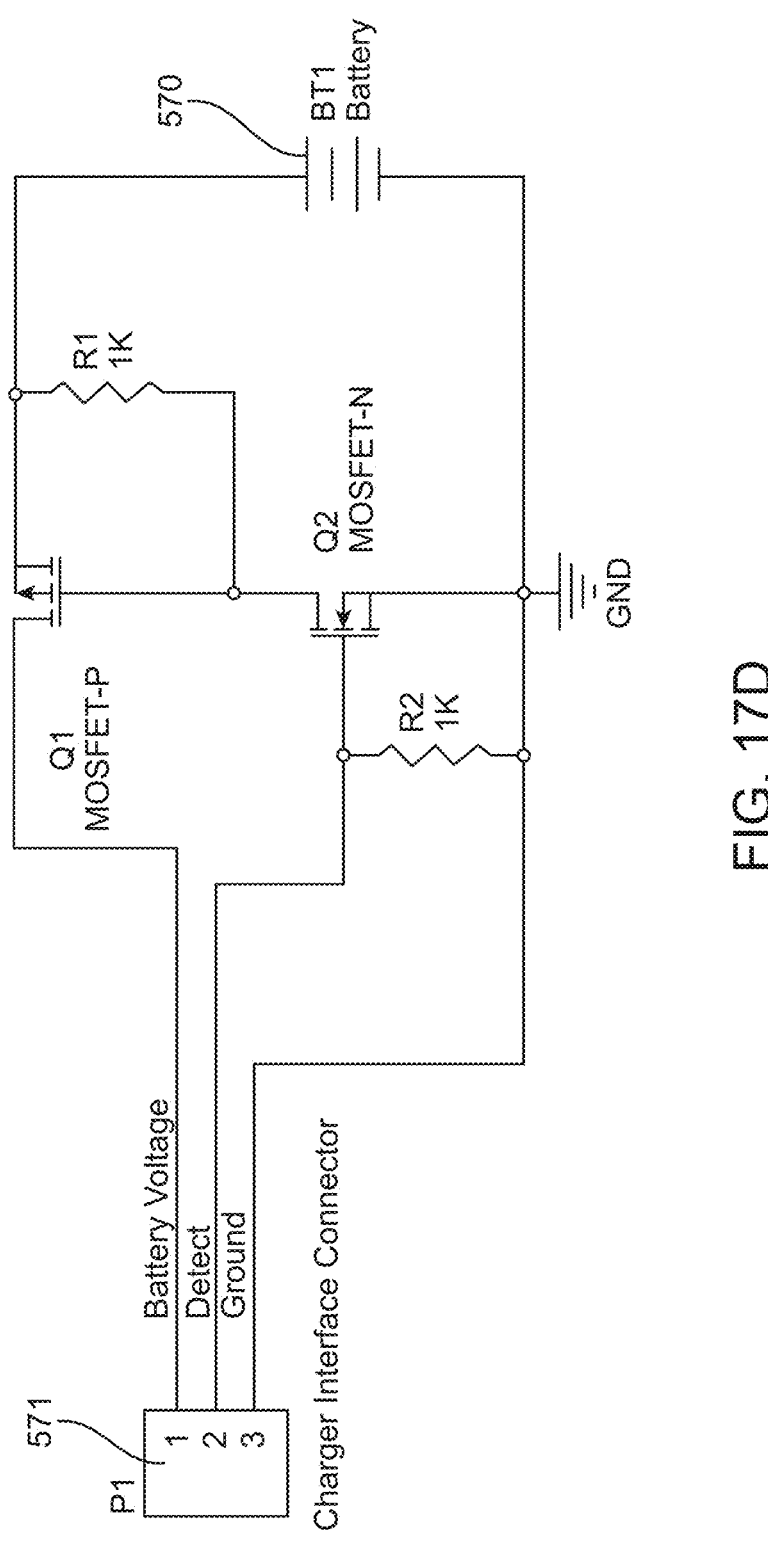

FIG. 17D is a schematic view of charging circuitry for an external device, consistent with the present inventive concepts.

Figure 18:
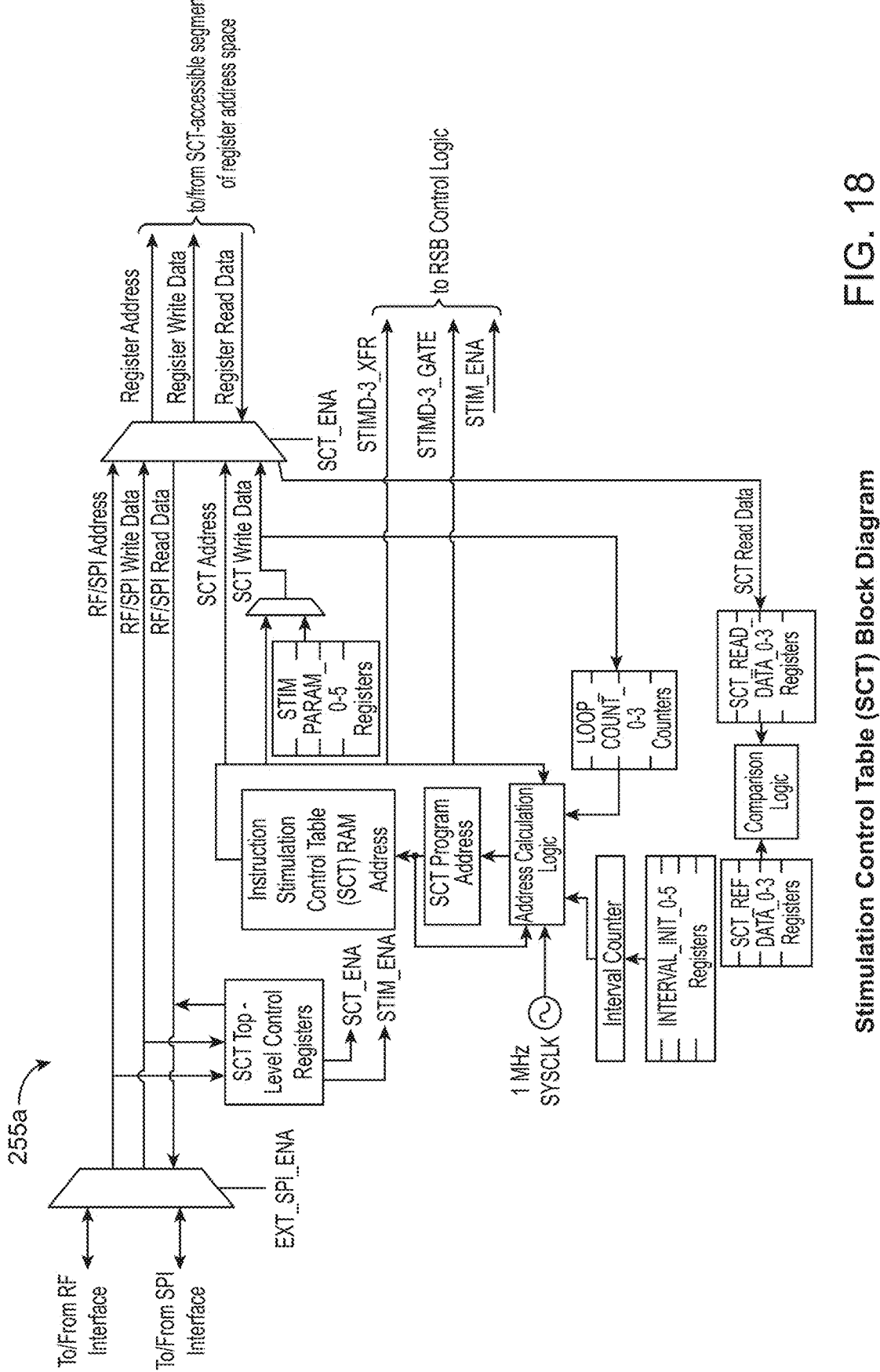

FIG. 18 is a schematic view of a portion of an electronic assembly of an implantable device, consistent with the present inventive concepts.

Figure 19:
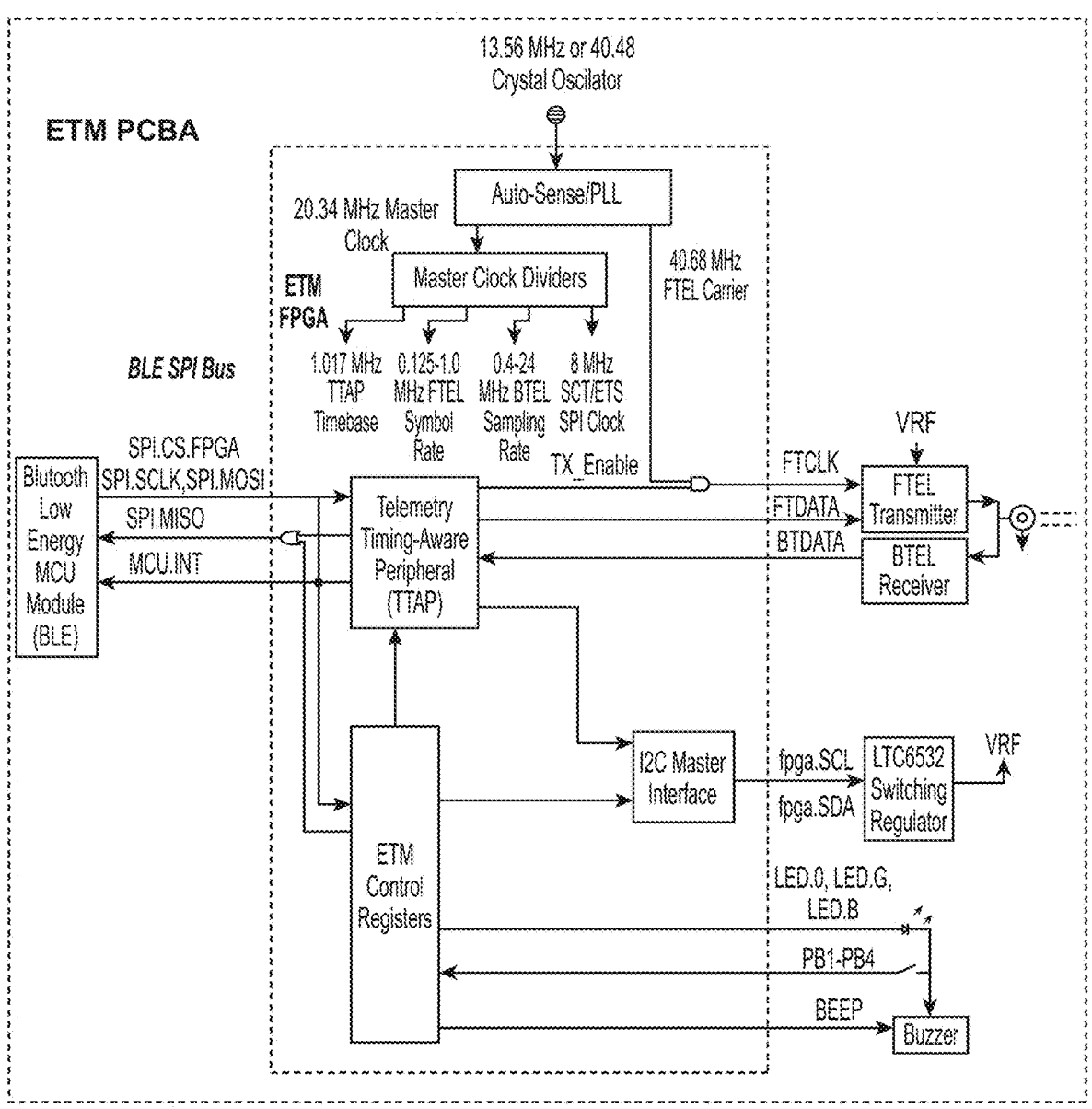

FIG. 19 is a representation of a TTAP packed description format, consistent with the present inventive concepts.

Figures 20A, 20B:
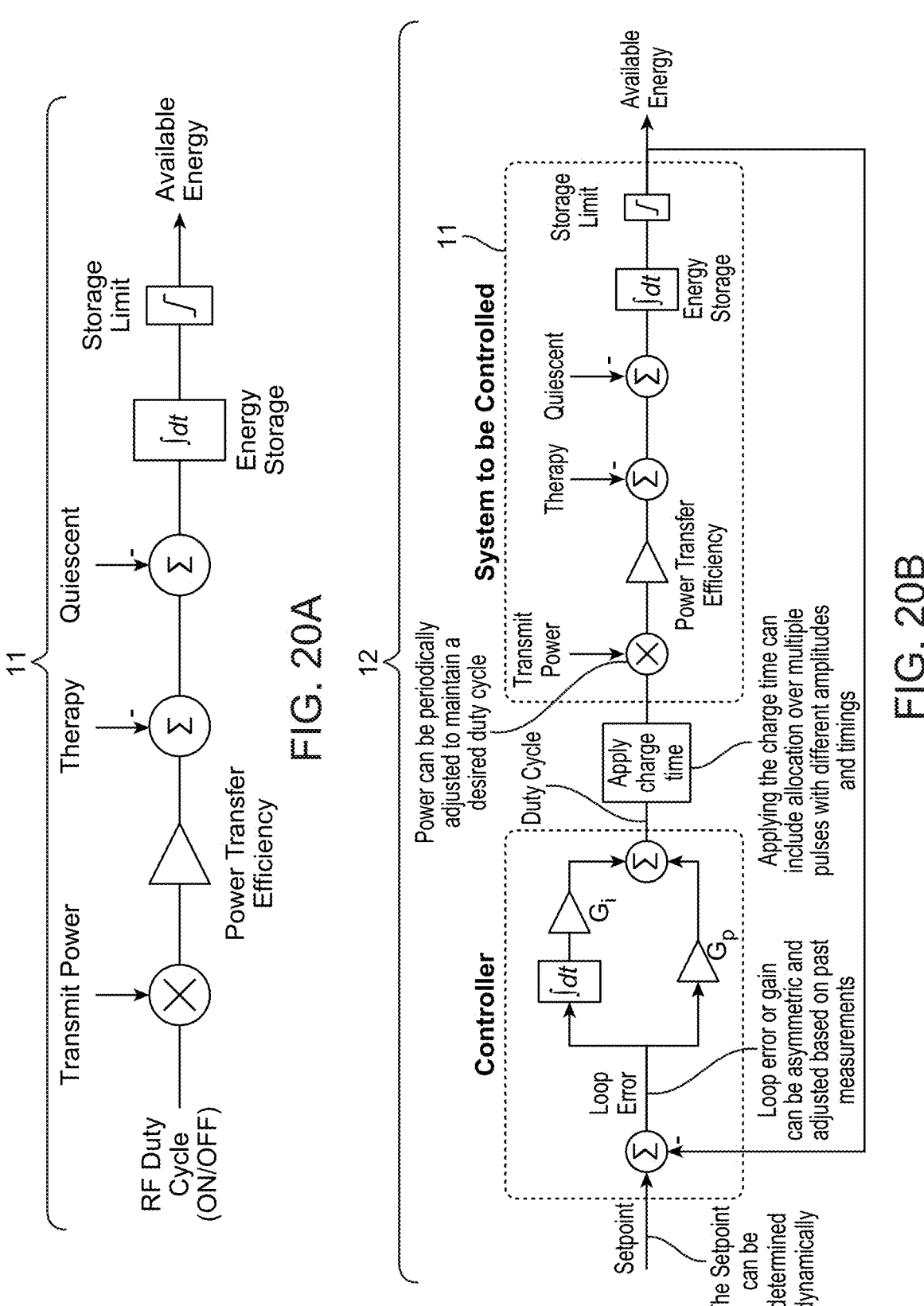

FIGS. 20A-B are schematic views of a power delivery and consumption arrangement of a stimulation apparatus, consistent with the present inventive concepts.

Figure 21:
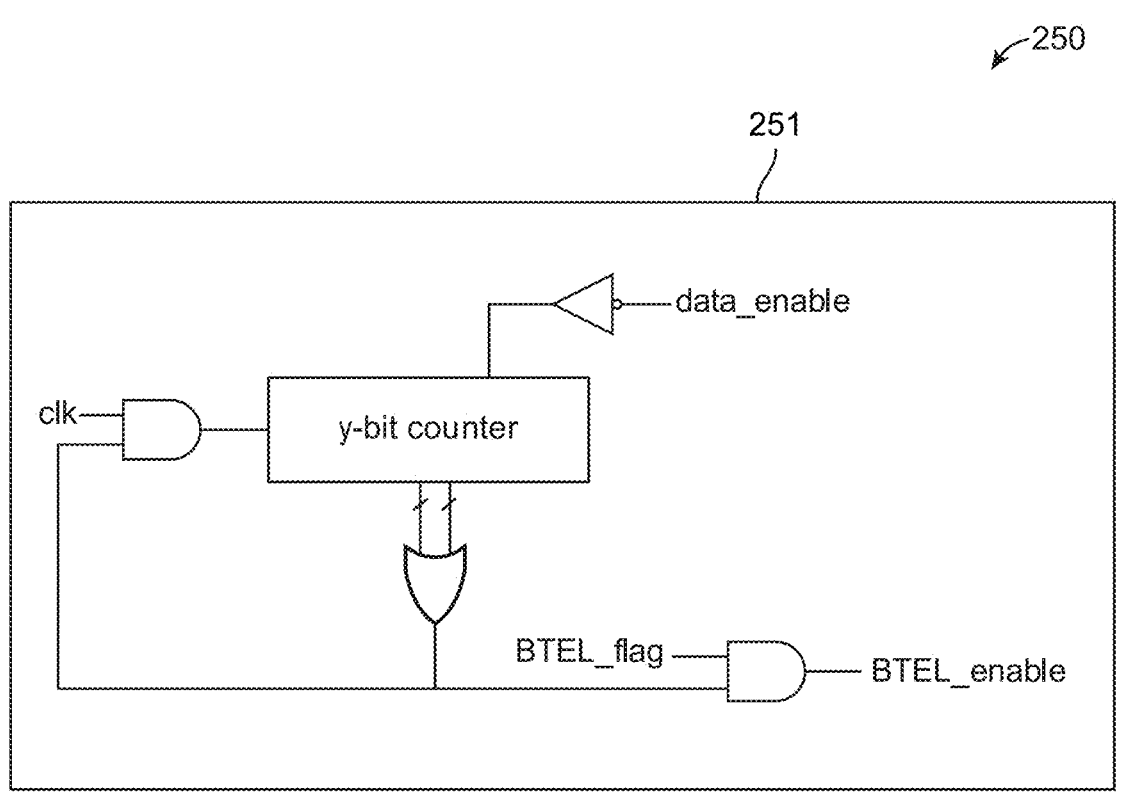

FIG. 21 is a schematic view of a back-telemetry circuit of an implantable device, consistent with the present inventive concepts.

FIGS. 22A-F are schematic views of various implantable device lead arrangements, consistent with the present inventive concepts.

Figure 23:
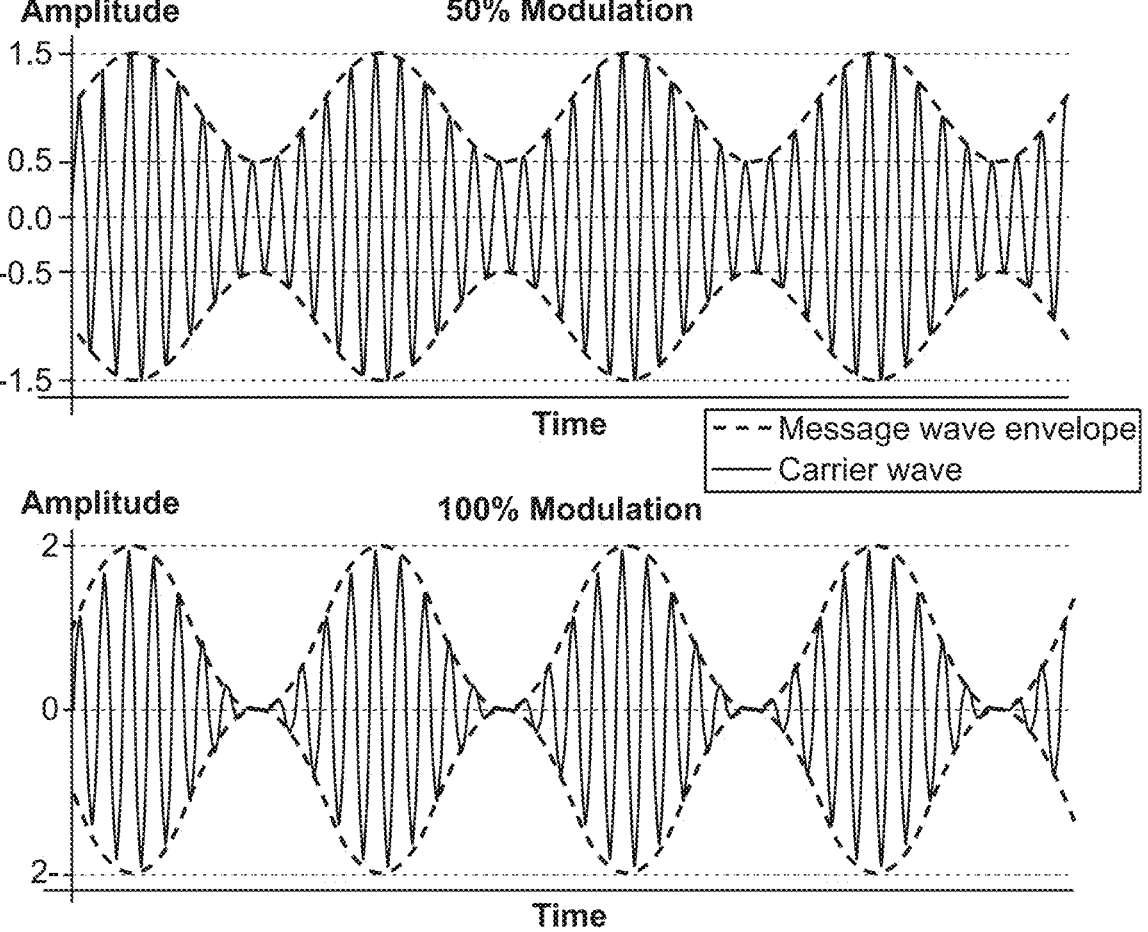

FIG. 23 is a graph of an amplitude modulation scheme, consistent with the present inventive concepts.

Figure 24A:
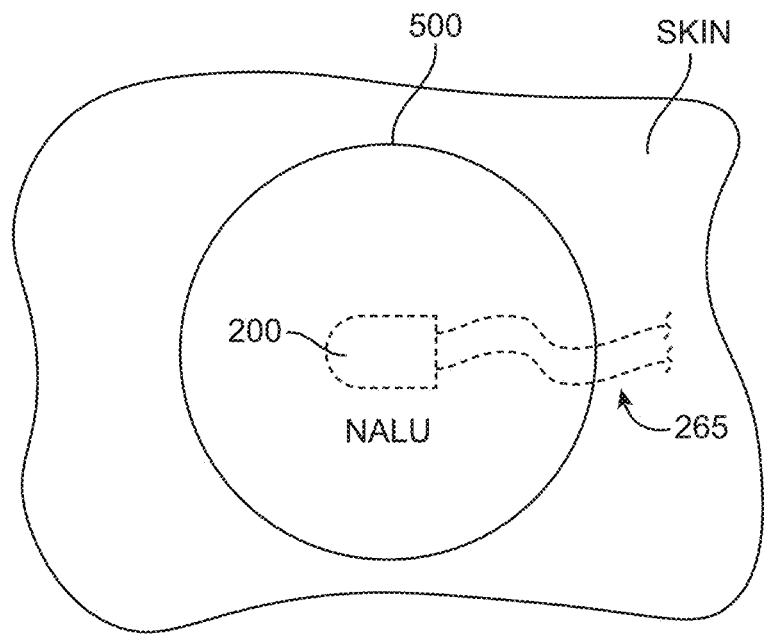
Figure 24B:
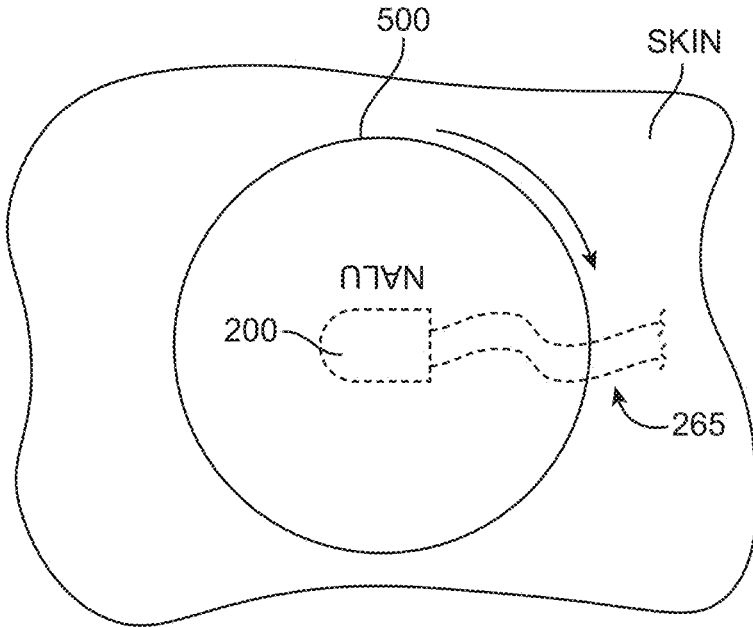

FIGS. 24A-B are top views of an external device positioned on a patient in a first orientation, and a second orientation, respectively, consistent with the present inventive concepts.

FIG. 25A is a schematic view of a reconfigurable stimulation block portion of an electronic assembly of an implantable device, consistent with the present inventive concepts.

FIG. 25B is a diagram of a control input sequence, consistent with the present inventive concepts.

FIG. 25C is a schematic view of a portion of an electronic assembly of an implantable device, consistent with the present inventive concepts.

Figure 26A:
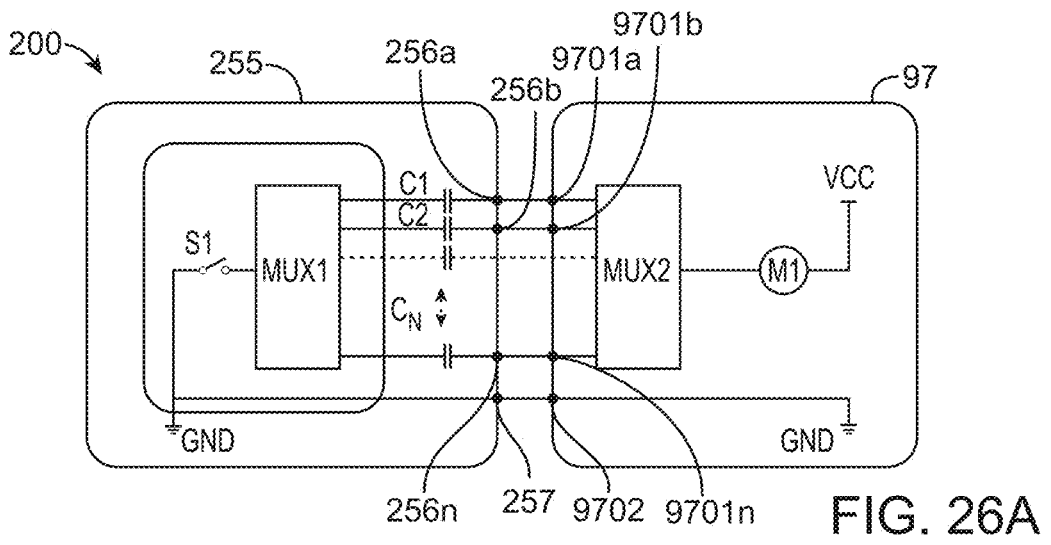
Figure 26B:
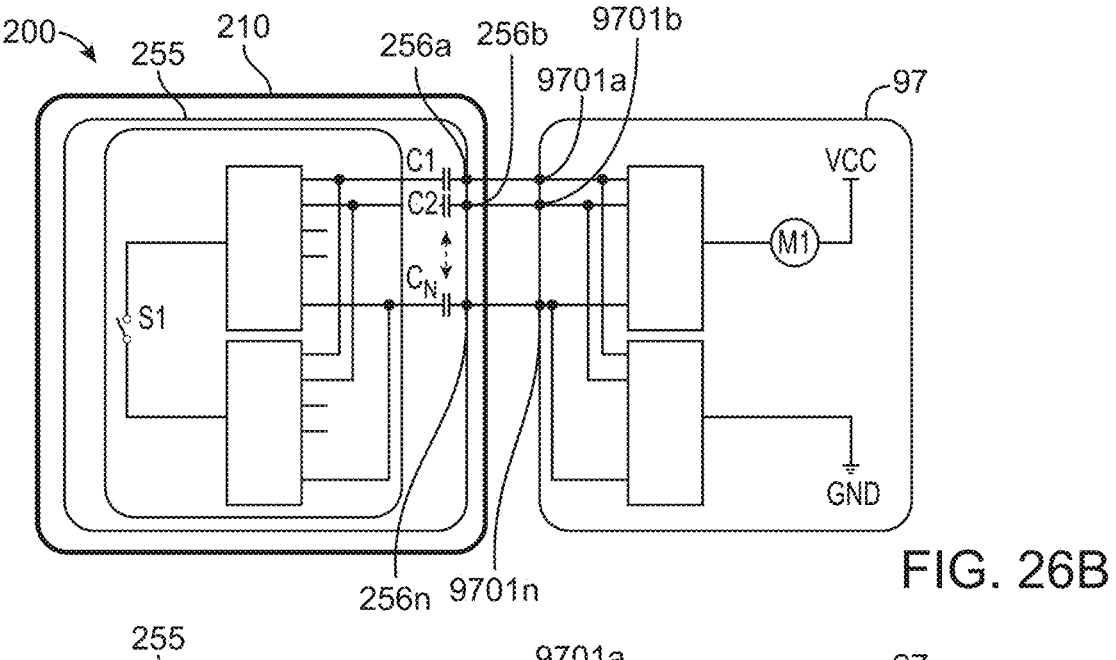
Figure 26C:
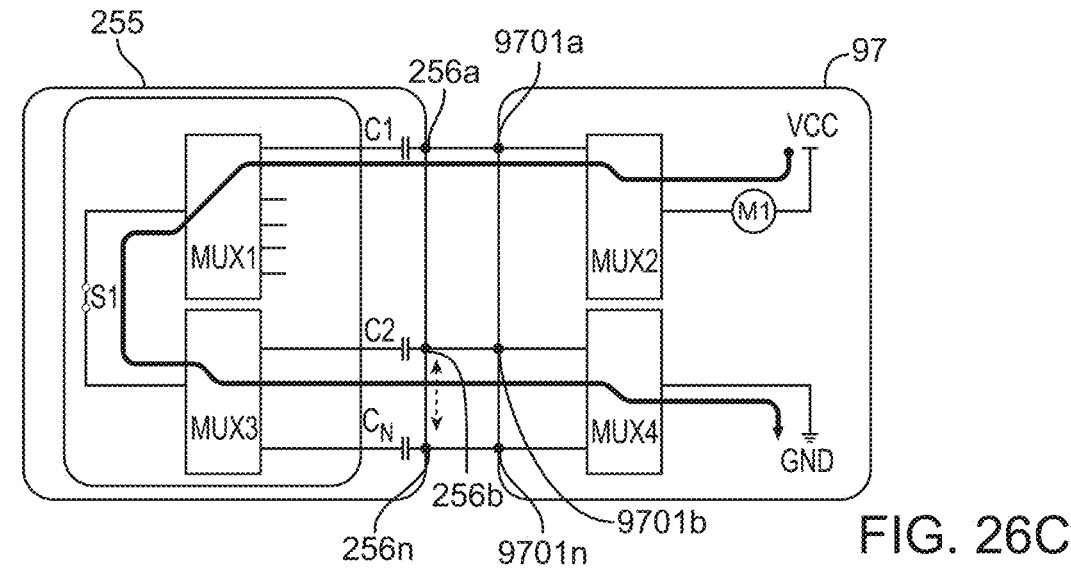

FIGS. 26A-C are schematic views of a test fixture arrangement for testing an electronic assembly of an implantable device, consistent with the present inventive concepts.

Figure 27A:
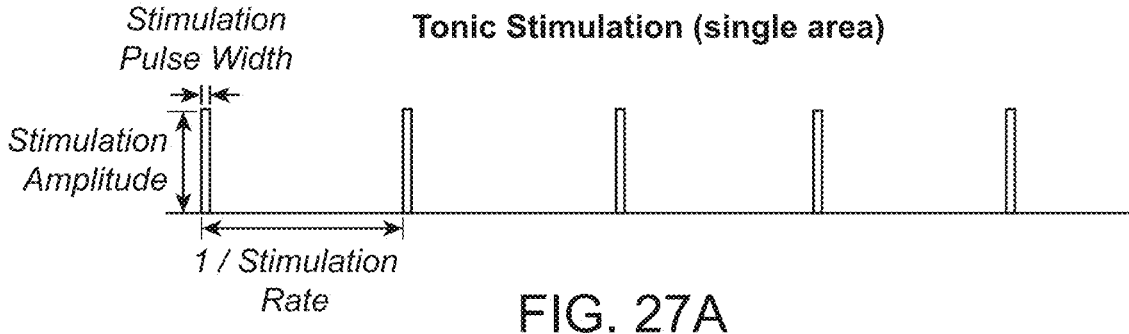
Figure 27B:
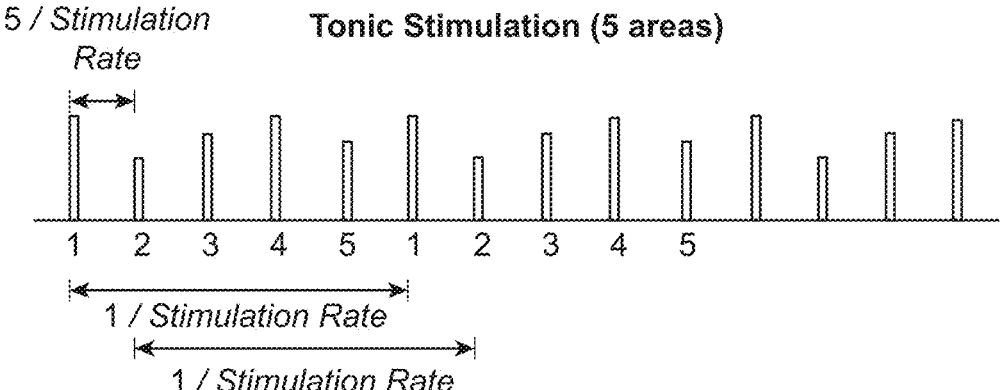
Figure 27C:
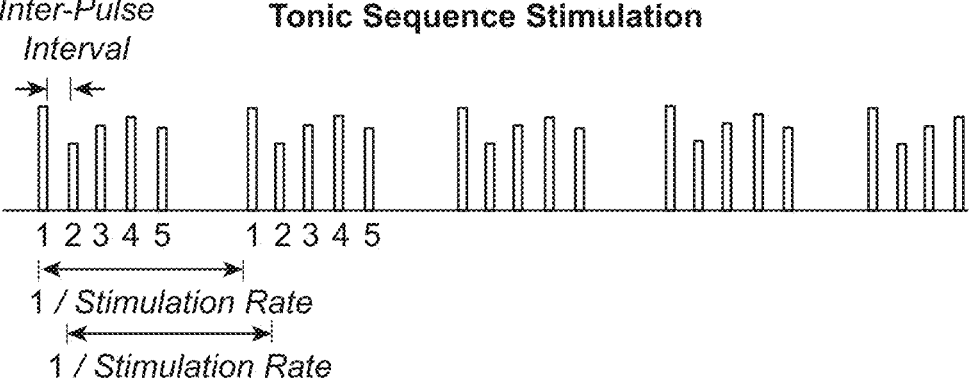

FIGS. 27A-C are a series of views of stimulations waveforms, consistent with the present inventive concepts.

Figure 28A:
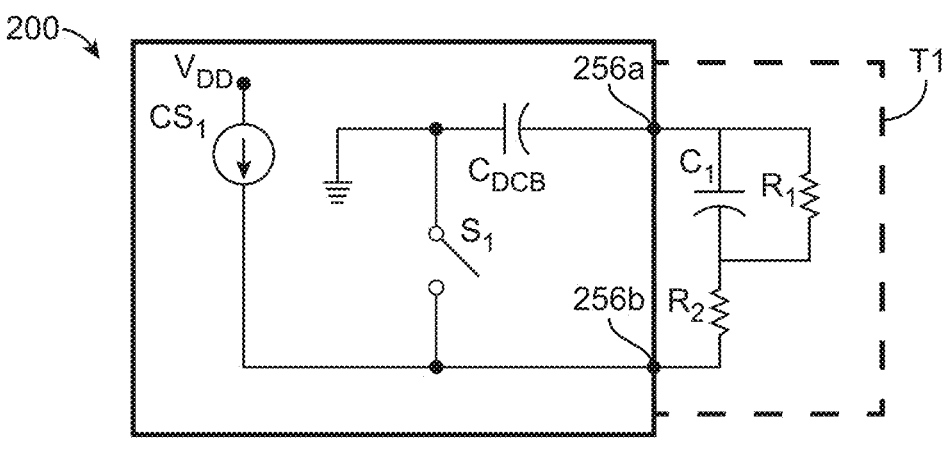
Figure 28B:
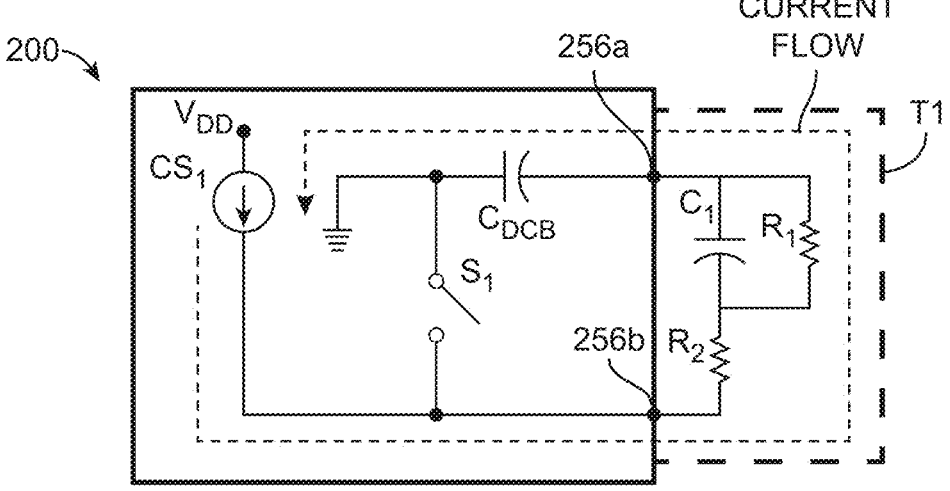
Figure 28C:
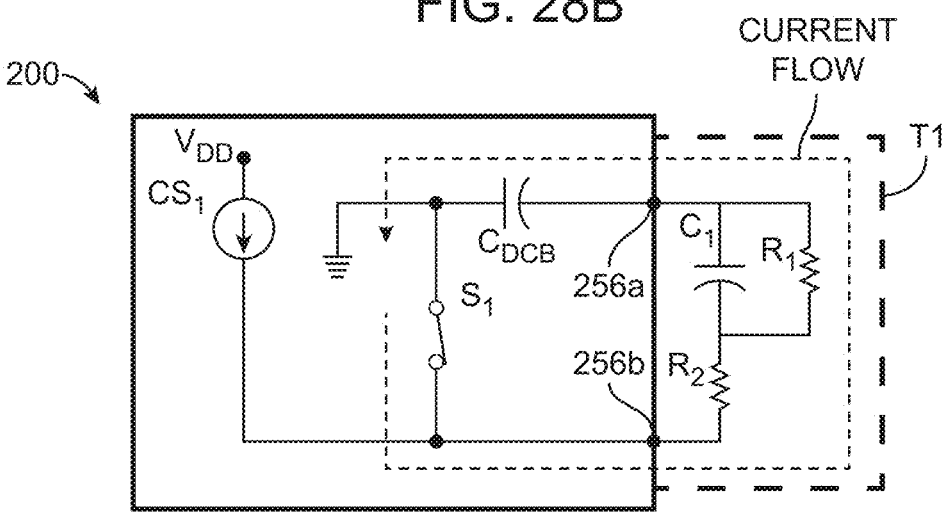

FIGS. 28A-C are schematic views of stimulation circuitry of an implantable device, consistent with the present inventive concepts.

Figure 28D:
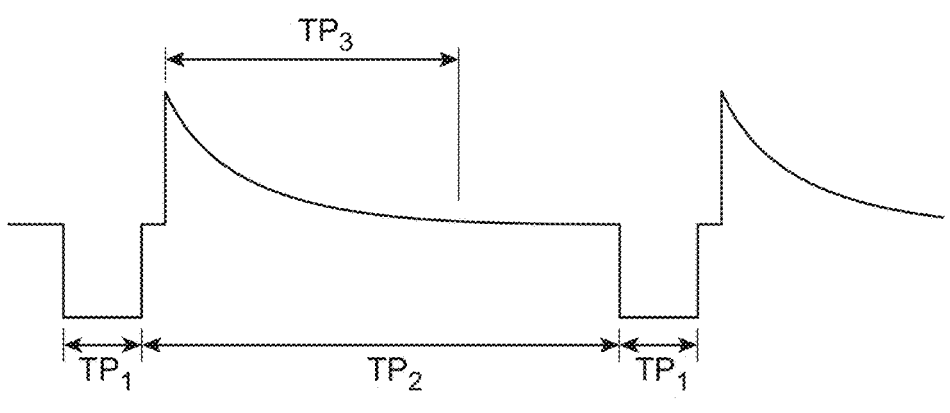
Figure 28E:
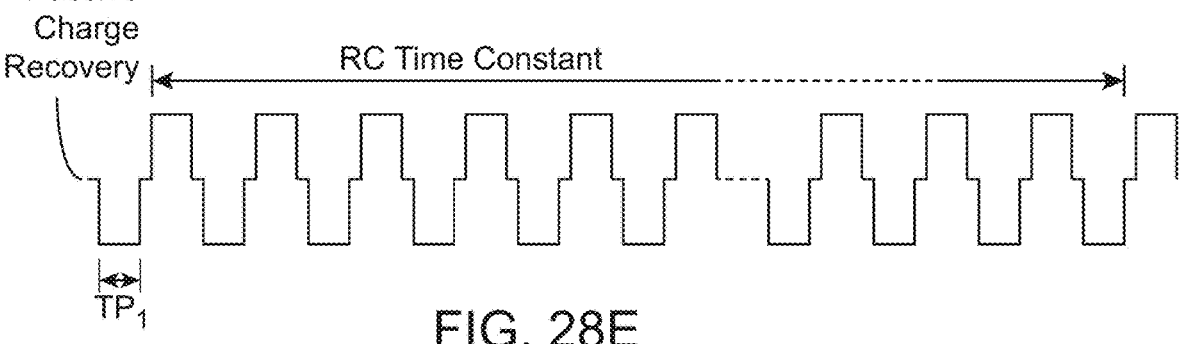

FIGS. 28D-E are views of stimulation and discharge waveforms, consistent with the present inventive concepts.

Figure 28F:
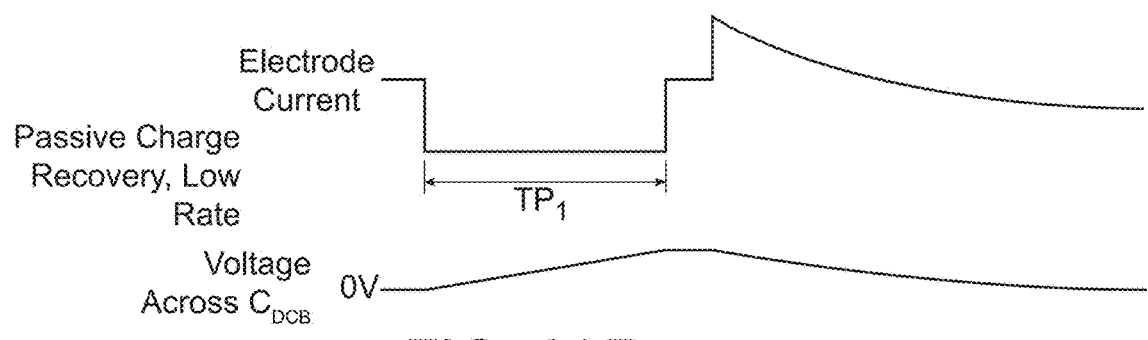
Figure 28G:
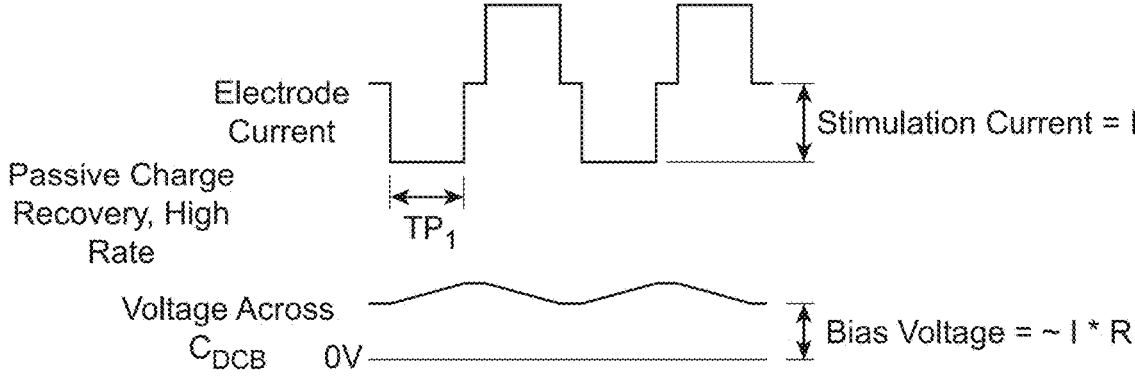

FIGS. 28F-G are views of stimulation and discharge waveforms, as well as a chart of voltage across a DC blocking capacitor, consistent with the present inventive concepts.

Figure 29:
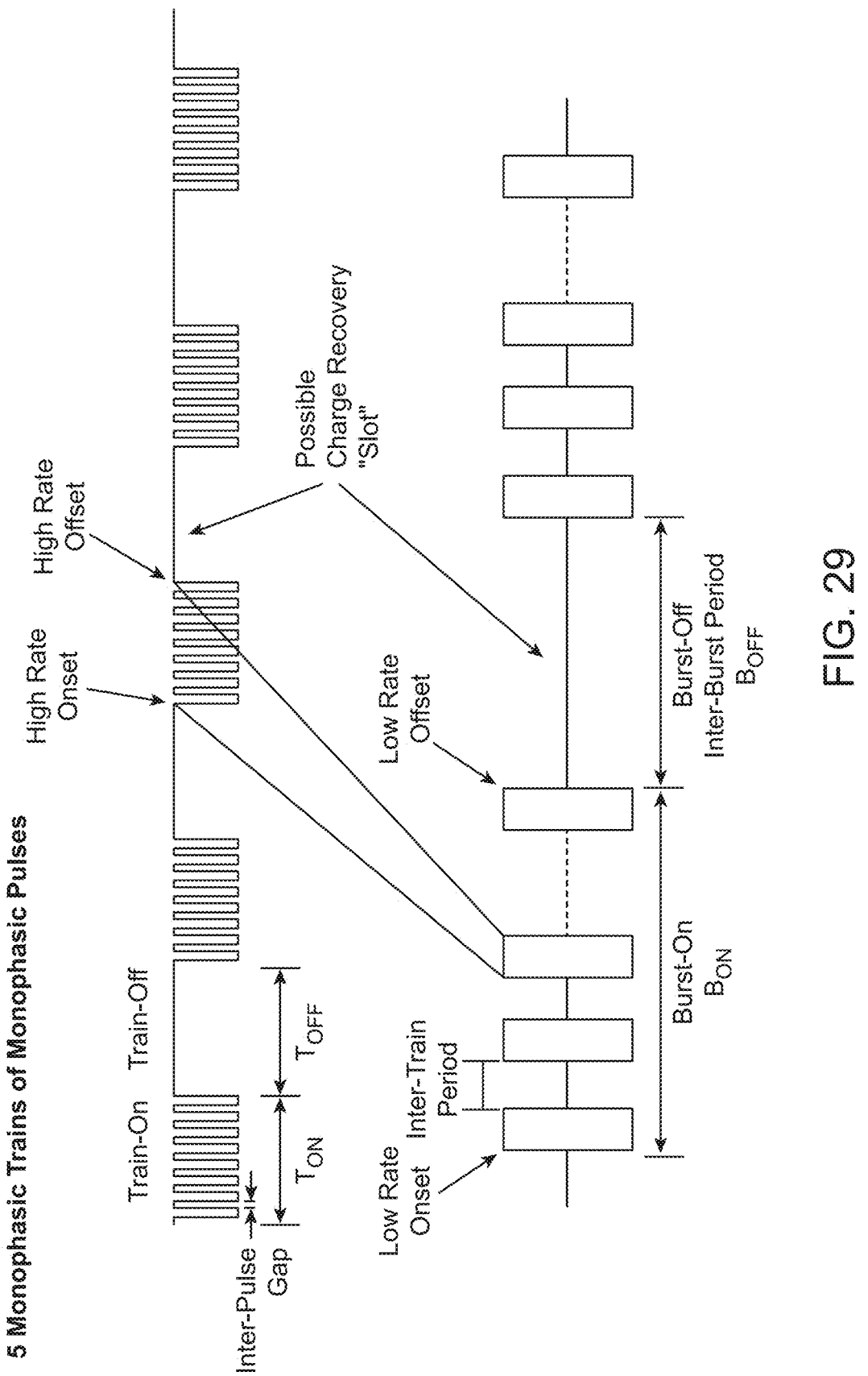

FIG. 29 is a stimulation waveform comprising multiple trains of monophasic pulses, consistent with the present inventive concepts.

Figures 29A, 29B:
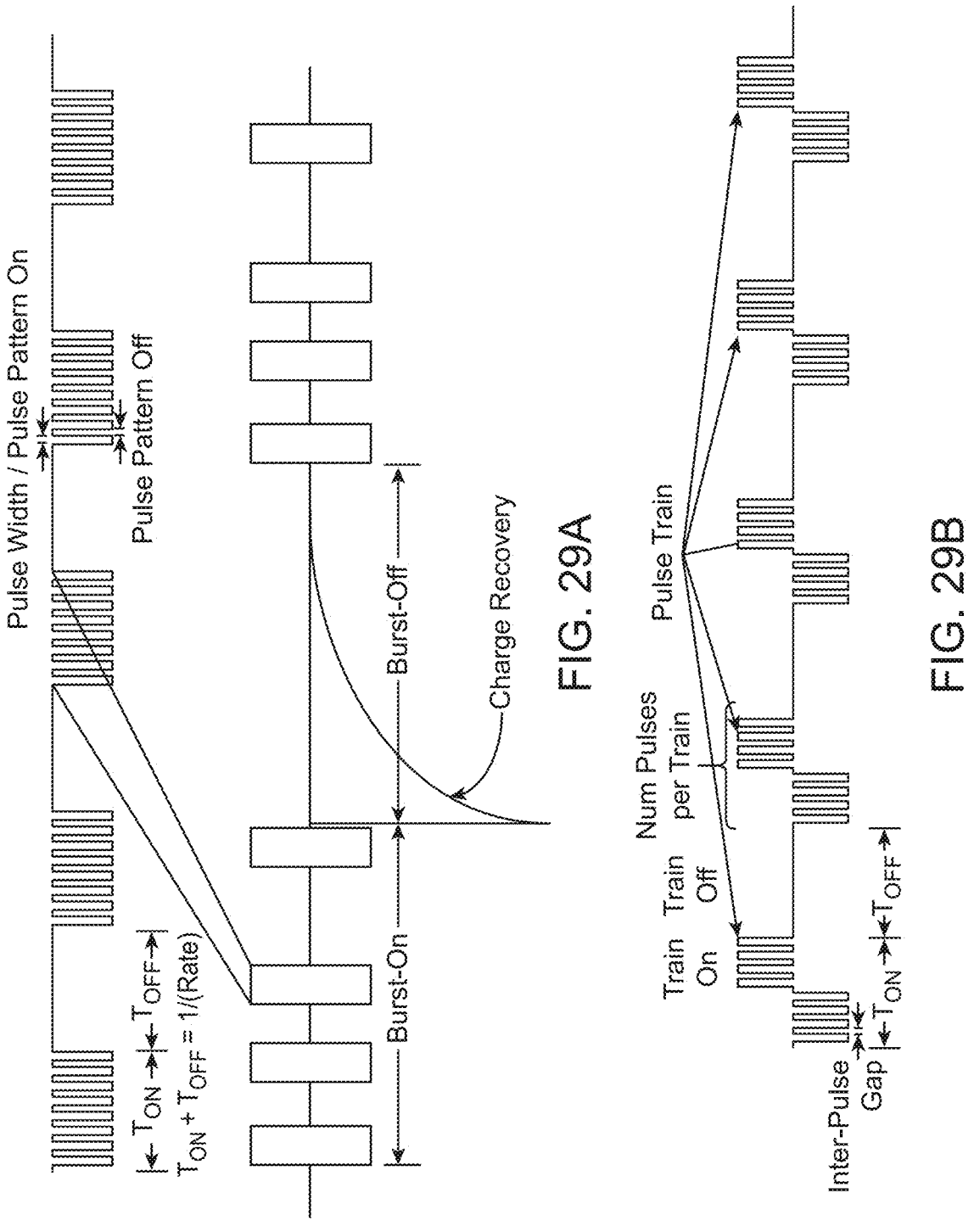

FIG. 29A is another stimulation waveform comprising multiple trains of monophasic pulses, consistent with the present inventive concepts.

FIG. 29B is another stimulation waveform comprising multiple trains of monophasic pulses, consistent with the present inventive concepts.

Figure 30:
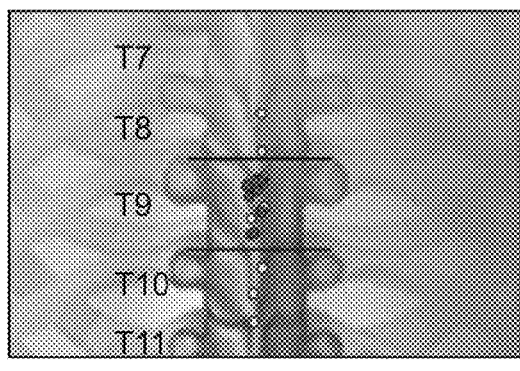

FIG. 30 is an anatomical illustration of various locations of lead placement in Applicant's study as well as a response rate for each, consistent with the present inventive concepts.

Figure 31A:
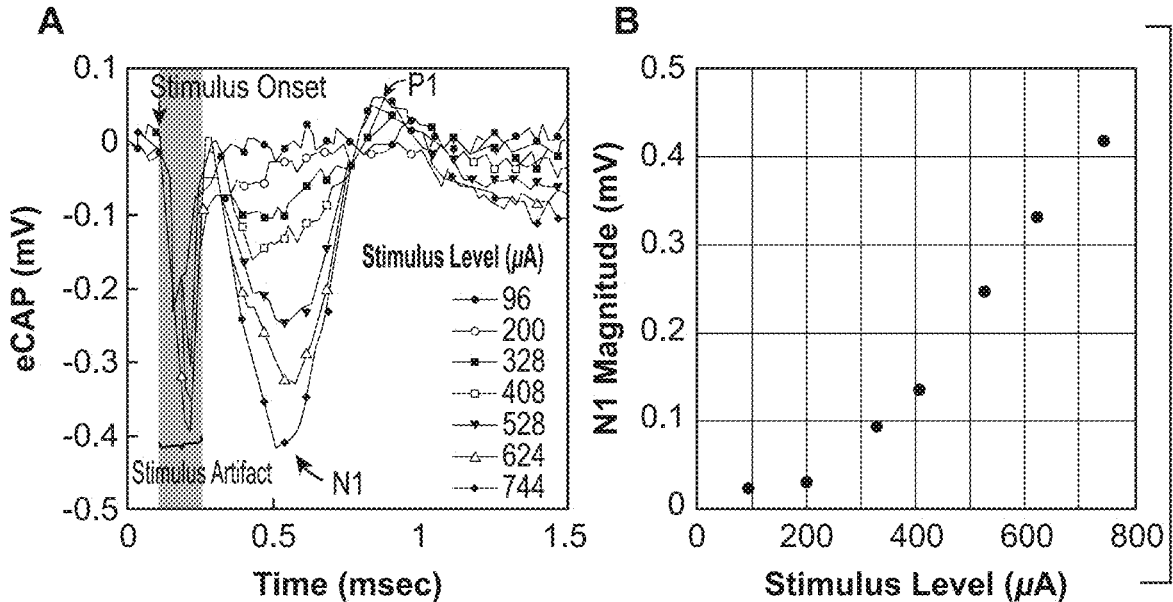

FIG. 31A is two graphs of electrically-evoked compound action potential signals, consistent with the present inventive concepts.

Figure 31B:
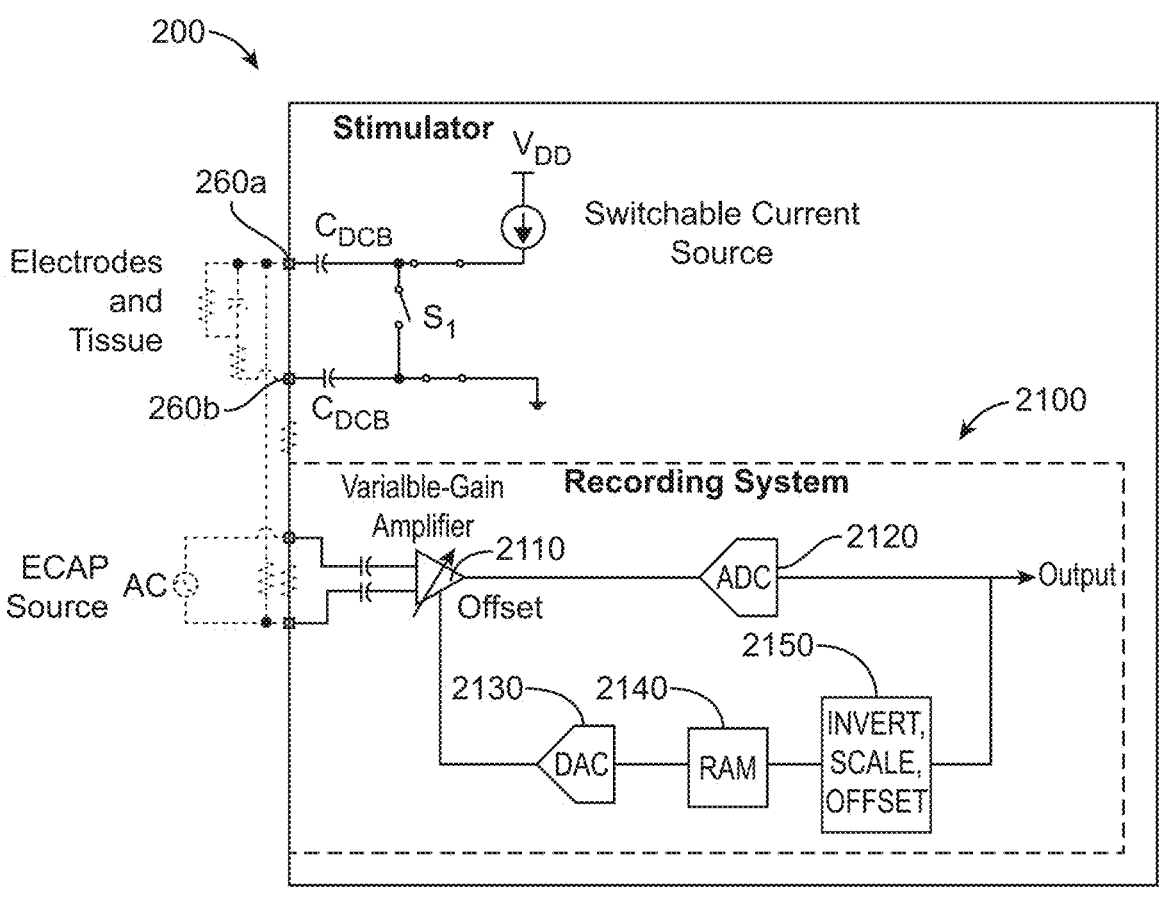
Figure 31C:
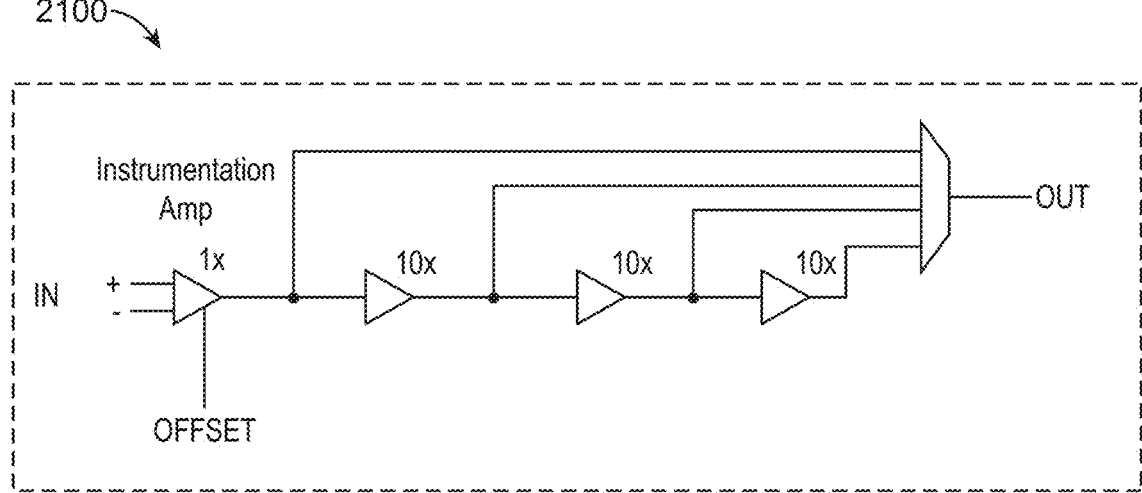

FIG. 31B-C are schematics of implantable device circuitry, consistent with the present inventive concepts.

FIG. 31D-H are graphs of artifact recordings and electrically-evoked compound action potential signals, consistent with the present inventive concepts.

Figure 32:
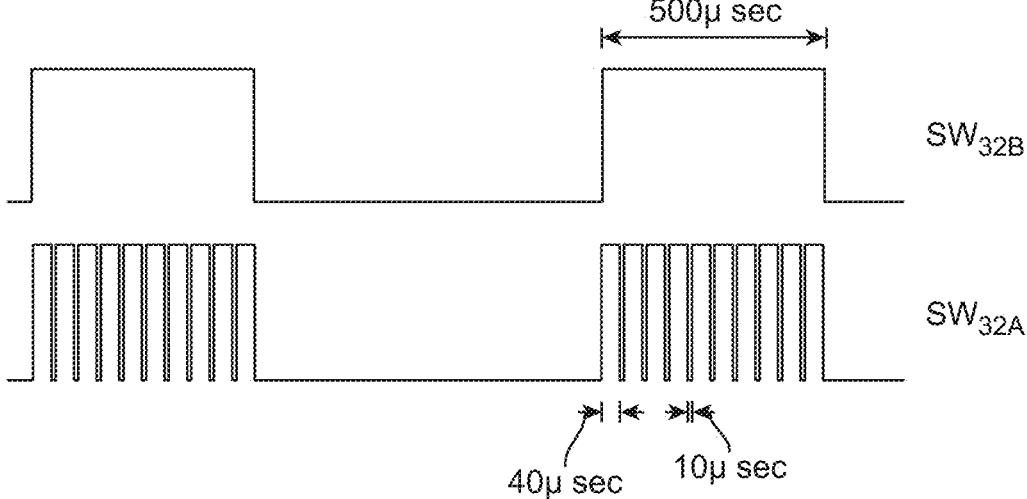

FIG. 32 is two graphs showing two different types of stimulation waveforms that produce a similar physiologic effect, consistent with the present inventive concepts.

Figure 33:
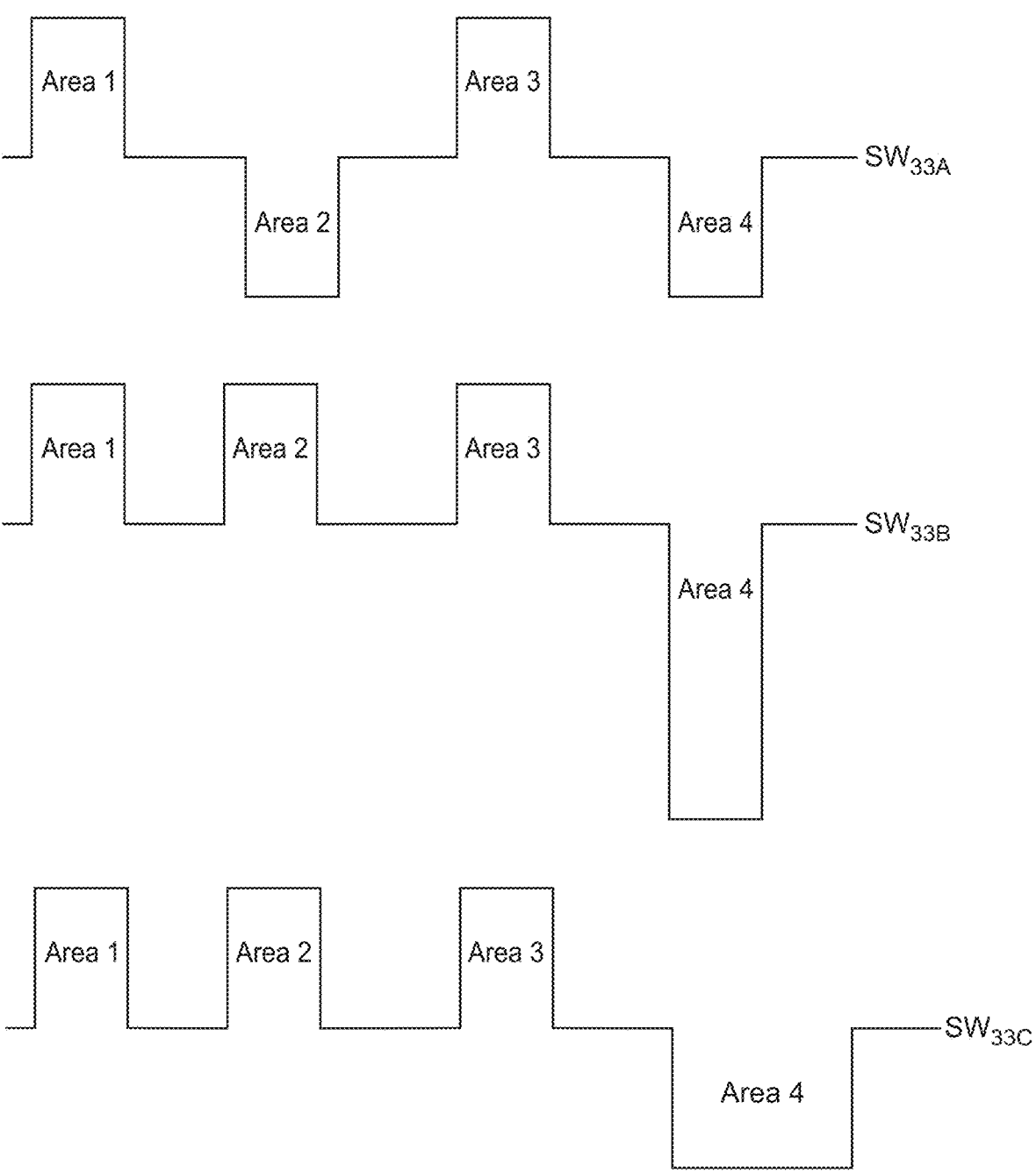

FIG. 33 is three graphs of stimulation waveforms for stimulating multiple anatomical areas of a patient, consistent with the present inventive concepts.

Figure 34:
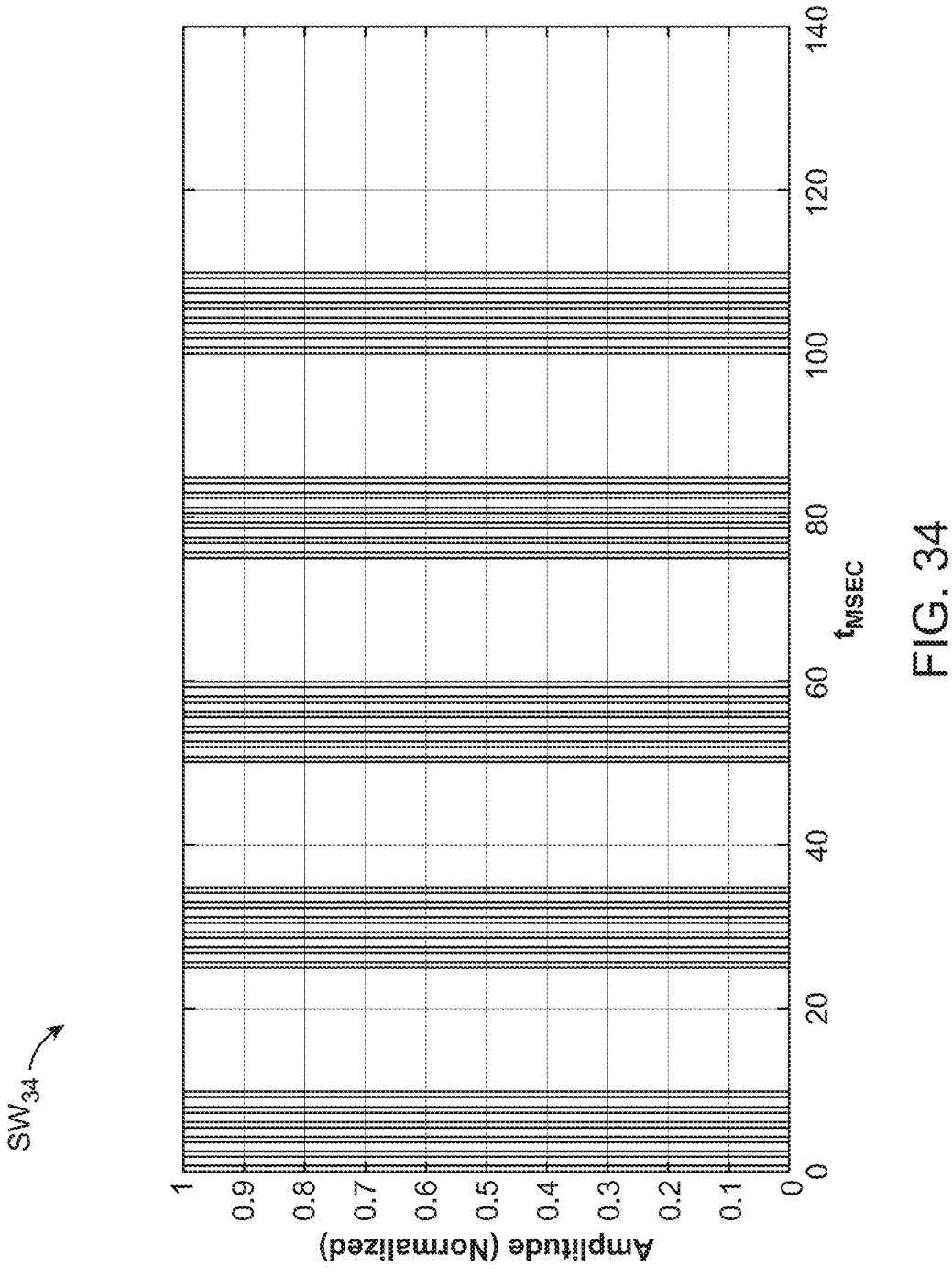

FIG. 34 is a graph of a stimulation waveform, consistent with the present inventive concepts.

Figure 35:
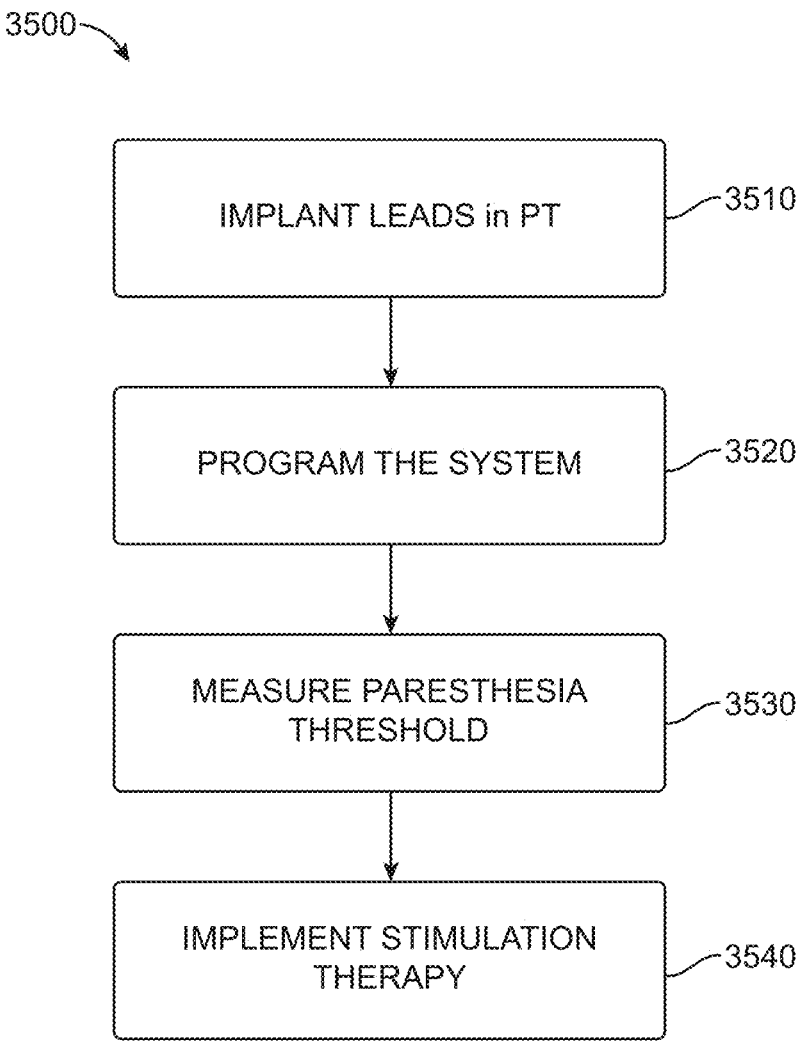

FIG. 35 is a flow chart of a method of implanting a stimulator and programming a stimulation system, consistent with the present inventive concepts.

Figure 35A:
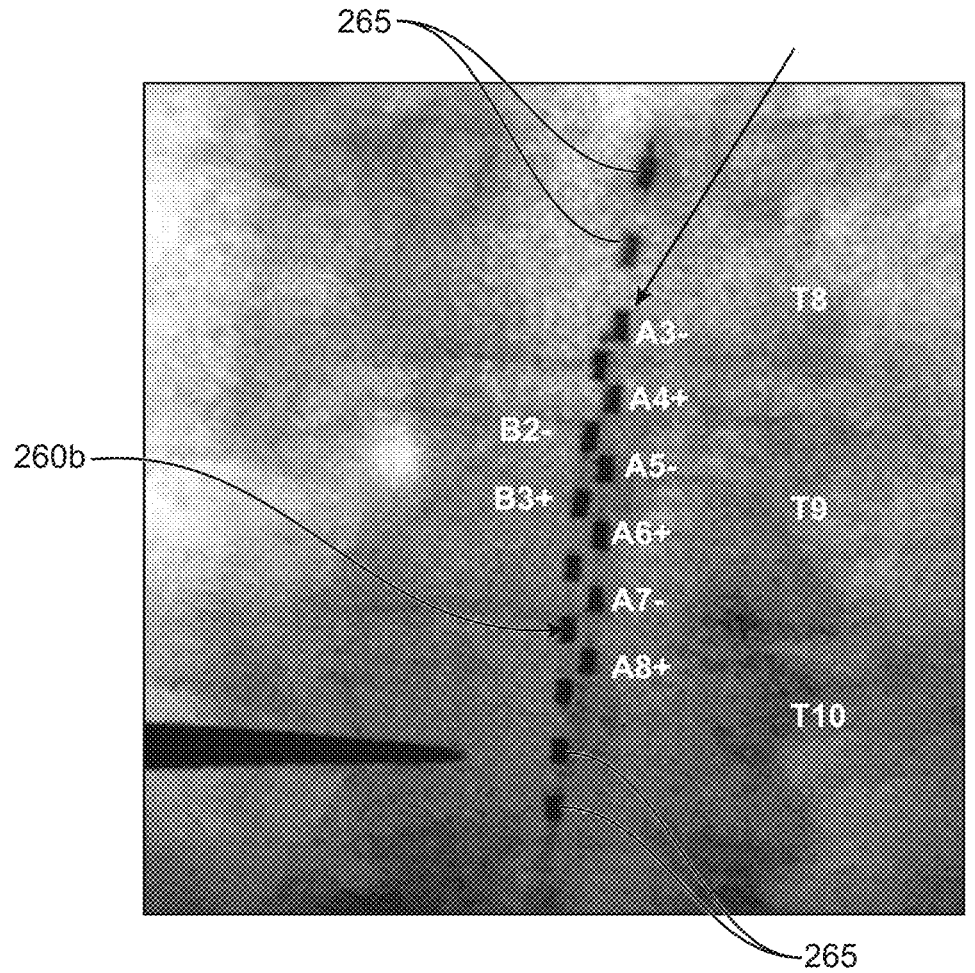

FIG. 35A is an X-ray image of a patient's spine with two implanted stimulation leads, consistent with the present inventive concepts.

Figure 36:
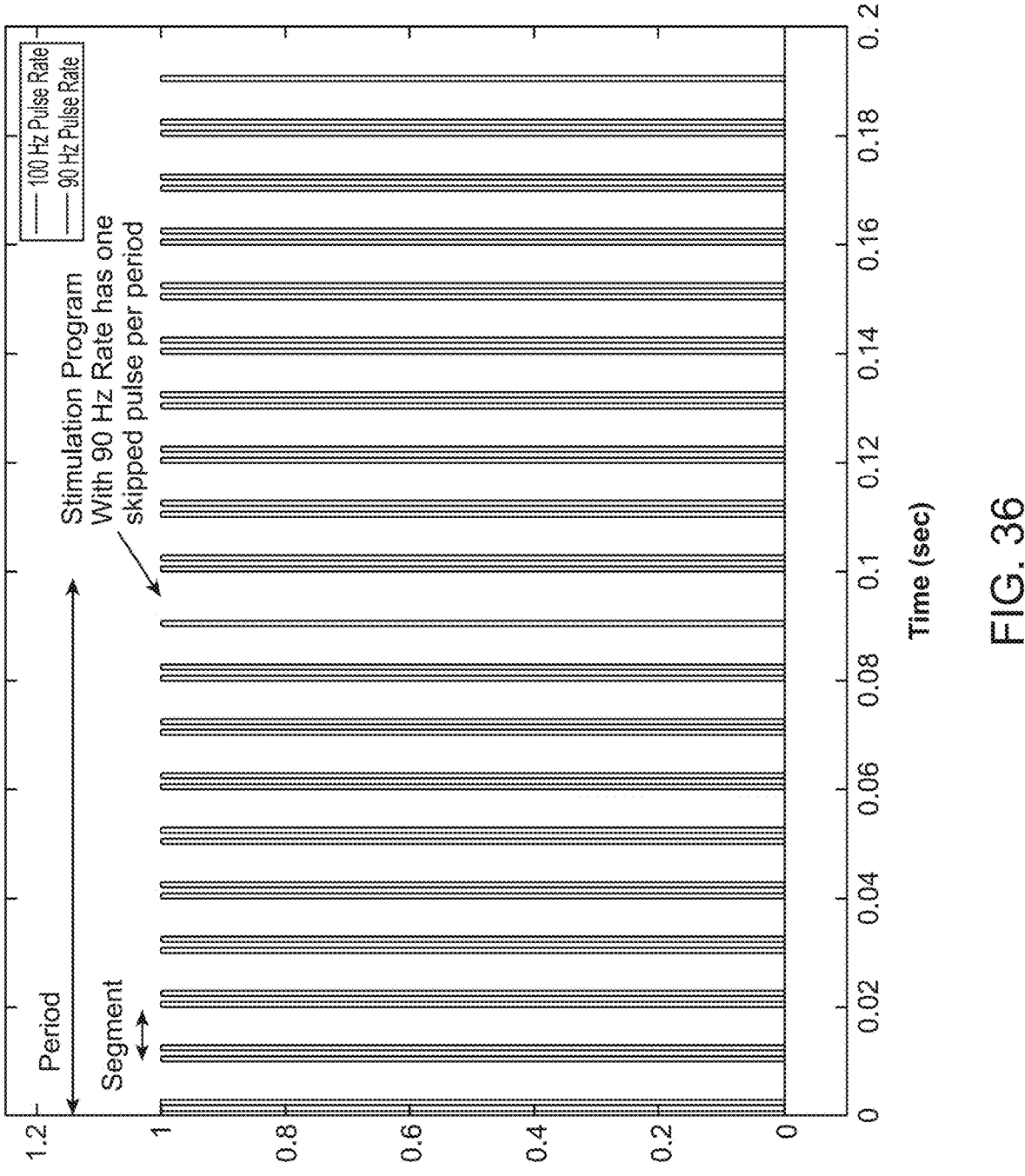

FIG. 36 is a graph of a delivery of two stimulation programs in a combined arrangement, consistent with the present inventive concepts.

FIGS. 37A-E are graphs of a series of stimulation waveforms that are modulated by an envelope signal, consistent with the present inventive concepts.

DETAILED DESCRIPTION OF THE DRAWINGS

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers, and/or sections, these limitations, elements, components, regions, layers, and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.). A first component (e.g. a device, assembly, housing or other component) can be "attached", "connected" or "coupled" to another component via a connecting filament (as defined below). In some embodiments, an assembly comprising multiple components connected by one or more connecting filaments is created during a manufacturing process (e.g. pre-connected at the time of an implantation procedure of the apparatus of the present inventive concepts). Alternatively or additionally, a connecting filament can comprise one or more connectors (e.g. a connectorized filament comprising a connector on one or both ends), and a similar assembly can be created by a user (e.g. a clinician) operably attaching the one or more connectors of the connecting filament to one or more mating connectors of one or more components of the assembly.

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

As used herein, the term "proximate" shall include locations relatively close to, on, in, and/or within a referenced component or other location.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross-sectional area as the cross section of the component being described.

The terms "major axis" and "minor axis" of a component where used herein are the length and diameter, respectively, of the smallest volume hypothetical cylinder which can completely surround the component.

The term "functional element" where used herein, is the be taken to include a component comprising one, two or more of: a sensor; a transducer; an electrode; an energy delivery element; an agent delivery element; a magnetic field generating transducer; and combinations of one or more of these. In some embodiments, a functional element comprises a transducer selected from the group consisting of: light delivery element; light emitting diode; wireless transmitter; Bluetooth device; mechanical transducer; piezo-electric transducer; pressure transducer; temperature transducer; humidity transducer; vibrational transducer; audio transducer; speaker; and combinations of one or more of these. In some embodiments, a functional element comprises a needle, a catheter (e.g. a distal portion of a catheter), an iontophoretic element or a porous membrane, such as an agent delivery element configured to deliver one or more agents. In some embodiments, a functional element comprises one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; orientation sensor; motion sensor; and combinations of one or more of these.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy, mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); thermal energy to tissue (e.g. heat energy and/or cryogenic energy); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include one or more signals transmitted using body conduction. Alternatively or additionally, a transmission signal can comprise reflected energy, such as energy reflected from any power and/or data signal.

The term "data signal" where used herein is to be taken to include a transmission signal including at least data. For example, a data signal can comprise a transmission signal including data and sent between a component external to the patient and one or more components implanted in the patient. Alternatively, a data signal can comprise a transmission signal including data sent from an implanted component to one or more components external to the patient. A data signal can comprise a radiofrequency signal including data (e.g. a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

The terms "attachment", "attached", "attaching", "connection", "connected", "connecting" and the like, where used herein, are to be taken to include any type of connection between two or more components. The connection can include an "operable connection" or "operable attachment" which allows multiple connected components to operate together such as to transfer information, power, and/or material (e.g. an agent to be delivered) between the components. An operable connection can include a physical connection, such as a physical connection including a connection between two or more: wires or other conductors (e.g. an "electrical connection"), optical fibers, wave guides, tubes such as fluid transport tubes, and/or linkages such as translatable rods or other mechanical linkages. Alternatively or additionally, an operable connection can include a non-physical or "wireless" connection, such as a wireless connection in which information and/or power is transmitted between components using electromagnetic energy. A connection can include a connection selected from the group consisting of: a wired connection; a wireless connection; an electrical connection; a mechanical connection; an optical connection; a sound propagating connection; a fluid connection; and combinations of one or more of these.

The term "connecting filament" where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term "connectorized" where used herein is to be taken to refer to a filament, housing or other component that includes one or more connectors (e.g. clinician or other user-attachable connectors) for operably connecting that component to a mating connector (e.g. of the same or different component).

The terms "stimulation parameter", "stimulation signal parameter" or "stimulation waveform parameter" where used herein can be taken to refer to one or more parameters of a stimulation waveform (also referred to as a stimulation signal). Applicable stimulation parameters of the present inventive concepts shall include but are not limited to: amplitude (e.g. amplitude of voltage and/or current); average amplitude; peak amplitude; frequency; average frequency; pulse width (also referred to as "pulse pattern on time"); period; phase; polarity; pulse shape; a duty cycle parameter (e.g. frequency, pulse width, and/or off time); inter-pulse gap (also referred to as "pulse pattern off time", or "inter-pulse interval"); polarity; burst-on (also referred to as "dosage on") period; burst-off (also referred to as "dosage off") period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations of one or more of these. A stimulation parameter can refer to a single stimulation pulse, multiple stimulation pulses, or a portion of a stimulation pulse. The term "amplitude" where used herein can refer to an instantaneous or continuous amplitude of one or more stimulation pulses (e.g. the instantaneous voltage level or current level of a pulse). The term "pulse" where used herein can refer to a period of time during which stimulation energy is relatively continuously being delivered. In some embodiments, stimulation energy delivered during a pulse comprises energy selected from the group consisting of: electrical energy; magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, stimulation energy comprises electrical energy and a pulse comprises a phase change in current and/or voltage. In these embodiments, an "inter-phase gap" can be present within a single pulse. The term inter-phase gap where used herein can refer to a period of time between two portions of a pulse comprising a phase change during which zero energy or minimal energy is delivered. The term "quiescent period" where used herein can refer to a period of time during which zero energy or minimal energy is delivered (e.g. insufficient energy to elicit an action potential and/or other neuronal response). The term "inter-pulse gap" where used herein can refer to a quiescent period between the end of one pulse to the onset of the next (sequential) pulse. The terms "pulse train" or "train" where used herein can refer to a series of pulses. The terms "burst", "burst of pulses" or "burst stimulation" where used herein can refer to a series of pulse trains, each separated by a quiescent period. The term "train-on period" where used herein can refer to a period of time from the beginning of the first pulse to the end of the last pulse of a single train. The term "train-off period"

where used herein can refer to a quiescent period between the end of one train and the beginning of the next train. The term "burst-on period" where used herein can refer to a period of time from the beginning of the first pulse of the first train to the end of the last pulse of the last train of a single burst. The term "burst-off period" where used herein can refer to a quiescent period between the end of one burst and the beginning of the next burst. The term "inter-train period" where used herein can refer to a quiescent period between the end of one train and the beginning of the next train. The term "inter-burst period" where used herein can refer to a quiescent period between the end of one burst and the beginning of the next burst. The term "train envelope" where used herein can refer to a curve outlining the amplitude extremes of a series of pulses in a train. The term "burst envelope" where used herein can refer to a curve outlining the amplitude extremes of a series of pulses in a burst. The term "train ramp duration" where used herein can refer to the time from the onset of a train until its train envelope reaches a desired target magnitude. The term "burst ramp duration" where used herein can refer to the time from the onset of a burst until its burst envelope reaches a desired target magnitude.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, such as to treat pain. The patient can comprise a human or other mammalian patient. The medical apparatus can comprise a stimulation apparatus. The medical apparatus can comprise an implantable system and an external system. The implantable system can comprise one or more similar and/or dissimilar implantable devices. Each implantable device comprises a housing surrounding one or more stimulation producing components. A lead comprising one or more stimulation elements can be pre-attached to the housing, or attachable to the housing (e.g. attached in a clinical procedure in which the implantable device is implanted in a patient).

The apparatus can include a trialing interface which provides energy to the stimulation elements during the implantation procedure, such as to confirm proper placement of the stimulation elements and/or to titrate the stimulation delivered. In embodiments in which the lead is pre-attached to the housing of the implantable device, the trialing interface can be configured to provide power (e.g. wireless power) to the implantable device, the implantable device providing stimulation energy to the stimulation elements derived from the power provided by the trialing interface. In embodiments in which the lead is attachable to the housing of the implantable device, the trialing interface can attach to the lead (prior to its attachment to the housing of the implantable device), and the trialing interface can then provide the stimulation energy directly to the stimulation elements.

In some embodiments, the implantable system comprises a first implantable device that delivers stimulation energy via energy received wirelessly from one or more external devices, and a second implantable device that delivers stimulation energy via an integral (e.g. implanted) battery. In these embodiments, the first implantable device can be configured to deliver stimulation energy during a limited period of time (e.g. a trial period in which stimulation settings are determined and/or acceptability of the apparatus is determined), and the second implantable device can be configured to deliver stimulation energy for a prolonged period of time in which long-term stimulation therapy is provided to a patient. In these embodiments, a single implantable lead comprising one or more stimulation energy delivery elements (e.g. electrodes) can be connected to the first implantable device and then the second implantable device. In some embodiments, a first implantable device can be configured to remain implanted in the patient for a limited period of time, such as to reduce cost of manufacture, and a second implantable device is configured for a longer implant life. The first implantable device can be used in a trialing procedure in which the stimulation apparatus is assessed for acceptable use (e.g. by the patient and/or clinician) and/or one or more stimulation settings are optimized or otherwise determined.

Each implantable device can comprise one or more implantable antennas configured to receive power and/or data. Each implantable device can comprise an implantable receiver configured to receive the power and/or data from the one or more implantable antennas. Each implantable device can comprise one or more implantable functional elements (e.g. an implantable stimulation element). An implantable functional element can be configured to interface with the patient (e.g. interface with tissue of the patient or interface with any patient location). Alternatively or additionally, an implantable functional element can interface with a portion of an implantable device (e.g. to measure an implantable device parameter). In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g. patient physiologic or patient environment information).

Each implantable device can comprise an implantable controller configured to control (e.g. modulate power to, send a signal to, and/or receive a signal from) the one or more implantable functional elements. In some embodiments, an implantable controller of a first implantable device is configured to control one or more other implantable devices. Each implantable device can comprise an implantable energy storage assembly (e.g. a battery and/or a capacitor) configured to provide power to the implantable controller (e.g. a controller comprising a stimulation waveform generator), the implantable receiver and/or the one or more implantable functional elements. In some embodiments, an implantable energy storage assembly is further configured to provide power to an assembly that transmits signals via the implantable antenna (e.g. when the implantable device is further configured to transmit data to one or more external devices). Each implantable device can comprise an implantable housing surrounding the implantable controller and the implantable receiver. In some embodiments, one or more implantable antennas are positioned within the implantable housing. Alternatively or additionally, one or more implantable antennas and/or implantable functional elements can be tethered (e.g. electrically tethered) to the implantable housing. In some embodiments, one or more implantable functional elements are positioned on an implantable lead, such as a flexible lead mechanically fixed or attachable to the implantable housing and operably connected (e.g. electrically, fluidly, optically and/or mechanically) to one or more components internal to the implantable housing. The implantable lead can be inserted (e.g. tunneled) through tissue of the patient, such that its one or more functional elements are positioned proximate tissue to be treated and/or positioned at an area in which data is to be recorded. In some embodiments, the implantable lead is configured to operably attach to and/or detach from, multiple implantable devices.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external programmer configured to control the external transmitter and/or an implantable device (e.g. when an external power transmitter is not included in the apparatus or otherwise not present during use). Each external device can comprise an external housing that surrounds at least the external transmitter. In some embodiments, the external housing surrounds the one or more external antennas, the external power supply and/or the external programmer.

The external programmer can comprise a discrete controller separate from the one or more external devices, and/or a controller integrated into one or more external devices. The external programmer can comprise a user interface, such as a user interface configured to set and/or modify one or more treatment and/or data recording settings of the medical apparatus of the present inventive concepts. In some embodiments, the external programmer is configured to collect and/or diagnose recorded patient information, such as to provide the information and/or diagnosis to a clinician of the patient, to a patient family member and/or to the patient themselves. The collected information and/or diagnosis can be used to adjust treatment or other operating parameters of the medical apparatus. In some embodiments, at least two external programmers are included, such as a first external programmer configured for use by the patient, and a second external programmer configured for use by a clinician of the patient.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue" or "nervous system tissue"). The stimulation apparatus comprises an external system configured to transmit power, and an implanted system configured to receive the power from the external system and to deliver stimulation energy to tissue. The delivered stimulation energy can comprise one or more stimulation waveforms, such as a stimulation waveform configured to enhance treatment of pain while minimizing undesired effects. The stimulation signal (also referred to as "stimulation energy" herein) delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Figure 1:
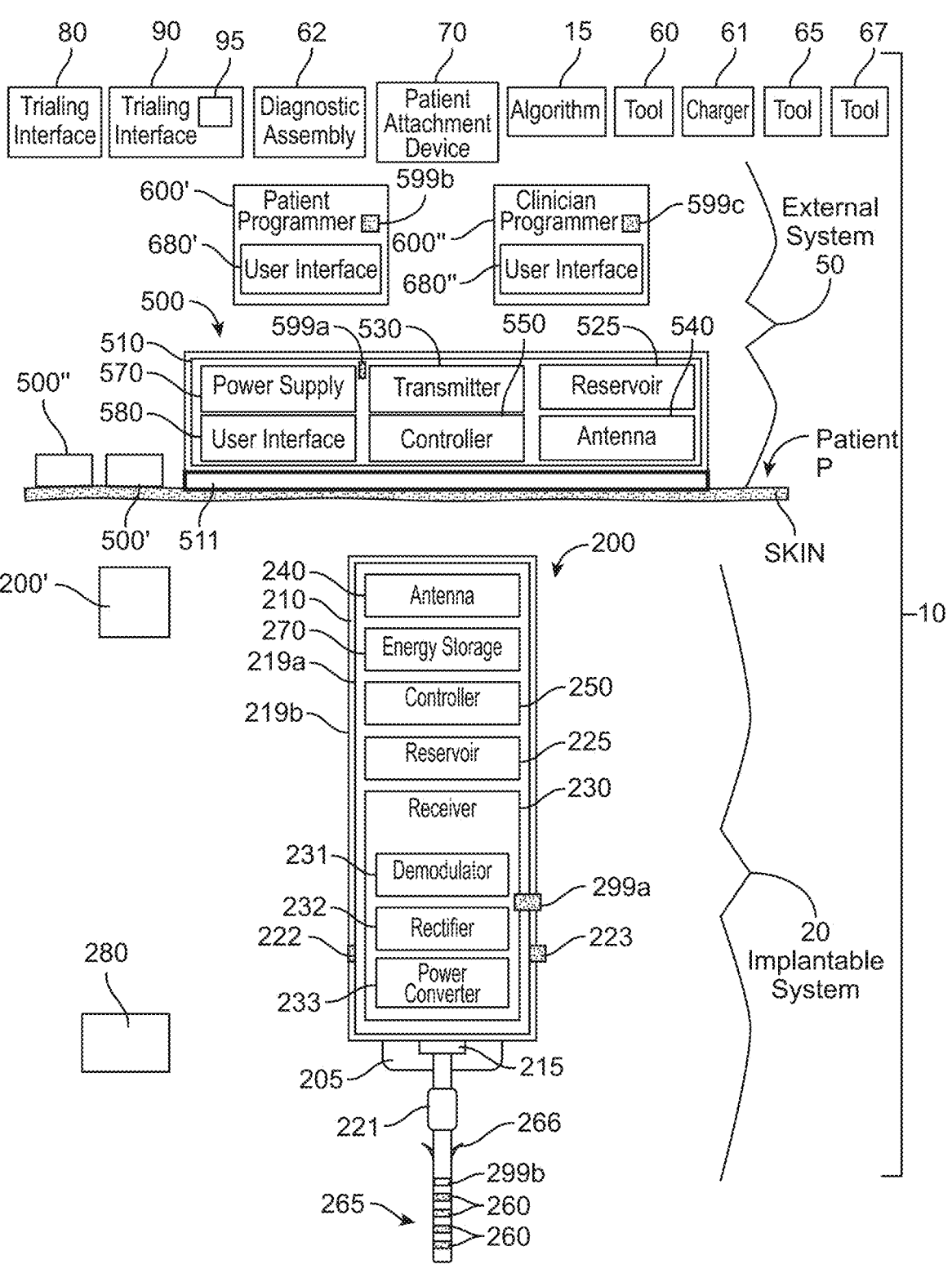
FIG. 1 is a schematic anatomical view of a medical apparatus comprising an external system and an implantable system, consistent with the present inventive concepts.

Referring now to FIG. 1, a schematic anatomical view of a stimulation apparatus for providing a therapy to a patient is illustrated, consistent with the present inventive concepts. Apparatus 10 comprises implantable system 20 and external system 50. External system 50 transmits transmission signals to one or more components of implantable system 20. These transmission signals can comprise power and/or data. Implantable system 20 comprises implantable device 200 shown implanted beneath the skin of patient P. In some embodiments, implantable system 20 comprises multiple similar or dissimilar implantable devices 200 (singly or collectively implantable device 200), such as is described in applicant's co-pending U.S. patent application Ser. No. 16/104,829, titled "Apparatus with Enhanced Stimulation Waveforms", filed Aug. 17, 2018. Each implantable device 200 can be configured to receive power and data from a transmission signal transmitted by external system 50, such as when stimulation energy delivered to the patient (e.g. to nerve or other tissue of the patient) by implantable device 200 is provided via wireless transmissions signals from external system 50. In some embodiments, implantable system 20 comprises at least two implantable devices, such as implantable device 200 and implantable device 200' shown in FIG. 1. Implantable device 200' can be of similar construction and arrangement to implantable device 200, and it can include components of a different configuration. Each implantable device 200 comprises one or more housings, housing 210 shown, which surrounds various other components of device 200. Each implantable device 200 comprises one or more stimulation and/or other functional elements, such as stimulation element 260 shown, where stimulation elements 260 are configured to deliver stimulation energy, a stimulating drug or other agent, and/or another form of stimulation (e.g. another form of tissue stimulation) to the patient. In some embodiments, one or more stimulation elements 260 are further configured as a sensor (e.g. when comprising an electrode configured to both deliver electrical energy and record electrical signals). Each implantable device 200 can include one or more leads, lead 265 shown, and each lead 265 can include one or more stimulation elements 260. Alternatively or additionally, one or more stimulation elements 260 can be positioned on housing 210 or one or more other components of implantable device 200.

Each implantable device 200 can comprise one or more other types of functional elements, such as functional element 299a shown positioned proximate housing 210 (e.g. within and/or on the external surface of housing 210) and/or functional element 299b shown positioned on lead 265. Functional element 299a and/or 299b (singly or collectively functional element 299) can comprise a transducer, a sensor, and/or other functional element as described herein. In some embodiments, a functional element 299 comprises a visualizable marker, such as a radiopaque marker, an ultrasonically visible marker, and/or a magnetic marker.

External system 50 can comprise an external device 500, which includes one or more housings, housing 510 shown, which surrounds various other components of device 500. In some embodiments, external system 50 comprises multiple external devices 500 (singly or collectively external device

500), such as an external device as is described in applicant's co-pending U.S. patent application Ser. No. 16/104,829, titled "Apparatus with Enhanced Stimulation Waveforms", filed Aug. 17, 2018. In some embodiments, external system 50 comprises at least two, or at least three external devices (e.g. at least two external devices configured to deliver power and/or data to one or more implantable devices 200), such as external device 500, external device 500', and external device 500" shown in FIG. 1. External device 500' and/or 500" can be of similar construction and arrangement to external device 500, and these devices can include components of a different configuration.

External system 50 can comprise one or more programming devices, programmer 600, such as patient programmer 600' and clinician programmer 600" shown. Patient programmer 600' and clinician programmer 600" (singly or collectively programmer 600) each comprise a user interface, such as user interfaces 680' and 680" shown (singly or collectively user interface 680). Programmer 600 can be configured to control one or more external devices 500. Alternatively or additionally, programmer 600 can be configured to control one or more implantable devices 200 (e.g. when no external device 500 is included in apparatus 10 or at least no external device 500 is available to communicate with an implantable device 200). Patient programmer 600' can be configured to be used by the patient, patient caregiver (e.g. clinician of the patient), and/or a family member of the patient.

Clinician programmer 600" can be of similar construction and arrangement to patient programmer 600'. In some embodiments, clinician programmer 600" provides additional functions not available in patient programmer 600'. In some embodiments, clinician programmer 600" can modify the programming of patient programmer 600' (e.g. modify the programming options available to the patient or family member of the patient).

Patient programmer 600' can be further configured as a smart phone and/or a music playing device (e.g. an mp3 player). For example, patient programmer 600' can comprise a smart phone or other commercial device onto which a software program of apparatus 10 is embedded to cause the commercial device to function as patient programmer 600'. Clinician programmer 600" can comprise a tablet-like device. For example, clinician programmer 600" can comprise a commercial tablet device onto which a software program of apparatus 10 is embedded to cause the commercial tablet to function as clinician programmer 600".

Clinician programmer 600" can configure multiple (e.g. all) external devices 500 used by a patient, as well as patient programmer 600', so that the set of devices are configured as a "trusted" network. After this configuration, patient programmer 600' can safely and effectively communicate with the one or more external devices 500 of the patient. The patient programmer 600' can upload (e.g. automatically upload) configuration information from an external device 500 (e.g. stimulation settings and the like). In some embodiments, patient programmer 600' and/or clinician programmer 600" uploads configuration information from an external device 500 any time certain information (e.g. stimulation information) on that external device 500 has changed (e.g. a change is detected by the programmer 600 or otherwise).

External system 50 can comprise one, two, three, or more functional elements, such as functional elements 599a, 599b, and/or 599c (singly or collectively functional element 599), shown positioned in external device 500, patient programmer 600', and clinician programmer 600", respectively.

Apparatus 10 can be configured to stimulate tissue (e.g. stimulate nerve tissue such as tissue of the central nervous system or tissue of the peripheral nervous system, such as to neuromodulate nerve tissue), such as by having one or more implantable devices 200 deliver and/or otherwise provide energy (hereinafter "deliver energy") and/or deliver an agent (e.g. a pharmaceutical compound or other agent) to one or more tissue locations, such as via one or more stimulation elements 260. In some embodiments, one or more implantable devices 200 deliver energy and/or an agent while receiving power and/or data from one or more external devices 500. In some embodiments, one or more implantable devices 200 deliver energy and/or an agent (e.g. continuously or intermittently) using energy provided by an internal power source (e.g. a battery and/or capacitor) without receiving externally supplied power, such as for periods of at least 1 hour, at least 1 day, at least 1 month or at least 1 year. In some embodiments, one or more stimulation parameters are varied (e.g. systematically and/or randomly), during that period.

In some embodiments, apparatus 10 is further configured as a patient diagnostic apparatus, such as by having one or more implantable devices 200 record a patient parameter (e.g. a patient physiologic parameter) from one or more tissue locations, such as while receiving power and/or data from one or more external devices 500. In some embodiments, during its use, one or more implantable devices 200 at least receives power from one or more external devices 500 (e.g. with or without also receiving data). Alternatively or additionally, one or more patient parameters can be recorded by an external device of apparatus 10, such as via a programmer 600 and/or an external device 500.

Apparatus 10 can be configured as a patient information recording apparatus, such as by having one or more implantable devices 200 and/or one or more external devices 500 record patient information (e.g. patient physiologic information and/or patient environment information). In some embodiments, one or more implantable devices 200 and/or one or more external devices 500 further collect information (e.g. status information or configuration settings) of one or more of the components of apparatus 10.

In some embodiments, apparatus 10 is configured to deliver stimulation energy to tissue to treat pain. In particular, apparatus 10 can be configured to deliver stimulation energy to tissue of the spinal cord and/or tissue associated with the spinal cord ("tissue of the spinal cord", "spinal cord tissue" or "spinal cord" herein), the tissue including roots, dorsal root, dorsal root ganglia, spinal nerves, ganglia, and/or other nerve tissue. The delivered energy can comprise energy selected from the group consisting of: electrical energy; magnetic energy; electromagnetic energy; light energy such as infrared light energy, visible light energy and/or ultraviolet light energy; mechanical energy; thermal energy such as heat energy and/or cryogenic energy; sound energy such as ultrasonic sound energy (e.g. high intensity focused ultrasound and/or low intensity focused ultrasound) and/or subsonic sound energy; chemical energy; and combinations of one or more of these. In some embodiments, apparatus 10 is configured to deliver to tissue energy in a form selected from the group consisting of: electrical energy such as by providing a controlled (e.g. constant or otherwise controlled) electrical current and/or voltage to tissue; magnetic energy (e.g. magnetic field energy) such as by applying controlled current or voltage to a coil or other magnetic field generating element positioned proximate tissue; and/or electromagnetic energy such as by providing both current to tissue and a magnetic field to tissue. A coil or other magnetic field generating element can surround (e.g. at least partially surround) the target nerve. Alternatively, or additionally, the magnetic energy can be applied externally and focused to specific target tissue via an implant comprising a coil and/or ferromagnetic materials. In some embodiments, the magnetic energy is configured to induce the application of mechanical energy. Delivered energy can be supplied in one or more stimulation waveforms, each waveform comprising one or more pulses of energy, as described in detail herebelow.

In some embodiments, apparatus 10 is configured as a stimulation apparatus in which external system 50 transmits a power signal to one or more implantable devices 200, and the one or more implantable devices 200 deliver stimulation energy to tissue with a stimulation signal (also referred to as a stimulation waveform), with the power signal and the stimulation signal having one or more different characteristics (e.g. as described herebelow). The power signal can be modulated with data (e.g. configuration or other data to be sent to one or more implantable devices 200). In these embodiments, the characteristics of the stimulation signal delivered (e.g. amplitude, frequency, duty cycle and/or pulse width), can be independent (e.g. partially or completely independent) of the characteristics of the power signal transmission (e.g. amplitude, frequency, phase, envelope, duty cycle and/or modulation). For example, the frequency and modulation of the power signal can change without affecting those or other parameters of the stimulation signal, and/or the parameters of the stimulation signal can be changed (e.g. via programmer 600), without requiring similar or any changes to the power signal. In some embodiments, implantable system 20 is configured to rectify the received power signal, and to produce a stimulation waveform with entirely different characteristics (e.g. amplitude, frequency and/or duty cycle) from the rectified power signal. Each implantable device 200 can comprise an oscillator and/or controller configured to produce the stimulation signal. In some embodiments, one or more implantable devices 200 is configured to perform frequency multiplication, in which multiple signals are multiplexed, mixed, added, and/or combined in other ways to produce a broadband stimulation signal.

In some embodiments, apparatus 10 is configured such that external system 50 transmits data (e.g. data and power) to implantable system 20, and implantable system 20 recovers (e.g. decodes, demodulates or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL); phase locked loop (PLL); high frequency clock; and/or crystal oscillator needed to perform the synchronization. Avoiding these components can also be correlated to reduced package size of each implantable device 200 (e.g. avoidance of a relatively large sized crystal oscillator). Asynchronous data transfer between external system 50 and implantable system 20 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591, 188, titled "Method of Making and Using an Apparatus for a Locomotive Micro-Implant using Active Electromagnetic Propulsion", filed Aug. 21, 2012. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013.

Apparatus 10 can be configured to treat pain, such as back pain and/or limb pain treated by stimulating dorsal root ganglia and/or other nerves or locations of the spinal cord or other nervous system locations. In some embodiments, apparatus 10 is configured to treat a type of pain selected from the group consisting of: back pain; joint pain; neuropathic pain; tennis elbow; muscle pain; shoulder pain; chronic, intractable pain of the back and/or limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these.

In some embodiments, apparatus 10 is configured to treat a patient disease or disorder selected from the group consisting of: chronic pain; acute pain; migraine; cluster headaches; urge incontinence; pelvic dysfunction such as overactive bladder; fecal incontinence; bowel disorders; tremor; obsessive compulsive disorder; depression; epilepsy; inflammation; tinnitus; hypertension; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

In some embodiments, apparatus 10 is configured to treat one or more diseases or disorders by delivering stimulation to perform renal modulation. In some embodiments, apparatus 10 is configured to treat hypertension, such as when apparatus 10 is configured to deliver stimulation to perform renal neuromodulation.

Apparatus 10 can be configured to treat heart disease, such as heart failure of a patient. In these embodiments, stimulation of the spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more stimulation elements 260 of one or more implantable devices 200 can be implanted at one or more spinal cord locations, such as to deliver stimulation to tissue proximate those locations. In some embodiments, stimulation elements 260 comprise two or more stimulation elements (e.g. electrodes) that span multiple vertebra of the spinal column (e.g. multiple stimulation elements that span at least T8 to T9 and/or T-9 to T-10). Power and/or data can be transmitted to the one or more implantable devices 200 via one or more external devices 500 of external system 50. One or more stimulation signals can be delivered to spinal cord tissue, such as to treat heart failure or other cardiac disease or disorder. In some embodiments, one or more stimulation elements 260 are configured to deliver energy (e.g. electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g. one or more stimulation elements 260, functional elements 299, functional elements 599 and/or other functional elements of implantable system 20) are configured (e.g. further configured) to record a patient parameter (e.g. stimulation element 260, functional element 299, functional element 599, and/or another functional element of apparatus 10 are configured as a sensor), such as a patient heart or spine parameter, and the information recorded is used to adjust the delivered stimulation signals. The at least one heart parameter can comprise a parameter selected from the group consisting of: EKG; blood oxygen; blood pressure; heart rate; ejection fraction; wedge pressure; cardiac output; and combinations of one or more of these.

Apparatus 10 can be configured to pace and/or defibrillate the heart of a patient. One or more stimulation elements 260 can be positioned proximate cardiac tissue and deliver a stimulation signal as described herein (e.g. based on power and/or data received by implantable system 20 from external system 50). The stimulation signal can be used to pace, defibrillate and/or otherwise stimulate the heart. Alternatively or additionally, apparatus 10 can be configured to record cardiac activity (e.g. by recording EKG, blood oxygen, blood pressure, heart rate, ejection fraction, wedge pressure, cardiac output, lung impedance and/or other properties or functions of the cardiovascular system via a sensor-based element 260, and/or other sensor of apparatus 10), such as to determine an onset of cardiac activity dysfunction or other undesired cardiac state. In some embodiments, apparatus 10 is configured to both record cardiac or other information and deliver a stimulation signal to cardiac tissue (e.g. stimulation varied or otherwise based on the recorded information). For example, apparatus 10 can be configured such that external system 50 transmits power and/or data to implantable system 20. Implantable system 20 monitors cardiac activity, and upon detection of an undesired cardiovascular state, implantable system 20 delivers a pacing and/or defibrillation signal to the tissue that is adjacent to one or more stimulation elements 260 configured to deliver a cardiac stimulation signal.

Apparatus 10 can be configured to perform a diagnostic procedure including measuring one or more patient parameters (e.g. patient physiologic or other patient parameters), such as are described in detail herebelow. In some embodiments, apparatus 10 is configured to measure a physiologic parameter that can be sensed from one or more sensor-based stimulation elements 260, functional elements 299, and/or functional elements 599 positioned in subcutaneous tissue. In these embodiments, external system 50 can comprise an external device 500 configured for placement proximate an implantable device 200 implanted in a position to record data from subcutaneous tissue (e.g. blood glucose data). External device 500 can comprise a wrist band, a wrist watch, and/or an arm band configuration such as when the implantable device 200 is positioned in subcutaneous tissue proximate the patient's wrist or upper arm. The external device 500 can comprise a leg, knee or ankle band configuration, such as when one or more implantable devices 200 are positioned in subcutaneous tissue proximate the patient's ankle, knee, and/or thigh. In some embodiments, external device 500 comprises a band or other attachment device for positioning about the thorax, neck, groin, and/or head of the patient. Power and/or data can be sent to the implantable device 200 from the external device 500, and data (e.g. blood glucose data) can be sent to external device 500 (or another component of external system 50) by implantable device 200, such as using a wireless communication configuration known to those of skill in the art. In some embodiments, external system 50 comprises a functional element 599 (e.g. functional element 599a, 599b, and/or 599c) configured to deliver an agent (e.g. insulin or glucose delivered by a needle-based functional element 599), based on the information received from implantable device 200. Alternatively, or additionally, implantable device 200 comprises a stimulation element 260 configured to deliver an agent (e.g. insulin or glucose delivered by a needle-based stimulation element 260), based on the information recorded by implantable device 200. Various closed loop sensing and agent delivery combinations and configurations should be considered within the spirit and scope of the present inventive concepts, including but not limited to: sensing a blood parameter such as white blood cell count and delivering a chemotherapeutic or other agent based on the blood parameter; sensing a hormone level and delivering a hormone or a hormone affecting agent; sensing blood pressure and delivering stimulation energy and/or a blood pressure affecting agent; sensing neural activity and delivering stimulation energy and/or a neural affecting agent or other agent based on the neural activity, such as for treating epilepsy; and combinations of one or more of these.

As described hereabove, external system 50 can be configured to transmit power and/or data (e.g. implantable system 20 configuration data) to one or more implantable devices 200 of implantable system 20. Implantable system 20 configuration data provided by external system 50 (e.g. via one or more antennas, antenna 540 shown, of one or more external devices 500) can include when to initiate stimulation delivery (e.g. energy delivery), and/or when to stop stimulation delivery, and/or it can include data related to the value or change to a value of one or more stimulation variables as described hereabove. The configuration data can include a stimulation parameter such as an agent (e.g. a pharmaceutical agent) delivery stimulation parameter selected from the group consisting of: initiation of agent delivery; cessation of agent delivery; amount of agent to be delivered; volume of agent to be delivered; rate of agent delivery; duration of agent delivery; time of agent delivery initiation; and combinations of one or more of these. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

As described hereabove, external system 50 can comprise one or more external devices 500. External system 50 can comprise one or more antennas 540, such as when a single external device 500 comprises one or more antennas 540, and/or when multiple external devices 500 each comprise one or more antennas 540. The one or more antennas 540 can transmit power and/or data to one or more antennas 240 of implantable system 20, such as when a single implantable device 200 comprises one or more antennas 240, and/or when multiple implantable devices 200 each comprise one or more antennas 240. In some embodiments, one or more antennas 540 define a radiation footprint (e.g. a footprint defining a volume, such as a volume of tissue, in which electromagnetic transmissions radiated by antennas 540 can be properly received by antennas 240), such as is described in applicant's co-pending U.S. patent application Ser. No. 15/664,231, titled "Medical Apparatus Including an Implantable System and an External System", filed Jul. 31, 2017.

External system 50 transmits power and/or data with a transmission signal comprising at least one wavelength λ. External system 50 and/or implantable system 20 can be configured such that the distance between an external antenna 540 transmitting the power and/or data and one or more implantable antennas 240 receiving the power and/or data transmission signal is equal to between 0.1λ and 10.0λ, such as between 0.2λ and 2.0λ. In some embodiments, one or more transmission signals are delivered by a transmitter, transmitter 530, at a frequency range between 10 MHz and 10.6 GHz, such as between 0.1 GHz and 10.6 GHz, between 10 MHz and 3.0 GHz, between 40 MHz and 1.5 GHz, between 10 MHz and 100 MHz, between 0.902 GHz and 0.928 GHz, in a frequency range proximate to 40.68 MHz, in a frequency range proximate to 866 MHz, or approximately between 863 MHz and 870 MHz. Transmitter 530 can comprise a transmitter that produces a transmission signal with a power level between 0.01 W and 4.0 W, such as a transmission signal with a power level between 0.01 W and 2.0 W or between 0.2 W and 1.0 W.

In addition to transmitting power and/or data to implantable system 20, external system 50 can be further configured to provide information (e.g. patient information and/or apparatus 10 performance information) to one or more other components of apparatus 10, such as tool 60 shown in FIG. 1 and described in detail herebelow.

One or more external devices 500 (singly or collectively external device 500) can be configured to transmit power and/or data (e.g. implantable system 20 configuration data) to one or more implantable devices 200 (singly or collectively implantable device 200). In some embodiments, one or more external devices 500 are configured to transmit both power and data (e.g. simultaneously and/or sequentially) to one or more implantable devices 200. In some embodiments, one or more external devices 500 are further configured to receive data from one or more implantable devices 200 (e.g. via data transmitted by one or more antennas 240 of one or more implantable devices 200). Each external device 500 can comprise housing 510, power supply 570, a transmitter 530, a controller 550, and/or one or more antennas 540, each shown in FIG. 1 and described in detail herebelow. Each external device 500 can further comprise one or more functional elements 599a, such as a functional element comprising a sensor, electrode, energy delivery element, a magnetic-field-generating transducer, and/or any transducer, also described in detail herebelow. In some embodiments, a functional element 599a comprises one or more sensors configured to monitor performance of external device 500 (e.g. to monitor voltage of power supply 570, quality of transmission of power and/or data to implantable system 20, temperature of a portion of an external device 500, and the like).

One or more housings 510 (singly or collectively housing 510) of each external device 500 can comprise one or more rigid and/or flexible materials which surround various components of external device 500 such as antenna 540, transmitter 530, controller 550, and/or power supply 570 shown in FIG. 1. In some embodiments, a single external device 500 comprises multiple discrete (i.e. separate) housings 510, two or more of which can each transfer data and/or other signals via a wired or wireless connection to the other, to an implantable device 200, and/or to another component of apparatus 10. In some embodiments, a housing 510 further surrounds a programmer 600 (e.g. programmer 600' or 600") and/or a power supply 570. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g. shielded to prevent transmission of electromagnetic waves), and an unshielded portion, such as an unshielded portion surrounding antenna 540.

Housing 510 can comprise an adhesive element (e.g. a spacer 511 configured as an adhesive element), such as an adhesive element configured to temporarily attach an external device 500 to the patient's skin. Alternatively or additionally, housing 510 can be constructed and arranged to engage (e.g. fit in the pocket of) a patient attachment device, such as patient attachment device 70 described herebelow.

One or more antennas 540 (singly or collectively antenna 540) can each comprise one, two, three, or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240, such as to adjust for movement of the array of the antennas 540 relative to the implanted antennas 240. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material. For antenna 540 to operate effectively at higher frequencies, the shield material can comprise a ferrite material that has a low conductivity and low magnetic loss tangent at a frequency of interest, and whereby a higher permeability is achieved. By placing a material with a high magnetic permeability ($\mu'$), low magnetic loss tangent ($\mu''/\mu'$), and low conductivity at the operating frequency (such as a high frequency ferrite) between the antenna and other elements of the transmitter, the losses or loading effects due to these elements can be dramatically reduced. In some cases, the magnetic field magnification of this shielding layer will enhance the overall performance. Additionally, this layer shields the outside environment from unwanted radiation from the antenna, and it protects the antenna from radiation originating in the environment.

In some embodiments, a spacing layer is positioned between antenna 540 and the shield material. The spacing layer can comprise a thickness of between 0 mm and 5 mm, such as between 0.25 mm and 1 mm. The spacing layer can comprise non-conductive dielectric materials, air, or other materials that have minimal impact on antenna performance. The spacing layer can also be incorporated into a board thickness, with the antenna being constructed on the opposite side of the board in relation to the shielding layer. The shielding layer can comprise a ferrite material as described hereabove, or any material with the desired permeability, magnetic loss, and conductivity at the frequency of interest. The thickness of the shielding layer can be dependent on its specific material properties and the application. In some embodiments, a conductive layer on the side of the shielding layer is positioned opposite the antenna to further shield unwanted radiation. To reduce weight, the shielding layer material can be porous or incorporate holes or slots spaced in a way to minimize the reduction in performance. The holes and spacings can be sized smaller than a wavelength of the RF signal. If no spacing layer is used, the shielding layer can extend inside the antenna. Additionally or alternatively, the shielding layer can be positioned on the other side or both sides of the antenna because of the field magnification effect. In some embodiments, the shielding layer is constructed to increase the directivity of the antenna or focus the electromagnetic energy.

One or more antennas 540 can be positioned in a housing 510 that is otherwise void of other components (e.g. void of power supply 570, controller 550 and/or transmitter 530), such as when an antenna 540 is positioned within a first housing 510 and communicates with components positioned in a second housing 510.

In some embodiments, one or more spacers, spacer 511 shown, is positioned between antenna 540 and the patient's skin, such as a spacer comprising a thickened portion of housing 510 or a discrete spacer 511 placed on a side of housing 510 (as shown) or on a side of antenna 540. Spacer 511 can comprise one or more materials that match the impedance of antenna 540 to the impedance of the patient's tissue. Spacer 511 can comprise a thickness of between 0.1 cm to 3 cm, such as a thickness between 0.2 cm and 1.5 cm. Spacer 511 can comprise materials which isolate heat (e.g. a spacer 511 comprising thermally insulating material). Alternatively, or additionally, housing 510 can comprise a heat insulating and/or dissipating material. Spacer 511 can comprise a soft or otherwise compressible material (e.g. foam) for patient comfort. Spacer 511 can be inflatable, such as to control the separation distance of an external antenna 540 from the patient's skin. An inflatable spacer 511 can be compartmentalized into several sections with independently controlled air pressure or volume to adjust the separation distance of an external antenna 540 and the patient's skin and/or its angle (e.g. tilt) with respect to the tissue surface.

In some embodiments, antenna 540 comprises a multi-feed point antenna, such as a multi-feed point antenna configured to: support beam shaping and/or focusing; allow adjustment of amplitude and/or phase of a transmission signal; increase the radiation footprint; or combinations of one or more of these.

In some embodiments, antenna 540 comprises one or more antennas selected from the group consisting of: patch antenna; slot antenna; array of antennas; a loop antenna (e.g.

a concentric loop antenna); antenna loaded with reactive elements; dipole antenna; polarizable antenna; selectable conductors that form an antenna; and combinations of one or more of these.

Antenna 540 can comprise a major axis between 1 cm and 10 cm, such as a major axis between 2 cm and 5 cm, and/or a major axis of approximately 4 cm. Antenna 540 can be further configured to receive a signal, such as when an antenna 240 is configured to transmit data to an external device 500. Antenna 540 can be positioned on (e.g. fabricated onto) a substrate, such as a flexible printed circuit board or other printed circuit board (e.g. a single or multiple layer printed circuit board comprising electrical traces connecting components).

A single external antenna 540 can be configured to transmit power and/or data to multiple implantable devices 200 (e.g. each containing one or more antennas 240). In some embodiments, a single external device 500, comprising one or more antennas 540 can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g. within housing 510). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200 operation depth; polarization; power efficiency; a radiation footprint; directional gain; beam shaping and/or focusing; sensitivity to implantable device 200 placement; patient comfort; patient usability; data transfer; and combinations of one or more of these. In some embodiments, the first antenna 540 is optimized for a different design parameter than the second antenna 540, and each antenna 540 can be activated independently or simultaneously to realize both benefits. In some embodiments, the first antenna 540 is similar to the second antenna 540 and placed in an array to increase the radiation footprint or placed in different external locations to operate with multiple implantable devices 200 implanted at different sites.

In some embodiments, a first external antenna 540 and a second external antenna 540 transmit power and/or data to a single implantable antenna 240. In some embodiments, a first antenna 540 and a second antenna 540 transmit power and/or data to one or more antennas 240, the transmissions performed simultaneously or sequentially. In sequential power and/or data transfers, a first external device 500 comprising a first one or more antennas 540 can be replaced (e.g. swapped) with a second external device 500 comprising a second one or more antennas 540. Alternatively or additionally, sequential power and/or data transfer can be initiated by one or more of the following conditions: when a first external antenna 540 moves (e.g. moves relative to an implanted antenna 240); when a second external device 500 comprising a second antenna 540 is turned on or otherwise activated; when a second antenna 540 provides improved power and/or data transfer to antenna 240 than that which is provided by a first antenna 540; and/or when power received from a first antenna 540 decreases (e.g. decreases below a threshold). In some embodiments, an antenna 240 receives power from a first antenna 540 and a second antenna 540, but only receives data from the first antenna 540. In some embodiments, a first antenna (e.g. an antenna 240 or an antenna 540) is driven with a different carrier signal than a second antenna (e.g. an antenna 240 or an antenna 540). The two carrier signals can comprise differences in amplitudes and/or relative phases as compared to each other. Each carrier signal can include a data transmission signal (e.g. data to be transmitted to an implantable device 200 from an external device 500 or to an external device 500 from an implantable device 200).

External device 500 can comprise an electronics module, controller 550 shown, configured to control one or more other components of external device 500.

One or more transmitters 530 (singly or collectively external transmitter 530) can each comprise one or more external transmitters that drive one or more antennas 540 (e.g. one or more antennas 540 positioned in a single external device 500 or multiple external devices 500). Transmitter 530 is operably attached to antenna 540 and is configured to provide one or more drive signals to antenna 540, such as one or more power signals and/or data signals transmitted to one or more implantable devices 200 of implantable system 20. Transmitter 530 can be configured to perform multi-level amplitude shift keying. The amplitude shift-keying can be configured to provide adjustable-depth modulation between 0-100% depth, such as between 5-75% depth, or such as between 10-50% depth.

As described herein, one or more external devices 500 can be configured to transmit data (e.g. configuration data) to one or more implantable devices 200, such as via a data transmission produced by transmitter 530 and sent to one or more antennas 540. In some embodiments, a transmitter 530 is configured to perform data modulation comprising amplitude shift keying with pulse width modulation. In these embodiments, the transmitter can be configured to perform multi-level amplitude shift keying. The amplitude shift-keying can be configured to provide adjustable-depth modulation between 0-100% depth, such as between 5-75% depth, or such as between 10-50% depth. In some embodiments, one or more external devices 500 transmit data to one or more implantable devices 200 using time division multiple access (TDMA). In some embodiments, one or implantable devices 200 are independently addressable through unique identification (ID) codes. Alternatively or additionally, transmitter 530 can be configured to transmit one or more data signals with a bandwidth between 1 kHz and 100 MHz, between 0.1 MHz and 100 MHz, or between 1 MHz and 26 MHz.

As described herein, one or more external devices 500 can be configured to transmit power to one or more implantable devices 200, such as via a power transmission produced by transmitter 530 and set to one or more antennas 540. One or more transmitters 530 can deliver power to one or more implantable devices 200 simultaneously or sequentially. In some embodiments, one or more transmitters 530 are configured to adjust the level of power transmitted to one or more implantable devices 200, such as by adjusting one or more duty cycling parameters. In these embodiments, power transmitted can be adjusted to: set a power transfer based on a stimulation level produced by implantable system 20; prevent oversaturation; to reduce interference with implantable system 20 data transmissions (e.g. when one or more implantable devices 200 are further configured to transmit data to external system 50); set a power transfer based on charge information and/or discharge information related to an implantable device 200 (e.g. charge rate and/or discharge rate of implantable energy storage assembly 270 described herebelow); and combinations of one or more of these. In some embodiments, implantable system 20 comprises a first receiver 230 (e.g. of a first implantable device 200) and a second receiver 230 (e.g. of a second implantable device 200'). One or more transmitters 530 can be configured to transmit a first power transmission to the first receiver 230, and a second power transmission to the second receiver 230. The first power transmission and the second power transmission can be adjusted or otherwise be different, such as to prevent oversaturation.

In some embodiments, transmitter 530 (and/or another component of external system 50) is further configured as a receiver (e.g. can further include a receiver, in addition to a transmitter or include a transmitter that further functions as a receiver), such as to receive data from implantable system 20. For example, a transmitter 530 can be configured to receive data via one or more antennas 240 of one or more implantable devices 200. Data received can include patient information (e.g. patient physiologic information, patient environment information or other patient information) and/or information related to an implantable system 20 parameter (e.g. an implantable device 200 stimulation parameter and/or other configuration parameter as described herein).

In some embodiments, transmitter 530 comprises a first transmitter to transmit power and/or data to one or more implantable devices 200, and a second transmitter to transmit data to a different device, as described herein. In these embodiments, a second transmitter of transmitter 530 can be configured to transmit data to tool 60 or another device such as a programmer 600; cell phone; computer; tablet; computer network such as the internet or a LAN; and combinations of one or more of these. In some embodiments, the second transmitter of transmitter 530 comprises a wireless transmitter; a Bluetooth transmitter; a cellular transmitter; and combinations of one or more of these. In some embodiments, a functional element 599 comprises a transmitter such as a Bluetooth transmitter.

Each power supply 570 (singly or collectively power supply 570) can be operably attached to a transmitter 530, and one or more other electrical components of each external device 500. Power supply 570 can comprise a power supplying and/or energy storage element selected from the group consisting of: battery; replaceable battery (e.g. via a battery door of housing 510); rechargeable battery; AC power converter; capacitor; and combinations of one or more of these. In some embodiments, power supply 570 comprises two or more batteries, such as two or more rechargeable batteries, such as to allow the first battery to be replaced (e.g. serially replaced) by the second battery (e.g. external device 500 can function with a single battery). In some embodiments, power supply 570 is configured to provide a voltage of at least 3 V. In some embodiments, power supply 570 is configured to provide a capacity between 1 Watt-hour and 75 Watt-hours, such as a battery or capacitor with a capacity of approximately 5 Watt-hours. In some embodiments, power supply 570 comprises an AC power source. Power supply 570 can include voltage and/or current control circuitry. Alternatively or additionally, power supply 570 can include charging circuitry, such as circuitry configured to interface a rechargeable battery with an external charging device. In some embodiments, apparatus 10 includes one or more charging devices, charger 61 shown, which can be configured to recharge a component of apparatus 10, such as to recharge power supply 570 of one or more external devices 500, such as is described herebelow in reference to FIGS. 17A-D.

Each external device 500 can include one or more user interface components, user interface 580 shown, such as to allow the patient or other user to adjust one or more parameters of apparatus 10. User interface 580 can include one or more user input components (e.g. buttons, slides, knobs, and the like) and/or one or more user output components (e.g. lights, displays and the like). In some embodiments, user interface 580 includes one or more controls configured to provide a water-ingress-resistant barrier, such as controls 581 described herebelow in reference to FIG. 3A-D.

Each patient programmer 600' or clinician programmer 600" (singly or collectively programmer 600) comprises a programming device configured to control one or more components of apparatus 10. Programmer 600 can comprise a user interface 680. Programmer 600 can send and/or receive commands to and/or from one or more external devices 500 via a wireless or wired connection (wired connection not shown but such as one or more insulated conductive wires). In some embodiments, one or more external devices 500 comprise all or a portion of programmer 600, such as when all or a portion of user interface 680 is integrated into housing 510 of external device 500. In some embodiments, apparatus 10 comprises multiple programmers 600, such as one or more patient programmers 600' and/or one or more clinician programmers 600".

Programmer 600 can be configured to adjust one or more parameters of apparatus 10, such as a stimulation parameter (e.g. a stimulation waveform parameter as described herein); a sensing parameter; a therapy parameter; a data recording parameter (e.g. a patient data recording parameter and/or an implantable device 200 data recording parameter); power transfer; data rate; activity of one or more external transmitters 530; activity of one or more external antennas 540; a stimulation element 260 parameter; a functional element 299 and/or 599 parameter; and combinations of one or more of these, such as is described hereabove. Programmer 600 can be further configured to provide information, such as patient physiologic information recorded by apparatus 10 (e.g. by one or more implantable devices 200 and/or one or more external devices 500), or apparatus 10 information, such as performance and/or configuration information (singly or collectively "status information") of one or more components of apparatus 10 (e.g. one or more external devices 500 and/or implantable devices 200). In some embodiments, programmer 600 uses information recorded by one or more implantable devices 200, apparatus 10 information, and/or information from external devices 500 to adapt configuration parameters of one or more components of apparatus 10.

In some embodiments, programmer 600 is configured to confirm that an adequate power transmission and/or an adequate data transmission has occurred between one or more external devices 500 and one or more implantable devices 200. In these embodiments, programmer 600 can comprise diagnostic assembly 62 described herebelow, or otherwise be configured to detect one or more of: power transmission to the implantable system 20 (e.g. to detect power transmission to implantable system 20 below a threshold); power transmission to the implantable system 20 trending in an undesired direction; improper and/or inadequate data transfer to the implantable system 20; and combinations of one or more of these. In some embodiments, programmer 600 monitors power transfer in real time and adjusts power transmission accordingly to optimize the rectifier efficiency (e.g. efficiency of rectifier 232 described herebelow) of one or more implantable devices 200. In some embodiments, apparatus 10 can be configured to adjust (e.g. in real time) the power transmission from one or more external devices 500 of external system 50 to one or more implantable devices 200 of implantable system 20, such as to optimize or otherwise improve an efficiency of apparatus 10, such as to improve the efficiency of transmissions between an external device 500 and an implantable device 200. These adjustments can include adjustment to one or more of: power transmission amplitude, duty cycle, frequency, phase, and periodicity.

In some embodiments, programmer 600 and/or another component of apparatus 10 comprises a matching network configured to match the impedance of one or more antennas 540 to one or more transmitters 530. The matching network can comprise an adjustable matching network. The matching network can comprise a directional coupler configured to measure a reflection coefficient. A transmitter 530 can comprise an output, and a programmer 600 can be configured to monitor a standing wave pattern at the output of the transmitter 530.

In some embodiments, programmer 600 comprises a lookup table of stimulation signal waveform patterns, such as to allow a clinician, patient and/or other operator of apparatus 10 to view and/or select a predetermined stimulation pattern (e.g. using user interface 680). In some embodiments, programmer 600 comprises a set of adjustable stimulation signal parameters configured to be varied to allow an operator to construct customized waveforms, such as to vary one or more stimulation parameters described hereabove. In some embodiments, programmer 600 is configured to allow an operator to create a customized waveform by specifying an amplitude of one or more discrete pulses or steps of a stimulation signal. In some embodiments, a clinician programmer 600" can include stimulation waveform customization options not provided by a patient programmer 600'.

In some embodiments, programmer 600 comprises a transmitter configured to transmit data to tool 60 or another device such as a cell phone; computer; tablet; computer network such as the internet or a LAN; and combinations of one or more of these. In these embodiments, programmer 600 can comprise a wireless transmitter; a Bluetooth transmitter; a cellular transmitter; and combinations of one or more of these. In some embodiments, programmer 600 comprises a receiver configured to receive data, or a transceiver configured to both transmit and receive data.

User interface 680 of programmer 600 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 599, such as functional elements 599a, 599b, and/or 599c, shown positioned in external device 500, programmer 600', and in programmer 600", respectively. Each functional element 599 can comprise a functional element as defined hereabove (e.g. a sensor, a transducer, and/or other functional element as described herein). In some embodiments, a functional element 599 comprises a needle, a catheter (e.g. a distal portion of a catheter), an iontophoretic element or a porous membrane, such as an agent delivery element configured to deliver one or more agents contained (e.g. one or more agents in a reservoir, such as reservoir 525 described herebelow) within an external device 500 and delivered into the patient (e.g. into subcutaneous tissue, into muscle tissue and/or into a blood vessel such as a vein).

In some embodiments, the functional element 599 comprises an electrode for sensing electrical activity and/or delivering electrical energy. In some embodiments, apparatus 10 is configured to cause stochastic resonance, and the addition of white noise can enhance the sensitivity of nerves to be stimulated and/or boost weak signals to be recorded by the one or more stimulation elements 260.

In some embodiments, one or more functional elements 599 comprise a sensor, such as a sensor configured to record data related to a patient parameter (e.g. a patient physiologic parameter), an external system 50 parameter and/or an implantable system 20 parameter. In some embodiments, operation of one or more implantable devices 200 (e.g. stimulation energy delivered by one or more implantable devices 200) is configured to be delivered based on the data recorded by one or more sensor-based functional elements 599, such as in a closed-loop energy delivery mode.

Functional element 599 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature; inflammation level; bacteria level; type of bacteria present; gas level; blood gas level; neural activity; neural spikes; neural spike shape; action potential; local field potential (LFP); EEG; muscular activity (e.g. as measured using electromyography, EMG); electrical activity produced by skeletal muscles (e.g. as measured using EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 599 can comprise one or more sensors configured to record data representing a parameter of external system 50 or any component of apparatus 10. Functional element 599 can comprise one or more sensors selected from the group consisting of: an energy sensor; a voltage sensor; a current sensor; a temperature sensor (e.g. a temperature of one or more components of external device 500 or programmer 600); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via controller 250 described herebelow) the data recorded by functional element 599 to assess one or more of: power transfer; link gain;

power use; energy within power supply 570; performance of power supply 570; expected life of power supply 570; discharge rate of power supply 570; ripple or other variations of power supply 570; matching of antennas 240 and 540; communication error rate between implantable device 200 and external device 500; integrity of transmission between implantable device 200 and external device 500; and combinations of one or more of these.

In some embodiments, one or more functional elements 599 are positioned on a housing 510. A functional element 599 can comprise a body conduction sensor, such as a body conduction sensor configured to record and/or receive data via skin conduction. A functional element 599 can be configured to record data associated with stimulation delivered by one or more implantable devices 200 (e.g. record data associated with stimulation energy delivered by one or more stimulation elements 260), such as to provide closed loop or semi-closed loop stimulation. A functional element 599 can be configured to record temperature, such as when apparatus 10 is configured to deactivate or otherwise modify the performance of an external device 500 when the recorded temperature (e.g. patient temperature and/or external device 500 temperature) exceeds a threshold.

In some embodiments, an external device 500, programmer 600', and/or programmer 600" comprises a temperature sensor, such as when functional elements 599a, 599b, and/or 599c, respectively, comprise a temperature sensor. The temperature-based functional element 599 can be positioned proximate a portion of programmer 600, housing 510 and/or one or more antennas 540 (e.g. to measure the temperature of one or more portions of a programmer 600 and/or external device 500). In these embodiments, the temperature data recorded by the functional element 599 is used to adjust one or more of: matching network; stimulation level (e.g. stimulation energy delivered by one or more implantable devices 200); power transmission level (e.g. level of power transmitted between one or more external devices 500 and one or more implantable devices 200); and combinations of one or more of these. In some embodiments, the temperature sensor-based functional element 599 is a part of a safety mechanism that deactivates programmer 600 and/or an external device 500 if the recorded temperature exceeds a threshold. Alternatively or additionally, a temperature sensor-based functional element 599 can be configured to measure temperature of the patient, such as when placed on housing 510, such as to adjust energy and/or agent delivery performed by implantable device 200 based on the recorded patient temperature.

In some embodiments, an external device 500, programmer 600', and/or programmer 600" comprise an accelerometer, vibration sensor, and/or other motion or shock sensor, such when functional elements 599a, 599b, and/or 599c comprise this type of sensor. In these embodiments, the functional elements 599 can comprise a sensor configured to produce a signal used to detect when an external device 500, programmer 600', and/or programmer 600" is dropped, as well as assess the forces generated during the drop. Alternatively or additionally, this sensor can be configured to produce a signal configured to detect a tap (e.g. on a housing) of the device, such that a tap gesture can be used in place of a control (e.g. a discrete switch) on the device.

As described hereabove, implantable system 20 comprises one or more implantable devices 200, such as one or more implantable devices 200 provided sterile or configured to be sterilized for implantation into the patient. A first implantable device 200 can be of similar or dissimilar construction and arrangement to a second implantable device 200'. Each implantable device 200 can be configured to treat a patient (e.g. treat pain of the patient) and/or record patient information, such as by delivering energy and/or an agent to tissue and/or by recording one or more physiologic parameters of the patient (e.g. parameters of tissue of the patient).

One or more portions of an implantable device 200 or other component of implantable system 20 can be configured to be visualized or contain a visualizable portion or other visualizable element, such as visualizable element 222 shown. Visualizable element 222 can comprise a material selected from the group consisting of: radiopaque material; ultrasonically reflective material; magnetic material; and combinations of one or more of these. In these embodiments, each implantable device 200 can be visualized (e.g. during and/or after implantation) via an imaging device such as a CT, X-ray, fluoroscope, ultrasound imager and/or MRI.

In some embodiments, implantable system 20 comprises multiple implantable devices 200 (e.g. implantable device 200 and implantable device 200' shown in FIG. 1) and implantable system 20 comprises a "multi-point ready" system, in which the operation (e.g. energy delivery, agent deliver, data recording and/or other function) of the multiple implantable devices 200 is performed simultaneously, asynchronously, and/or sequentially. The implantable devices 200 can be part of a network including one or more external devices 500 (e.g. external device 500 and external device 500' shown in FIG. 1) in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single and/or multiple external devices 500, which can further be synchronized (e.g. to a single clock). Each implantable device 200 of implantable system 20 can receive a power signal and/or a data signal from one or more external devices 500. In some embodiments of the multi-point ready implantable system 20, each implantable device 200 comprises a unique ID, such that each implantable device 200 is individually addressed (e.g. receive unique signals from external system 50). In some embodiments, external system 50 transmits high-bandwidth signals to implantable system 20, such that time-domain multiple access communication is performed while operating in near real time. In some embodiments, implantable system 20 is configured as a multi-point ready system such that stimulation energy delivered by implantable system 20 is independent of power received by implantable system 20 from external system 50.

Two implantable devices 200, or two discrete components of a single implantable device 200 (e.g. two components comprising or positioned in different housings), can be attached to each other by a connecting filament as defined hereabove. In some embodiments, a connecting filament comprises a user-attachable (e.g. clinician-attachable) connector on at least one end. The filament connector is configured to operably attach to a mating connector on a component (e.g. a housing 210) of an implantable device 200.

Each implantable device 200 is configured to receive power and/or data (e.g. implantable system 20 configuration data) from one or more external devices 500. In some embodiments, one or more implantable devices 200 are configured to receive both power and data (e.g. simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (generally "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

Each implantable device 200 can comprise one or more stimulation elements 260, configured to stimulate, deliver energy to, deliver an agent to, record information from and/or otherwise interface with the patient. Alternatively or additionally, the one or more stimulation elements 260 can be configured as a sensor, such as to record patient information. Each implantable device 200 can comprise housing 210, receiver 230, controller 250, energy storage assembly 270 and/or one or more antennas 240, each described in detail herein. Each stimulation element 260 can comprise a sensor and/or any transducer, as described in detail herein. One or more stimulation elements 260 can be positioned on a lead, lead 265 shown (e.g. a flexible filament including wires or other conductors that connect each stimulation element 260 to electronics within housing 210). Each implantable device 200 can comprise one or more leads 265, such as two leads attached to a single housing 210, or a first lead 265 attached to a first housing 210 and a second lead 265 attached to a second housing 210. Each implantable device 200 can comprise one or more other functional elements, such as functional elements 299a and 299b described herein. Each implantable device 200 can further comprise one or more anchoring or other fixation elements, anchor element 223 shown, as described in detail herebelow.

In some embodiments, one or more implantable devices 200 are further configured to transmit data to one or more external devices 500, such as via one or more antennas 240 transmitting a signal to one or more antennas 540, or otherwise. Data transmitted by an implantable device 200 can comprise patient information (e.g. patient physiologic information recorded by one or more stimulation elements 260 configured as a physiologic sensor), or implantable device 200 information (e.g. data recorded by one or more stimulation elements 260 configured as a sensor and positioned in implantable device 200, or other implantable device 200 configuration and/or performance data).

Housing 210 of each implantable device 200 can comprise one or more rigid and/or flexible materials which surround various components, such as antenna 240, energy storage assembly 270, controller 250 and/or receiver 230 as shown in FIG. 1. In some embodiments, one or more stimulation elements 260 are positioned in, on and/or within housing 210. In some embodiments, housing 210 surrounds a substrate, such as a flexible and/or foldable printed circuit board, such as multiple discrete or continuous printed circuit boards positioned in different planes (e.g. a flexible or foldable printed circuit board).

Housing 210 can comprise one or more shapes or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210 can comprise a major axis and a minor axis, defined hereabove. In some embodiments, housing 210 comprises a major axis less than or equal to 20 mm, such as a major axis less than or equal to 15 mm, 12 mm or 10 mm. In some embodiments, housing 210 comprises a minor axis less than or equal to 8 mm, such as a minor axis less than or equal to 6 mm, or less than or equal to 5 mm. Housing 210 can comprise a wall thickness between 0.1 mm and 1.0 mm, such as a wall thickness between 0.2 mm and 0.5 mm, such as a wall thickness of approximately 0.3 mm. Housing 210 can comprise a displacement volume less than or equal to 2000 mm$^3$, such as less than or equal to 600 mm$^3$.

Housing 210 can comprise one or more portions that are transmissive to radiofrequency (RF) signals. In some embodiments, housing 210 comprises glass. In some embodiments, housing 210 comprises a material selected from the group consisting of: glass; ceramic; stainless steel; titanium; polyurethane; an organic compound; liquid crystal polymer (LCP); gold; platinum; platinum iridium; tungsten; epoxy; a thermoplastic; a thermoset plastic; and combinations of one or more of these. In some embodiments, one or more portions of housing 210 comprises one or more coatings, such as one or more coatings configured to cause or prevent a physiologic reaction and/or a coating configured to block (e.g. shield) an electromagnetic transmission.

Housing 210 can comprise one or more passageways or other feedthroughs, such as for the passage of a lead, wire, optical fiber, fluid delivery tube, mechanical linkage and/or other conduit through a wall of housing 210, such as is described in applicant's co-pending U.S. patent application Ser. No. 15/664,231, titled "Medical Apparatus Including an Implantable System and an External System", filed Jul. 31, 2017.

In some embodiments, one or more inner or outer surfaces (or portions of surfaces) of housing 210 includes an insulating and/or shielding layer (e.g. a conductive electromagnetic shielding layer), such as inner coating 219a and/or outer coating 219b shown (singly or collectively coating 219). Coating 219 can comprise an electrically insulating and/or a thermally insulating layer or other coating. In some embodiments, one or more portions of housing 210 comprise an electrically shielding coating, coating 219, while other portions are transmissive to electromagnetic signals such as radiofrequency signals.

In some embodiments, housing 210 comprises an array of feedthroughs, not shown. In some embodiments, housing 210 is surrounded (e.g. partially or fully surrounded) by a covering, such as a flexible and/or non-conductive covering, such as a covering made of an elastomer.

In some embodiments, implantable device 200 and/or another component of apparatus 10 can include one or more features to prevent or at least reduce migration of implant 200 within the patient's body. In some embodiments, one or more implantable devices 200 comprises one or more anchor elements configured to secure one or more portions of implantable device 200 to tissue (e.g. anchor element 223 described hereabove and/or an anchor element in an overmold positioned about a portion of housing 210). Anchor element 223 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these. While anchor element 223 is shown proximate housing 210 (e.g. to fixedly attach housing 210 to tissue), in some embodiments anchor element 223 surrounds or is otherwise proximate lead 265 (e.g. to fixedly attach lead 265 to tissue), such as is described herebelow in reference to FIGS. 8A-C. In some embodiments, anchor element 223 comprises a porous mesh that surrounds all or a portion of housing 210. The porous mesh can be configured to promote tissue ingrowth, such as to prevent or at least limit ("prevent" herein) migration of housing 210 when implantable device 200 is implanted in the patient. In some embodiments, anchor element 223 comprises a mesh that is attached to the top side of implantable device 200 (side in closest proximity to the patient's skin), such as to prevent housing 210 from migrating away from the patient's skin (e.g. prevent from migrating deeper into the patient).

One or more antennas 240 (singly or collectively antenna 240) can be configured to receive power and/or data, and receiver 230 can receive the power and/or data from the one or more antennas 240. Each antenna 240 can comprise one or more implantable antennas, such as one or more antennas positioned within housing 210, and/or one or more antennas electrically attached to a connecting filament. In some embodiments, one or more implantable devices 200 comprise at least two antennas 240, or at least three antennas 240. Antenna 240 can be configured to receive power and/or data from one or more external devices 500, such that an attached receiver 230 receives the power and/or data. In some embodiments, implantable system 20 comprises at least two implantable devices 200, each of which comprise one or more (e.g. two or three) antennas 240 which are positioned within a housing 210 and/or electrically tethered to a housing 210. In some embodiments, an implantable device 200 comprises a first antenna 240 positioned in a first plane and a second antenna 240 positioned in a second plane. The first plane and second plane can be relatively orthogonal planes, or planes oriented between 30° and 90° relative to each other, such as between 40° and 90°, approximately 30°, approximately 45° and/or approximately 60° relative to each other. In some embodiments, an implantable device 200 comprises a first antenna 240 positioned in a first plane, a second antenna 240 positioned in a second plane, and a third antenna 240 positioned in a third plane.

In some embodiments, implantable device 200 comprises one or more antennas 240 positioned on a substrate, such as a printed circuit board (PCB), a flexible printed circuit board and/or a foldable substrate (e.g. a substrate comprising rigid portions and hinged portions). In some embodiments, the substrate is folded or otherwise pivoted to position the various antennas 240 on differently oriented planes, such as multiple planes oriented between 5° and 90° relative to each other, such as two antennas 240 positioned on two planes oriented between 30° and 90° or between 40° and 90° relative to each other, or three antennas 240 positioned on three planes oriented between 5° and 60° relative to each other. Two or more antennas 240 can be positioned on two or more different planes that are approximately 45° relative to each other, or approximately 60° or approximately 90° relative to each other.

Implantable device 200 can comprise three antennas 240. In some embodiments, a first antenna 240 comprises an electrical dipole antenna, and the second and third antennas 240 can be positioned in different planes than the first antenna 240. In some embodiments, the three antennas 240 each comprise a loop antenna, such as when each loop antenna is positioned on a different plane. In some embodiments, a first antenna 240 comprises an electrical dipole antenna, and a second antenna 240 and a third antenna 240 each comprise a loop antenna. In these embodiments, the second antenna 240 and the third antenna 240 can be positioned relatively orthogonal to each other (e.g. positioned on two relatively orthogonal planes). In some embodiments, a first antenna (e.g. an electrical dipole antenna) is positioned outside of housing 210, while a second antenna (e.g. a loop antenna) and a third antenna (e.g. a loop antenna) are each positioned on, in and/or within housing 210. In some embodiments, implantable device 200 comprises one or more antennas 240 in which any combination of antenna types (as described herein) are used in combination.

One or more antennas 240 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240 can comprise a loop antenna, such as an elongated loop antenna or a multiple-turn loop antenna.

One or more antennas 240 can comprise a multi-turn spiral loop antenna, such as a multi-turn spiral loop antenna configured to desensitize coupling sensitivity and/or boost input voltage. In some embodiments, one or more antennas 240 comprise multiple concentric loops with varied dimensions, such as concentric loops configured to desensitize coupling sensitivity. In these embodiments, the multiple concentric loops can be a arranged as follows: connected in parallel and driven from the same feed point; driven from the same feed point and connected using one or more of a capacitor, inductor, varactor, and combinations of one or more of these; and/or driven from multiple feed points.

One or more antennas 240 can comprise a minor axis and a major axis. In some embodiments, one or more antennas 240 comprise a minor axis between 1 mm and 8 mm, such as between 2 mm and 5 mm. In some embodiments, one or more antennas 240 comprise a major axis between 3 mm and 15 mm, such as between 4 mm and 8 mm. In some embodiments, one or more antennas 240 comprise a major axis above 3 mm, such as between 3 mm and 15 mm, such as when the antenna 240 is positioned outside of housing 210.

One or more antennas 240 can comprise a foldable and/or unfoldable antenna, such as is described in applicant's co-pending U.S. patent application Ser. No. 14/975,358, titled "Method and Apparatus for Minimally Invasive Implantable Modulators", filed Dec. 18, 2015.

One or more antennas 240 can be positioned inside of housing 210. Alternatively or additionally, one or more antennas 240 can be positioned outside of housing 210.

Implantable system 20, one or more implantable devices 200 and/or one or more antennas 240 can be configured to be positioned at a desired depth beneath the patient's skin, such as at a depth between 0.5 cm and 7.0 cm, such as a depth of between 1.0 cm and 3.0 cm.

One or more energy storage assemblies 270 (singly or collectively energy storage assembly 270) can comprise one or more implantable energy storage components, such as one or more batteries (e.g. rechargeable batteries) and/or capacitors (e.g. a supercapacitor). Energy storage assembly 270 can be configured to provide power to one or more of: one or more stimulation elements 260; controller 250; receiver 230; and combinations of one or more of these. In some embodiments, energy storage assembly 270 further provides power to one or more antennas 240 and/or circuitry configured to transmit data via antenna 240. In some embodiments, energy storage assembly 270 includes digital control for charge/discharge rates, voltage outputs, current outputs, and/or system power distribution and/or management.

Energy storage assembly 270 can comprise one or more capacitors with a single or collective capacitance between 0.01 μF and 10 F, such as a capacitance between 1 μF and 1.0 mF, or between 1 μF and 10 μF. The energy storage assembly 270 can comprise one or more capacitors with capacitance between 1 mF and 10 F, such as when energy storage assembly 270 comprises a super-capacitor and/or an ultra-capacitor. Such large capacitance can be used to store sufficient charge to maintain operation (e.g. maintain delivery of stimulation energy and/or delivery of an agent) without the use (e.g. sufficient proximity) of an associated external device 500. A capacitor or other energy storage element (e.g. a battery) can be chosen to provide sufficient energy to maintain operation for at least 30 seconds, at least 2 minutes, at least 5 minutes, at least 30 minutes, and up to several hours or more (e.g. during showering, swimming or other physical activity). In some embodiments, energy storage assembly 270 is configured to provide continuous and/or intermittent stimulation energy for at least one charge-balanced pulse (e.g. for the duration of at least one charge-balanced pulse). In some embodiments, a capacitor, battery or other energy storage element is configured to provide stimulation energy without receiving externally supplied power for periods of at least 1 hour, at least 1 day, at least 1 month or at least 1 year. Energy storage assembly 270 can comprise one or more capacitors with a breakdown voltage above 1.0 V, such as a breakdown voltage above 1.5 V, 4.0 V, 10 V, or 15 V. In some embodiments, energy storage assembly 270 can comprise capacitors distributed outside of housing 210, such as when one or more capacitors are distributed along lead 265. Energy storage assembly 270 can comprise one or more capacitors with low self-leakage, such as to maintain stored energy for longer periods of time.

In some embodiments, energy storage assembly 270 comprises a temporary energy storage component, such as a super-capacitor, configured to store a sufficient quantity of energy to provide uninterrupted stimulation, such as during time periods in which the link gain may be of poor quality or it may be temporarily unavailable (e.g. an external device 500 not being in place such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more stimulation elements 260 to deliver stimulation energy during subsequent (intended or unintended) unavailability of one or more external devices 500 (e.g. an external device 500 is intentionally removed or unintentionally falls off or otherwise loses its position sufficiently proximate one or more implantable devices 200). An energy storage assembly 270 comprising one or more high capacity energy storage components can be beneficial in applications where therapy interruption provides a significant risk or is otherwise relatively unacceptable, such as for life support therapies, cardiac resynchronization therapies, and the like. The high capacity energy storage components of energy storage assembly 270 can be positioned in an assembly positioned within housing 210, on an inner or outer surface of housing 210, within a separate housing, and/or within lead 265.

In some embodiments, during use (e.g. during period of providing stimulation or other function) implantable device 200 receives power regularly from external system 50 (e.g. relatively continuously while implantable device 200 delivers stimulation energy), and energy storage assembly 270 comprises a relatively small battery or capacitor, such as a battery or capacitor that has an energy storage capacity of less than or equal to 0.6 Joules, 7 Joules or 40 Joules.

One or more controllers 250 (singly or collectively controller 250) can be configured to control one or more stimulation elements 260, such as a stimulation element 260 comprising a stimulation-based transducer (e.g. an electrode or other energy delivery element) and/or a sensor (e.g. a physiologic sensor and/or a sensor configured to monitor an implantable device 200 parameter). In some embodiments, controller 250 is configured to transmit a stimulation signal (e.g. transmit stimulation energy configured in one or more stimulation waveforms) to one or more stimulation elements 260 (e.g. one or more stimulation elements 260 comprising an electrode and/or other energy delivery element), independent of the power signal received by one or more antennas 240 (e.g. independent of power transmitted by external system 50), such as by using energy stored in energy storage assembly 270. In these embodiments, the power signal and/or the RF path for the power signal can be adjusted to optimize power efficiency (e.g. by tuning matching network on transmitter 530 and/or receiver 230; configuring antennas 540 and/or 240 in an array; tuning operating frequency; duty cycling the power signal; adjusting antenna 540 and/or 240 position; and the like), and a stimulation signal can be precisely delivered (e.g. by using energy stored on energy storage assembly 270 and generating stimulation signal locally on the implantable device 200) to ensure clinical efficacy. Also, if the power signal transmission (also referred to as "power link") is perturbed unexpectedly, the stimulation signal can be configured so that it is not significantly affected (e.g. unaffected). In some configurations, the stimulation signal being delivered by one or more implantable devices 200 is insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250 can receive commands from receiver 230, such as one or more commands related to one or more implantable device 200 configuration parameters selected from the group consisting of: stimulation parameter; data rate of receiver; data rate of data transmitted by the first implantable device 200 at least one implantable antenna 240; stimulation element 260 configuration; state of controller 250; antenna 240 impedance; clock frequency; sensor configuration; electrode configuration; power management parameter; energy storage assembly parameter; agent delivery parameter; sensor configuration parameter; and combinations of one or more of these.

In some embodiments, one or more stimulation elements 260 comprise a stimulation element configured to deliver energy (e.g. one or more electrodes configured to deliver monopolar or bipolar electrical energy) to tissue, and controller 250 is configured to control the energy delivery, such as to control one or more stimulation parameters. Each of these stimulation parameters can be held relatively constant, and/or varied, such as a variation performed in a continuous or intermittent manner. In some embodiments, one or more stimulation parameters are varied in a random or pseudo-random (hereinafter "random") manner, such as a variation performed by apparatus 10 using a probability distribution as described in applicant's co-pending U.S. patent application Ser. No. 16/104,829, titled "Apparatus with Enhanced Stimulation Waveforms", filed Aug. 17, 2018. In some embodiments, stimulation (e.g. stimulation comprising high frequency and/or low frequency signal components) is varied randomly to eliminate or at least reduce synchrony of neuronal firing with the stimulation signal (e.g. to reduce paresthesia or other patient discomfort). In some embodiments, one or more stimulation elements 260 comprise a stimulation element configured to stimulate a target (e.g. nerve tissue such as spinal nerve tissue and/or peripheral nerve tissue). The amount of stimulation delivered to the target can be controlled by varying a parameter selected from the group consisting of: stimulation element 260 size and/or configuration (e.g. electrode size and/or configuration); stimulation element 260 shape (e.g. electrode shape, magnetic field generating transducer shape or agent delivering element shape); shape of a generated electric field; shape of a generated magnetic field; stimulation signal parameters; and combinations of one or more of these.

In some embodiments, one or more stimulation elements 260 comprise an element configured to deliver electrical energy to tissue (e.g. one or more electrodes configured to deliver monopolar or bipolar electrical energy), and controller 250 is configured to control charge balance, such as to actively and/or passively control charge balance, as described herebelow. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.01 mA to 15 mA (such as between 0.1 mA and 15 ma, between 0.1 mA and 12 mA, or between 0.1 mA and 10 mA), depending on the treatment, the error in charge balance can be on the order of 0.001% to 0.01%. Alternatively or additionally, controller 250 can comprise AC coupling capacitors that are configured to balance stimulation waveforms passively. The AC coupling capacitance can be fairly large (e.g. greater than 10 μF), in order to pass the stimulation waveform with minimal filtering. In some embodiments, apparatus 10 is configured to perform active charge balancing. In some embodiments, an implantable device 200 comprises a precise resistor in series with a stimulation electrode-based stimulation element 260. The precise resistor can be used to measure outflow and inflow currents, such as when controller 250 comprises an analog to digital converter (ADC). Controller 250 can integrate current over time during a first phase in which stimulation energy is delivered, and during a second phase in which a reverse current is applied (e.g. a reverse current used to balance charge). Controller 250 can be configured to balance the total charge in the two phases, to ensure that the net DC current is approximately zero. The integration can be achieved using an analog integrator and/or a digital summer of controller 250, with controller 250 keeping track of one or more parameters of the pulses delivered (e.g. pulses delivered within a train or a burst). Implantable device 200 can comprise a precise series resistance comprising an "on-chip" trimmed resistor or an "off-chip resistor". In some embodiments, implantable device 200 comprises a bank of trimmed resistors that are used to control the net series resistance, such as to adjust resistance based on stimulation amplitude requirements (e.g. to take advantage of the full dynamic range of an ADC of controller 250). In some embodiments, controller 250 comprises a shunt path with an RC-based low pass filter used for both outflow and inflow of current. RC elements of controller 250 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse. The ADC resolution can be high enough to ensure the residual error is less than what would cause an undesired charge accumulation. ADC resolution requirements can be further reduced by reducing the net capacitance in a shunt RC circuit, to cause accelerated charging of the capacitor. The capacitor can be discharged every time the voltage exceeds a certain predefined threshold, while controller 250 keeps track of the number of times the capacitor has been charged and reset. By resetting the capacitor through a low resistance path, the discharge time can be insignificant compared to the charge time, reducing the error due to the discharge period. Since the net charge equivalent to full scale voltage on the ADC can be divided into multiple cycles, the required resolution of the ADC to achieve the same residual error can be divided by the number of cycles.

In some embodiments, controller 250 is configured to produce a stimulation signal comprising a waveform or a waveform pattern (hereinafter stimulation waveform), for one or more stimulation elements 260 configured as a stimulation element (e.g. such that one or more stimulation elements 260 deliver stimulation energy comprising or at least resembling that stimulation waveform). Controller 250 can produce a stimulation signal comprising a waveform selected from the group consisting of: square wave; rectangle wave; sine wave; sawtooth; triangle wave (e.g. symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to produce a stimulation signal comprising a waveform including a combination of two or more waveforms selected from the group consisting of: square wave; rectangle wave; sine wave; triangle wave (symmetric or asymmetric); ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to construct a custom waveform (e.g. an operator customized waveform), such as by adjusting amplitude at specified time steps (e.g. for one or more pulses). In some embodiments, controller 250 is configured to generate a waveform including one or more random parameters (e.g. random timing of pulses or random changes in frequency, rate of change or amplitude).

In some embodiments, controller 250 is configured to provide a stimulation signal comprising waveforms and/or pulses repeated at a frequency (e.g. includes a frequency component) between 1.0 Hz and 50 KHz, such as between 10 Hz and 500 Hz, between 40 Hz and 160 Hz and/or between 5 KHz and 15 KHz. In some embodiments, controller 250 is configured to produce a stimulation signal comprising a frequency between 1 Hz and 1000 Hz, such as a stimulation signal with a frequency between 10 Hz and 500 Hz. In some embodiments, controller 250 is configured to produce a stimulation signal comprising a duty cycle between 0.1% and 99%, such as a duty cycle between 1% and 10% or between 1% and 25%. In some embodiments, controller 250 is configured to produce a stimulation signal comprising a frequency modulated stimulation waveform, such as a stimulation waveform comprising a frequency component (e.g. signal) between 1 kHz and 20 kHz. In some embodiments, controller 250 is configured to produce a stimulation signal comprising a mix and/or modulation of low frequency and high frequency signals, which comprise any of the waveform types, shapes and other configurations. In these embodiments, the stimulation signal can comprise low frequency signals between 1 Hz and 1000 Hz, and high frequency signals between 600 Hz and 50 kHz, or between 1 kHz and 20 kHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse width and/or frequency of the pulses.

Controller 250 can comprise a clamping circuit configured to allow fast charging and/or discharging of the energy storage assembly 270, stimulation element 260 drivers (e.g. electrode drivers) of controller 250, and/or other components of implantable device 200. The clamping circuit can improve pulse shape by offering additional control and/or configuration of rise and fall times in the shape of the waveform (e.g. to create rapid rise or fall times). In some embodiments, the clamping circuit can be configured to limit the rise and/or fall time to be less than or equal to one-tenth (10%) of the pulse width of an applied stimulation pulse (e.g. less than or equal to 1 μsec rise and/or fall time for a 10 μsec stimulation pulse).

In some embodiments, controller 250 comprises a matching network configured to match the impedance of a first antenna 240 with the impedance of the receiver 230. In these embodiments, controller 250's matching network can be adjustable. Alternatively or additionally, controller 250 can comprise an adjustable loading impedance to stabilize the load seen at an antenna 240 under different operating conditions. In some embodiments, the adjustable loading impedance is controlled according to the charge rate of the energy storage assembly 270.

Controller 250 and/or any other component of each implantable device 200 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230 (singly or collectively receiver 230) can comprise one or more components, such as demodulator 231, rectifier 232, and/or power converter 233 shown in FIG. 1. In some embodiments, receiver 230 can comprise a DC-DC converter such as a boost converter. Receiver 230 can comprise a data receiver, such as a data receiver including an envelope detector and demodulator and/or an envelope averaging circuit. In some embodiments, one more antennas 240 separately connect to one or more receivers 230. In some embodiments, one or more antennas 240 connect to a single receiver 230, such as via a series connection or a parallel connection.

One or more implantable devices 200 can be configured to transmit a data signal to external system 50. In some embodiments, receiver 230 is configured to drive one or more antennas 240 to transmit data to external system 50 (e.g. to an antenna 540 of an external device 500). Alternatively or additionally, implantable device 200 can be configured to transmit a data signal by having receiver 230 adjust a load impedance to backscatter energy, such as a backscattering of energy which can be detected by external system 50. In some embodiments, data transmission is accomplished by receiver 230 manipulating a signal at a tissue interface, such as to transmit a data signal using body conduction.

In some embodiments, receiver 230 comprises a matching network, such as a matching network configured to detune to prevent oversaturation. For example, implantable system 20 can comprise two or more implantable devices 200 each of which includes a receiver 230 comprising a matching network. A first implantable device 200's receiver 230's matching network can be configured to detune based on power received by the second implantable device 200's receiver 230.

Demodulator 231 can comprise circuitry that asynchronously recovers signals modulated on the power signal provided by external system 50, and that converts the modulated signals into digital signals. In some embodiments, demodulator 231 asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, demodulator 231 recovers a digital signal that is used as timing information for an implantable device 200, similar to an on-chip clock. The recovered clock signal can also be used to synchronize an on-chip clock generator of controller 250, such as through the use of a frequency and/or phase locked loop (FLL or PLL).

Rectifier 232 can comprise a power signal rectifier, such as to provide power to the energy storage assembly 270 and/or controller 250. In some embodiments, rectifier 232 comprises one or more self-driven synchronous rectifier (SDSR) stages connected in charge-pump configuration, to boost the voltage from input RF amplitude to the rectifier to a higher voltage. The boosted voltage can directly charge energy storage assembly 270, or it can be further boosted by a DC-DC converter or boost converter. In some embodiments, rectifier 232 comprises diode-capacitor ladder stages instead of, or in addition to, SDSR stages. On-chip diodes, such as Schottky diodes, or off-chip diodes can be used in one or more rectifier 232 stages. For maximum efficiency, the rectification elements, such as diodes, can be optimized to minimize forward conduction and/or reverse conduction losses by properly sizing the components and selecting appropriate number of stages based on the input RF voltage and load current.

Power converter 233 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters 233 can interface with energy storage assembly 270 and charge up associated energy storage components to desired voltages. In some embodiments, power converter 233 receives control signals from controller 250, such as to configure voltages, currents, charge/discharge rates, switching frequencies, and/or other operating parameters of power converter 233.

One or more implantable leads 265 (singly or collectively lead 265) can be attached to one or more housings 210, such as a lead 265 comprising one or more stimulation elements 260. Lead 265 can comprise one or more stimulation elements 260 configured as a stimulation element (e.g. an electrode configured to deliver electrical energy in monopolar or bipolar mode or an agent delivery element such as an output port fluidly connected to a reservoir within housing 210). Alternatively or additionally, lead 265 can comprise one or more stimulation elements 260 and/or functional elements 299b that is configured as a physiologic sensor (e.g. an electrode configured to record electrical activity of tissue or another physiologic sensor as described herein). Alternatively or additionally, lead 265 can comprise one or more stimulation elements 260 and/or functional elements 299b that is configured to transmit signals through tissue to external system 50, such as through body conduction.

In some embodiments, implantable device 200 comprises a connector, connector 215, that operably attaches (e.g. electrically attaches) one or more stimulation elements 260 to one or more components (e.g. electronic components) internal to housing 210 (e.g. to transfer power and/or data therebetween). Connector 215 can be constructed and arranged as described herebelow in reference to any of FIGS. 13A-C and/or 14A-B. In some embodiments, connector 215 is operably attached (e.g. in a manufacturing process) or attachable (e.g. in a clinical procedure) to lead 265 as shown in FIG. 1. Alternatively, connector 215 can be operably attached and/or attachable to a lead connection assembly, assembly 280, which in turn can be attached to a lead 265, such as is described herebelow in reference to any of FIGS. 7A-D, 13A-C, and/or 14A-B. In some embodiments, connector 215 passes through an opening in housing 210, in a feed-through arrangement. In some embodiments, an overmold or other sealing element, sealing element 205 shown, provides a seal about connector 215, the opening in housing 210 and/or the interface between connector 215 and housing 210.

In some embodiments, lead 265 comprises a removable stylet configured to aid in the implantation of lead 265, such as is described in applicant's co-pending U.S. patent application Ser. No. 15/664,231, titled "Medical Apparatus Including an Implantable System and an External System", filed Jul. 31, 2017. In some embodiments, implantable system 20 comprises more than one lead 265, comprising one or more stimulation elements 260 and attached to one or more housings 210 of one or more implantable devices 200. In some embodiments, one or more leads 265 can be attached to a single housing 210.

In some embodiments, lead 265 comprises a diameter between 1 mm and 4 mm, such as a diameter between 1 mm and 2 mm, such as a lead with a diameter of approximately 1.35 mm. In some embodiments, lead 265 comprises a length between 3 cm and 60 cm, such as a length between 6 cm and 30 cm. One or more leads 265 can include between 2-64 stimulation elements 260, such as when a lead 265 comprises between 2 and 64 electrodes, such as between 4 and 32 electrodes. In some embodiments, lead 265 comprises a paddle lead. In some embodiments, lead 265 comprises a single or multi-lumen catheter, such as when an attached implantable device 200 is configured as an agent delivery apparatus as described herein (e.g. a stimulation element 260 configured as a catheter comprises at least a portion of lead 265).

In some embodiments, lead 265 comprises one or more anchoring elements, anchor element 221 shown, that can be configured to anchor lead 265 to tissue (e.g. configured to allow an implanting clinician to anchor lead 265 to tissue using suture, staples, and the like. Anchor element 221 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these.

In some embodiments, lead 265 comprises one or more tines, such as tines 266 shown. Tines 266 can be configured to anchor or otherwise stabilize ("anchor" or "stabilize" herein) lead 265 relative to patient tissue, such as to prevent undesired movement during and/or after an implantation procedure for lead 265. One or more tines 266 can be configured to biodegrade after implantation in the patient, such that the stabilization provided is temporary. Tines 266 can be configured to biodegrade over a time period of approximately 4 to 12 weeks. In some embodiments, biodegradable tines 266 are configured to be incorporated when lead stimulation elements 260 are positioned to stimulate a peripheral nerve (e.g. lead 265 is implanted such that one or more stimulation elements 260 are positioned proximate one or more peripheral nerves).

In some embodiments, one or more tines 266 are configured to be deployed, such as via an operator-accessible control.

One or more stimulation elements 260 (singly or collectively stimulation element 260) and/or functional element 299 (e.g. functional element 299a and/or 299b) can comprise one or more sensors, transducers and/or other functional elements. In some embodiments, one or more stimulation elements 260 and/or functional elements 299 comprise at least one sensor and/or at least one transducer (e.g. a single stimulation element 260 or multiple stimulation elements 260). In some embodiments, stimulation element 260 and/or functional element 299 comprises a functional element configured to provide a therapy, such as one or more stimulation elements 260 configured to deliver an agent to tissue (e.g. a needle or catheter), to deliver energy to tissue and/or to otherwise therapeutically affect tissue. In some embodiments, stimulation element 260 and/or functional element 299 comprises one or more functional elements configured to record patient information, such as when stimulation element 260 and/or functional element 299 comprises one or more sensors configured to measure a patient physiologic parameter, as described herein. In some embodiments, stimulation element 260 and/or functional element 299 comprises one or more sensors configured to record an implantable device 200 parameter, also as described herein.

One or more stimulation elements 260 can be positioned on lead 265 as shown in FIG. 1. Alternatively or additionally, one or more stimulation elements 260 can be positioned on housing 210. One or more functional elements 299 can be positioned on lead 265 (e.g. functional element 299b shown) and/or positioned on and/or within housing 210 (e.g. functional element 299a shown).

Stimulation element 260 can comprise one or more stimulation elements positioned at one or more internal body locations. Stimulation element 260 can comprise one or more stimulation elements positioned to interface with (e.g. deliver energy to and/or record a physiologic parameter from) spinal cord tissue, spinal canal tissue, epidural space tissue, spinal root tissue (dorsal or ventral), dorsal root ganglion, nerve tissue (e.g. peripheral nerve tissue, spinal nerve tissue or cranial nerve tissue), brain tissue, ganglia (e.g. sympathetic or parasympathetic) and/or a plexus. In some embodiments, stimulation element 260 comprises one or more elements positioned proximate and/or within one or more tissue types and/or locations selected from the group consisting of: one or more nerves; one or more locations along, in and/or proximate to the spinal cord; peripheral nerves of the spinal cord including locations around the back; the knee; the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; the spine; the vagus nerve; the renal nerve; an organ; the heart; the liver; the kidney; an artery; a vein; bone; and combinations of one or more of these, such as to stimulate and/or record data from the tissue and/or location in which the stimulation element 260 is positioned proximate to and/or within. In some embodiments, apparatus 10, implantable device 200 and/or stimulation element 260 are configured to stimulate spinal nerves, peripheral nerves and/or other tissue as described in applicant's co-pending U.S. patent application Ser. No. 16/993,999, titled "Apparatus for Peripheral or Spinal Stimulation", filed Aug. 14, 2020.

In some embodiments, stimulation element 260 and/or functional element 299 comprises one or more sensors configured to record data representing a physiologic parameter of the patient. Stimulation element 260 and/or functional element 299 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 (e.g. via stimulation element 260, functional element 299, and/or functional element 599) can be configured to record a patient parameter (e.g. patient physiologic and/or patient environment parameter) selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity (e.g. as measured using EMG); skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, stimulation element 260 and/or functional element 299 comprises one or more sensors configured to record data representing a parameter of implantable device 200. In these embodiments, stimulation element 260 and/or functional element 299 can comprise one or more sensors selected from the group consisting of: an energy sensor; a voltage sensor; a current sensor; a temperature sensor (e.g. a temperature of one or more components of implantable device 200); a contamination detector (e.g. to detect undesired material that has passed through housing 210); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via implantable controller 250, programmer 600 and/or diagnostic assembly 62 described herebelow) the data recorded by stimulation element 260 and/or functional element 299 to assess one or more of: power transfer; link gain; power use; energy within energy storage assembly 270; performance of energy storage assembly 270; expected life of energy storage assembly 270; discharge rate of energy storage assembly 270; ripple or other variations of energy storage assembly 270; matching of antenna 240 and 540; communication error rate between implantable device 200 and external device 500; integrity of transmission between implantable device 200 and external device 500; and combinations of one or more of these. A stimulation element 260 can be configured to record temperature, such as when apparatus 10 is configured to deactivate or otherwise modify the performance of an implantable device 200 when the recorded temperature exceeds a threshold.

In some embodiments, one or more stimulation elements 260 comprise a transducer configured to deliver energy to tissue, such as to treat pain and/or to otherwise stimulate or affect tissue. In some embodiments, stimulation element 260 comprises a stimulation element, such as one or more transducers selected from the group consisting of: an electrode; an energy delivery element such as an electrical energy delivery element, a light energy delivery element, a laser light energy delivery element, a sound energy delivery element, a subsonic sound energy delivery element and/or an ultrasonic sound delivery element; an electromagnetic field generating element; a magnetic field generating element; a mechanical transducer (e.g. delivering mechanical energy to tissue); a tissue manipulating element; a heat generating element; a cooling (e.g. cryogenic or otherwise heat extracting energy) element; an agent delivery element such as a pharmaceutical drug delivery element; and combinations of one or more of these.

In some embodiments, one or more stimulation elements 260 comprises a drug or other agent delivery element, such as a needle, port, iontophoretic element, catheter, or other agent delivering element that is connected to a reservoir of agent positioned within housing 210 (e.g. reservoir 225 described herebelow). In some embodiments, one or more stimulation elements 260 comprise a drug eluting element configured to improve biocompatibility of implantable system 20.

In some embodiments, one or more stimulation elements 260 comprise one or more electrodes configured to deliver energy to tissue and/or to sense a patient parameter (e.g. electrical activity of tissue or other patient physiologic parameter). In these embodiments, one or more stimulation elements 260 can comprise one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, apparatus 10 (e.g. via stimulation element 260, functional element 299, and/or functional element 599) is configured to both record one or more patient parameters, and also to perform a medical therapy (e.g. stimulation of tissue with energy and/or an agent). In these embodiments, the medical therapy can be performed in a closed-loop fashion, such as when energy and/or agent delivery is modified based on the measured one or more patient physiologic parameters.

In some embodiments, one or more stimulation elements 260 comprise an agent delivery element, such as a fluid delivery element (e.g. a catheter, a porous membrane, an iontophoretic element or a needle) in fluid communication with a reservoir of the agent positioned within housing 210, such as reservoir 225 described herebelow.

In some embodiments, apparatus 10 comprises one or more tools, tool 60 shown. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g. patient physiologic information) recorded by implantable system 20; patient environment information recorded by implantable system 20; and combinations of one or more of these. Tool 60 can be configured to receive data from wired or wireless (e.g. Bluetooth) means. Tool 60 can comprise a tool selected from the group consisting of: a data logging and/or storage tool; a data analysis tool; a network such as a LAN or the Internet; a cell phone; and combinations of one or more of these.

In some embodiments, tool 60 comprises a battery charging assembly, such as an assembly configured to recharge one or more power supplies 570 comprising a rechargeable battery or capacitor.

Apparatus 10 can include one or more placement tools, positioning tool 67 shown, which can be configured to aid in the positioning and/or maintenance of one or more external devices 500 on the patient's skin (e.g. at a location proximate an implanted implantable device 200).

Apparatus 10 can include one or more implantation tools, tool 65 shown. Implantation tool 65 can comprise an introducer, tunneller (e.g. tunneling tool 6504 described herein), and/or other implantation tool constructed and arranged to aid in the implantation of housing 210, implantable antenna 240, lead 265 and/or one or more stimulation elements 260. In some embodiments, tool 65 comprises a component configured to anchor implantable device 200 to tissue, such as a mesh or wrap that slides around at least a portion of implantable device 200 and is configured to engage tissue (e.g. via tissue ingrowth) or be engaged with tissue (e.g. via suture or clips).

In some embodiments, one or more components (and/or portions of components) of tool 65 comprises a lubricious coating and/or a lubricous material ("lubricious coating" herein), such as to reduce tissue trauma and/or reduce pain to the patient. For example, tool 65 can comprise an introducer, tunneller, pocket formation tool, needle, and/or other insertion tool with at least a portion comprising a lubricious coating configured to ease insertion of the tool. Typical coatings and materials include but are not limited to: a polytetrafluoroethylene coating or material; a hydrophilic coating or material; and combinations of these.

In some embodiments, one or more components (and/or portions of components) of tool 65 comprises one or more "visualizable portions", such as a radiopaque portion that is visible in X-ray imaging (e.g. fluoroscopy) and/or ultrasonically visible portion that is visible in ultrasound imaging. For example, tool 65 can comprise an introducer including an ultrasonically visible or otherwise visible portion that is used to position the introducer, such as during the implantation of lead 265 or another portion of implantable device 200.

In some embodiments, lead 265 comprises a paddle lead or other stimulating lead and tool 65 comprises an introducer (e.g. a needle or an extended-width introducer) configured to deliver at least a distal portion of lead 265 into an epidural space of a patient. Tool 65 can comprise an introducer comprising a Tuohy needle, such as a Tuohy needle of 12 gauge or smaller. Tool 65 can comprise a handle for manipulating lead 265. Tool 65 can be configured to place lead 265 at an entry point above the lumbar spinal column (e.g. between L1 and L2 vertebrae). Tool 65 can include extension tubing used to insert lead 265. Tool 65 can further comprise a tool configured to anchor lead 265, such as when tool 65 comprises sutures, clips, other anchoring elements and/or an anchor securing tool (e.g. a needle or a stapling device), such as to secure lead 265 in subcutaneous tissue. Lead 265 and/or tool 65 can comprise extension tubing used to place lead 265, such as extension tubing that remains in place after removal of an introducer of tool 65. Tool 65 can be configured to place lead 265 against the dura of the spinal cord of the patient.

In some embodiments, tool 65 and/or lead 265 are constructed and arranged to implant lead 265 to stimulate one or more multifidus (MF) muscle fascicles, such as at least three sets of multifidus muscle fascicles. Lead 265 can be secured to a vertebra (e.g. on the transverse process, lamina or vertebral body). Lead 265 can be placed via tool 65 such that one or more stimulation elements 260 (e.g. electrodes) are positioned within the multifidus muscle structures. One or more stimulation elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Stimulation elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, stimulation elements 260 are positioned to cause transvascular stimulation (e.g. transvascular stimulation from arteries and/or veins in a leg or arm). In some embodiments, stimulation elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, stimulation elements 260 are configured to deliver stimulation energy to contract the multifidus muscle. In some embodiments, stimulation elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool 60 comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described herein. Alternatively or additionally, two more external system 50 components and/or two or more implantable system 20 components transmit information and/or power via a wireless transmitter (e.g. an RF transmitter), magnetic coupling, inductive coupling; capacitive coupling and/or other wireless transmission means.

Apparatus 10 can include one or more positioning devices, such as patient attachment device 70 shown in FIG. 1, that is used to attach one or more components of external system 50 to a location on or at least proximate the patient. In some embodiments, patient attachment device 70 is constructed and arranged as described in applicant's co-pending U.S. patent application Ser. No. 16/408,989, titled "Method and Apparatus for Neuromodulation Treatments of Pain and Other Conditions", filed May 10, 2019.

Patient attachment device 70 can comprise one or more elements configured to attach one or more external devices 500 and/or programmer 600 at one or more locations on or proximate the patient's skin, that are relatively close to one or more implantable devices 200 that have been implanted in the patient. Patient attachment device 70 can comprise a component selected from the group consisting of: belt; belt with pockets; belt with adhesive; adhesive; strap; strap with pockets; strap with adhesive shoulder strap; shoulder band; shirt; shirt with pockets; clothing; clothing with pockets; epidural electronics packaging; clip (e.g. patient attachment device 70a described herebelow in reference to FIG. 3A-D); bracelet; wrist band; wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g. at least one antenna 540 mounted to or otherwise positioned on a printed circuit board such as a flexible printed circuit board). Patient attachment device 70 can include one or more pockets, such as one or more pockets configured to collectively surround one or more of: external device 500; one or more antennas 540; power supply 570; programmer 600; and combinations of one or more of these. In some embodiments, patient attachment device 70 comprises multiple pockets, such as to allow repositioning of an external antenna 540, programmer 600, external transmitter 530 and/or external power supply 570 to various different locations, such as to improve transmission of power and/or data to one or more implantable devices 200 and/or improve patient comfort. In some embodiments, one or more antennas 540, power supplies 570, and/or transmitters 530 are connected through flexible cables positioned in patient attachment device 70. In some embodiments, the flexible cables are small coax cables that accommodate the power levels and frequencies of the carried signals. In some embodiments, the one or more antennas 540 are connected to one or more additional components of external device 500 through a single cable with a local power splitting component and/or active matching element that adjusts signal power to each of the one or more antennas 540.

In some embodiments, patient attachment device 70 and/or external device 500 can be configured to prevent adversely affecting portions of the skin contacted by either device. Alternatively or additionally, patient attachment device 70 and/or external device 500 can be configured to clean and/or to promote healing of one or more skin-contacting portions. For example, patient attachment device 70 can include an agent (e.g. a coating or other included agent) selected from the group consisting of: a bactericidal agent; an anti-fungal agent; and combinations thereof.

In some embodiments, an anchoring-based tool, patient attachment device 70, is used on a patient-by-patient basis, such as when used on overweight patients and/or to otherwise avoid migration of implantable device 200 sideways and/or downward (e.g. into fat tissue).

Apparatus 10 can comprise a device configured to operate (e.g. temporarily operate) one or more implantable devices 200, such as trialing interface 80 shown in FIG. 1. Trialing interface 80 can be configured to wirelessly deliver power to an implantable device 200, wirelessly deliver data to an implantable device 200, and/or wirelessly receive data from an implantable device 200. Trialing interface 80 can be configured to interface with one or more implantable devices 200 during an implantation procedure in which one or more implantable devices 200 are implanted in a patient (e.g. a sterile clinical procedure in which an implantable device 200 comprising a pre-attached lead 265 is implanted in a patient). Trialing interface 80 can be configured to be sterilized one or more times. Trialing interface 80 can comprise one or more antennas, such as an antenna similar to antenna 540 of an external device 500. Trialing interface 80 can comprise a transmitter, such as a transmitter similar to transmitter 530 of external device 500, and a power supply, such as a power supply similar to power supply 570 of external device 500. In some embodiments, trialing interface 80 is of similar construction and arrangement to the trialing interface described in applicant's co-pending U.S. patent application Ser. No. 16/408,989, titled "Method and Apparatus for Neuromodulation Treatments of Pain and Other Conditions", filed May 10, 2019. In some embodiments, trialing interface 80 includes a housing to be positioned proximate at least a portion of implantable device 200, such as a housing 210 that surrounds an antenna and a transmitter that is configured to operatively couple to (e.g. transmit power and/or data to) one or more antennas 240 of one or more implantable devices 200.

In some embodiments, trialing interface 80 is constructed and arranged as described an applicant's co-pending U.S. patent application Ser. No. 16/672,921, titled "Stimulation Apparatus", filed Nov. 4, 2019, the entire content of which is incorporated herein by reference in its entirety for all purposes.

As described hereabove, trialing interface 80 can be used in clinical procedures in which an implantable device 200 including a pre-attached lead 265 is implanted. In some embodiments, implantable device 200 includes an attachable lead 265, and apparatus 10 includes trialing interface 90. Trialing interface 90 can be configured to operably (e.g. electrically) attach to lead 265, such as to deliver stimulation energy via a wired connection during a trialing procedure, as described herein. For example, trialing interface 90 can deliver stimulation energy to one or more stimulation elements 260 of lead 265 during a trialing procedure in which proper position of stimulation element 260 is confirmed and/or modified, and/or one or more stimulation waveforms are tested. Trialing interface 90 can include an interface connector 95 configured to operably attach (e.g. electrically attach) trialing interface 90 to lead 265 (e.g. after lead 265 has been implanted in tissue of the patient). Connector 95 can be configured to be used in a single trialing procedure (e.g. on a single patient), while the remainder of trialing interface 90 can be reused (e.g. in multiple trialing procedures for multiple patients). Trialing interface 90 can comprise a device that is sterilized, and it can be a device that can be re-sterilized (e.g. to be used in multiple sterile clinical procedures). In some embodiments, interface connector 95 and other portions of trialing interface 90 are constructed and arranged as described herebelow in reference to FIGS. 12A-B. In some embodiments, trialing interface 80 and trialing interface 90 include similar components, (e.g. similar components used to create similar stimulation waveforms to be used in a trialing procedure).

In some embodiments, one or more implantable devices 200 of implantable system 20 comprises an implantable transmitter configured to transmit data, such as to transmit data (e.g. stimulation information, patient physiologic information, patient environment information, implantable device 200 performance and/or configuration information, and the like) to one or more external devices 500. In these embodiments, receiver 230 can be configured as both a receiver and a transmitter. One or more implantable devices 200 can be configured to transmit data by sending a signal to (i.e. "driving") one or more antennas 240 or another antenna of implantable device 200. An implantable device 200 can be configured to transmit data using one or more of: load modulation; a signal carrier; and/or body conduction. An implantable device 200 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 62 shown in FIG. 1. In some embodiments, programmer 600 and/or implantable controller 250 comprise all or a portion of diagnostic assembly 62. Diagnostic assembly 62 can be configured to assess, monitor, determine and/or otherwise analyze patient information and/or implantable device 200 information, such as when one or more stimulation elements 260, functional elements 299, and/or functional elements 599 are configured as a sensor configured to record patient information (e.g. patient physiologic information and/or patient environment information) and/or apparatus 10 information (e.g. implantable device 200 information) as described herein. Diagnostic assembly 62 can be configured to analyze communication and/or the power link between an implantable device 200 and an external device 500. In some embodiments, such a communication link analysis can be performed by measuring bit error rate (BER) of a known data stream during communication signal transmission (also referred to as "communication link") measurement phase (e.g. such as during a calibration procedure). The BER can be tracked by the implant controller 250 or programmer 600, such as to monitor and keep track of any trends in the link. This trend can be used to adjust the link and/or provide feedback to an operator of apparatus 10 (e.g. the patient), in case the link cannot be automatically adjusted to compensate for a negative trend (e.g. such that the operator can perform physical re-adjustment of the external system 50). Alternatively or additionally, a power link analysis can be performed by monitoring charge/discharge rate of the implanted energy storage assembly 270. Similar to the communication link, the power link status and/or trending can be monitored and recorded for link adjustment and/or feedback purposes. Diagnostic assembly 62 can be configured to analyze a result of stimulation energy delivered by implantable device 200, such as when a stimulation element 260 comprises an electrode to record electrical activity of tissue (e.g. in addition to delivering electrical energy to stimulate tissue). A stimulation element 260, a functional element 299, and/or a functional element 599 can comprise a sensor configured to record neural activity and/or muscular activity, and the diagnostic assembly configured to analyze the recorded sensor data. In some embodiments, diagnostic assembly 62 is configured to analyze impedance, such as when a stimulation element 260, a functional element 299, and/or functional element 599 comprises a sensor configured to record data related to impedance, such as when implantable device 200 performs a frequency sweep, performs an impulse response and/or compares voltage and current of a stimulation waveform. In some embodiments, diagnostic assembly 62 is configured to assess the impedance of one or more implantable antennas 240 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 62 is configured to test or otherwise assess the link between one or more implantable antennas 240 and one or more external antennas 540 (e.g. during a procedure in which one or more implantable devices 200 are implanted in a patient). In these embodiments, diagnostic assembly 62 can be configured to perform a test prior to anchoring housing 210 to tissue (e.g. prior to initial or final suturing into tissue such as the fascia layer). For example, lead 265 can be implanted at a location to stimulate target tissue (e.g. one or more nerves identified to treat pain or another patient condition). Prior to suturing housing 210 in its implant location, diagnostic assembly 62 can be configured to confirm that one or more external antenna 540 transmission links to one or more implantable antennas 240 are above an efficiency threshold, for example such that sufficient power will be received by the one or more implantable devices 200. Additionally, the procedure can be performed to optimize or otherwise improve the position of the one or more implantable devices 200 to be implanted and subsequently secured to tissue.

In these link testing embodiments, diagnostic assembly 62 can comprise a handheld assembly (e.g. a sterile assembly comprising a wand or other handheld housing). Diagnostic assembly 62 can be configured to send a simple signal to one or more implantable devices 200 (e.g. a diagnostic assembly 62 with similar power and/or data transmission capabilities as an external device 500). Each implantable device 200 can respond (e.g. via data sent via an implantable antenna 240 or other transmitter) with information related to the quality of the transmission link (e.g. information about the power received by the one or more implantable devices 200). Diagnostic assembly 62 could provide a user interface (e.g. a speaker, a text screen and/or a video display) that provides quality or other information (go/no go information, digital or other discrete level information, and/or analog information). Diagnostic assembly 62 could be further configured to provide information confirming detection of one or more implantable devices 200, status of one or more implantable devices 200 (e.g. parameter level and/or fault detection status), and/or self-diagnostic status (i.e. diagnostic assembly 62 status).

Each implantable device 200 can be configured to specifically identify and/or specifically reply to diagnostic assembly 62 (e.g. in a different form than communications with an external device 500). Each implantable device 200 can be configured to provide information related to one or more of: the charge and/or discharge rate of energy storage assembly 270 (e.g. the charge and/or discharge rate of a capacitor or battery of energy storage assembly 270); or the frequency of a voltage-controlled oscillator that is driven by an unregulated voltage of power converter 233. Diagnostic assembly 62 can be configured to perform numerous performance tests (e.g. of one or more implantable devices 200 or implantation locations for one or more implantable devices 200), prior to completion of the implantation procedure (e.g. prior to closing one or more incisions).

In some embodiments, apparatus 10 is configured to provide a therapy by delivering stimulation energy to tissue, such as electrical energy delivered to tissue by one or more stimulation elements 260 comprising one or more electrodes. Alternatively or additionally, apparatus 10 can be configured as an agent-delivery apparatus (e.g. a pharmaceutical or other agent delivery apparatus). In some embodiments, apparatus 10 comprises one or more reservoirs for storing the agent, such as reservoir 525 of external device 500 and/or reservoir 225 of implantable device 200, each shown in FIG. 1. Reservoirs 525 and/or 225 can be fluidly connected to one or more functional elements 599 and/or functional elements 299, respectively (e.g. via one or more tubes). Reservoirs 525 and/or 225 can comprise one or more chambers (e.g. independent chambers configured to separately contain incompatible drugs or otherwise prevent undesired multiple drug interactions). Reservoirs 525 and/or 225 can comprise a volume (e.g. a volume to store one or more agents) between 0.1 ml and 50 ml, such as between 0.1 ml and 3.0 ml, or between 0.1 ml and 1.0 ml. Reservoirs 525 and/or 225 can comprise pressurized reservoirs or otherwise comprise a fluid pumping mechanism (e.g. a peristaltic mechanism, syringe pump or other fluid pump). Reservoirs 525 and/or 225 and can comprise refillable reservoirs (e.g. when reservoir 225 of an implantable device 200 comprises a valved opening such as a silicone septum or a mechanical valve, either accessible via a needle for refilling). The fluidly attached functional elements 599 and/or functional elements

299 can comprise a fluid delivery element selected from the group consisting of: a catheter; a porous membrane; an iontophoretic element; a needle; or combinations of one or more of these. Delivered and/or stored (e.g. in a reservoir) agents can comprise an agent selected from the group consisting of: an analgesic agent such as morphine, fentanyl, lidocaine or other agent delivered to treat pain; a chemotherapeutic agent such as a chemotherapeutic agent delivered systemically (e.g. throughout the blood system of the patient) and/or to a location in or proximate an organ such as the liver or brain to treat cancer; an antibiotic configured to treat or prevent an infection; a hormone such as a hormone delivered intravenously in hormonal therapy; heart medications such as nitroglycerin, a beta blocker or a blood pressure lowering medication; a carbohydrate such as glucose or dextrose delivered to treat a low blood sugar condition; insulin such as to treat a high blood sugar condition; a diabetic medication; a neurological medication; an epilepsy medication; and combinations of one or more of these. In some embodiments, apparatus 10 comprises the one or more agents stored in reservoir 225 and/or 525. In some embodiments, apparatus 10 is constructed and arranged to deliver the agent (e.g. via a catheter-based functional element 599, functional element 299, and/or stimulation element 260) to a patient location selected from the group consisting of: a vessel; a blood vessel; a vein; an artery; heart; brain; liver; spine; epidural space; intrathecal space; subcutaneous tissue; bone; intraperitoneal space, intraventricular space, and combinations of one or more of these.

In some embodiments, an external device 500 is attached to the patient via a patient attachment device 70 comprising a wrist band, wrist watch, leg band, ankle band or other band configured to position an external device 500 about a limb of the patient (i.e. arm or leg of the patient). In these embodiments, one or more implantable devices 200 are implanted under the skin proximate the intended (limb) location of external device 500 and patient attachment device 70. Apparatus 10 can be configured such that external device 500 comprises one or more antennas 540; one or more implantable devices 200 each comprise one or more antennas 240; and each implantable device 200 one or more antennas 240 receive power and/or data from the one or more antennas 540 of the limb-attached external device 500. The limb-attached external device 500 can comprise one or more reservoirs 525 described hereabove and/or one or more functional elements 599 configured as agent delivery elements and/or sensors. The one or more implantable devices 200 can comprise one or more reservoirs 225 described hereabove and/or one or more stimulation elements 260 configured as agent delivery elements and/or sensors.

In some embodiments, apparatus 10 comprises an agent delivery apparatus and agent is delivered into the patient (e.g. into a blood vessel, muscle or subcutaneous tissue) by an external device 500 functional element 599 (e.g. a needle) based on signals recorded by an implantable device 200 functional element 299 and/or stimulation element 260 (e.g. a sensor). Alternatively or additionally, agent can be delivered into the patient (e.g. into a blood vessel, muscle or subcutaneous tissue) by an implantable device 200 stimulation element 260 (e.g. a needle, catheter, porous membrane or iontophoretic delivery element). The amount of agent delivered by stimulation element 260 can be based on signals recorded by an implantable device 200 stimulation element 260 (e.g. a sensor) and/or an external device 500 functional element 599_a_ (e.g. a sensor). External device 500 can provide power to one or more implantable devices 200 and/or it can send data (e.g. sensor data from a functional element 599) to implantable device 200, such as to control agent delivery by implantable device 200.

Apparatus 10 can be configured to prevent an electromagnetic field (e.g. an electromagnetic field produced by one or more devices not included in apparatus 10 and/or other present in the patient environment) from adversely affecting and/or otherwise affecting the patient treatment and/or patient information recording (e.g. patient tissue stimulation and/or patient physiologic information gathering) performed by apparatus 10. Electromagnetic fields from one or more apparatus 10 devices and/or otherwise present in the patient environment can potentially interfere with apparatus 10. The architecture of the wireless signal transmissions of apparatus 10 can be configured to include certain unique and/or identifiable patterns in the signals transmitted by apparatus 10 to confirm (upon receipt) that the signal originated from a component of apparatus 10. Alternatively or additionally, the stimulation signal produced by an implantable device 200 can be created independent from a power signal received from an external device 500, so that any electromagnetic interference in the wireless link does not affect generation and delivery of the stimulation signal. In some embodiments, each implantable device 200 and/or external device 500 includes unique identification codes that are required to be transmitted prior to any changes in stimulation or other implantable device 200 configuration, ensuring correct operation in the presence of interference. Alternatively or additionally, the communication link can incorporate handshaking protocols, confirmation protocols, data encryption and/or scrambling, coding and other security measures to ensure that interfering signals do not adversely affect the implantable system 20 performance (e.g. stimulation). In some embodiments, external system 50 and/or implantable system 20 incorporate electromagnetic absorptive and/or reflective materials to minimize external interference from other sources and/or minimize the probability of apparatus 10 interfering with other systems. Alternatively or additionally, apparatus 10 can incorporate error detection and protocols for entering an alarm state (e.g. and shutting down normal operation) and/or otherwise ensuring safe operation.

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200, via one or more of its stimulation elements 260 (e.g. electrodes) can be configured to provide localized (e.g. targeted) magnetic and/or electrical stimulation. Combined electrical field stimulation and magnetic field stimulation can be applied by using superposition, and this combination can reduce the overall energy requirement. In some embodiments, implantable apparatus 10 comprises one or more stimulation elements 260 comprising a magnetic field generating transducer (e.g. microcoils or cuff electrodes positioned to partially surround or otherwise be proximate to one or more target nerves). Stimulation elements 260 comprising microcoils can be aligned with nerves to minimize affecting non-targeted tissue (e.g. to avoid one or more undesired effects to non-target tissue surrounding or otherwise proximate the target tissue). In some embodiments, the target tissue comprises dorsal root ganglia (DRG) tissue, and the non-target tissue comprises ventral root tissue (e.g. when the stimulation energy is below a threshold that would result in ventral root tissue stimulation).

In some embodiments, external system 50 of apparatus 10 is configured to provide mechanically adjustable alignment of one or more external antennas 540 alignment. Link gain between one or more external antennas 540 and one or more implantable antennas 240 can degrade over time due to physical misalignment of the antennas, relative orientation changes between antennas and/or relative angular misalignment between antennas. In order to compensate for misaligned antennas, electrical beam steering can be included in apparatus 10. Antennas comprising a multi-feed antenna structure and/or those comprising an array of antennas can be incorporated (e.g. into external antenna 540, implantable antenna 240 or both) for electrical beam steering. Alternatively or additionally, mechanical antenna steering can be implemented to physically realign one or more external antennas 540 with one or more implanted antennas 240 (or vice versa). A substrate of an implantable antenna 240 and/or an external antenna 540 can be flexible and/or rigid (e.g. a substrate comprising polyamide, polyimide, liquid crystal polymer (LCP), Rogers, FR4, or a similar material). One or more antennas 540 can be connected to electronics (e.g. a transmitter, receiver or transceiver) using a flexible waveguide or cable (e.g. 50 ohm 0.047" coaxial cable designed to provide patient comfort) and/or a flexible PCB substrate transmission line. Mechanical or physical realignment of antennas 240 and/or 540 can be accomplished using one or more of: use of motorized positioners, such as a mechanism including one or more small pulleys and/or tensioners used to translate one or more antennas 240 and/or 540 about one or more axes; an actuator (e.g. a piezoelectric actuator) with directional gears configured to translate one or more antennas 240 and/or 540 about one or more axes; a micro-pump with fluid reservoir (e.g. liquid or gas reservoir) configured to hydraulically and/or pneumatically translate one or more antennas 240 and/or 540 about one or more axes, such as by creating a local pressure difference. In some embodiments, a micro-pump with fluid reservoir is used to move one or more antennas 240 and/or 540, such as to move an external antenna 540 away from tissue to reduce specific absorption rate (SAR). In these embodiments, external antenna 540 can be positioned in mechanical contact with an expandable reservoir (e.g. a balloon) that is positioned between external antenna 540 and tissue. The reservoir can be inflated or deflated to control the separation distance of the external antenna 540 from the patient's skin surface. In some embodiments, apparatus 10 comprises one or more algorithm positioning algorithms, algorithm 15, that is configured to provide beam steering functionality and/or mechanical antenna steering as described in applicant's co-pending U.S. patent application Ser. No. 14/975,358, titled "Method and Apparatus for Minimally Invasive Implantable Modulators", filed Dec. 18, 2015, and U.S. patent application Ser. No. 15/664,231, titled "Medical Apparatus Including an Implantable System and an External System", filed Jul. 31, 2017, the content of each of which is incorporated herein in its entirety for all purposes.

In some embodiments, implantable system 20 of apparatus 10 is configured to provide paresthesia-reduced (e.g. paresthesia-free) high frequency pain management and rehabilitation therapy (e.g. via delivery of a stimulation signal above 600 Hz or 1 kHz, or other stimulation signal resulting in minimal paresthesia). Apparatus 10 can be configured to provide both low frequency (e.g. <1 kHz) stimulation and high frequency stimulation, such as when providing low frequency stimulation to elicit feedback from a patient during intraoperative or other (e.g. post-implantation) stimulation configuration. For example, trialing interface 80 and/or 90 can be used during an intra-operative titration of stimulation configuration using low frequency stimulation (e.g. to position and/or confirm position of one or more stimulation elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intraoperative and/or post-implantation titration or other stimulation configuration procedures. Intentional elicitation of paresthesia (e.g. via low frequency stimulation and/or high frequency stimulation) is beneficial during stimulation element 260 (e.g. electrode) implantation because a patient can provide feedback to the implanting clinician to ensure that the stimulation elements 260 are positioned close to the target neuromodulation or energy delivery site. This implantation position-optimizing procedure can advantageously reduce the required stimulation energy due to stimulation elements 260 being closer to target tissue, since a minimum threshold for efficacious stimulation amplitude is proportional to the proximity of stimulation elements 260 to target tissue (e.g. target nerves). The patient can inform the clinician of the sensation of paresthesia coverage, and the clinician can adjust stimulation element 260 position to optimize stimulation element 260 location for efficacious treatment while minimizing unintentional stimulation of non-target tissue (e.g. motor nerves or other nerves which are not causing the patient's pain). These paresthesia-inducing techniques (e.g. using low frequency stimulation and/or high frequency stimulation) can be used during or after implantation of one or more implantable devices 200.

In some embodiments, apparatus 10 is configured to deliver low frequency stimulation energy (e.g. electrical energy comprising a low frequency signal) to stimulate motor nerves, such as to improve tone and structural support (e.g. physical therapy). In these embodiments, apparatus 10 can be further configured to provide high frequency stimulation, such as to treat pain (e.g. suppress and/or control pain). The combined effect can be used not only for pain management but also muscle strengthening and gradual healing of supportive structures. Alternatively or additionally, as described herein, apparatus 10 can be configured to deliver low frequency stimulation energy (e.g. electrical energy) to induce paresthesia, which can also be accompanied by the delivery of high frequency stimulation (e.g. to suppress and/or control pain). In some embodiments, apparatus 10 is configured to deliver low frequency stimulation (e.g. electrical energy comprising a low frequency signal) and burst stimulation, delivered simultaneously or sequentially. The low frequency stimulation and the burst stimulation can be delivered on similar and/or dissimilar stimulation elements 260 (e.g. similar or dissimilar electrode-based stimulation elements 260).

As described herein, apparatus 10 can be configured for treating numerous disease and disorders, such as when apparatus 10 is configured to deliver electrical or other stimulation energy to treat pain (e.g. by delivering electrical or other energy to the spine or other neural location). Apparatus 10 can be configured to stimulate tissue with various stimulation waveforms, such as those described in applicant's co-pending U.S. patent application Ser. No. 16/104,829, titled "Apparatus with Enhanced Stimulation Waveforms", filed Aug. 17, 2018.

Apparatus 10 can be configured to treat neuropathy, neuralgia and/or other nerve pain that is related to: surgery; trauma; infection (e.g. a herpetic infection); and/or diabetes (e.g. diabetic neuropathy). One or more stimulation elements 260 can be configured to deliver stimulation energy (e.g. electrical energy, magnetic energy, light energy, thermal energy, sound energy, and/or chemical energy (e.g. energy from a drug or reagent) to nerve tissue such as tissue of the central nervous system and/or peripheral nervous system. One or more leads 265 (each comprising one or more stimulation elements 260) can be implanted in and/or proximate the spinal cord, the groin and/or a joint such as the hip. For example, apparatus 10 can be configured to treat one or more of: post-surgical neuralgia (e.g. following hernia repair such as a hernia repair including an implanted mesh); headache (e.g. due to occipital neuralgia); post-herpetic neuralgia; chronic pelvic and/or hip pain; knee pain; and combinations of one or more of these.

To treat pain related to hernia or hernia repair, one or more stimulation elements 260 (e.g. on a lead 265 and/or on a housing 210) can be positioned to stimulate tissue of the peripheral nervous system and/or the central nervous system. In some embodiments, one or more stimulation elements 260 are positioned to stimulate the cutaneous branch of the ilioinguinal, inguinal and/or genital branch of the genitofemoral nerves. In some embodiments, one or more stimulation elements 260 are positioned to stimulate corresponding branches of spinal nerves correlating to one or more dermatomes related to pain associated with at least one of hernia or hernia repair.

Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these. In some embodiments, apparatus 10 is configured to treat hernia pain by delivering a low frequency stimulation signal (e.g. an electrical signal less than or equal to 1 kHz delivered by one or more electrode-based stimulation elements 260). Alternatively or additionally, apparatus 10 can treat hernia pain with a high frequency stimulation signal, such as a signal comprising a frequency greater than 1 kHz. Stimulation can be accomplished either via subcutaneous field stimulation and/or by stimulation elements 260 positioned adjacent or at least near the nerves and/or their branches. In some embodiments, stimulation is accomplished transvascularly (e.g. stimulation including low and/or high frequencies).

The apparatus of the present inventive concepts can be configured to stimulate the ilioinguinal nerve, genitofemoral nerve and/or iliohypogastric nerves, such as to ameliorate pain following hernia repair. One or more leads 265 (e.g. one or more leads 265 comprising one or more electrode-based or otherwise stimulation-based stimulation elements 260) can be inserted over the inguinal region (which may include the inguinal ring) to stimulate any or all three of these nerves (e.g. in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more stimulation elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g. the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g. transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g. percutaneous or paddle) including stimulation-based stimulation elements 260 can be placed over the dorsal columns, over the dorsal roots and/or in the dorsal root entry zone, in a unilateral, bilateral and/or midline fashion.

To treat occipital neuralgia, also known as C2 neuralgia, one or more stimulation elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more stimulation elements 260, are implanted transversely, either unilaterally or bilaterally, at the level of the appropriate target cervical nerve (C1, C2, etc.). The C1, 2, 3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more stimulation elements 260 are positioned to stimulate the trigeminal and/or occipital nerves. One or more leads 265 can be anchored to the fascia proximate the tissue to be stimulated.

To treat post-herpetic neuralgia (e.g. neuralgia associated with shingles), one or more stimulation elements 260 can be positioned to stimulate corresponding branches of the spinal nerves and/or peripheral nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; accidental bowel leakage; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g. using bilateral and/or unilateral stimulation) one or more of the targets listed below.

In some embodiments, the stimulated targets include the sacral nerves (roots) S2, S3 and/or S4. One or more leads 265 (e.g. each including one or more stimulation-delivering stimulation elements 260) can be positioned to stimulate any or all of the three roots, on a single side or both sides, in any bilateral or unilateral combination. The roots can be accessed, with the patient lying in the prone position, by positioning one or more leads 265 (e.g. percutaneously), with or without the use of fluoroscopy, ultrasound or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal, and spanning one or more foramina.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound or other imaging modality), up to the cauda equina, where the S2, S3 and/or S4 roots can be stimulated where they enter the spinal cord, and/or the conus medullaris can be stimulated directly (e.g. in the same location).

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals and urethra. Pelvic and voiding disorders can be treated by stimulating pudendal nerve fibers. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g. fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g. through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g. fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g. voiding dysfunction). In order to provide stimulation of the tibial nerve, lead 265 can be inserted at a location close to the knee and/or at a location near the ankle. For example, the tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g. a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e. stimulation energy delivered from inside a blood vessel to nerve tissue proximate the blood vessel), such as via the femoral vein and/or artery, each of which provide intraluminal access to many other blood vessels (e.g. using standard interventional techniques). The tibial nerve can be transvascularly stimulated by the popliteal vein and/or artery (e.g. by placing one or more stimulation elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat pelvic dysfunction, overactive bladder, and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more stimulation elements 260 are positioned to stimulate tissue of the central nervous system or tissue and/or tissue of the peripheral nervous system to treat overactive bladder, such as to stimulate one or more nerves that control and/or are otherwise related to bladder function (e.g. to increase bladder capacity, improve bladder emptying, reduce urge incontinence and/or reduce stress incontinence). For example, one or more stimulation elements 260 are be positioned to stimulate tibial nerve tissue and/or sacral nerve tissue (e.g. at least the S3 nerve root) to treat overactive bladder. In some embodiments, one or more stimulation elements 260 can be positioned to stimulate sacral nerve tissue to treat urinary urgency, urinary frequency (e.g. urinary urgency frequency), and/or painful bladder syndrome. In some embodiments, lead 265 is constructed and arranged to be positioned along one or more locations of the tibial nerve, such as a positioning performed using percutaneous technique (e.g. when lead 265 comprises a cylindrical SCS-type lead) and/or surgical (cut-down) techniques (e.g. when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g. transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more stimulation elements 260 are positioned proximate (e.g. in contact) with the sacral nerve root(s). The housing 210 can be placed anywhere in the groin, perineum, scrotum, pelvis, hip, thigh, leg, behind the knee, buttocks, abdomen and/or low back. Lead 265 (e.g. a lead 265 comprising a lead extension) can be extended underneath the skin (e.g. tunneled) to a second incision (e.g. across the flank to the lower abdomen, across the midline to the buttocks, or low back), and a third incision can be made (e.g. in the abdomen, back or buttocks) where housing 210 can be inserted and connected to lead 265. Alternatively, housing 210 can be inserted at another internal location. If lead 265 is already connected (e.g. attached in manufacturing) to housing 210, lead 265 can be advanced in the opposite direction, such as from the third incision, to the second incision, to the first incision (if three incisions are made), or housing 210 can be advanced under the tissue from incision 1 to incision 2 or from incision 2 to incision 3. In some embodiments, only 1 or 2 incisions are performed. In some embodiments, such as when lead 265 is already connected (e.g. attached in manufacturing) to housing 210, lead 265 and housing 210 are implanted. In some embodiments, a first lead 265 and a first housing 210 (pre-attached or attachable) are utilized in a dose titration or other "trialing procedure", and a second lead 265 and housing 210 (pre-attached or attachable) are implanted in the patient for subsequent treatment of the patient.

In some embodiments, one or more stimulation elements 260 are positioned to perform posterior tibial nerve stimulation (PTNS), such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more stimulation elements 260 are positioned to perform retrograde stimulation of the sacral nerve plexus and restore the balance between bladder inhibitory and excitatory control systems of the bladder. One or more stimulation elements 260 can be positioned above the ankle, proximate and/or into the tibial nerve. Implantable device 200 can deliver stimulation energy to the stimulation elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, implantable system 20 is configured to deliver a series of repeated stimulation periods, such as a regimen of approximately: weekly thirty-minute sessions of stimulation for twelve weeks. In some embodiments, implantable system 20 is configured to provide weekly, daily and/or hourly sessions that deliver stimulation for between 10 minutes and 60 minutes. Implantable system 20 can deliver stimulation for any number of minutes per day. In some embodiments, apparatus 10 is configured to achieve an approximate 50% reduction in urinary urge incontinence and/or urinary urgency/frequency episodes.

In some embodiments, apparatus 10 is configured to provide temporary stimulation of tissue to treat overactive bladder, such as by using trialing interface 80 and/or 90 described hereabove, such as to provide power and/or data to one or more implantable devices 200 to confirm acceptable improvement of the patient's overactive bladder (e.g. successful stimulation of one or more sacral nerves, tibial nerves or other tissue), before closing an incision or otherwise fully implanting one or more implantable devices 200. In some embodiments, a temporary stimulation (for overactive bladder or in a trialing procedure for any therapy) is provided for up to one week, up to one month, more than 1 month, more than 2 months, or more than 3 months. In some embodiments, one or more implantable devices 200 are left in place if the temporary stimulation period is successful or unsuccessful (e.g. left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more stimulation elements 260 are positioned to stimulate periurethral muscles. In some embodiments, one or more stimulation elements 260 are positioned to stimulate tissue of the vagina or anus. In some embodiments, one or more stimulation elements 260 are positioned to stimulate sphincter muscles for controlling the bladder, such as two stimulation elements 260 positioned on either side of the urethral orifice. In these embodiments, housing 210 can be implanted in suprapubic region or in the perineum. In some embodiments, lead 265 comprises (e.g. on a distal portion) a pessary ring comprising two stimulation elements 260. In some embodiments, stimulation elements 260 comprise periurethral electrodes configured to stimulate pudendal afferents.

As described above, apparatus 10 can be configured for treating numerous diseases, disorders or other undesirable patient conditions, such as fecal incontinence. Injury of nerves that sense stool in the rectum can lead to fecal incontinence. In some embodiments, one or more stimulation elements 260 (e.g. one or more electrical, magnetic, light or other energy delivery elements) of one or more leads 265 and/or one or more implantable devices 200 are configured to stimulate tissue to treat fecal incontinence, such as to treat tissue selected from the group consisting of: sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more stimulation elements 260 are configured to deliver energy to sacral nerve or other tissue.

In some embodiments, apparatus 10 is configured to treat fecal incontinence, overactive bladder (i.e. overactive bladder and/or urinary incontinence), and/or pelvic disorders, and implantable device 200: comprises between 1 and 16 stimulation elements 260, such as four or more electrodes; delivers electrical stimulation energy at a range of approximately between 10 Hz and 15 Hz (or a range of between 5 Hz and 25 Hz); delivers electrical stimulation energy with a pulse width of approximately between 180 μsec and 240 μsec (or between 1 μsec and 200 μsec); provides electrical stimulation energy with an amplitude of approximately 0.1V to 8.5V (e.g. providing a current between 0.1 mA to 10 mA, which can be adjusted in increments between 0.01 mA and 0.1 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; or an on time of several hours followed by an off time of several hours (such as 8 hours of stimulation ON and 16 hours of stimulation OFF or 16 hours on and 8 hours off, and 12 hour on and 12 hours off; delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more stimulation elements 260 (e.g. small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratroclear; sphenopalantine (SPG); and combinations of one or more of these.

In some embodiments, apparatus 10 is configured to treat neuralgia, such as a neuralgia resulting from surgery (e.g. groin, shoulder, lung and/or amputation), trauma and/or phantom pain, and one or more stimulation elements 260 are positioned to stimulate nerve tissue.

In some embodiments, apparatus 10 is configured to treat neuralgia, such as a neuralgia resulting from groin surgery (e.g. hernia or other groin surgery), and one or more stimulation elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more stimulation elements 260 are positioned to stimulate axial nerve tissue (e.g. one or more stimulation elements 260 positioned on a lead 265 implanted in a suprascapular location).

In some embodiments, apparatus 10 is configured to treat neuralgia, such as a neuralgia resulting from lung surgery, and one or more stimulation elements 260 are positioned to stimulate intercostal nerve tissue.

In some embodiments, apparatus 10 is configured to treat neuralgia, such as a neuralgia associated with carpal tunnel syndrome, and one or more stimulation elements 260 are positioned to stimulate median nerve tissue.

In some embodiments, apparatus 10 is configured to treat neuralgia, such as a neuralgia associated with temporomandibular joint disorder (TMJ), and one or more stimulation elements 260 are positioned to stimulate V2 of trigeminal nerve tissue.

In some embodiments, apparatus 10 is configured to treat neuralgia, such as a facial neuralgia, and one or more stimulation elements 260 are positioned to stimulate trigeminal nerve tissue.

In some embodiments, apparatus 10 is configured to treat neuralgia, such as a leg (sciatic) neuralgia, and one or more stimulation elements 260 are positioned to stimulate nerve tissue proximal a contributing lesion.

In some embodiments, apparatus 10 is configured to treat pelvic pain, such as interstitial cystitis and/or bladder pain, and one or more stimulation elements 260 are positioned to stimulate peripheral nervous system tissue (e.g. pudendal tissue and/or S-2, S-3 and/or S-4 roots) and/or central nervous system tissue (e.g. lower spinal cord and/or S3 neural foramen).

In some embodiments, apparatus 10 is configured to treat pelvic pain, such as anal pain, and one or more stimulation elements 260 are positioned to stimulate peripheral nerve tissue such as pudendal tissue and/or S-2, S-3 and/or S-4 roots.

In some embodiments, apparatus 10 is configured to treat subcutaneous pain, and one or more stimulation elements 260 (e.g. paddle electrodes) are positioned to stimulate nerve tissue.

In some embodiments, apparatus 10 is configured to treat diabetic neuropathy, such as painful diabetic neuropathy, and one or more stimulation elements 260 are positioned proximate the lower spinal cord (e.g. to stimulate S3 nerves) or other body location to stimulate nerve tissue.

In some embodiments, apparatus 10 is configured to treat visceral pain, angina and/or other pain, and one or more stimulation elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g. such that one or more stimulation elements 260 are positioned proximate the nerve to be stimulated). In some embodiments, lead 265 is positioned to stimulate the dorsal root ganglia to treat diabetic neuropathy (e.g. diabetic neuropathy of the hand and/or foot). Lead 265 can be implanted percutaneously and/or surgically as described herein. Lead 265 and/or one or more stimulation elements 260 can comprise a paddle electrode, such as one or more paddle electrodes implanted in the foot, leg and/or arm. Lead 265 and/or one or more stimulation elements 260 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g. to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of trunk, neck, head, back, foot, leg, arm and/or hand disorders.

One or more leads 265 (e.g. each including one or more stimulation elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibular (peroneal) innervates top of both medial and lateral foot. In some embodiments, stimulation element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius and soleus muscles where it can be accessed surgically or percutaneously. It then surfaces just as it warps around the anterior aspect of the medial malleolus where it supplies the medial posterior foot in front of heel. The medial sural cutaneous nerve comes off the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more stimulation elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more stimulation elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 is configured to transvascularly stimulate at least one of a median nerve, an ulnar nerve or a radial nerve, and stimulation element 260 comprises one or more electrodes positioned in a vessel selected from the group consisting of: brachial vein; brachial artery; basilic vein; basilic artery; deep vein of the arm; deep artery of the arm; and combinations of one or more of these. In some embodiments, apparatus 10 is configured to transvascularly stimulate at least one of a median nerve or an ulnar nerve, and stimulation element 260 can comprise one or more electrodes positioned in a vessel selected from the group consisting of: brachial vein; brachial artery; and combinations of one or more of these. In some embodiments, apparatus 10 is configured to transvascularly stimulate the radial nerve, and stimulation element 260 comprises one or more electrodes positioned in a vessel selected from the group consisting of: deep vein of arm; deep artery of arm; basilic vein; radial collateral vein; radial collateral artery; medial collateral vein; medial collateral artery; radial vein; radial artery; and combinations of one or more of these. In some embodiments, apparatus 10 can be configured to transvascularly stimulate the medial cutaneous nerve, and stimulation element 260 comprises one or more electrodes positioned in the basilic vein. In some embodiments, apparatus 10 is configured to transvascularly stimulate the ulnar nerve, and stimulation element 260 comprises one or more electrodes positioned in a vessel selected from the group consisting of: ulnar collateral vein; ulnar collateral artery; ulnar vein; ulnar artery; and combinations of one or more of these. In some embodiments, apparatus 10 is configured to transvascularly stimulate the median nerve, and stimulation element 260 can comprise one or more electrodes positioned in a vessel selected from the group consisting of: brachial vein; brachial artery; ulnar vein; ulnar artery; and combinations of one or more of these.

As described herein, one or more leads 265 can be positioned to stimulate the spinal cord, such as via percutaneous insertion of a lead 265 in the epidural space or surgical implantation of the lead 265 (e.g. a paddle lead) in the epidural space. A lead 265 can be placed such that one or more stimulation elements 260 (e.g. one or more electrodes) are positioned from T5-S5, such as to capture the area of pain or reduced circulation of the leg or foot. One or more stimulation elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more stimulation elements 260 (e.g. one or more electrodes attached to one or more leads 265) can be positioned to transvascularly stimulate one or more nerves, such as one or more nerves in the foot, leg and/or arm, such as when the one or more stimulation elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more stimulation elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more stimulation elements 260 (e.g. one or more electrodes attached to one or more leads 265) can be positioned to stimulate dorsal root ganglia that supply the following nerves (e.g. to treat the leg and/or foot): common peroneal (L4-S2); tibial (L4-S3); femoral (L2-L4); and combinations of one or more of these. One or more stimulation elements 260 (e.g. one or more electrodes attached to one or more leads 265) can be positioned to stimulate dorsal root ganglia that supply the following nerves (e.g. to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e., stump pain), such as by using a high frequency alternating current (HFAC) block approaches. In these embodiments, one or more leads 265 can be implanted such that one or more stimulation elements 260 stimulate one or more nerves in the leg, arm and/or sacrum. One or more leads 265 can be surgically implanted, such as when lead 265 comprises a paddle electrode positioned near a nerve in the foot, leg or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg or arm, such as when one or more stimulation elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g. which arise from C2 and C3); the greater and/or lesser auricular nerves (e.g. which also arise from C2/C3); the third (least) occipital nerve (e.g. which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g. a cylindrical SCS-type lead) can be inserted percutaneously either subcutaneously or under the muscle. Alternatively, surgery (e.g. direct cut-down) can be performed to insert lead 265 (e.g. a cylindrical lead, a paddle lead, a cuff or hemi-cuff electrode) proximate, one and/or around these nerves. Alternatively or additionally, the nerves can be accessed transvascularly as described herein (e.g. when one or more stimulation elements 260 are implanted in a blood vessel). Housing 210 can be implanted anywhere in the head under the skin, including: behind the ear, back of the head, the neck, in the face, and the like, where one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210 can be placed anywhere in the head under the skin, as described herein.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approaches. In these embodiments, one or more leads 265 can be implanted such that one or more stimulation elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg, torso and/or arm, such as when one or more stimulation elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these. In these embodiments, apparatus 10 can be configured to deliver stimulation to median nerve tissue; ulnar nerve tissue and/or radial nerve tissue.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations of one or more of these.

In some embodiments, apparatus 10 is configured to treat knee pain. Knee pain from joint degeneration or join replacement surgery can be treated via stimulation of the nerves innervating the knee and/or via stimulation of the tissue surrounding the knee (sometimes referred to as peripheral field stimulation). Apparatus 10 can comprise between one and eight leads 265 whose stimulation elements 260 are placed near and around the knee. In some embodiments, four leads 265 are placed, in locations medial, lateral, superior and inferior to the knee. The leads 265 can be placed subcutaneously for field stimulation, or they can be placed directly adjacent to specific nerve targets. Applicable nerve targets are as follows: medial knee can include medial femoral cutaneous and infrapatellar cutaneous branches of saphenous nerve; lateral knee can include constant articular branches of common peroneal, lateral retinacular nerve; anterior knee can include lateral, medial, and anterior cutaneous femoral nerve, infrapatellar branch of saphenous nerve, medial and lateral retinacular nerve and articular branches of peroneal nerve; posterior knee can include obturator, posterior tibial and sciatic nerves. In addition, the following nerves can be stimulated via stimulation elements 260 to treat knee pain: nerves arising from the tibial nerve such as the superior, middle and inferior genicular nerves; nerves arising from the common peroneal such as the superior lateral, inferior lateral, and recurrent genicular nerves; and nerves arising from the obturator nerve such as the genicular branch of obturator; and nerves arising from the femoral nerve such as the saphenous nerve. Each of these targets can be stimulated transvascularly by one or more stimulation elements 260.

In some embodiments, implantable device 200 has an internal battery or other power supply such that stimulation (e.g. stimulation energy and/or a stimulation agent) is delivered to one or more locations within a patient for an extended time period (e.g. at least 1 hour, at least 1 day, at least 1 month or at least 1 year), without receiving a power transmission (e.g. as described herein from an external device such as external device 500) during that time period. In some embodiments, at least a portion of a single pulse of energy (e.g. at least a single phase) is delivered by implantable device 200 using energy provided by an internal power supply 570 such as a battery or a capacitor. In these embodiments, data can be transmitted by one or more of an external device 500 and/or programmer 600, such as to activate or modify stimulation being delivered, with or without also transmitting power.

In some embodiments, implantable device 200 comprises one or more components configured to receive transmitted power (e.g. via an external device 500), receive transmitted data (e.g. via an external device 500 and/or programmer 600) and/or deliver stimulation (e.g. deliver stimulation energy and/or a stimulation agent).

In some embodiments, one or more implantable devices 200 are configured to deliver stimulation energy (e.g. via one or more stimulation elements 260 comprising an electrode) with a stimulation waveform comprising one or more high frequency signals (e.g. a signal comprising one or more high frequency components). For example, one or more implantable devices 200 can deliver one or more stimulation waveforms comprising one or more signals above 600 Hz, such as one or more signals above 1.0 kHz, 1.2 kHz, 5 kHz, 10 kHz or 25 kHz.

In these embodiments, the delivered stimulation waveform can be configured to be void of (i.e. not include) one or more lower frequency signals, such as by not including any signals at a frequency below 100 Hz, below 500 Hz, below 1000 Hz, below 1200 Hz or below 1500 Hz.

One or more implantable devices 200 can be configured to deliver stimulation energy with a stimulation waveform that varies over time. In some embodiments, one or more stimulation parameters of the stimulation waveform are randomly varied over time, such as by using a probability distribution as described in applicant's co-pending U.S. patent application Ser. No. 16/104,829, titled "Apparatus with Enhanced Stimulation Waveforms", filed Aug. 17, 2018. Each stimulation waveform can comprise one or more pulses, such as a group of pulses that are repeated at regular and/or irregular intervals. In some embodiments, a pulse can comprise delivery of electrical energy, such as electrical energy delivered in one or more phases (e.g. a pulse comprising at least a cathodic or anodic portion followed by passive capacitive recovery with an optional open circuit time between the first portion and recovery). In some embodiments, a group of pulses is delivered, each pulse comprising an anodic or cathodic portion that can include charge recovery after each pulse, such as charge recovery comprising active (opposite polarity pulse) recovery, and/or passive (capacitive) recovery. In some embodiments, there is no recovery between pulses, but instead active or passive recovery is included at the end of the set of the first (anodic or cathodic) portions. In some embodiments, single or groups of pulses are provided at time-varying modes of repetition (e.g. regular intervals for a period, then a period of irregular intervals) or at regular intervals with occasional (random) spurious pulses inserted (creating a single irregular event in an otherwise regular series). Non-limiting examples of waveform variations include: a variation in frequency (e.g. frequency of one or more signals of the waveform); variation of a signal amplitude; variation of interval time period (e.g. at time period between pulses or a time period between pulse trains); variation of a pulse width; multiple piecewise or continuous variations of one of more stimulation parameters in a single pulse (e.g. multi-step, multi-amplitude in one "super-pulse"); variation of pulse symmetry (e.g. via active drive, passive recovery and/or active-assisted passive recovery); variation of stimulation energy over a time window and/or overlapping time windows; variation of the power in the frequency spectrum of the stimulation waveform; and combinations of one or more of these. In some embodiments, apparatus 10 and/or implantable device 200 can be configured to vary a stimulation waveform "systematically" such as a variation performed temporally (e.g. on predetermined similar or dissimilar time intervals) and/or a variation performed based on a parameter, such as a measured parameter that can be based on a signal produced by a sensor of implantable device 200 or another component of apparatus 10. Alternatively or additionally, apparatus 10 and/or implantable device 200 can be configured to vary a stimulation waveform randomly. Random variation shall include discrete or continuous variations that can be selected from a distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. Random pulses or groups of pulses can be generated based on randomly varying one or more stimulation signal parameters. One or more stimulation parameters can be varied randomly through the use of one or more probability distributions, as described herebelow.

In some embodiments, the amplitude of a signal delivered by one or more implantable devices 200 is adjusted to prevent discomfort to the patient (e.g. paresthesia or other undesired condition) from the stimulation signal. In some embodiments, the amplitude of the stimulation signal can be ramped (e.g. up and/or down), a single time or multiple times (e.g. continuously or intermittently). In some embodiments, a titration procedure is performed to "set" one or more stimulation parameters based on avoiding patient discomfort.

In some embodiments, one or more implantable devices 200 are configured to deliver stimulation energy (e.g. via one or more stimulation elements 260 comprising an electrode) with a stimulation waveform comprising one or more waveform patterns. The stimulation waveforms delivered can be configured to treat various conditions of a patient. Each stimulation waveform can comprise a series of continuous pulses, intermittent pulses, and/or spurious pulses (e.g. occasional events in an otherwise continuous stream). Each pulse can comprise a pulse train that is repeatedly delivered by implantable device 200, the train comprising one or more cathodic pulses and/or one or more anodic pulses. In some embodiments, implantable device 200 delivers a multiphasic pulse comprising at least two cathodic pulses and/or anodic pulses, with or without any time between each pulse. For example, implantable device 200 can deliver a biphasic pulse comprising a cathodic pulse followed by an anodic pulse, a triphasic pulse comprising a cathodic pulse followed by an anodic pulse followed by a second cathodic pulse, or any series of two or more cathodic and/or anodic pulses. In some embodiments, delivered pulses are exponential in nature (e.g. comprise an exponential portion), such as dynamic return pulses that exceed a minimum current (e.g. at least 1 mA, 10 mA or 50 mA) for a short duration (e.g. for approximately 1 µsec), and then decay to lower current levels (e.g. a level of approximately 100 nA), with a time constant on the order of 1 µsec to 100 µsec.

The stimulation waveforms delivered by implantable device 200 can comprise one or more high frequencies. The stimulation waveform frequency or other stimulation parameter can be set and/or adjusted (hereinafter "adjusted") to optimize therapeutic benefit to the patient and minimize undesired effects (e.g. paresthesia or other patient discomfort). In some embodiments, a stimulation waveform is adjusted based on a signal produced by a sensor of apparatus 10 (e.g. a sensor of implantable device 200, such as a stimulation element 260 configured as a sensor or other sensor of implantable device 200 as described hereabove). Adjustment of a stimulation waveform parameter can be performed automatically by the implantable device 200 and/or via an external device 500 and/or programmer 600).

In some embodiments, a pulse shape of a stimulation waveform can be varied, such as a pulse shape comprising: a sinusoidal geometry; a square geometry (e.g. a waveform comprising a square wave); a rectangular geometry; a triangular geometry; (e.g. symmetric or asymmetric); a trapezoidal geometry; a sawtooth geometry; a ramped geometry; an exponential geometry; a piece-wise step function geometry; a root-raised cosine geometry; and combinations of one or more of these.

In some embodiments, a charge recovery phase (e.g. anodal phase) of a stimulation waveform is varied by implantable device 200.

Inter-pulse gap, the time between one or more pulses (e.g. a biphasic or other multiphasic pulse that is repeated continuously), can be varied systematically and/or randomly by implantable device 200. In some embodiments, inter-pulse gap between one or more pulses comprises zero time (i.e. a first pulse is immediately followed by a similar or dissimilar second pulse). In some embodiments, inter-pulse gap is varied systematically, such as on a routine basis (i.e. temporally) and/or varied based on a signal produced by a sensor of apparatus 10. Alternatively or additionally, inter-pulse gap can be varied randomly, such as a random variation based on a distribution (e.g. a probability distribution with a pre-determined shape) as described herebelow.

In some embodiments, implantable device 200 delivers a stimulation waveform comprising a series of frequency modulated (FM) pulses, such that the frequency of stimulation varies. Implantable device 200 can be configured to deliver a frequency modulated stimulation waveform comprising a carrier signal, at a carrier frequency, that is modulated continuously between a first frequency and a second frequency. For example, implantable device 200 can deliver a stimulation waveform that modulates between 2.0 kHz and 3.0 kHz every second (e.g. comprising a carrier signal at 2.5 kHz that is modulated at 1 Hz) with a modulation range (the excursion from the carrier signal) of +/−500 Hz. In some embodiments, implantable device 200 can deliver a stimulation waveform that comprises: a carrier frequency between 1 kHz and 50 kHz, a modulation frequency between 0.1 Hz and 10 kHz and/or a modulation range between 1 Hz and the carrier frequency.

In some embodiments, implantable device 200 delivers a stimulation waveform comprising a series of amplitude modulated (AM) pulses, such that the amplitude of stimulation varies (e.g. varying the amplitude of the voltage and/or current of the stimulation signal). The amplitude of delivered current can be varied in a single amplitude modulated sweep, such as a sweep from 2 mA to 3 mA. In some embodiments, amplitude of a signal can be varied continuously, such as when current is varied between 2 mA and 3 mA every second (e.g. a signal comprising a modulation frequency of 1 Hz). In these embodiments, the depth of modulation would be 33%, where depth of modulation is equal to 1-[lower range/upper range]. In some embodiments, amplitude of delivered current fluctuates between 1 mA and 3 mA (i.e. a depth of modulation of 66%), while in other embodiments, current fluctuates between 0 mA and 10 mA (e.g. a depth of modulation of 100%). In some embodiments, implantable device 200 is configured to deliver an amplitude modulated signal comprising: a carrier frequency between 1 Khz and 50 kHz; a modulation frequency between 0.1 Hz and the carrier frequency and/or a depth of modulation between 0.1% and 100%.

In some embodiments, implantable device 200 delivers a stimulation waveform comprising delivery of continuously balanced analog current waveforms, for example from a differential Howland current source. In these embodiments, there are not independent pulses, but rather there is true analog frequency and amplitude modulation. Periods of delivering stimulation (or presence of balanced differential analog stimulation) and periods of no stimulation (e.g. a quiescent period) can be included. In some embodiments, controller 250 comprises one or more reconfigurable stimulation blocks including one or more Howland or other current sources. The one or more current sources (e.g. two or more current sources) can each be attached to a stimulation element 260 (e.g. in a monopolar configuration when the current source is also connected to housing 210 or in a bipolar configuration when the current source is connected to a pair of stimulation elements 260). Alternatively, controller 250 can comprise one or more current sources that are attached to a matrix of switches that selectively connect the one or more current sources to multiple stimulation elements 260 (e.g. connect a single current source to 2, 4, 8, 12 or 16 electrodes). In some embodiments, controller 250 is configured such that a stimulation waveform signal provided to the current source passes through a capacitor (e.g. capacitor C1 shown), the capacitor providing DC balance.

In some embodiments, implantable device 200 delivers a stimulation waveform comprising delivery of multiple trains of pulses that are delivered intermittently, a "burst stimulation" waveform as defined hereabove. For example, implantable device 200 can be configured to deliver a series or train of five pulses, each with a 1 msec pulse width. The each of the five pulses can be separated by an inter-pulse gap of 4 msec, creating a train-on period of 16 msec. These five pulses can be repeated every 25 msec (the "inter-train period"). In some embodiments, implantable device 200 can be configured to deliver a burst stimulation waveform comprising a pulse width between 5 μsec and 1 msec. Implantable device 200 can deliver a train or burst stimulation waveform comprising pulses with constant pulse widths and/or varying pulse widths, such as when the pulse widths (and/or other stimulation parameters) are varied randomly and/or systematically. Implantable device 200 can deliver a train or burst stimulation waveform with a varied or constant pulse shape selected from the group consisting of: sinusoid; square, rectangle; triangle (symmetric or asymmetric); trapezoid; sawtooth; ramp (e.g. a linear ramp); exponential curve; piece-wise step function; and combinations of one or more of these. Implantable device 200 can deliver a train or burst stimulation waveform with an inter-pulse gap less than inter-train period. The inter-pulse gap can be relatively constant, and/or it can be varied, such as when implantable device 200 randomly varies the inter-pulse gap or varies the inter-pulse gap systematically. In some embodiments, the inter-pulse gap between any two pulses within a pulse train (or burst) can be varied between 0.1 μsec and the inter-train period (or inter-burst period). Implantable device 200 can deliver a train stimulation waveform with an inter-pulse gap between 1 μsec and 1 second. Implantable device 200 can deliver a burst stimulation waveform with an inter-train period between 1 μsec and 1 second. Implantable device 200 can deliver a burst stimulation waveform with an inter-burst period between 20 μsec and 24 hours. The inter-burst period can be relatively constant, and/or it can be varied, such as when implantable device 200 randomly varies the inter-burst period or varies the inter-burst period systematically. In some embodiments, inter-burst period is varied by the user, such as via a user using programmer 600. In these embodiments, user activation can be regulated with one or more safeguards or other limits such as those incorporated into patient-controlled analgesia devices. The inter-train period can be varied between 1 μsec and 24 hours. Implantable device 200 can deliver a train or burst stimulation waveform with a train-on period (the time between the onset of a first pulse in a pulse train to the end of the last pulse in a pulse train) between 10 μsec and 24 hours. The train-on and/or burst-on period can be relatively constant, and/or it can be varied, such as when implantable device 200 randomly varies the train-on and/or burst-on period or varies the train-on and/or burst-on period systematically. Implantable device 200 can deliver a train or burst stimulation waveform with a train or burst envelope selected from the group consisting of: cosine; cosine-squared; sine; square; rectangle; triangle (symmetric or asymmetric); trapezoid: sawtooth; ramp (e.g. linear ramp); and combinations of one or more of these. Implantable device 200 can deliver a train and/or burst stimulation waveform with a train ramp duration or burst ramp duration between 1 μsec to 10 minutes. Implantable device 200 can deliver a train and/or burst stimulation waveform with a depth of modulation between train and/or bursts of between 1% and 99%. For example, between some or all of the trains and/or bursts (burst-off or train-off periods), a signal may be present and may contain the same or different elements contained in the train-on and/or burst-on period. These burst-off or train-off periods may comprise a quiescent period. The amplitude of the signal contained in these quiescent periods can be from 0% to 99% of the signal amplitude during the train-on and/or burst-on period, such as a signal with an amplitude less than 50% of the signal amplitude during the train-on and/or burst-on period or another amplitude below a neuronal excitation threshold.

In some embodiments, apparatus 10 is configured to deliver stimulation energy to dorsal root ganglion and/or spinal cord tissue to treat a condition such as pain. In these and other embodiments, apparatus 10 can be configured to provide a stimulation waveform comprising: a combination of low frequency stimulation (e.g. electrical energy comprising a low frequency signal) and burst stimulation; burst stimulation (e.g. burst stimulation alone); a combination of low frequency stimulation and high frequency stimulation; a combination of low frequency stimulation, high frequency stimulation and burst stimulation; and combinations of one or more of these. The stimulation energy provided by apparatus 10 can be delivered to tissue via one or more stimulation elements 260, such as two or more electrodes which deliver similar or dissimilar stimulation waveforms simultaneously and/or sequentially. Each of the stimulation waveforms can comprise one or more pulses comprising an entire phase or at least a portion of a phase at a superthreshold level. Alternatively or additionally, each of the stimulation waveforms can comprise one or more pulses comprising an entire phase or at least a portion of a phase at a subthreshold level.

In some embodiments, apparatus 10 is configured to vary one or more stimulation parameters. The stimulation parameters can be varied to optimize (e.g. balance the benefits of) therapeutic benefit, system efficiency, stimulation efficiency, avoidance and/or reduction of paresthesia, and/or reduction of charge.

Figure 2:
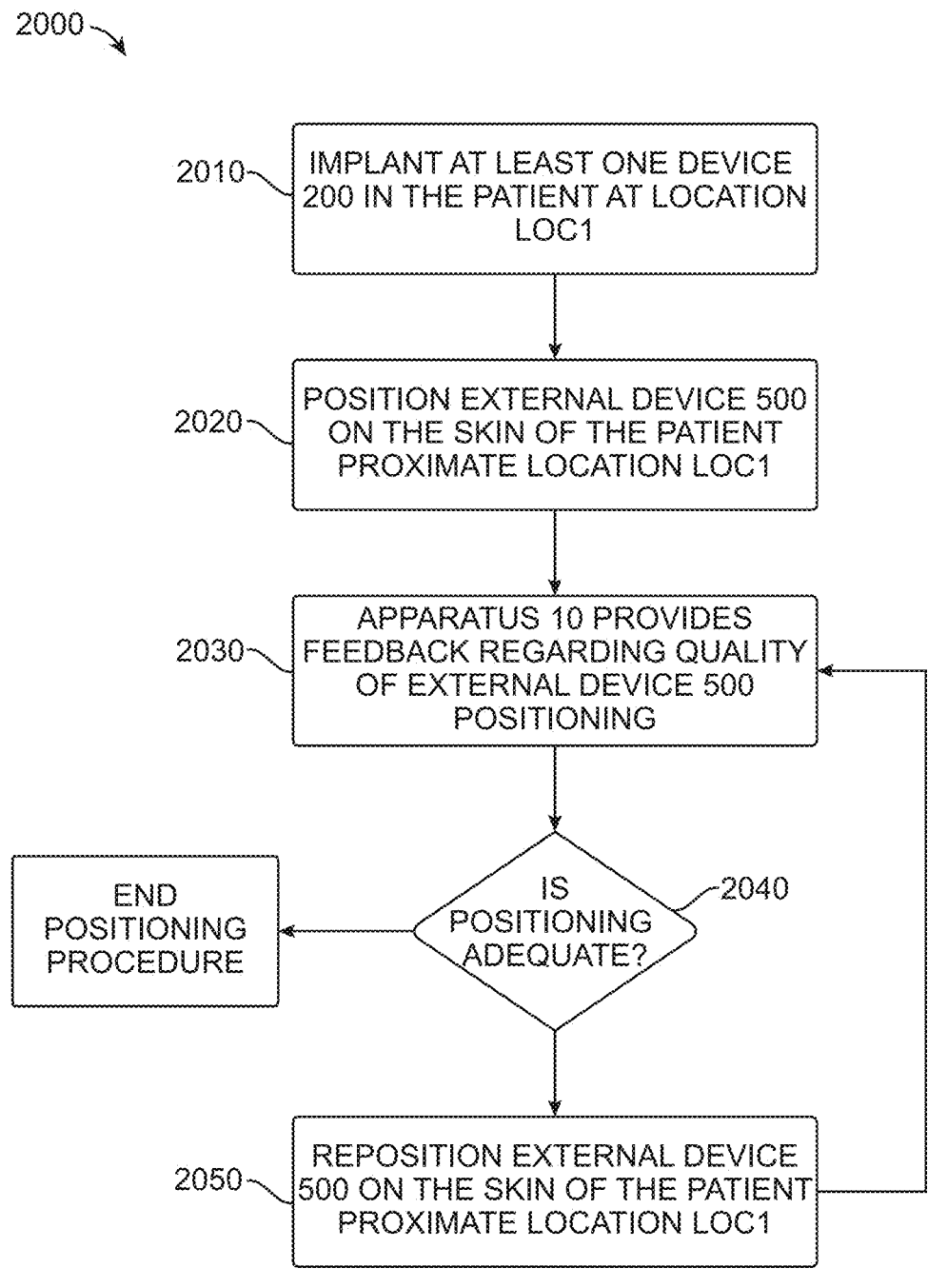
FIG. 2 is a flow chart of a method for positioning an external device on the skin of a patient, consistent with the present inventive concepts.

Referring now to FIG. 2, a flow chart of a method for positioning external device 500 on the skin of the patient is illustrated, consistent with the present inventive concepts. Method 2000 of FIG. 2 includes multiple steps for placing, orienting, and/or otherwise positioning ("positioning" herein) external device 500 on or otherwise proximate ("on" or "proximate" herein) the skin of the patient to ensure proper transfer of data and/or power to one or more implantable devices 200 that are positioned under the skin of the patient (e.g. ensure a proper communication link will be maintained). Method 2000 is described using the various components of apparatus 10 described herein.

In STEP 2010, one or more implantable devices 200 are implanted in the patient at an implant location LOC1, such as a location under the skin on the patient's back. After recovery from the implantation procedure, STEP 2020 is performed in which an external device 500 is positioned on the patient's skin proximate location LOC1, such as a location on the skin of the patient's back.

In STEP 2030, apparatus 10 provides feedback regarding the quality of the positioning of external device 500. Quality of the external device 500 position can be determined via analysis of test transmissions sent from external device 500 to implantable device 200. For example, external device 500 can send a power and/or data transmission, after which implantable device 200 sends feedback, such as a received signal strength indicator (RSSI), to external device 500 related to the quality of the transmissions (e.g. the "link"). In some embodiments, a reference RSSI can be used to compare a measured signal level to reference to determine the quality of the link. The reference can comprise a reference that is: determined during a manufacturing process of apparatus 10; based on a characterization of a population of previously manufactured external devices 500 and implantable devices; determined over time, during patient use of apparatus 10 (e.g. "learned" during actual use of one or more external devices 500 transmitting power and/or data with one or more implantable devices 200); and/or determined during a calibration process performed during programming. There can be multiple distinct link quality levels output by the RSSI, such as via a numeric scale (e.g. 1 through 4). Positioning of external device 500 can be modified (e.g. moved) to increase the determined link quality. In some embodiments, link quality (e.g. due to the position of external device 500) can be determined based on an assessment of the voltage generated by the power system of implantable device 200 (e.g. the voltage of rectifier 232), such as when information regarding this voltage is transmitted from implantable device 200 to external device 500.

In some embodiments, transmission quality (link quality) can be determined by measuring power consumption of the system, and external device 500 positioning can be optimized (e.g. moved) based on the power consumption measurement. For example, each external device 500 can include an energy measurement circuit (e.g. a current measurement circuit) that can be used to determine energy draw (e.g. current draw) of the device 500. By either calibrating at time of programming and/or learning over time during use (e.g. delivery of therapy to the patient), apparatus 10 can be configured to assess link quality by measuring the energy used (e.g. current draw).

In some embodiments, apparatus 10 assesses transmission quality by both measuring power consumption as well as using a reference RSSI, each as described hereabove.

Feedback of this transmission quality can be provided (e.g. to the patient) by one or more user output components (e.g. an alphanumeric screen, a red light/green light, speaker or other audible device, and the like). Feedback can comprise a simple "good/bad" assessment, or a more detailed (e.g. 3 or more level) assessment of external device 500 position quality (e.g. to assess better versus worse placement of external device 500). In some embodiments, quality of placement is indicated by a changing graph (e.g. bar chart) and/or a changing quantity on a display; and/or a changing tone (from a speaker).

In STEP 2040, the feedback provided is assessed (e.g. by the patient), and if acceptable, the positioning procedure of Method 2000 can be ended. If not acceptable (or if better positioning is desired), STEP 2050 can be performed where external device 500 is repositioned on the patient's skin, at a different location that is still proximate to location LOC1.

STEPS 2030 thru 2050 can be repeated multiple times, such as to compare various positions of external device 500 and/or to optimize external device 500 placement.

In some embodiments, external device 500 is positioned on the skin of the patient via patient attachment device 70 (e.g. a belt, strap, vest, and/or other attachment device), and positioning (in STEP 2020) and/or repositioning (in STEP 2050) is performed using patient attachment device 70.

In some embodiments, apparatus 10 can be configured to provide guidance in repositioning of external device 500 (e.g. relative to an implanted implantable device 200), such as directional guidance (e.g. up, down, left, right, and the like). For example, the user could enter information about a first repositioning motion (e.g. directional information provided using programmer 600), and apparatus 10 can use that information to provide subsequent repositioning guidance (e.g. feedback received from the repositioning performed via Steps 2030-2040).

Figures 3A, 3B, 3C, 3D:
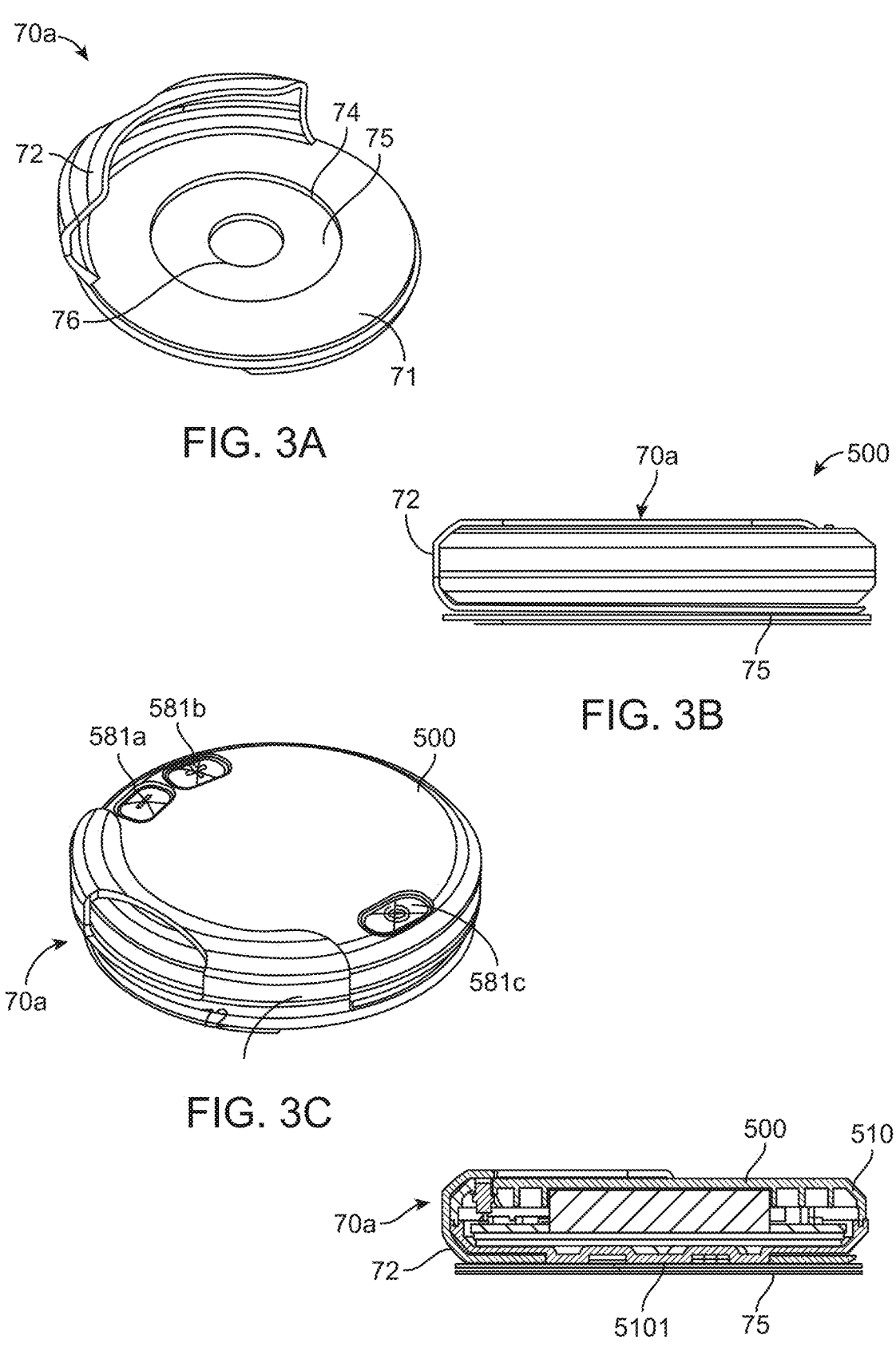
FIGS. 3A-D are various views of a patient attachment device and an external device, consistent with the present inventive concepts.

Referring now to FIGS. 3A-D various views of a patient attachment device 70 and an external device 500 are illustrated, consistent with the present inventive concepts. FIG. 3A is a perspective view of patient attachment device 70a. FIG. 3B is a side view of an external device 500 inserted into the patient attachment device 70a. FIG. 3C is a perspective view of the external device 500 inserted into the patient attachment device 70a. FIG. 3D is a side sectional view of the external device 500 inserted into the patient attachment device 70a.

Patient attachment device 70a can be configured to removably attach to external device 500, such as to first position patient attachment device 70a on the patient's skin, and subsequently insert external device 500 into the skin-attached device 70a. After a time period (e.g. after a time period of stimulation and/or other use, such as when power supply 570 is relatively depleted, and/or pain has been sufficiently reduced), external device 500 can be removed from attachment device 70a and replaced with a second (e.g. fully charged) external device 500. This replacement procedure can be repeated numerous times.

Patient attachment device 70a of FIGS. 3A-D includes a housing, housing 71, that includes a retaining portion 72 and an opening 74, as shown. Retaining portion 72 can be sized and arranged to frictionally engage a portion of each external device 500. Housing 71 can comprise a shape that approximates the shape of at least a portion of an external device 500. For example, a contour of housing 71 can approximate a contour of a mating surface of external device 500 (e.g. a surface of a portion of housing 510 of external device 500). Additionally or alternatively, the "footprint" of attachment device 70a (i.e. perimeter shape) can match and/or approximate the "footprint" of housing 510 of external device 500 (e.g. a circle as shown).

Opening 74 can be positioned near the center of patient attachment device 70a, such as to aid the user in positioning patient attachment device 70a over implantable device 200. For example, the user can palpate the patient's skin through opening 74 to locate implantable device 200 beneath the tissue and position patient attachment device 70a accordingly. Patient attachment device 70a can include an attachment element comprising an adhesive patch, adhesive 75 shown, which can be positioned on the bottom side of housing 71 (e.g. the side positioned proximate the patient's skin). Alternatively or additionally, patient attachment device 70a can include a strap, belt or other attachment element, such as is described hereabove in reference to patient attachment device 70 of FIG. 1. Adhesive 75 can comprise one or more openings, such as opening 76 shown. Opening 76 can be included to allow viewing of the patient's skin through opening 76 (e.g. during and/or after placement). Opening 76 can be included to limit the amount of skin covered by adhesive 75.

Patient attachment device 70a is constructed and arranged such that device 70a can be positioned on the patient by the patient themselves, and the positioning can be done with a single hand (e.g. when the patient's other hand is used to perform a palpation procedure to locate implantable device 200 as described herein). Patient attachment device 70a can be attached to the patient in any orientation, since when an external device 500 is inserted into patient attachment device 70a, patient attachment device 70a applies retention forces that prevent dislodgement of external device 500 (e.g. prevent dislodgement due to gravity).

In some embodiments, adhesive 75 is configured to be re-activated (e.g. via a washing, cleaning and/or other process) and/or be replaced (e.g. removed and reattached to housing 71). Alternatively or additionally, adhesive 75 can comprise multiple independent, removable layers of adhesive, which can be sequentially removed to reactivate adhesive 75. In these embodiments, patient attachment device 70a can be attached to the patient's skin (e.g. as described herein) for a first time period (e.g. a time period in which one, two, or more external devices 500 are inserted and/or removed). After the first time period, device 70a can be removed from the patient's skin, adhesive 75 reactivated and/or replaced, and device 70a again positioned on the patient's skin for a second time period (e.g. a time period in which one, two, or more external devices 500 are inserted and/or removed).

When external device 500 is to be positioned on the patient's back (e.g. when an implantable device 200 is implanted under the skin of the patient's back), it can be difficult to position external device 500 to ensure proper power and data transmission with implantable device 200. Patient attachment device 70a is configured to simplify attachment of patient attachment device 70a as well as subsequent insertion and removal of each external device 500 into and out of, respectively, device 70a.

In some embodiments, external device 500 includes a projection, projection 5101, that mates with opening 74 of device 70a. Housing 510 and projection 5101 of device 500, as well as housing 71 and retaining portion 72 of device 70a comprise materials of construction and a geometry such as to have external device 500 remain captured by (e.g. secure within) device 70a, even when external forces are imparted on either component (e.g. forces encountered during running and/or other reasonable physical activity). For example, if device 500 begins to disengage due to such a force, retention forces provided by the engagement of the mating portions of device 500 and device 70a tend to reposition device 500 back into the secure, captured position.

External device 500 can be configured to be relatively water tight, such as when external device 500 is constructed and arranged to resist ingress of water when submerged 1 meter deep in a tank of water for 30 minutes. For example, housing 510 can include one or more portions that are attached via adhesive, welding, and the like, such as to resist water ingress. In some embodiments, external device 500 includes one or more controls 581 (e.g. controls 581a, 581b, and 581c shown in FIG. 3C) that are positioned on the external surface of housing 510, and these controls may be constructed and arranged to be relatively water-tight, such as at the level described hereabove. In some embodiments, controls 581 comprise one or more controls that are manufactured using in-mold decorating (IMD) technology, where a flexible printed plastic film applique is utilized with rigid substrate insert molding. Control 581 can comprise one or more switches or other controls comprising an engagement surface (e.g. a membrane that is pressed by a finger of the patient to activate control 581) that is continuous with housing 510, such as to avoid a gap between housing 510 and control 581. In some embodiments, a water-tight design of external device 500 comprises a housing 510 including at least a portion with a sufficiently thin wall thickness to allow flexing sufficient such that a user (e.g. a user's finger) can flex the housing and activate a mechanical switch positioned within housing 510 proximate the flexible portion. Alternatively or additionally, a water-tight design of external device 500 can comprise a housing 510 including one or more holes into which a mechanical switch can be inserted or accessed (e.g. via a finger of a user) combined with a water-tight overmold (e.g. silicone overmold) positioned over at least a portion of the housing 510 (e.g. over at least the holes in housing 510).

Figure 4A:
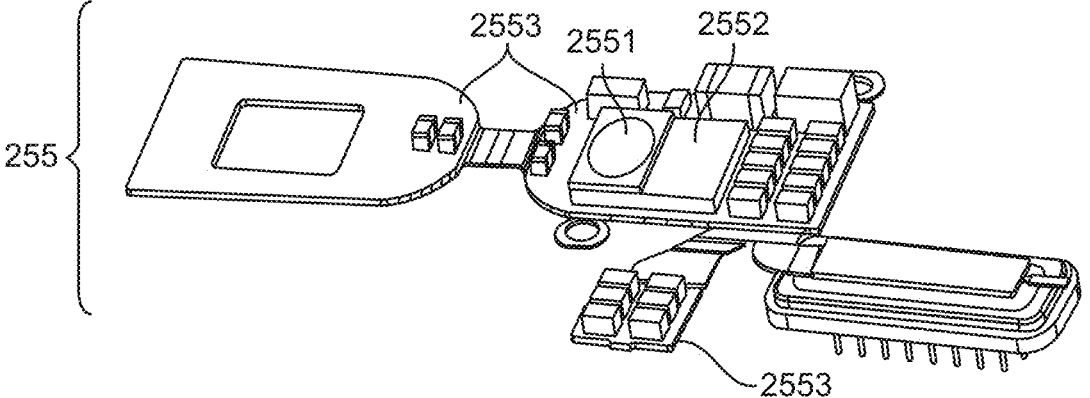
FIGS. 4A-B are perspective views of an electronic assembly of an implantable device in unfolded and folded states, respectively, consistent with the present inventive concepts.
Figure 4B:
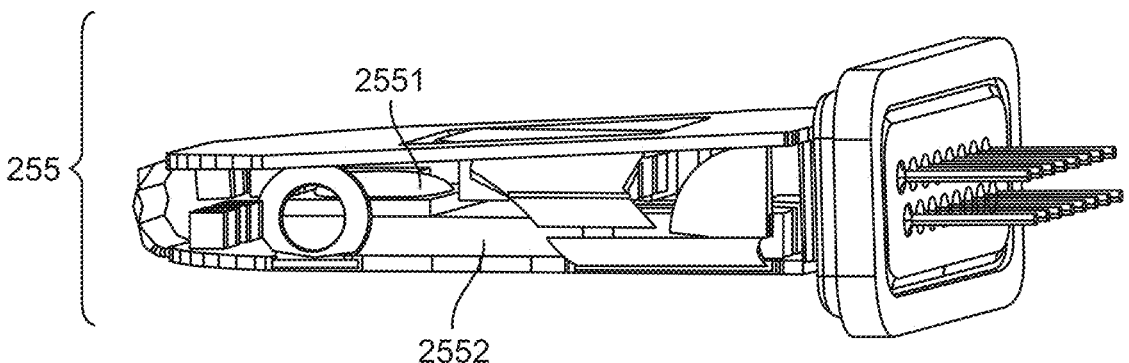

Referring now to FIGS. 4A-B, perspective views of an electronic assembly of implantable device 200 are shown, consistent with the present inventive concepts. In FIG. 4A, electronic assembly 255 is shown in an unfolded state, and in FIG. 4B, electronic assembly 255 is shown in its manufactured, folded state. Electronic assembly 255 can include a desiccant and/or other drying agent, drying agent 2551. Drying agent 2551 can be configured to remove any moisture that is captured within housing 210 during the manufacturing process, and/or any moisture that enters the interior of housing 210 after manufacturing (e.g. while implanted in the patient via a small leak). In some embodiments, drying agent 2551 comprises getter material. Implantable device 200 can be constructed such that the "free space" within housing 210 is relatively small (e.g. due to efficient packaging of implantable device 200 components within housing 210). The relatively small free space has a negative impact on the tolerance to moisture, and thus drying agent 2551 provides a significant advantage. In some embodiments, electronic assembly 255 comprises an integrated circuit 2552 which is operatively connected to circuit board 2553, and drying agent 2551 (e.g. getter material) is positioned on a top surface of integrated circuit 2552, as shown in FIGS. 4A-B. In some embodiments, drying agent 2551 is positioned at multiple locations within housing 210.

Referring now to FIGS. 5A-H, various views of an electronic assembly of implantable device 200 are illustrated, consistent with the present inventive concepts. Electronic assembly 255 is shown in various unfolded, folded, and partially folded states, such as is described hereabove in reference to FIGS. 4A-B. Electronic assembly 255 can comprise one or more of: portion 2553*a* which includes feedthrough 2556; portion 2553*c*, which includes one or more capacitors 2554*c*; portion 2553*d*, which can include antenna 240 (not shown) and opening 2557*b*; and/or portion 2553*b* which is operably connected to portions 2553*a*, 2553*c*, and/or 2553*d*; each as shown. Electronic assembly 255 can further include tabs 2553*e* and 2553*f* as shown, which can be used to secure portions of electronics assembly 255 to each other.

Figures 5A, 5B, 5C, 5D, 5E, 5F, 5G, 5H:
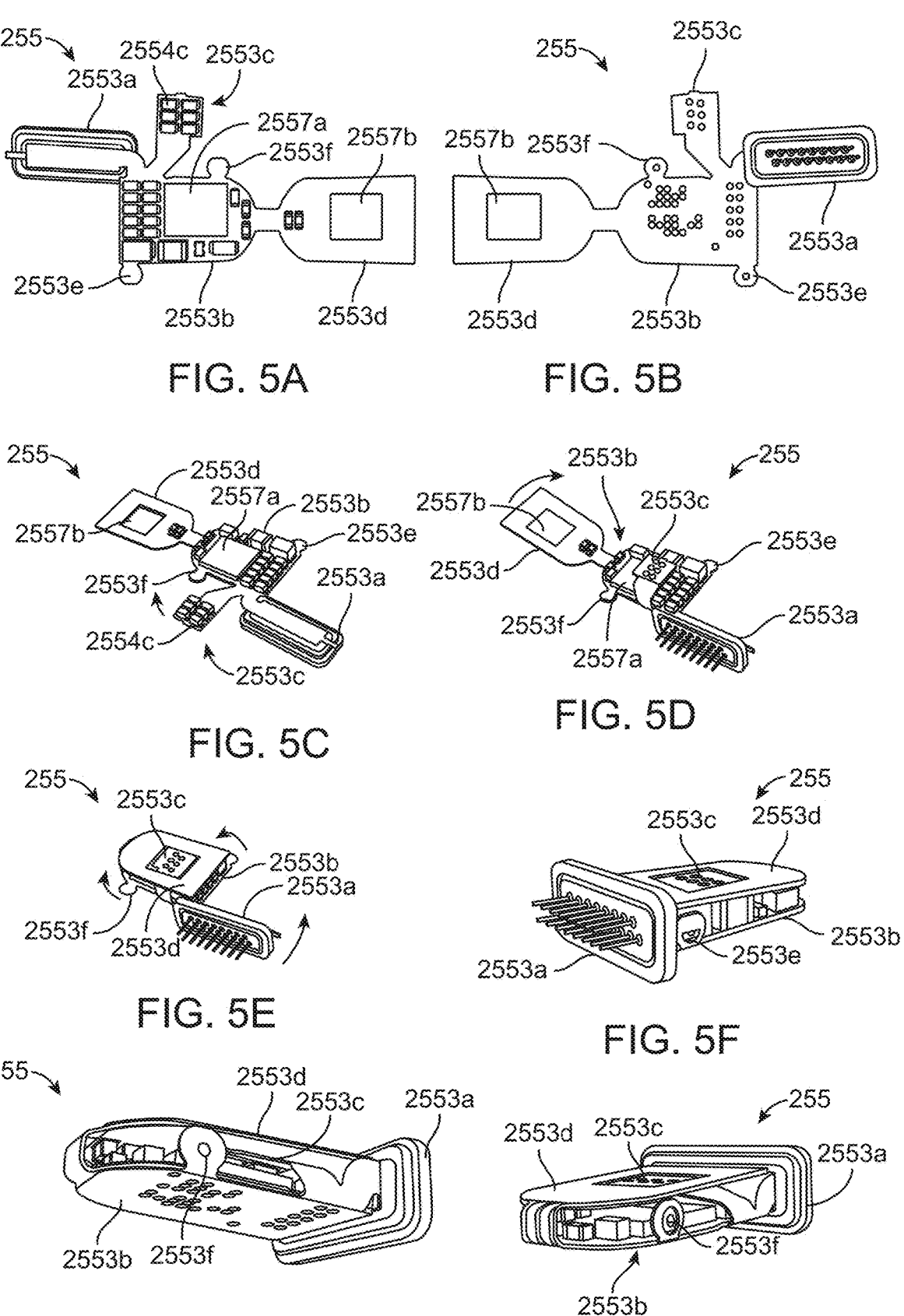
FIGS. 5A-H are various views of an electronic assembly of an implantable device in various states of a folding process, consistent with the present inventive concepts.

FIGS. 5C through 5F show a series of steps of folding electronic assembly 255. In FIG. 5C, the arrow shown indicates the direction portion 2553*c* is to be subsequently folded (e.g. rotated as performed by a person or machine of a manufacturer of implantable device 200). In FIG. 5D, portion 2553*c* has been folded approximately 180° as shown, portion 2553*a* has been rotated approximately 90° also as shown, and the arrow shown in FIG. 5D indicates the direction portion 2553*d* is to be subsequently folded. In FIG. 5E, portion 2553*d* has been folded approximately 180° as shown, and the arrow shown in FIG. 5E indicates the direction portion 2553*a* is to be subsequently folded. In FIG. 5F, portion 2553*a* has been folded approximately 90° as shown.

When electronic assembly 255 is in its folded final state, as shown in FIGS. 5F-H, capacitors 2554*c* of portion 2553*c* are positioned in an open space, space 2557*a* of the assembly, providing volumetric efficiency (e.g. reduced size of the final assembly). In some embodiments, opening 2557*b* and portion 2553*c* are sized and arranged to frictionally engage, such as to cause electronic assembly 255 to tend to remain (e.g. during the manufacturing process) in the folded state shown in FIGS. 5F-H.

Figure 6A:
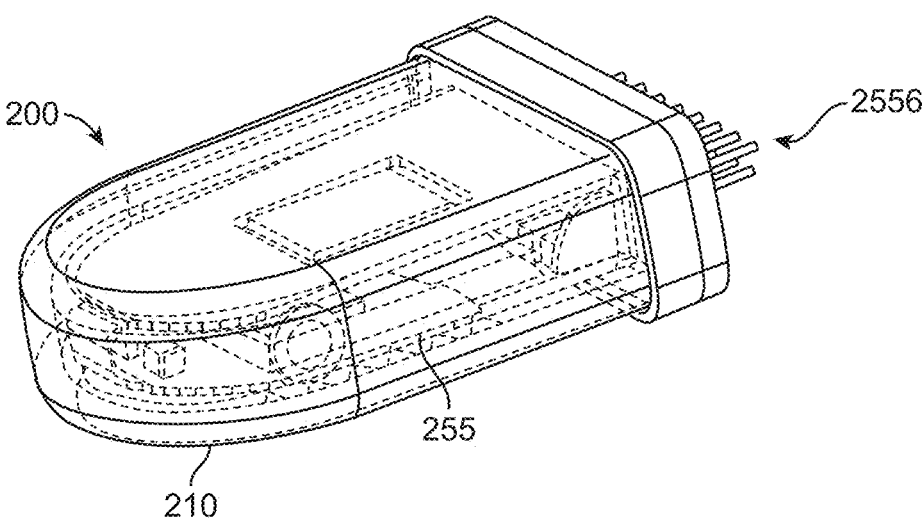
FIGS. 6A-C are a perspective, end, and side view, respectively, of a partially assembled portion of an implantable device, consistent with the present inventive concepts.
Figure 6B:
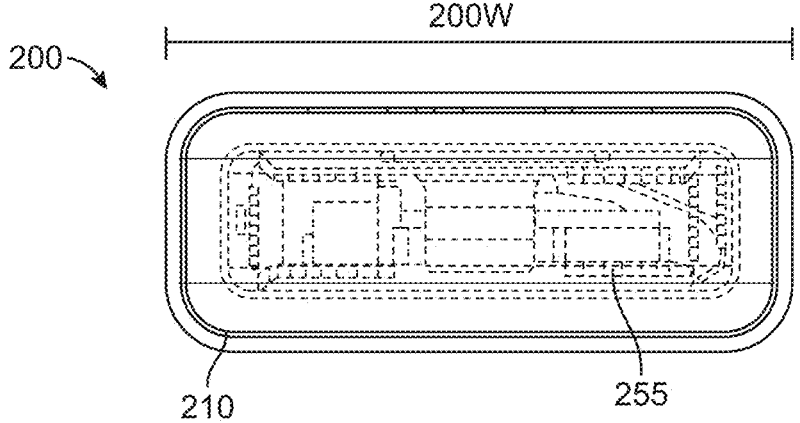
Figure 6C:
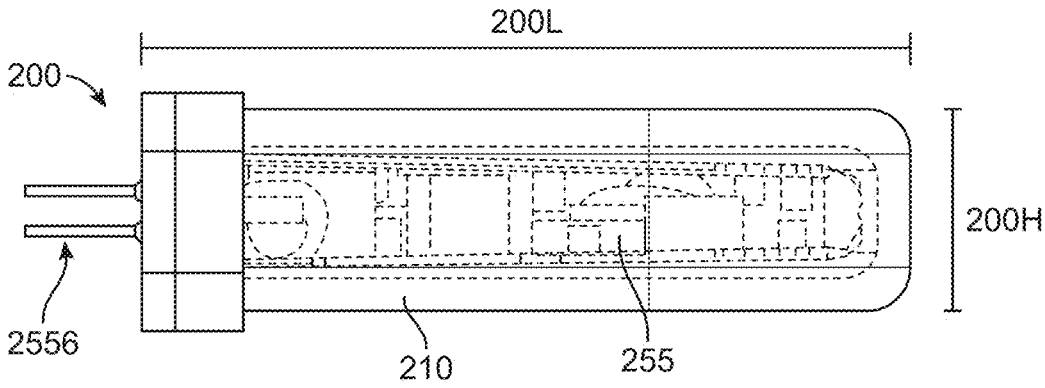

Referring now to FIGS. 6A-C, perspective, end, and side views of a partially assembled portion of implantable device 200 is illustrated, consistent with the present inventive concepts. Implantable device 200 includes housing 210, which is shown partially transparent for illustrative clarity. In some embodiments, electronic assembly 255 is manufactured with a supporting frame, such as to improve volumetric efficiency of electronic assembly 255 and housing 210 (e.g. minimize the volume of implantable device 200). The various components of implantable device 200 within housing 210, such as electronic assembly 255 (including its components) can be assembled as described herein, without a separate frame (e.g. without a separate stabilizing frame). Electronic assembly 255 can be stabilized (e.g. solely stabilized) via attachment to feedthrough 2556, which is in turn attached to housing 210, as shown.

In some embodiments, implantable device 200 comprises a length, length 200L shown, that is at least two times the magnitude of the height of device 200, height 200H shown. In these embodiments, implantable device 200 can comprise a width, width 200W shown, that is also at least 1.5 times the magnitude of the height 200H. These minimum aspect ratios (the ratios of each of length 200L and width 200W as compared to height 200H) can be chosen to prevent flipping of device 200 after implantation.

Figures 7A, 7B, 7C, 7D:
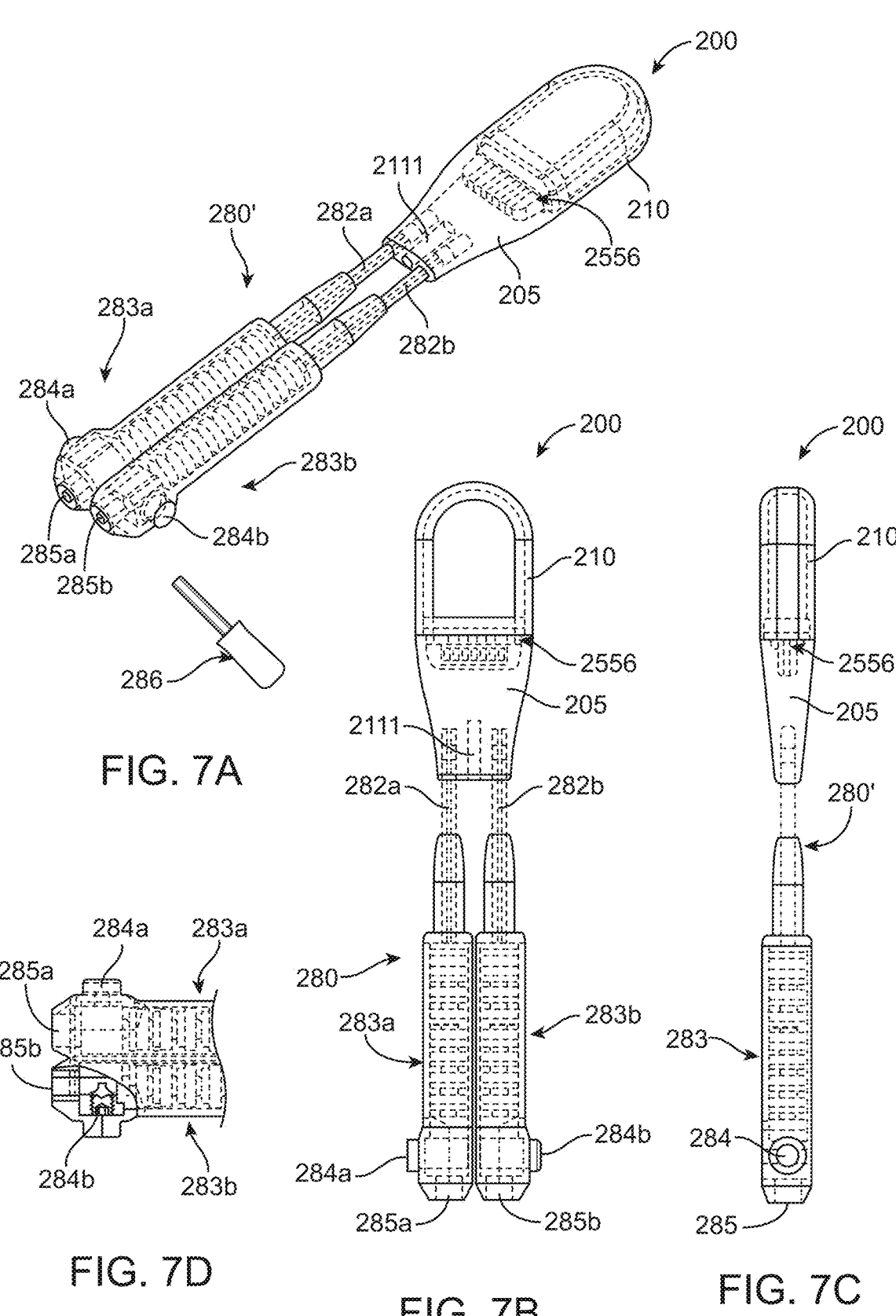
FIGS. 7A-C are a perspective, top, and side view, respectively, of an implantable device including a connector for attaching to two leads, consistent with the present inventive concepts.
FIG. 7D is a top view of the end portion of the connector of FIGS. 7A-C.

Referring now to FIGS. 7A-C, perspective, top, and side views of an implantable device 200 are shown, the device 200 including a connector for attaching to two leads 265, consistent with the present inventive concepts. FIG. 7D shows a magnified view of a distal portion of connector 280', including fastener 284. Implantable device 200, with certain components shown as partially transparent for illustrative clarity, includes a pigtail or other connecting assembly, connector 280' shown, which is attached to housing 210 and surrounds feedthrough 2556. In the embodiment of FIGS. 7A-C, connector 280' comprises a dual connector configured to operably attach (e.g. electrically and mechanically attach) to two leads 265 (e.g. leads 265 not shown but configured to be attached during a clinical procedure in which implantable device 200 is implanted in a patient). Connector 280' can be configured to electrically, mechanically, fluidly, optically, and/or sonically attach one or more components within housing 210 to one or more components (e.g. one or more stimulating elements 260) of lead 265. Connector 280' includes two conduits, conduits 282*a* and 282*b* as shown. Connector 280' also includes two engagement assemblies 283*a* and 283*b* (singly or collectively connector 283), which each include a set screw and/or other securing element, fasteners 284*a* and 284*b* (singly or collectively fastener 284). Each engagement assembly 283 includes an opening, ports 285*a* and 285*b* (singly or collectively port 285). Each port 285 is configured to slidingly receive the proximal portion of a lead 265, such as to operably connect (e.g. electrically or otherwise operably connect) to one or more conduits (e.g. wires, linkages, tubes, optical fibers, and/or wave guides) of lead 265 that are operably attached to one or more stimulating elements 260 (e.g. electrode-based stimulating elements) or other components of lead 265. Each port 285 connects to one or more filaments (e.g. wires) of the associated conduit 282 (filaments not shown but traveling proximally and electrically and/or otherwise operably connecting via feedthrough 2556 to one or more components internal to housing 210). Each fastener 284 is configured to be rotated by a screwdriver or other tool, driver 286 (shown in FIG. 7A), when the proximal portion of lead 265 is inserted into a port 285, such that engagement assembly 283 frictionally engages lead 265 (via fastener 284) such as to prevent detachment of lead 265 from connector 280'.

In some embodiments, each engagement assembly 283 comprises a portion that protrudes outward from the body portion of connector 280' creating a "bump" portion. In some embodiments, engagement assemblies 283 are positioned such that the bump portion extends along a line parallel with the top and bottom surfaces of implantable device 200, such that when the implantable device 200 is implanted in the patient, with its top surface parallel to the patient's skin, the bump portions of engagement assemblies 283*a* and 283*b* do not exert a force (e.g. does not exert a rubbing force) to the patient's skin (since the bump portion of each engagement assembly 283 extends in a direction parallel to the skin surface as opposed to orthogonal to it).

Housing 210 of implantable device 200 can include an extension portion, sealing element 205 shown. Sealing element 205 can surround feedthroughs 2556, and it can be created in a molding process (e.g. a molding process in which an overmold is applied to the feedthrough portion of housing 210). In some embodiments, a first portion (e.g. a first molded portion) of sealing element 205 is applied to feedthroughs 2556 (e.g. to create a seal around feedthroughs 2556 and the associated electrical connections), and a second portion (e.g. a second molded portion) of sealing element 205 is subsequently applied to the first portion and other locations of housing 210. Sealing element 205 can comprise epoxy.

Implantable device 200 can comprise a mechanical port, such as port 2111 shown, which is configured to engage an insertion tool (e.g. insertion tool 6511 described herein). Port 2111 can comprise a recess in sealing element 205 (e.g.

the cylindrical recess shown in FIGS. 7A-B), or it can comprise a recess positioned in another location of housing 210.

While the embodiment of FIGS. 7A-D shows an implantable device 200 with a dual connector 280' which can be attached to two leads 265, it should be appreciated that a connector 280 can be configured to attach to a single lead 265, and the bump portion of the single engagement assembly 283 can extend in a direction parallel to the patient's skin surface.

Figure 8A:
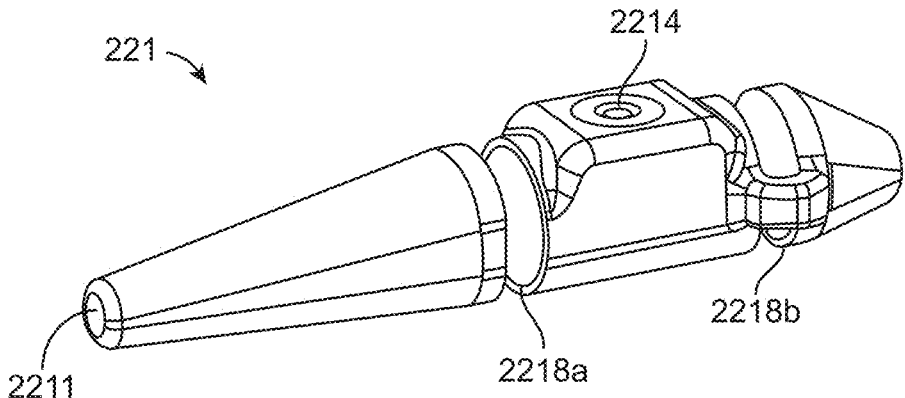
FIGS. 8A-C are a perspective, side sectional, and perspective transparent view, respectively, of an anchoring element, consistent with the present inventive concepts.
Figure 8B:
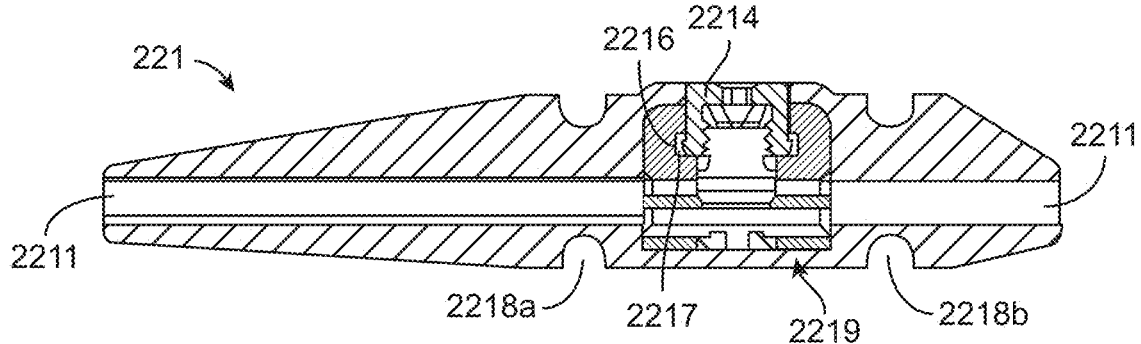
Figure 8C:
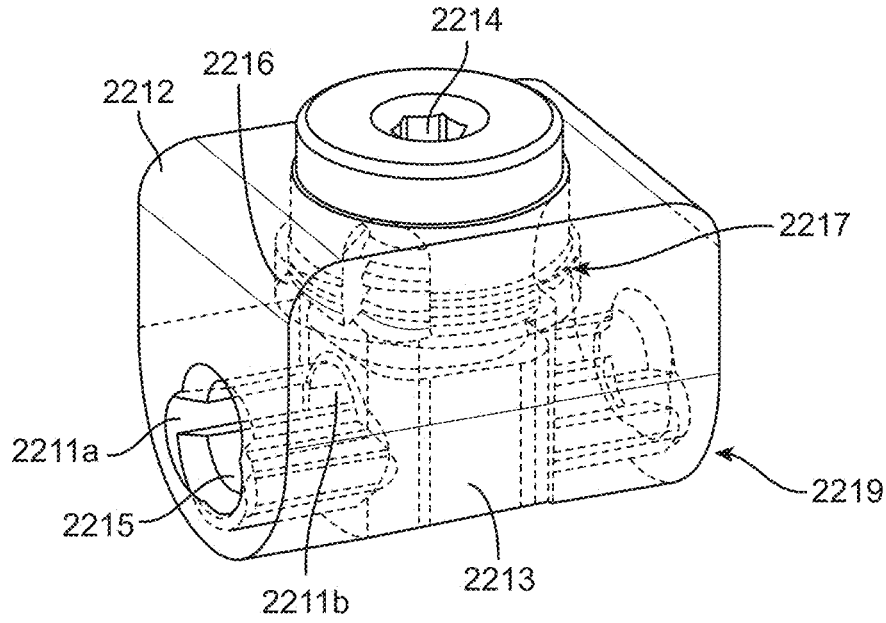

Referring now to FIGS. 8A-C, perspective, side sectional, and perspective transparent views of an anchoring element are illustrated, consistent with the present inventive concepts. As described hereabove in reference to FIG. 1, implantable device 200 can include one or more anchoring elements, such as anchoring element 221 shown in FIGS. 8A-C. Anchor element 221 can be configured to slidingly receive, via lumen 2211, an elongate portion of lead 265 (e.g. not shown, but such that the elongate portion of lead 265 passes thru lumen 2211 from one end of anchor element 221 to the other). Anchor element 221 includes a compression assembly 2219. Compression assembly 2219 can include a housing 2212, with lumen 2211a therethrough. A translatable element 2213 is operably attached to a set screw 2214, and element 2213 is positioned within housing 2212 such that translatable element 2213 translates in a direction perpendicular to the axis of lumen 2211 when set screw 2214 is rotated. Translatable element 2213 includes a lumen 2211b. Lumen 2211b can be positioned coaxial with lumen 2211a, such as when set screw 2214 is rotated such that lumen 2211b is aligned with lumen 2211a. Housing 2212 can comprise a shaped opening, configured to slidingly receive translatable element 2213, such that translatable element 2213 can translate as described, but not rotate. Housing 2212 can comprise a circular opening, configured to receive set screw 2214, such that set screw 2214 can rotate within housing 2212 and rotatably engage translatable element 2213. Housing 2212 can comprise a recess 2216, configured to engage a flange 2217 of set screw 2214. Flange 2217 can engage with recess 2216 such that set screw 2214 can rotate within housing 2212, but not translate within housing 2212, therefore capturing set screw 2214 (e.g. such that set screw 2214 is always maintained within compression assembly 2219, regardless of the number of times set screw 2214 is rotated in either direction). Compression assembly 2219 can include a compression sleeve 2215, positioned within lumens 2211a,b, as shown. Rotation of set screw 2214 in a first direction (e.g. in a clockwise direction) causes translatable element 2213 to translate towards set screw 2214, and this translation causes compression sleeve 2215 to frictionally engage an inserted lead 265 that is positioned within lumen 2211. Subsequent rotation of set screw 2214 in the opposite direction, causes translatable element 2213 to translate in the opposite direction, disengaging sleeve 2215 from lead 265.

Compression assembly 2219 can comprise a compression length (i.e. the length of lead 265 that is compressed by assembly 2219) that is above a minimum threshold, such as to compress lead 265 along a sufficiently long segment of lead 265 (e.g. a sufficiently long segment to avoid adversely crimping lead 265), such as a segment of at least one times, or at least two times the diameter of the lead (e.g. the diameter of the lead at the point of compression). In some embodiments, the compression length of compression assembly 2219 comprises a length of at least 0.051 mm, at least 0.102 mm, or at least 0.200 mm. In some embodiments, compression assembly 2219 compresses lead 265 along two or more discrete segments.

Compression assembly 2219 can be configured to radially compress lead 265 at least 10% of the diameter of the lead (e.g. a lead with an uncompressed diameter of 1.3 mm would be compressed at least 0.13 mm), and/or no more than 33% of the diameter of the lead (e.g. a lead with a compressed diameter of 1.3 mm would be compressed no more than 0.43 mm).

Anchor element 221 can include one or more fixation points, circumferential recess 2218 (e.g. such as recesses 2218a and 2218b shown). Surgical clips or sutures can be placed around a recess 2218 and into tissue, such as to fixate anchor element 221 and an inserted lead 265 to tissue.

Figure 9:
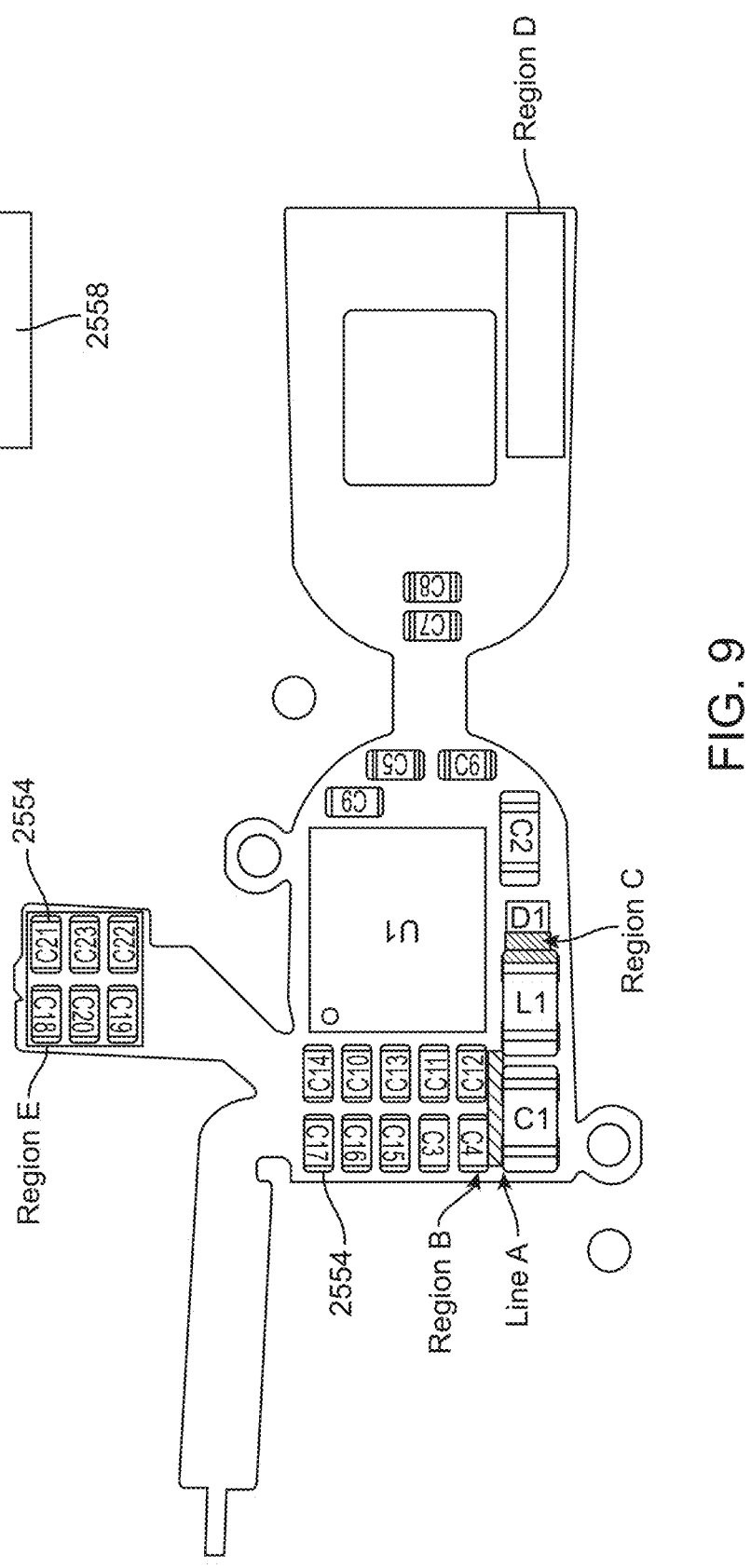
FIG. 9 is a top view of an electronic assembly of an implantable device, consistent with the present inventive concepts.

Referring now to FIG. 9, a top view of an electronic assembly of implantable device 200 is illustrated, consistent with the present inventive concepts. Electronic assembly 255 is shown in an unfolded state. Electronic assembly 255 comprises various portions, such as regions B, C, D, and E shown. Electronic assembly 255 can comprise one or more portions of insulating tape (e.g. a polyimide tape) and/or other insulating material portions, insulator 2558 shown. In some embodiments, an insulator 2558 is positioned over one or more regions of electronic assembly 255 such that when assembly 255 is folded in manufacturing (e.g. as described hereabove in reference to FIGS. 5A-H), opposing electrically conductive portions of assembly 255 do not contact each other. For example, an insulator 2558 can be positioned such that a DC blocking capacitor 2554 and a DC node do not electrically short together. Insulator 2558 can comprise a portion that is positioned along the sides of components C1 and L1 shown (e.g. along line A). Insulator 2558 can comprise an upper boundary that is no lower than the top surface of component L1 and no higher than the top surface of component C1. In some embodiments, adhesive is applied between components at region B and region C. In some embodiments, insulator 2558 can comprise a portion that is positioned over components C18-C23 shown (e.g. components positioned in region E). In some embodiments, a serial number label is positioned in region D.

Figure 10:
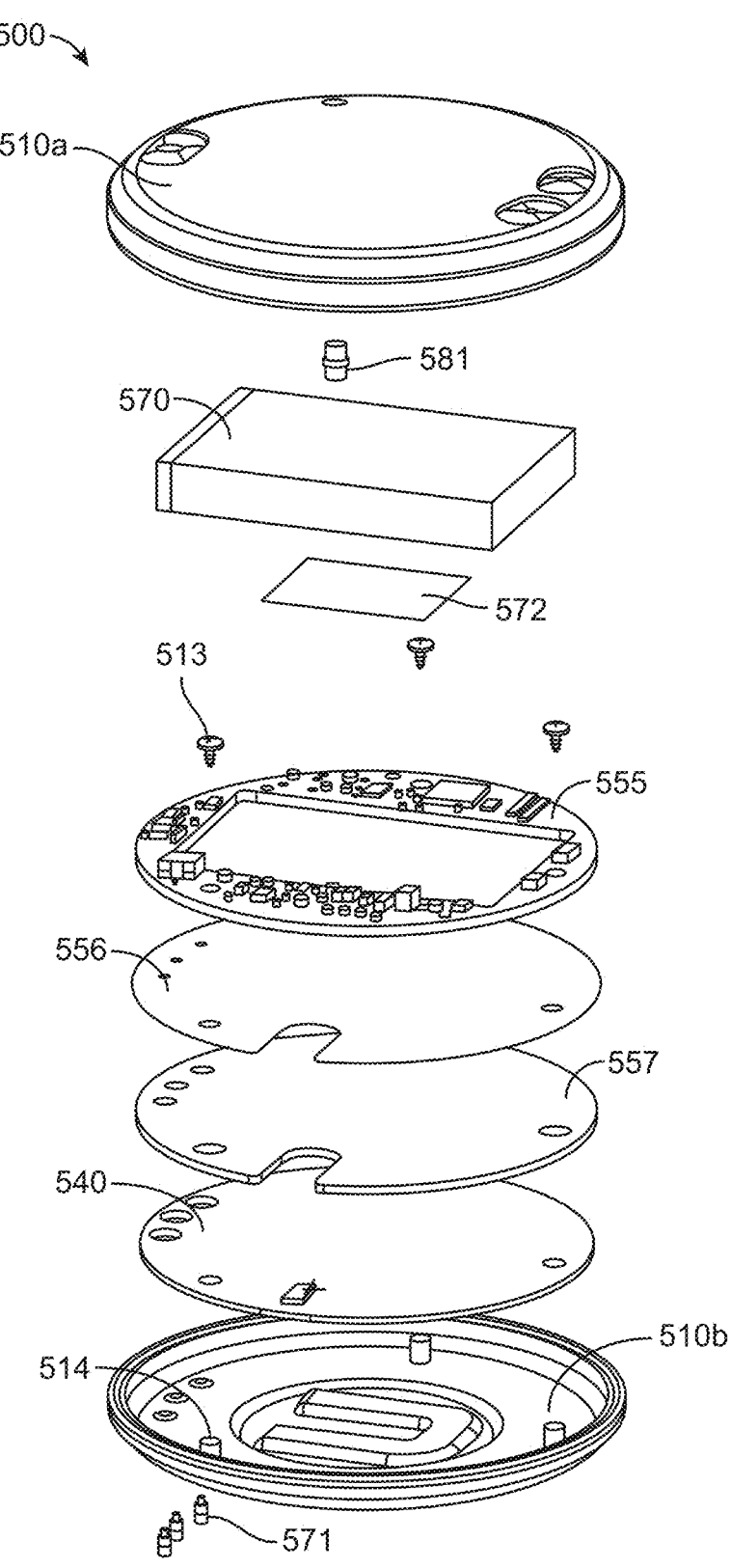
FIG. 10 is an exploded view of an external device, consistent with the present inventive concepts.

Referring now to FIG. 10, an exploded view of an external device is illustrated, consistent with the present inventive concepts. External device 500 includes housing 510, comprising top housing 510a and bottom housing 510b. Housing 510 can comprise one or more metal and/or plastic materials, such as polycarbonate and/or acrylonitrile butadiene styrene (ABS). Positioned between housings 510a-b are various components configured to transmit power and/or data to an implantable device 200, and perform other functions, as described herein. External device 500 includes electronic assembly 555, which is shown positioned on top of a copper shield, shield 556 shown. Copper shield 556 is positioned on top of a ferrite disk, disk 557, which in turn is positioned on top of antenna assembly 540. One or more screws, screws 513 (three shown), attach components 555, 556, 557, and 540 to bottom housing 510b via mating bosses 514 (three shown) into which screws 513 rotatably engage (e.g. engage threads of boss 514). In some embodiments, screws 513 are rotatably engaged with a minimum torque (e.g. to minimize gaps between the layers), such as a torque of at least 10 in-oz, such as at least 14 in-oz, or at least 16 in-oz. In some embodiments, copper shield 556 is adhered to ferrite disk 557. In some embodiments, antenna 540 is adhered to ferrite disk 557. In some embodiments, both copper shield 556 and antenna 540 are adhered to ferrite disk 557 (e.g. in the orientation shown in FIG. 10), such as to create a laminate construction which maximizes the effectiveness of the shielding provided, and/or eliminates or at least minimizes gaps between layers that could result in detuning.

External device 500 includes a battery, capacitor, or other energy storage element, power supply 570 shown. Power supply 570 can be attached to electronic assembly 555 via connector 572 shown. Connector 572 can comprise a double-sided adhesive pad. Power supply 570 can be replaceable and/or rechargeable. In some embodiments, power supply 570 comprises a lithium ion battery. External device 500 can comprise one or more contacts positioned on the external surface of housing 510, such as contacts 571 (three shown). Contacts 571 can comprise pogo pins or other contacts that are electrically connected to charging circuitry of electronic assembly 555, such as to allow charging of power supply 570. For example, contacts 571 can be constructed and arranged to receive power from mating contacts of charger 61 as described herebelow in reference to FIGS. 17A-C.

External device 500 can comprise one or more user interface components, such as indicator 581 shown. Indicator 581 can comprise an indicator light and/or a display. In some embodiments, indicator 581 comprises a light pipe which is positioned above a light-emitting device such as above an LED of electronic assembly 555. In some embodiments, indicator 581 comprises a speaker or other audio output component (e.g. a buzzer). Indicator 581 can provide various information to the patient or other user, such as: status of connection with implantable device 200; battery status (e.g. battery level, low battery, and the like); program information (e.g. program number); therapy information (e.g. amplitude or other therapy level); programmer 600 connection status; and combinations of one or more of these.

Figure 11A:
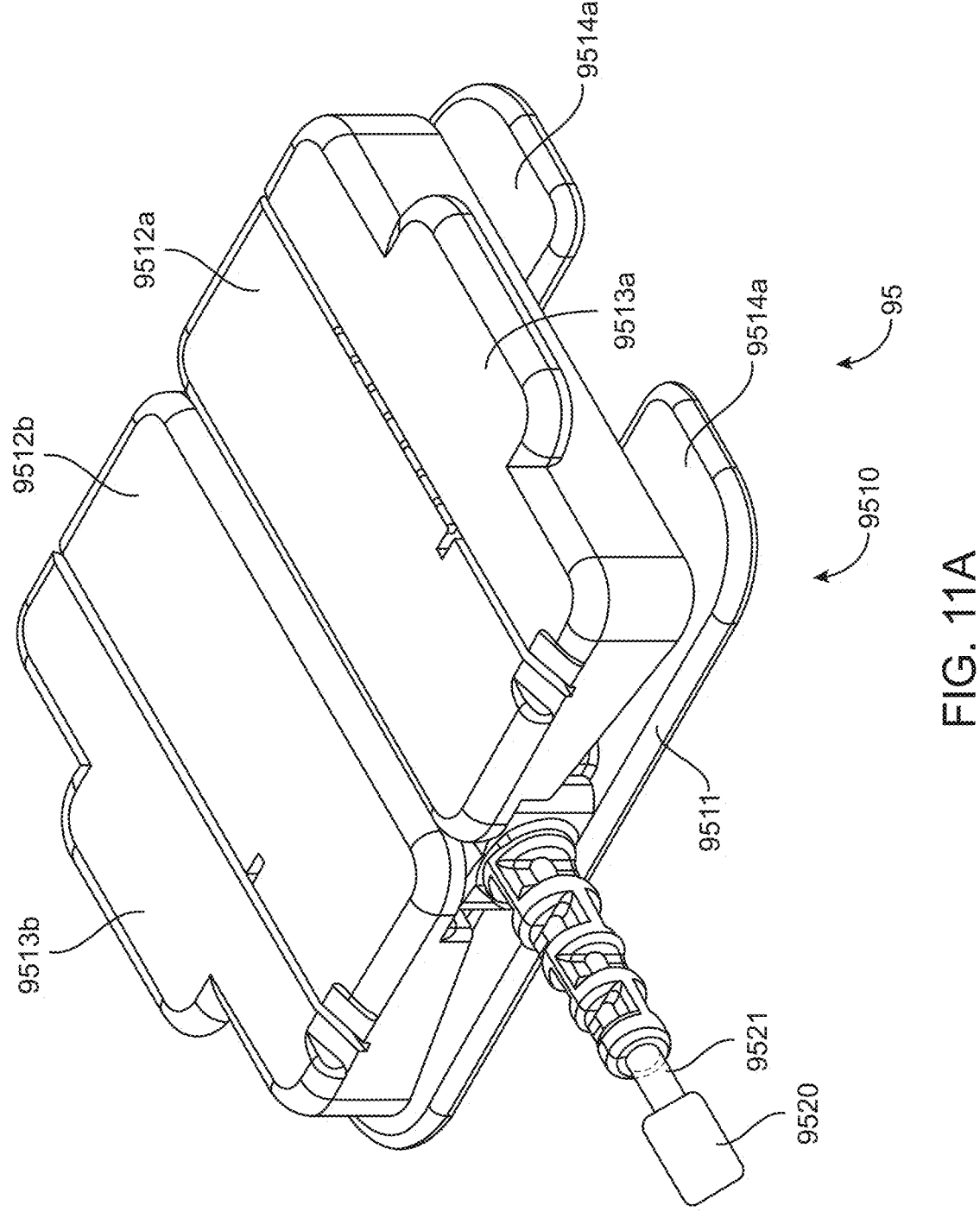
FIGS. 11A-D are a perspective top view, a side view, a side sectional view, and another side sectional view, respectively, of an interface assembly for operably attaching a trialing interface to two lead assemblies, consistent with the present inventive concepts.
Figure 11B:
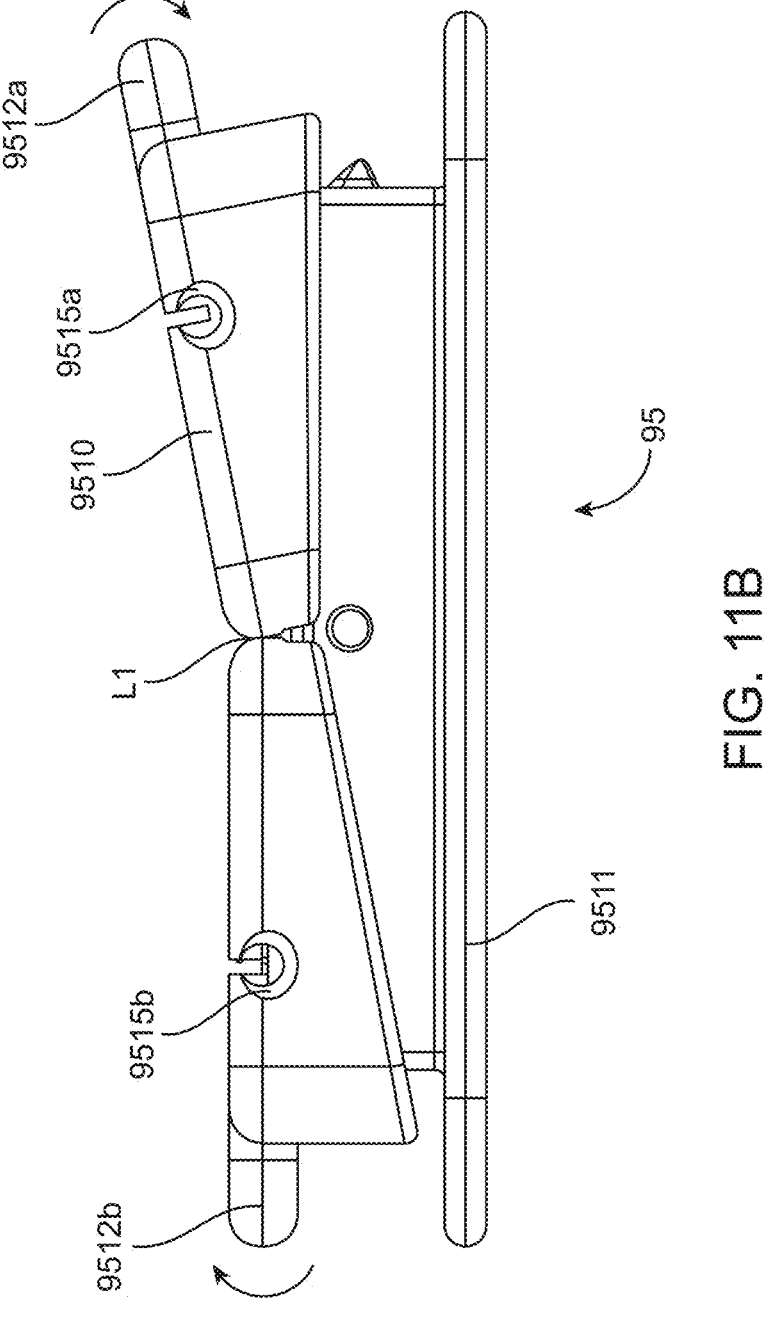
Figures 11C, 11D:
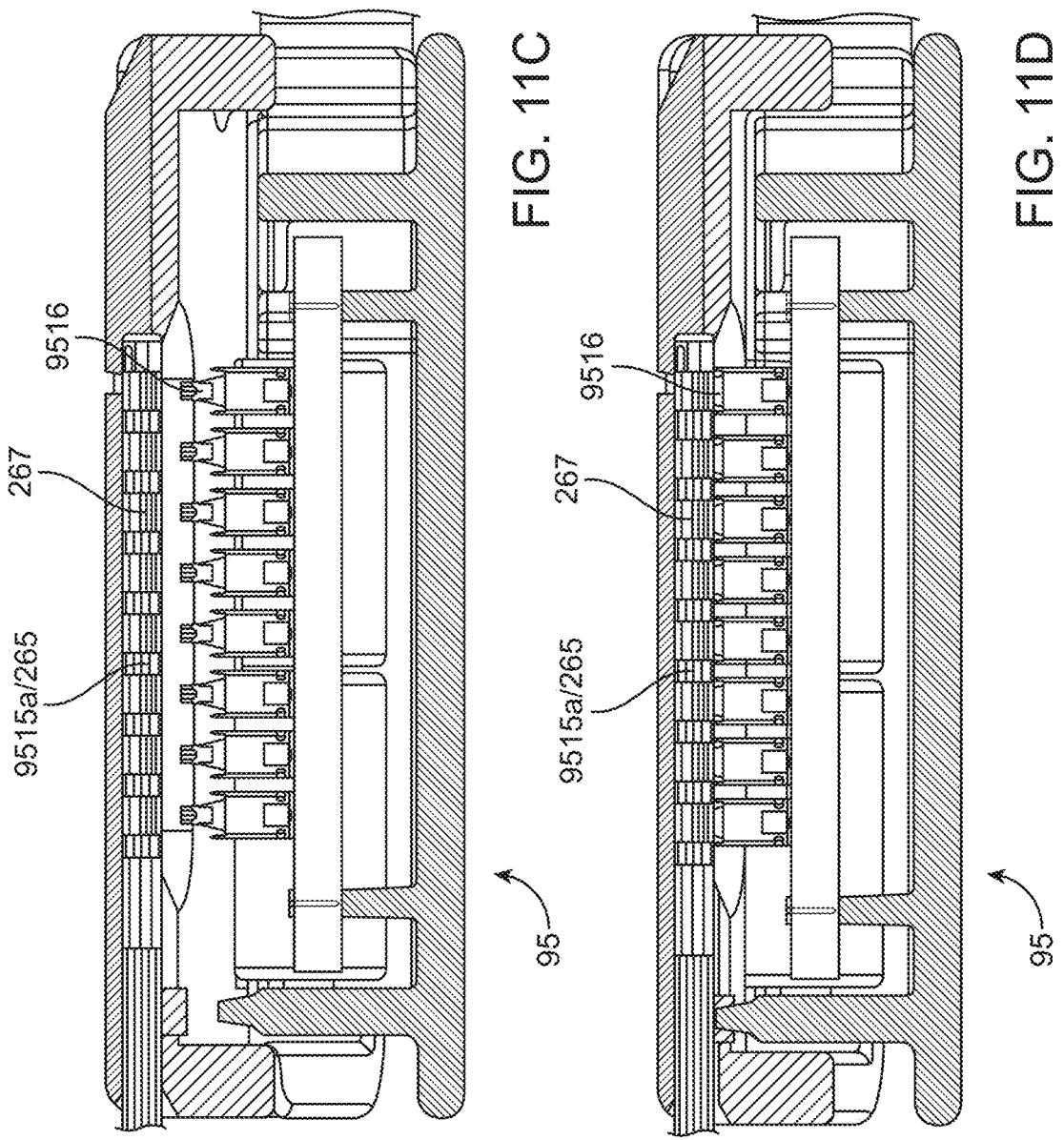

Referring now to FIG. 11 A-D, a perspective top view, a side view, a side sectional view, and another side sectional view and of an interface assembly for operably attaching a trialing interface 90 to two lead assemblies 265 is illustrated, consistent with the present inventive concepts. Interface connector 95 comprises housing 9510 including base 9511 and first hinged portion 9512a and second hinged portion 9512b (singly or collectively hinged portion 9512). Hinged portions 9512a and 9512b are rotatably attached to a mid portion of base 9511, and each can rotate in the directions shown in FIG. 11B. In FIG. 11B, hinged portion 9512a is shown in an "open" position (e.g. a position in which a lead 265 can be inserted or removed), and hinged portion 9512b is shown in a "closed position" (e.g. position in which the proximal end of a lead 265 is secured in place and electrically and/or otherwise operably connected to trialing interface 90).

In some embodiments, interface connector 95 is constructed and arranged such that hinged portion 9512a-b interfere with each other during rotation, such as to limit the amount of rotation each can undertake. For example, rotation of hinged portion 9512a is limited to the point at which hinged portion 9512a contacts hinged portion 9512b, e.g. location L1 shown in FIG. 11B. In some embodiments, only one of hinged portions 9512 can be opened (e.g. fully opened) at a time (e.g. due to a mechanical stop provided by contact between the hinged portion 9512a and 9512b when one is in an open position).

Hinged portions 9512a and 9512b can include one or more projections, such as tabs 9513a and 9513b, respectively, as shown. Similarly, base 9511 can comprise one or more projections, such as the two tabs 9514a shown relatively opposite projection 9513a (e.g. and similar tabs 9514b not shown but relatively opposite projection 9513b). Interface connector 95 can be constructed and arranged such that a user (e.g. a clinician that implants one or more implantable devices 200) can rotate a hinged portion 9512 by engaging a hinged portion 9512 (e.g. grasping a projection 9513) and engaging base 9511 (e.g. gasping at a projection 9514) and applying a force to cause a rotation (e.g. a pivoting force to transition hinged portion 9512 from an open to closed condition, or vice versa). In some embodiments, interface connector 95 is constructed and arranged such that a user can use a single hand to transition a hinged portion 9512 from an open condition to a closed condition, or vice versa (e.g. fingers of a single hand apply opposing forces to base 9511 and a hinged portion 9512).

Each hinged portion 9512 includes a lumen 9515 through which a lead 265 can be inserted when the associated hinged portion is in an open position. Subsequent closure of the hinged portion 9512 causes lead 265 to be secured within interface connector 95 and to operably connect with various components of lead 265. For example, conductive portions of lead 265, contacts 267 (e.g. contacts which are each electrically connected to a stimulation element 260), can electrically connect to one or more pogo pins or other electrical contacts of connector 95, contacts 9516.

Securing of a lead 265 via inserting of lead 265 into a lumen 9515 and rotation of the associated hinged portion 9512 to a closed position, electrically and/or otherwise operably connects lead 265 to interface connector 95. Interface connector 95 includes connector 9520 which is operably attached to at least contacts 9516 via cable 9521. Connector 9520 can be operably connected to a trialing interface, such as trialing interface 90 described herebelow in reference to FIGS. 12A-B.

Figure 12A:
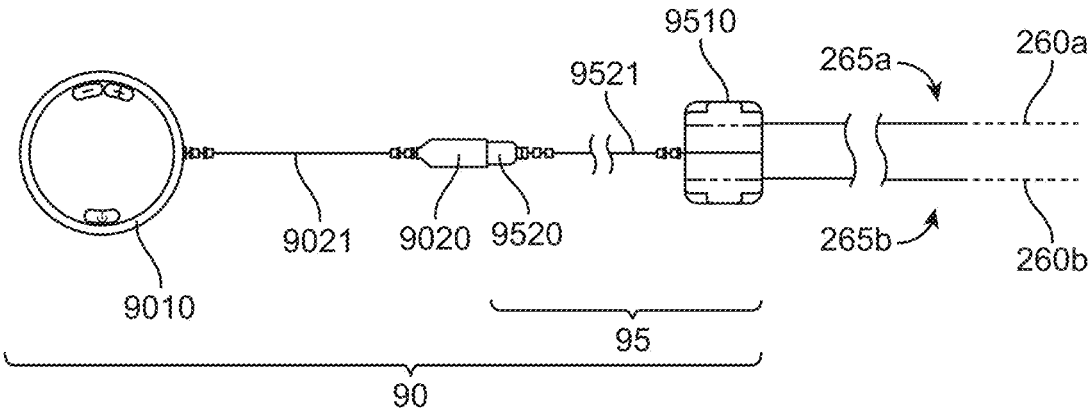
FIGS. 12A-B are a perspective view and a schematic view, respectively, of a stimulation apparatus comprising a trialing interface and a lead connector, consistent with the present inventive concepts.
Figure 12B:
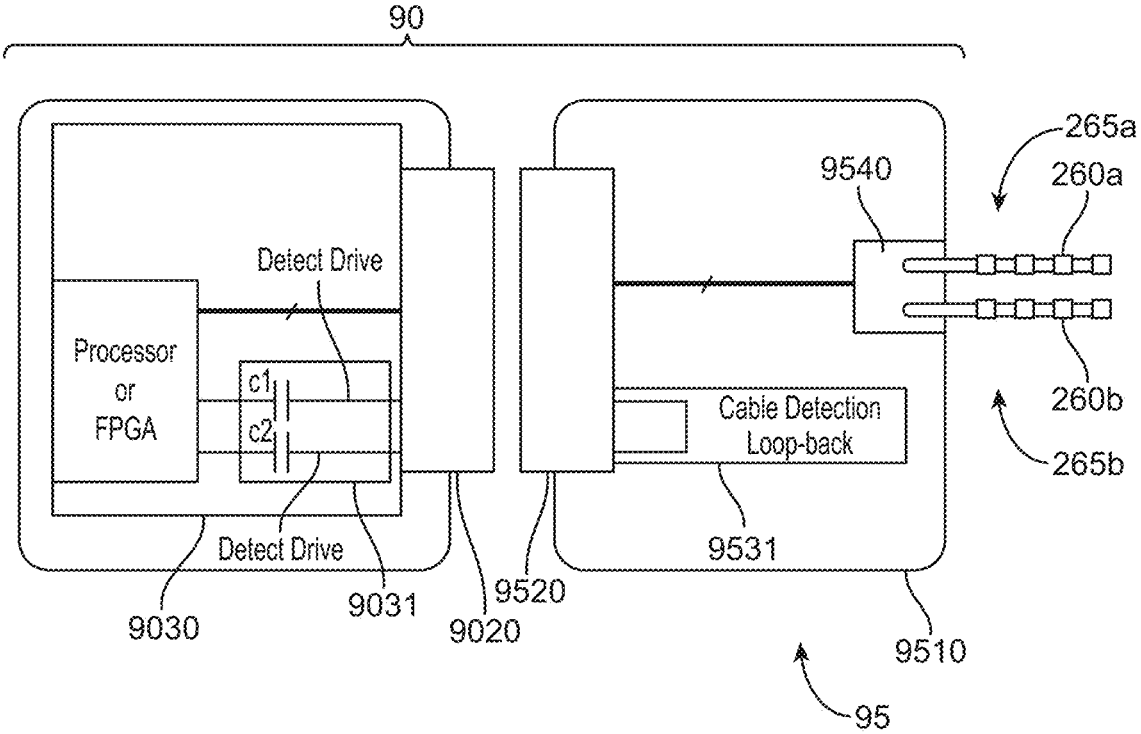

Referring now to FIG. 12A-B, a perspective view and a schematic view of a stimulation apparatus comprising a trialing interface and a lead connector are illustrated, consistent with the present inventive concepts. Trialing interface 90 comprises a housing, housing 9010, which surrounds an electronic assembly, assembly 9030. Electronic assembly 9030 is electrically attached to a connector, connector 9020, such as a connector with at least 10 contacts, such as approximately 18 contacts. Electronic assembly 9030 can be electrically attached to connector 9020 via cable 9021 (as shown in FIG. 12A). Trialing interface 90 further comprises interface connector 95, which includes connector 9520. Connector 9520 is configured to electrically attach to connector 9020 (e.g. connector 9520 comprises mating contacts, such as at least 10 contacts, such as approximately 18 contacts).

Interface connector 95 includes housing 9510. Interface connector 95 is configured to operably (e.g. at least electrically) attach to one or more leads 265 (leads 265a and 265b shown in FIGS. 12A-B). Each lead 265 can include one or more stimulation elements 260a and 260b, respectively (e.g. two, four, six, eight, or more stimulation elements 260). Each lead 265 connects to interface connector 265 via connector 9540 as shown. In some embodiments, housing 9510 comprises two hinged portions, which can be positioned (e.g. via a single hand of an operator) about one or more leads 265 (e.g. as described hereabove in reference to FIGS. 11A-D). In some embodiments, interface connector 95 is configured to operably attach to a single lead 265. In some embodiments, interface connector 95 is configured to operably attach to three or more leads 265, such as four leads 265. Interface connector 95 can include cable 9521, as shown in FIG. 12A, which electrically attaches connector 9520 to connector 9540.

Electronic assembly 9030 is configured to provide stimulation energy to one or more stimulation elements 260 of one or more leads 265 (e.g. via connectors 9020, 9520, and 9540). As described hereabove in reference to FIG. 1, interface connector 95 can comprise a single-use disposable component, used in a single clinical procedure on a single patient, while the remaining portions of trialing interface 90 (e.g. housing 9010 and its surrounded components) are for use in multiple clinical procedures (e.g. on the same or multiple patients).

In some embodiments, electronic assembly 9030 includes detection circuitry 9031, and interface connector 95 comprises detection circuitry 9531. Detection circuitry 9031 is electrically connected to one or more contacts of connector 9020, and detection circuitry 9531 is connected to one or more mating contacts of connector 9520. Via circuitry 9031 and 9531, trialing interface 90 is configured to detect proper connection of connector 9520 to connector 9020. In some embodiments, detection circuitry 9531 comprises a connection (e.g. an electric short or other known resistance connection) between two or more contacts of connector 9520, and electronic assembly 9030, via detection circuitry 9031 can detect a proper connection between connectors 9020 and 9520 has been made. In some embodiments, the connection is determined using an alternating current (AC) signal. Avoidance of a direct current (DC) signal is advantageous as it avoids uncomfortable and/or unsafe stimulation of the patient (e.g. due to a bend and/or break in lead 265, or other event that causes shorting of wires of lead 265). In some embodiments, the AC signal provided by electronic assembly 9030 comprises a digital pulse (e.g. with a pulse width of approximately 2 μsec and at a voltage level less than 10V, such as less than 5 V, or approximately 3 V). Electronic assembly 9030 is configured to detect a "high" state during the pulse, and then a "low" state after the pulse. This detection is repeated (e.g. at approximately a 10 Hz rate), and it can detect if a connect or disconnect of connectors 9020 and 9520 occurs (e.g. a connect or disconnect of interface connector 95 from the remaining portion of trialing interface 90).

In some embodiments, trialing interface 90 is configured to detect proper connection of one or more leads 265. For example, trialing interface 90 can be configured to perform an impedance measurement that provides information about the state of connectivity of lead 265 with both trialing interface 90 and tissue. A high (e.g. open) impedance is indicative of an improper connection.

In some embodiments, if trialing interface 90 detects connectors 9020 and 9520 being connected, and electronic assembly 9030 is currently (e.g. at the time of the connection) attempting to deliver a stimulation waveform to the patient (e.g. via stimulation element 260), electronic assembly 9030 can be configured to stop signal delivery (e.g. stop full amplitude signal delivery to the patient), and initiate a new stimulation delivery in which amplitude level is slowly ramped up (e.g. to avoid the patient getting full stimulation energy at the time of connection). For example, the amplitude can be ramped up over a period of 1 s to 10 s to avoid full amplitude delivery at the time of a connection that may be perceived as unpleasant by the patient.

Referring now to FIG. 13A-C, perspective views of a single connector 215' attached to a connector 220 and a dual connector 215" attached to a connector 220, respectively, are illustrated, consistent with the present inventive concepts. As shown in FIG. 13A, the array of pins 206 of connector 220 are slidingly received by the array of receptacles 216 of connector 215'. Connector 215' includes single conduit 262 of lead 265 or a single conduit 282 of lead connection assembly 280. As shown in FIG. 13B, the array of pins 206 of connector 220 are slidingly received by the array of receptacles 216 of connector 215". Connector 215" includes dual conduits 262a, 262b of two leads 265 or conduits 282a, 282b of two lead connection assemblies 280 or a dual lead connection assembly 280'. In some embodiments, as shown in both FIGS. 13A and 13B, a sealing element 205 is applied to surround at least a portion of housing 210, connector 220, and/or connector 215, such that sealing element 205 prevents contamination from entering locations within housing 210 and/or adversely affecting the connection made between connector 215 and an attached component.

Referring additionally to FIG. 13C, apparatus 10 can include one or more stylets 1700, such as stylets 1700a and 1700b shown, and implantable device 200 can comprise one or more stylet entry ports, such as ports 207a and 207b shown. Each entry port 207 can be connected to a lumen of a lead 265 and/or lead connection assembly 280, such as lumens 208a and 208b. Each stylet 1700 can include an elongate filament 1701 which can be connected to a handle 1702, (e.g. filaments 1701a and 1701b connected to handles 1702a and 1702b, respectively). Each filament 1701 can be inserted into a lumen 208 such as to provide rigidity in the advancement of the lead 265 (or lead connection assembly 280) through tissue. Filament 1701 can comprise a filament that is flexible and/or malleable, such as a malleable filament whose shape can be curved or otherwise modified as desired to assist in the insertion of a lead 265 through tissue (e.g. a lead comprising one or more stimulation elements 260 as shown). In some embodiments, a single stylet 1700 is used to sequentially advance a first lead 265a and then a second lead 265b. Each entry port 207 includes an opening with a trajectory that allows stylet 1700 to be positioned eccentric to the associated lumen 208. In other words, the proximal portion of each lumen 208 (the portion proximate opening 207 is curved as shown. This configuration of lumen 208 and opening 207 avoids any additional volume needed to be added to housing 210, while allowing stylet 1700 to remain centered in the associated lead 265 such that insertion of lead 265 is performed with a similar technique to that used when inserting a lead not attached to a stimulator housing.

In some embodiments, sealing element 205 (or another portion of housing 210) comprises a receptacle for engaging an implantation tool (e.g. insertion tool 6511 described herein), such as port 2111 described hereabove in reference to FIGS. 7A-B.

Referring now to FIGS. 14A-B, perspective views of an implantable device 200 are illustrated, consistent with the present inventive concepts. Implantable device includes housing 210, and connector 220 as described herein. Connector 220 comprises an array of pins 206 that are slidingly received by an array of receptacles 216 of connector 215". Connector 215" includes dual conduits 262a, 262b of two leads 265 or conduits 282a, 282b of two lead connection assemblies 280 or a dual lead connection assembly 280'. In some embodiments, a sealing element 205 is applied to surround at least a portion of housing 210, connector 220, and/or connector 215, such that sealing element 205 prevents contamination from entering locations within housing 210 and/or adversely affecting the connection made between connector 215 and an attached component.

Implantable device 200 can comprise one or more stylet entry ports, such as ports 207a and 207b shown. Each entry port 207 can be connected to a lumen of a lead 265 and/or lead connection assembly 280, such as lumens 208a and 208b, such as to cooperate with a stylet 1700 as described hereabove in reference to FIG. 13C.

A set of wires 217 are electrically connected to the array of pins 206. For illustrative clarity, only 4 wires 217 are shown in FIGS. 14A-B, however each pin 206 is electrically connected to a separate wire 217 (e.g. 32 pins 206 are connected to 32 separate wires 217). The array wires 217 travel into dual conduits 262a, 262b of two leads 265 or conduits 282a, 282b of two lead connection assemblies 280 or a dual lead connection assembly 280'. Wires 217, at their point of connection to pins 206, can be arranged in 2 linear arrays of wires positioned in 2 planes (e.g. when pins 206 are arranged in two rows as shown). Each wire 217 can travel, in a path comprising a curvilinear trajectory, and in a relatively parallel arrangement to one or more wires 217 in proximity to it, and enter into a conduit 262a, 262b of a two lead 265 or a conduit 282a, 282b of a connection assembly 280 or a dual lead connection assembly 280'. The collective pathways of wires 217 can be arranged to avoid the lumen of ports 207.

Referring now to FIGS. 15A-L, a series of views of an implantation procedure for implantable device 200 is illustrated, consistent with the present inventive concepts. Implantable device 200 can be configured as a "ported-version", in which leads 265 are attachable by the clinician, and/or an "integrated-version" (a pre-attached-version), in which leads 265 are attached during the manufacturing of implantable device 200. As described herebelow, each implantable device 200 can be implanted in the patient using a single incision (i.e. avoiding multiple incisions). Implantable device 200 can be implanted using both a tunneling tool, tool 6504, for creating a tunnel in tissue, a lead pushing tool, tool 6505, configured to push lead 265 through that tunnel, and/or other tools as described herebelow. Tunneling tool 6504 can comprise a handheld device (e.g. with an effective length of approximately 10 cm) that is used to create a subcutaneous pathway and pocket for the placement of implantable device 200. The implantation steps below are described in reference to positioning implantable device 200 proximate the patient's spine.

The patient can be positioned, prepped, and draped per clinical protocols. A local anesthetic can be injected at the needle insertion site. A needle assembly 6506 including a needle 6506a and a stylet 6506b can be inserted into the epidural space, such as with a bevel of the needle facing up at an angle of 45° or less. The stylet 6506b is then removed from the needle 6506a. Proper positioning of the needle tip in the epidural space can be performed using the "loss-of-resistance" technique.

Lead 265 can include a pre-loaded bent stylet, stylet 6507. This stylet 6507 can extend to the tip of the lead. The lead 265 including its stylet 6507 can be inserted through the insertion needle 6505a. In some embodiments, lead 265 includes multiple stylets 6507 (e.g. multiple different stylets 6507a, 6507b, and so on). If exchange of a stylet 6507 is desired, the existing stylet (e.g. a stylet 6507a) can be carefully pulled out of the lead 265, and a different stylet (e.g. a stylet 6507b) inserted. If resistance is encountered during a stylet 6507 insertion, rotation of the lead 265 and/or stylet 6507 can be performed (e.g. a rotation that occurs after a small withdrawal of the stylet 6507).

Lead 265 including a stylet 6507 can be advanced to the appropriate vertebral level under fluoroscopic guidance. A sufficient length of lead 265 (e.g. at least 10 cm, or approximately three vertebrae) should reside in the epidural space (e.g. to aid in stabilization of lead 265).

If multiple leads 265 are to be implanted, the above steps can be repeated for each lead 265.

Figure 15A:
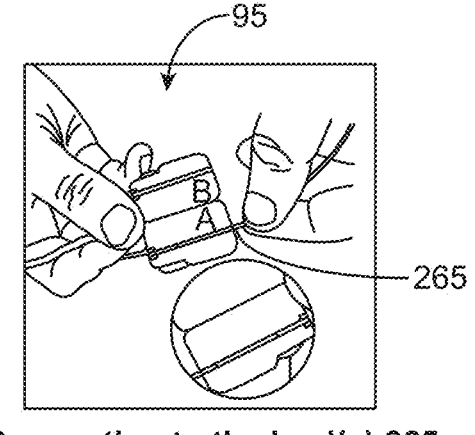

Referring to FIG. 15A, while holding lead 265 in place, the interface connector 95 is connected to the proximal end of each lead 265 by opening a hinged lid of connector 95 and inserting the proximal end of each lead 265 into the access port on the side of the lid. A verification that lead 265 is fully inserted into connector 95 can be performed, such as through a visual observation port on the top of the hinged lid(s). The lid(s) is then closed, which can be confirmed by the presence of a snapping sound provided by connector 95. If a single lead 265 is inserted, it can be inserted into a predetermined port of connector 95 (e.g. the bottom access port A shown in FIG. 15a).

In some embodiments, the female end of interface connector 95 (e.g. a larger end) can be connected to an extension cable of apparatus 10. This extension cable can be connected to a trial stimulator device of apparatus 10, such as trialing interface 80 and/or 90 described herein.

In some embodiments, the connections can be tested (e.g. impedance tested), such as by using clinician programmer 600" described herein. Inadequate connections can be reconnected and retested until a satisfactory result is achieved.

If paresthesia coverage is desired, an appropriate set of stimulation parameters can be identified, such as parameters beginning at a relatively medium pulse width and frequency range. The stimulation can be delivered, and an increase in amplitude performed while asking the patient questions (e.g. close-ended questions) to identify that patient's perception threshold, a discomfort threshold, and/or an area of coverage (e.g. paresthesia coverage).

In some embodiments, a fluoroscopic, ultrasonic, and/or other image of placement of lead 265 is taken, such as for record-keeping purposes.

Figure 15B:
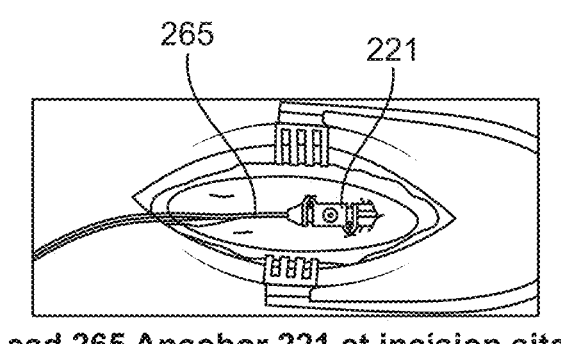

If performing a "staged trial", using a lead 265 to be permanently implanted, interface connector 95 can be detached from lead 265, and anchoring of lead 265 can be performed (e.g. as described herebelow in reference to FIG. 15B). If performing a "temporary trial" using a short term temporary implanted lead (e.g. a temporarily implanted lead 265), the excess portion of lead 265 can be coiled and the lead 265 and interface connector 95 can be covered (e.g. with gauze and dressing).

Referring now to FIG. 15B, anchoring of lead 265 can be performed by first removing the lead 265 stylet 6506, such as using fluoroscopy or other imaging to ensure that the lead 265 position does not change. As shown in FIG. 15B, a small midline incision can be made at the lead 265 skin entry site. An anchor element 221 can be placed over lead 265 and down to the supraspinous ligament or down to the deep fascial tissue. A confirmation that the tip of the anchor element 221 has been pushed into the ligamentous tissue can be performed.

A suture can be placed in the supraspinous ligament or deep facia, then lead 265 can be inserted through the suture and the suture tied off (e.g. to an eyelet of anchor element 221). After suturing to the eyelet, a set screw of anchor element 221 can be tightened (e.g. using a torque wrench, such as torque wrench 6508 described herein). A clicking sound can be provided when anchor 211 is locked. After the set screw is tightened, a second eyelet of anchor element 221 can be sutured to the supraspinous ligament or deep fascia. The secure attachment of lead 265, via anchor element 221, can be checked. A check can be performed to ensure that lead 265 has not moved, such as by performing a test stimulation and/or using imaging (e.g. fluoroscopic imaging) as necessary. If it is determined that lead 265 has undesirably migrated, the set screw can be loosened, lead 265 repositioned, and the set screw retightened. This process described in reference to FIG. 15B can be repeated for placement of additional leads 265.

Implantation of a ported-version of implantable device 200 is described herebelow in reference to FIGS. 15C-G.

If a staged trial was performed, as described hereabove, the following steps 1-5 are performed. If it wasn't a staged trial, only steps the 3-5 are performed.

(1) The lead extension is cut (e.g. with scissors or other cutting tool of apparatus 10), proximal to its connector. The remaining portion of the lead extension is pulled out through the exit wound site and discarded.

(2) Using torque wrench 6508, a set screw of a connector boot of the lead extension is loosened (e.g. rotated until a click is heard). The connector boot is removed and discarded.

Steps (1) and (2) can be repeated for additional leads 265 that have been inserted into the patient.

(3) The proximal end of the lead 265 can be cleaned, and then inserted into the implantable device 200 connector (e.g. until it is fully inserted and a set screw ring is located directly under the set screw).

(4) A check that the lead 265 is fully inserted is performed.

(5) Using torque wrench 6508, the set screw of implantable device 200 is tightened (e.g. until a click is heard, indicating the lead 265 is properly secured).

Steps (3) through (5) can be repeated for any additional leads 265 that have been inserted into the patient.

Figure 15C:
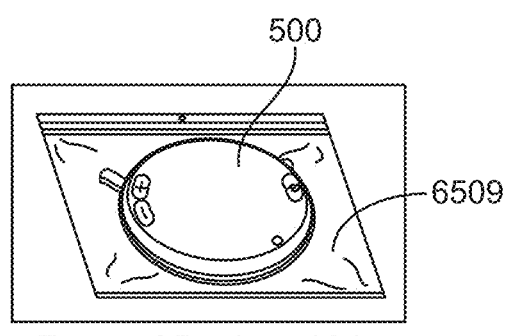

Referring now to FIG. 15C, an external device 500 can be included in a sterile bag, sterile bag 6509, as shown. The external device 500 can be positioned proximate the implantable device 200 that has been implanted in the patient, such as to perform a test stimulation. A check of a desired physiologic response can be performed during the test stimulation. External device 500 can be oriented such that any buttons or other controls of user interface 580 of external device 500 are facing away from the implantable device 200 when performing the test stimulation.

Figure 15D:
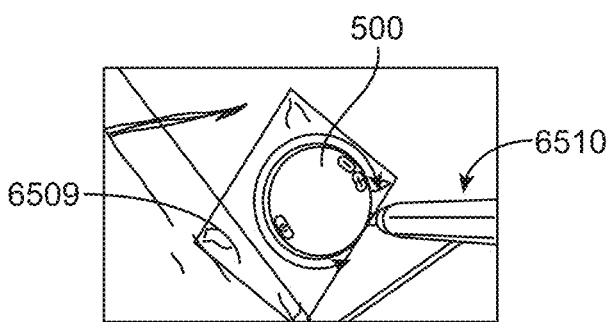

Referring now to FIG. 15D, the desired implantation site for the implantable device 200 can be located lateral to the midline incision. This final implantation site can be predetermined via consultation with the patient prior to the implantation procedure. With the external device 500 still in the sterile bag 6509, the periphery of the external device 500 can be traced with a surgical marker of apparatus 10, sterile marking tool 6510 shown, such as while the external device 500 is centered over the desired implantation site of implantable device 200.

Referring now to FIG. 15E, the lower distal end of a tunneling tool of apparatus 10, such as tunneling tool 6504 described herein, is inserted into the midline incision, with the top portion of tunneling tool 6504 positioned above the skin (e.g. to function as a depth guide and/or to gauge length). Using blunt dissection, a subcutaneous tissue path from the midline incision site to the final implant location of implantable device 200 is performed by advancing the tip of tunneling tool 6504 until the tip of tunneling tool 6504 is approximately the length of implantable device 200 from the center of the traced outline of external device 500 described hereabove. Tunneling tool 6504 can include markings 6504a (e.g. markings equidistantly spaced, such as at a separation distance of 1 cm) that are used to measure the distance from the incision site to the final implant location of implantable device 200. Tunneling tool 6504 can be maintained relatively shallow during tissue tunneling, without puncturing the skin. The pocket can be irrigated, such as with sterile saline solution and/or antibiotic solution. Tunneling tool 6504 is configured to cause implantable device 200 to be positioned below the skin at a constant depth and approximately parallel to the skin, such as to ensure successful transmissions of power and/or data between implantable device 200 and an external device 500 during use.

Referring now to FIG. 15F, tunneling tool 6504 can be used as a template. Tunneling tool 6504 can be placed on the skin and the tunneling path traced using the top portion of the tool 6504 from the midline incision to the center of the outline of the external device 500 location.

The tip of a tool configured to insert implantable device 200, insertion tool 6511 (shown in FIG. 15G), is inserted into a receptacle of implantable device 200 (e.g. port 2111 described hereabove in reference to FIG. 7A-B), such as a receptacle proximate the location where lead 265 or a lead extension protrudes from housing 210 of implantable device 200. Insertion tool 6511 can be sized and configured to frictionally engage implantable device 200 during the positioning process.

Referring now to FIG. 15G, the tunneling tool 6504 (not shown in FIG. 15G) can be withdrawn until only its tip portion remains within the tissue tunnel (e.g. in order to retain the tunnel location and path). The insertion tool 6511, with attached implantable device 200 is made available (e.g. positioned proximate the tunnel location) as shown. The tunneling tool 6504 is then completely removed, and soon thereafter the implantable device 200 is advanced into the tissue tunnel (e.g. in a particular orientation, such as with a logo or other marker facing toward the patient's skin). Forceps can be used to lift the superior edge of the midline incision to further facilitate insertion.

The implantable device 200 is advanced with a pushing motion along the subcutaneous tissue path until the device 200 is located at the center of the external device 500 marked outline. Verification of proper placement can be performed, such as using palpation.

If excessive resistance is encountered upon initial insertion of the implantable device 200 into the tissue tunnel created by tunneling tool 6504, a check that the implantable device 200 is positioned (e.g. oriented) properly within the tissue tunnel can be performed. If insertion tool 6511 is detached from the implantable device 200, a gentle pull back on the lead(s) 265 can be performed to remove the implantable device 200 from the tissue tunnel.

If excessive resistance inserting the implantable device 200 is encountered after multiple attempts, alternative tools, such as forceps, can be used for placement.

Once properly positioned, while slight pressure is applied to the implantable device 200, insertion tool 6511 is detached (e.g. by simultaneously applying a pulling force), leaving the implantable device 200 in place.

A check of connections can be performed, such as using an impedance measurement (e.g. as described herein). If impedance is at an undesired level, connections can be checked and/or remade, and an impedance check repeated.

Any excess length of lead 265 can be looped and/or tucked into the incision site and/or tissue tunnel.

The midline incision is closed, and the wound dressed.

While the method described in reference to FIGS. 15C-G provides one method of implanting a ported-version of an implantable device 200, alternative methods can be performed. For example, one alternative method is described immediately herebelow.

Leads 265 are placed and anchored, for example as described hereabove.

The final pocket site for the implantable device 200 is located as desired (e.g. a location pre-determined with the patient prior to the implantation surgery). With an external device 500 in a sterile bag 6509, the outline of the external device 500 is traced with sterile marking tool 6510 with the external device 500 centered over the desired implantable device 200 final pocket site.

A small incision is made near the desired pocket site.

The desired route of the tissue tunnel is marked on the patient's skin.

A local anesthetic is administered along the intended tissue tunnel path.

If necessary or at least desired, a tissue tunneling device, tunneling tool 6512, is bent to conform to the patient's body. Tunneling tool 6512 can comprise a handle, a malleable (e.g. stainless steel) rod with a sharp tip that is used to create a tissue tunnel (i.e. a subcutaneous pathway) for the passage of lead 265 and/or a lead extension. Tunneling tool 6512 can further include a sleeve (e.g. a plastic sleeve).

Tunneling tool 6512 can be used to create a subcutaneous tunnel between the lead(s) 265 incision site and the implantable device 200 pocket incision site until the tool 6512 is visible and accessible at the exit point (e.g. the exit of the tunnel at the surface of the skin).

Once in place in the created tissue tunnel, a handle (e.g. a loop) of tunneling tool 6512 can be grasped with one hand, while holding its sleeve with the other hand. The shaft of the tool 6512 can be pulled out through the sleeve, leaving the sleeve in place.

A lead 265 (or lead extension) can be pushed through the tool 6512 sleeve, and then the sleeve withdrawn from the tissue tunnel.

The proximal end(s) of the lead 265 can be pulled out of the exit point.

The proximal end(s) of the lead 265 can be cleaned, and then inserted into the implantable device 200 connector (e.g. until it is fully inserted and a set screw ring is located directly under the set screw), such as is described hereabove in reference to FIG. 15B hereabove. Further implantation steps can be performed as described in reference to FIGS. 15B-G.

Implantation of an integrated-version of implantable device 200 is described herebelow in reference to FIGS. 15H-K.

Figure 15H:
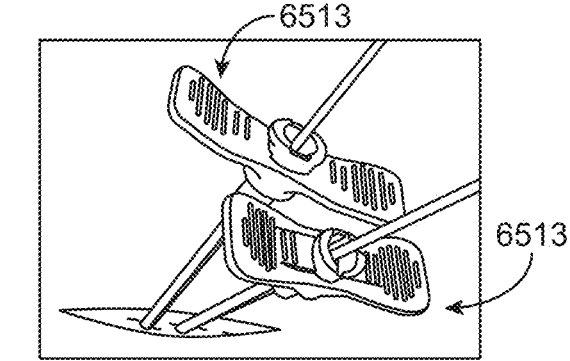
Figure 15I:
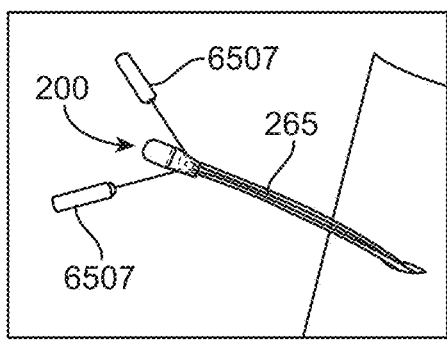

Referring now to FIG. 15H, the patient is positioned, prepared, and draped. A local anesthetic is injected at the needle insertion site. Under fluoroscopic guidance, the distal portion of a tearaway introducer, introducer 6513, has been inserted into the patient (e.g. into the epidural space of the patient). In the embodiment of FIG. 15H, two introducers 6513 have been inserted (e.g. to implant two leads 265).

Introducer 6513 can include needle 6513a, stylet 6513b, and sheath 6513c. During insertion, the angle of the insertion needle 6513a of introducer 6513 can be maintained at an angle of 45° or less. Steep angles increase the insertion force of stylet 6513b, and can also present more of an opportunity for stylet 6513b to pierce lead 265 and cause tissue damage. The distance between the sheath 6513c opening and the needle 6513a opening, can be below a maximum, such as is described herebelow in reference to FIG. 16. This distance can be considered by the clinician when entering the epidural space.

Stylet 6513b is then removed from sheath 6513c. Entry into the epidural space can be verified (e.g. using the loss-of-resistance technique).

Needle 6513a is then removed from sheath 6513c.

Lead 265 is loaded (e.g. pre-loaded) with stylet 6507, such that stylet 6507 extends to the tip of lead 265. In some embodiments, multiple leads 265 are each loaded with a stylet 6507, such as the two leads 265 and two stylets 6507 shown in FIG. 15I. Subsequently, each lead 265 and loaded stylet 6507 is slowly inserted through a sheath 6513c.

In some embodiments, an exchange of stylet 6507 can be performed (e.g. with a stylet 6507 of a different configuration to the stylet loaded into lead 265), such as a stylet 6507 exchange as described hereabove.

Figure 15J:
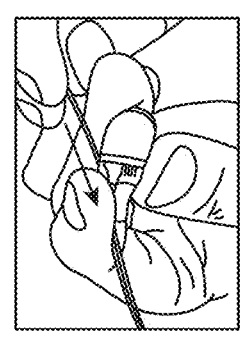

In some embodiments, to facilitate loading of a stylet 6507 into an integrated lead 265, the lead 265 is first aligned with the general direction of the stylet lumen path of the implantable device 200, as shown in FIG. 15J. Once aligned, the tip of the stylet 6507 can be inserted into the associated opening of implantable device 200 and stylet 6507 advanced into lead 265.

Figure 15K:
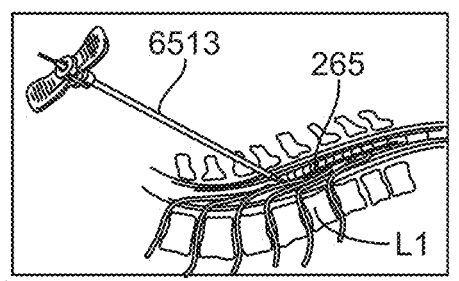

Subsequently, lead 265 can be advanced to the appropriate vertebral level, such as an advancement performed under visual guidance (e.g. fluoroscopy and/or ultrasound imaging), as shown in FIG. 15K. Sufficient length of lead 265 (e.g. at least 10 cm and/or approximately three vertebrae) should reside in the epidural space (e.g. to aid in stabilization of lead 265).

If implantable device 200 comprises dual leads 265, the second lead 265 can be implanted in a similar fashion.

While holding the one or more leads 265 in place, impedance levels can be checked and/or test stimulation can be performed (e.g. using an external device 500 positioned in sterile bag 6509). If paresthesia coverage is desired, an appropriate set of stimulation parameters can be identified, such as parameters beginning at a relatively medium pulse width and frequency range. The stimulation can be delivered, and an increase in amplitude performed while asking the patient questions (e.g. close-ended questions) to identify that patient's perception threshold, a discomfort threshold, and/or an area of coverage (e.g. paresthesia coverage).

Figure 15L:
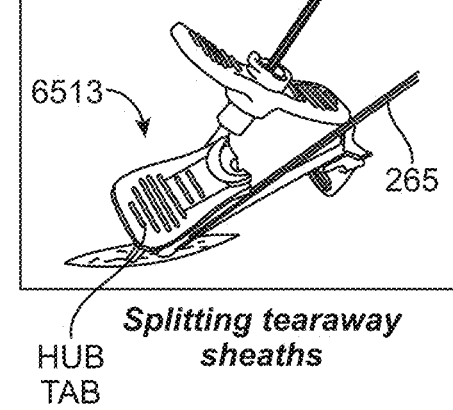

The tearaway introducer sheath 6513c can be removed (e.g. each half at a time) by grasping hub tabs of the sheath 6513c as shown in FIG. 15L.

Anchoring of lead 265 can be performed, such as using anchor element 221 as described hereabove in reference to FIG. 15B.

Proximal to the one or more anchor elements 221, a small loop in the lead 265 can be created (e.g. to create slack).

Implantable device 200 can be implanted in the final pocket site, as described hereabove.

In some embodiments, a lead extension is positioned between implantable device 200 and lead 265 (e.g. between housing 210 and lead 265). In these embodiments, a desired location of a tissue tunnel is marked (e.g. on the patient's skin). Anesthetic is administered along the intended tissue tunnel path.

If necessary or at least desired, a tissue tunneling device, tunneling tool 6512 described hereabove, is bent to conform to the patient's body.

A small incision is created at the desired exit site, and the tunneling tool 6512 is prepared for use (e.g. a protective cap is removed if present).

A tissue tunnel is created in the subcutaneous tissue between the midline incision and the exit site until the shaft of the tunneling tool 6512 is visible and accessible at the exit point. In order to minimize the risk of infection, tunneling can be performed away from the initial incision site, in the contralateral and superior direction.

Once in place in the created tissue tunnel, a handle (e.g. a loop) of tunneling tool 6512 can be grasped with one hand, while holding its sleeve with the other hand. The shaft of the tool 6512 can be pulled out through the sleeve, leaving the sleeve in place.

The proximal end of the lead 265 can be cleaned, and then inserted into a connector of the lead extension (e.g. until it is fully inserted and a set screw ring is located directly under the set screw). If an obstruction is suspected when inserting lead 265 into the lead extension, the set screw can be loosened (e.g. using torque wrench 6508) and/or the lead 265 can be gently rotated.

Once proper insertion of the lead 265 is confirmed, the set screw can be tightened (e.g. using torque wrench 6508), such as a tightening that proceeds until a clicking sound is observed.

An appropriately-sized pocket in the tissue is formed (e.g. using blunt dissection), on either side of the midline for coiled excess lead 265 and/or lead extension.

A small loop is created in lead 265 for slack.

The free end of the lead extension is passed through the sleeve of tunneling tool 6512 until it emerges from the exit site. Excess slack is removed by pulling the lead extension from the exit site.

These steps can be repeated for a second lead extension.

Interface connector 95 can be attached to the lead extension, such as is described hereabove in reference to FIGS. 11A-D, and a test stimulation performed to verify desired response of the implantable device 200.

If a staged trial using a permanent lead 265 is being performed, a small suture can be used to close the exit site of the lead extension. Tape can be placed and a stress relief loop created in the lead extension, and the wound dressed.

The midline incision can be closed and covered with gauze and dressing. The lead extension can be coiled and covered with gauze and dressing at the exit site.

In some embodiments, implantable device 200 is implanted to perform peripheral nerve stimulation. For example, implantable device 200 can be implanted to stimulate one or more peripheral nerves selected from the group consisting of: suprascapular nerve; brachial plexus nerve; intercostal nerve; ulnar nerve; median nerve; radial nerve; cluneal nerve; femoral nerve; ilioinguinal nerve; sacral nerve; scrotal nerve; pudendal nerve; sciatic nerve; peroneal nerve; sural nerve; tibial nerve; and combinations of these.

In an implantation procedure in which peripheral nerve stimulation is to be accomplished, the patient can be positioned, prepped, and draped per clinical protocols. The area of the patient's peripheral nerve(s) to be stimulated can be mapped and the planned trajectory marked on the skin.

A local anesthetic can be injected at the needle insertion site.

If necessary or desired, a puncture incision can be made before inserting a needle or introducer.

A needle and/or introducer can be advanced through the incision in the direction of the peripheral nerve. If using a needle, an included stylet can be removed, leaving the needle in place. If using an introducer, an included needle can be removed leaving a sheath in place.

One or more leads 265 are provided, such as including bent stylet 6507. The stylet 6507 should be positioned to extend to the tip of the lead 265. The lead 265, including stylet 6507, is slowly inserted, through the insertion needle or sheath.

If an exchange of stylet 6507 is desired, the existing stylet 6507 can be pulled out, and a different stylet 6507 inserted, as described hereabove.

These steps can be repeated if a second lead 265 is to be implanted.

While holding lead 265 in place, the needle or sheath is pulled back to expose contacts of lead 265.

Figure 15M:
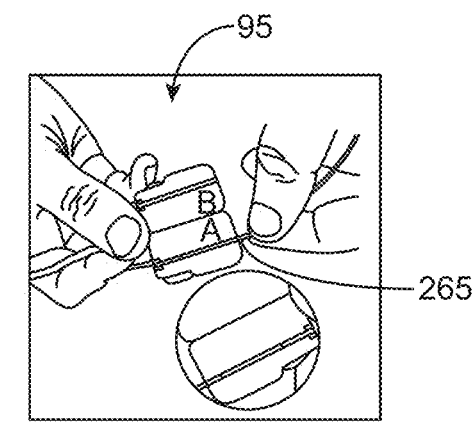

While holding lead 265 in place, interface connector 95 is connected to the proximal end of lead 265 by opening the hinged lid(s) of connector 95 and inserting the proximal end of lead(s) 265 into the access port on the side of the lid. A verification that the lead 265 is fully inserted can be performed (e.g. through a visual observation port on the top of the hinged lid). The lid is closed (e.g. until a snapping sound is observed). If a single lead 265 is to be attached, the lead 265 can be connected to access port A, as shown in FIG. 15M.

In some embodiments, a cable extension can be used to connect lead 265 to interface connector 95, such as to position the interface connector 95 outside of the sterile field.

A check of connections (e.g. an impedance measurement) can be performed, such as using a programmer 600 (e.g. clinician programmer 600″).

If paresthesia coverage is desired, an appropriate set of stimulation parameters can be identified, such as parameters beginning at a relatively medium pulse width and frequency range. The stimulation can be delivered, and an increase in amplitude performed while asking the patient questions (e.g. close-ended questions) to identify that patient's perception threshold, a discomfort threshold, and/or an area of coverage (e.g. paresthesia coverage).

In some embodiments, a fluoroscopic, ultrasonic, and/or other image of placement of lead 265 is taken, such as for record-keeping purposes.

If performing a "staged trial", using a lead 265 to be permanently implanted, interface connector 95 can be detached from lead 265, and anchoring of lead 265 can be performed (e.g. as described hereabove in reference to FIG. 15B). If performing a "temporary trial" using a short term implanted lead (e.g. a temporarily implanted lead 265), the excess portion of lead 265 can be coiled and the lead 265 and interface connector 95 can be covered (e.g. with gauze and dressing).

Anchoring of the lead 265 can be performed as described hereabove in reference to FIG. 15B.

Implantation of implantable device 200 can be performed as described hereabove in reference to FIGS. 15C through 15L.

In some embodiments, one or more implantable devices 200 that have been implanted in a patient are explanted. An explantation procedure is described immediately herebelow.

The initial incision and/or lead 265 skin entry site is located. This identification can be performed by palpation, observation of existing surgical artifacts (i.e., previous sites as indicated by scarring), patient interviews, and/or by using fluoroscopy.

A small midline incision is made at this entry site.

Sutures are cut and removed from the anchor elements 221.

Lead 265 is uncoiled, and pulled on the slack end(s) of the lead 265 loop(s), until the distal tip of the lead(s) 265 emerges from the epidural space.

Once the distal end of the lead(s) 265 has been removed from the epidural space, the remaining slack in the lead(s) 265 is pulled in order to dislodge and remove the implantable device 200.

After the implantable device 200 has been removed, all components can be verified to be intact, and that all previously implanted materials are accounted for (e.g. removed or intentionally left in place).

The midline incision is closed and covered with gauze and dressing.

Referring now to FIG. 16A-B, a side view of an introducer tool, and a magnified side view of the distal portion of the introducer tool is illustrated, consistent with the present inventive concepts. Implantation tool 65 can comprise an introducer with a tear-away sheath, introducer 6513 shown. Introducer 6513 can include introducer needle 6513*a*, and tear-away sheath 6513*c*. Needle 6513*a* can include a beveled distal end, bevel 6513*d* shown. Sheath 6513*c* and needle 6513*a* comprise lengths such that when needle 6513*a* is fully inserted into sheath 6513*c*, bevel 6513*d* is completely outside of sheath 6513*c*, but within a relatively small distance, D$_1$, of the distal end of sheath 6513*c*, such as to reduce the likelihood of needle 6513*a* entering a target location of interest (e.g. the epidural space), without the distal end of sheath 6513*c* also entering that target location. In some embodiments, D1 comprises a length of no more than 3 mm, or no more than 2 mm.

Referring now to FIGS. 17A-C, views of an external device and a charging device are illustrated, consistent with the present inventive concepts. FIG. 17A is a perspective view of charger 61, and FIG. 17B is an exploded view of charger 61. FIG. 17C is a view of an external device 500 positioned just above a charging position within charger 61. As described hereabove in reference to FIG. 1, one or more external devices 500 can comprise an integrated power supply 570 comprising one or more rechargeable elements, such as a rechargeable battery. Each external device 500 can be configured to engage a charging device, charger 61 shown, such that power supply 570 can be recharged. Charger 61 can be configured to attach to standard wall AC power, and/or it can include an integral battery (e.g. a replaceable or rechargeable battery).

Charger 61 comprises housing 6110, which includes top housing 6110*a* and bottom housing 6110*b*. One or more contacts, contacts 6120, can be positioning on housing 6110*a* and can be configured to electrically connect to mating contacts of external device 500, contacts 571, as shown in FIG. 17C. Contacts 6120 are connected to energy-providing circuitry of charger 61 (not shown), and contacts 571 are connected to charging circuitry of power supply 570 of external device 500.

Charger 61 can comprise one or more features to maintain the position of an external device 500 during charging. For example, charger 61 can comprise flange 6112 which is configured to frictionally engage the perimeter of each external device 500. Alternatively or additionally, charger 61 can comprise recess 6111 which is configured to slidingly receive a mating projection of each external device 500, projection 512, each shown in FIG. 17C. In some embodiments, charger 61 comprises two or more recesses 6111 and external device 500 comprises two or more mating projections 512. In some embodiments, one or more recesses 6111 of charger 61 comprises a projection, and one or more projections 512 of external device 500 comprises a mating recess. Recess 6111 and/mating projection 512 are positioned and include a geometry (e.g. the "N" shape shown or other geometry that allows a single rotational orientation of device 500) such that when external device 500 is inserted into charger 61, contacts 6120 make contact with the corresponding contacts 571 (e.g. the contacts are vertically aligned when projection 512 mates with recess 6111).

In some embodiments, charger 61 comprises one or more magnets, magnet 6113, which can be configured to magnetically attract a magnetic material of each external device 500, such as ferrite disk 557 described hereabove in reference to FIG. 10. In some embodiments, charger 61 comprises one or more magnets 6113 as well as one or more other external device 500 retention features (e.g. flange 6112 and/or recesses 6111 described hereabove). Alternatively or additionally, external device 500 can comprise mating magnets or other magnetic material (e.g. magnetic material which provides correct orientation of contacts 6120 and 571 as described hereabove).

Contacts 6120 and 571 can comprise mating conductive surfaces which make sufficient electrical contact when an external device 500 is properly positioned in a charger 61. Alternatively, the pair of charging contacts can comprise a standard micro or mini USB port and plug.

Charger 61 can comprise one or more features which cause external device 500 to tend to remain properly engaged with charger 61, once in place. For example, flange 6112 (which mates with housing 510) and/or magnets 6113 (which attract ferrite disk 557 or other magnetic material of device 500) can be configured to work singly or in combination to cause external device 500 to remain in place.

In some embodiments, charger 61 comprises a memory module 6114 which includes electronic memory and circuitry configured to record and process information related to charge and/or discharge cycles of one or more external devices 500, as well as record other characteristics, each of which can be used to predict power supply 570 condition, expected longevity and the like, which can be presented to a user or manufacturer of external device 500 (e.g. via a user interface of charger 61, not shown, or other user interface of apparatus 10).

In some embodiments, charger 61 comprises an interface module 6115 which is configured to interface with a communication network via a wired or wireless communication, such as a communication network selected from the group consisting of: cellular service; the Internet; LAN; WAN; computer network; and combinations thereof. In these embodiments, communication with an external device 500 attached to charger 61 can be performed remotely, such as by a clinician of the patient or a manufacturer of external device 500. The communication can include downloading of apparatus 10 use information, and/or programming of external device 500 or other apparatus 10 component.

In some embodiments, charger 61 comprises a light, display, or other user output component, indicator 6121 shown. Indicator 6121 can comprise a ring-geometry, such as a ring that is positioned between two portions of housing 6110 as shown in FIG. 17B. Indicator 6121 can comprise one or more light emitting diodes or other visual indicators, ("LEDs" herein), such as one or more LEDs that change color (e.g. from yellow to orange to green) to indicate different charging status of the power supply 570 of the external device 500 being charged. The LEDs can be positioned under a ring of translucent plastic or other translucent material.

In some embodiments, charger 61 provides charging energy to power supply 570 of external device 500 via wireless transfer of energy (e.g. avoiding the need for contacts 6120 and 571). For example, charger 61 and external device 500 can comprise corresponding mating inductive coils for energy transfer.

Referring additionally to FIG. 17D, a schematic of external device 500 charging circuitry is illustrated, consistent with the present inventive concepts. External device 500 can be configured to prevent corrosion of contacts 571. External device 500 (e.g. controller 550 and/or power supply 570) can include circuitry configured as a passivation module (e.g. to prevent corrosion on contacts 571, such as in the presence of salts, sweat, and the like). When an external device 500 is not operably connected to charger 61 (e.g. as detected by external device 500), external device 500 removes the voltage from being present at contacts 571. As shown in FIG. 17D, when external device 500 is not operably connected to charger 61, Q1 acts as an open switch, and power supply 570 is disconnected from pins 571. When external device 500 is operably connected to charger 61, a voltage is sent on the "detect" pin, which closes Q2, which in turn closes Q1, connecting power supply 570 to pins 571 (which in turn is connected to charger 61 pins 6120, such as to charge power supply 570).

In some embodiments, external device 500 is configured to detect an operable (e.g. successful) connection to charger 61. In these embodiments, when such a connection is detected, external device 500 can be configured to shut down one or more transmissions to an implantable device 200 (e.g. a transmission comprising transmission of stimulation energy and/or data to an implantable device 200), such as when external device 500 enters a "sleep state" when attached to a charger 61, to prevent undesired load on power supply 570 while charging.

Dual levels of power supply 570 protection can be included, such as protection circuitry including active circuitry and/or passive components (e.g. a thermal or other resettable fuse). In some embodiments, power supply 570 includes a battery including protective circuitry. In some embodiments, external device 500 and/or charger 61 includes circuitry to protect power supply 570.

Referring now to FIG. 18, a schematic view of a portion of electronic assembly 255 is illustrated, consistent with the present inventive concepts. Electronic assembly 255 comprises portion 255a which includes various components configured to safely and effectively deliver stimulation energy to tissue. Electronic assembly portion 255a includes address-mapped registers that can be written directly from external device 500 via a forward-telemetry (FTEL) link, but bandwidth constraints of that link could limit the rate at which stimulation delivered by implantable device 200 can occur. To overcome this limitation, a digital control structure known as the Stimulation Control Table (SCT) is used. Electronic assembly portion 255a of implantable device 200 includes a configurable state machine (Stimulation Control Table—SCT) that can execute autonomously (e.g. within pre-determined limits) to generate stimulation pulses and maintain fine grained (e.g. precision) stimulation control of timing and amplitude. Being a state machine (as opposed to a microcontroller) the SCT cannot perform computations or make decisions, and therefore its behavior is deterministic and highly predictable. Specifically, the following types of parameters can be encoded in the registers and parameters that drive the state table: pulse width; inter-phase gap; and/or inter-pulse gap. The SCT can also specify the amplitude of stimulation from a register. Alternatively, the amplitude (and timing) can be specific directly in the sequence or it can be provided dynamically.

Layered above a pulse or series of pulses, a "loop" can be used to play a sequence repeatedly (e.g. the SCT includes 4 nested loop levels). The loops also allow for long sequences of pulses to be played without involvement from external device 500 (thereby reducing telemetry traffic, such as to improve EMI and/or power efficiency). With a local clock source, the SCT can execute commands without any external involvement for significant periods of time (depending on the stability and accuracy of the clocks of external device 500 and implantable device 200). Loops can also be used to implement trains of stimulation pulses and/or bursts of stimulation pulses.

The SCT can include the ability to implement a 1-level sub-routine. The sub-routine minimizes the usage of program memory (allowing the electronic circuitry to be smaller). Additionally or alternatively, the sub-routine can allow for complex and arbitrary waveforms to be implemented.

The stimulation amplitude, loop counters and intervals (which can be used for pulse width, inter-pulse gap, etc.) can be modified by the external device 500 at run time and are used by the SCT when a subsequent start command is received. In this manner, significant change can be made to the stimulation patterns with minimal telemetry information needing to be transmitted from external device 500 to implantable device 200. The SCT can trigger measurements. The SCT can check status registers (whose contents can be set from comparisons between registers and/or measured quantities) and relay results to the external device 500 and/or autonomously take action as a result of the checking. The SCT can halt stimulation if errors are detected.

Referring additionally to FIG. 19 a representation of a TTAP packet description format is illustrated, consistent with the present inventive concepts. External device 500 includes a digital control structure called the Telemetry Timing Aware Peripheral (TTAP). The TTAP works with the SCT described hereabove to ensure reliable and efficient operation of apparatus 10. The TTAP starts the sequence of stored instructions in the SCT program table, where the SCT executes the sequence once and waits for further TTAP start commands.

In this manner, the autonomous execution time can be controlled while starting a new sequence with minimal telemetry. The TTAP can turn the external device 500 on and off to coincide with the stimulation pulses delivered by implantable device 200, within a sequence, to ensure optimal and sufficient power delivery. The TTAP uses a crystal-controlled clock source, and is the master time base for apparatus 10. The rate at which the TTAP issues start commands to the SCT can determine the overall stimulation rate.

In some embodiments, the stimulation control table can store multiple sets of instructions that can be invoked by the TTAP. Each time the TTAP issues a start command to the SCT, the TTAP can request to start the previous set of instructions or a start a new set (generally stored at a different starting address). Such a configuration can be implemented to efficiently execute complex waveforms (for instance, combining a train stimulation waveform with a traditional tonic waveform).

Referring now to FIG. 20A, a schematic view of a power delivery and consumption arrangement of a stimulation apparatus is illustrated, consistent with the present inventive concepts. Apparatus 10 of the present inventive concepts can include arrangement 11 which can be configured to enhance reliability of apparatus 10 (e.g. enhance reliability of therapy delivery and/or other functionality). Arrangement 11 can be performed by and/or can include one or more components positioned within external device 500, implantable device 200, and/or another component of apparatus 10. In some embodiments, arrangement 11 can be configured to reduce power consumption (e.g. enhance battery or other power supply 570 life of an external device 500). In some embodiments, an implantable device 200 receives wireless power from an external device 500, and arrangement 11 is configured to both enhance reliability (e.g. enhance reliability of therapy delivery by the implantable device 200) and reduce power consumption (e.g. enhance battery life of the external device 500). For example, arrangement 11 can be configured to avoid time periods in which insufficient power is received by an implantable device 200. Simultaneously, arrangement 11 can include one or more algorithms, algorithm 15 (e.g. one or more "optimization" algorithms), which routinely (e.g. continuously) and intelligently adapt to the physical environment of one or more components of apparatus 10, while external device 500 provides power above a minimum threshold required for reliable operation (e.g. reliable stimulation of implantable device 200). These algorithms 15 can also adapt to diverse therapy configurations (e.g. diverse amounts of stimulation energy being delivered) and/or adapt to various implantable device 200 state conditions, and the algorithms 15 can manage transitions in these configurations and conditions.

Each implantable device 200 is desired to be relatively small, and therefore can have limited energy storage capacity (e.g. limited energy storage capacity of energy storage assembly 270). When there is a change in power transfer (e.g. a sudden change that can occur with patient motion) and/or there is a change in power consumption (e.g. due to a change in delivery of stimulation energy), arrangement 11, via algorithm 15, can be configured to rapidly adapt so that power delivery from an external device 500 to the implantable device 200 remains sufficient for safe and reliable operation.

Apparatus 10 can include multiple mechanisms for adjusting power delivery between an external device 500 and an implantable device 200. For example, a first mechanism can adjust the amplitude of power transmitted by external device 500 to change the output power of the transmission signal (e.g. an RF signal). Alternatively or additionally, a second mechanism can turn the power transmitted by external device 500 on and off, such as via a duty cycle that includes a ratio of "on time" versus "off time" that is set and/or adjusted by an algorithm 15 (e.g. an optimization algorithm of arrangement 11, such as an algorithm 15 of external device 500). Power is wasted if energy stored on implantable device 200 reaches a maximum value (e.g. further charging can't occur) and external device 500 continues to deliver power. This energy storage maximum can be limited by an acceptable input voltage of a rectifier (e.g. rectifier 232) of implantable device 200, the rectifier operating as a charge pump, providing a voltage multiplication of an input voltage of an antenna (e.g. antenna 240) of implantable device 200. Implantable device 200 can include other electronic componentry that limits a maximum voltage for energy storage (e.g. the circuitry includes a voltage clamp that prevents an excessive voltage from damaging an electronic component).

Arrangement 11 can be configured to perform duty cycle modulation of power transferred by an external device 500 based on an amplifier of external device 500 being more efficient when charging at particular power levels (e.g. high-power levels) that do not saturate circuitry of implantable device 200 and/or do not cause reduced efficiency by exceeding an optimal input voltage of a rectifier 232 of implantable device 200. As described hereabove, power can be delivered in bursts via duty cycle modulation which can deliver power before and after stimulation pulses (e.g. in a symmetric pattern). Power delivery before stimulation can prevent a significant voltage drop (e.g. of energy storage assembly 270) when implantable device 200 transitions from operating at a quiescent current to delivering stimulation energy to tissue. If sufficient energy is available, boosting circuitry of implantable device 200 can operate with a minimum conversion ratio, which increases efficiency and maximizes the instantaneous power implantable device 200 can deliver (e.g. stimulation energy delivered to tissue). Power delivery after stimulation can replenish energy used during stimulation, and it can reduce impact of disturbances in power transfer. Duty cycle modulation can be applicable to idle (e.g. no stimulation) modes and/or lower frequency stimulation modes (e.g. stimulation below approximately 1.5 kHz or below 1 kHz). When varying power transfer with duty cycle, an optimization algorithm 15 of arrangement 11 can measure stored energy in implant 200 (e.g. stored in energy storage assembly 270) once every stimulation period (e.g. a period of time in which one or more forms of stimulation energy is delivered), and algorithm 15 can adjust the duty cycle based on an analysis of energy requirements for that stimulation period. Energy measurements (e.g. voltage measurements) can be taken (e.g. immediately) prior to a first stimulation pulse in the stimulation period, a point in which the stored energy can be high. To measure a target energy level effectively, a target voltage of energy storage assembly 270 can be set slightly below the maximum allowed value. An optimization algorithm 15 can determine a target (maximum) value of energy storage by increasing (or maximizing) the duty cycle for a (short) time period, and subsequently measuring the energy level. Alternatively or additionally, the energy level can be occasionally increased over time until a constant error is observed (e.g. a maximum has been achieved), which also indicates a limit has been reached. The target energy level used by algorithm 15 can then be adjusted slightly below the maximum thereby allowing optimized energy storage with the described control loop (also referred to as "tracking loop" or "feedback loop" herein). During optimization, the duty cycle at each stimulation cycle can be fed to a lowpass digital filter with a time constant that is much slower than the stimulation rate, and the output of this filter can be sampled after several time constants. The filtered value is the average duty cycle during the sampling period. If the average duty cycle is too high, then the output power of the transmitter 530 of external device 500 can be increased. If the average duty cycle is too low, then the output power of the transmitter can be decreased. Controlling the average duty cycle can allow the power transmitter 530 of external device 500 to operate at an optimized point, and it can allow a feedback loop of arrangement 11 to quickly raise duty cycle in response to a disturbance in power.

Arrangement 11 can utilize duty cycle modulation when there are multiple stimulation pulses delivered in a stimulation period. The power transferred from external device 500 to implantable device 200 can be allocated based on energy of stimulation pulses, as well as when the pulses occur in the stimulation period. With multiple stimulation pulses, the periodic measurement of available energy in implantable device 200 can be performed immediately prior to the stimulation pulse delivering the greatest energy. In other words, if a stimulation period consists of multiple pulses, a timing of a stimulation period can be defined such that the largest energy pulse is the first pulse.

Arrangement 11 of FIG. 20A demonstrates the available energy over time, as power is transmitted and used by the device. As described above, power transmission is represented by two parameters, the amplitude of the transmission signal, and the duty cycle of transmission. Power consumption by each implantable device 200 comprises: energy delivered during stimulation; energy delivered performing other functions (e.g. sensing functions, data transmission function, and/or other functions); and/or quiescent energy required by implantable device 200 during minimal operation. Integrating the sum of power used over time determines energy to be stored in implantable device 200, which can have one or more limits as described hereabove. If the energy storage element of assembly 270 is a capacitor or battery, this limit will be reflected as a limit in the voltage as described hereabove. Circuitry of implantable device 200 can also have a maximum operating voltage that limits the energy that can be stored, also as described hereabove.

The power transfer efficiency between an external device 500 and an implantable device 200 represents the ability of external device 500 to provide energy to the implantable device 200 and represents the quality of the wireless link between two devices. This efficiency can vary over time (such as with patient motion and/or changes in environment), and the efficiency can be tracked by arrangement 11 such that the implantable device 200 neither loses power (causing an interruption in stimulation delivery and/or other implantable device 200 operation), nor is excessively charged (wasting power).

When apparatus 10 reaches a steady state, the duty cycle of power transmission can be stable. For example, over a (repeated) period of time of a control loop (a control loop managed by an optimization algorithm 15 of arrangement 11), the energy transmitted from external device 500 to implantable device 200 can be approximately equal to the sum of: the energy for therapy (e.g. stimulation energy delivered); the energy required for other functions of implantable device 200; and the quiescent energy requirements of implantable device 200. As a result, the available energy of implantable device 200 will rise and fall the same amount during each time period. Furthermore, the maximum energy will be maintained at a value slightly lower than a limit (e.g. a maximum voltage).

In some embodiments, algorithm 15 only modulates duty cycle. In some embodiments, algorithm 15 modulates both duty cycle and the voltage (e.g. to modulate the average power being transmitted). These modulations can be performed in relation to the current stimulation parameters.

Referring now to FIG. 20B, a schematic view of a power delivery and consumption arrangement of a stimulation apparatus is illustrated, consistent with the present inventive concepts. Apparatus 10 of the present inventive concepts can include arrangement 12 which can be configured to enhance reliability of apparatus 10 (e.g. enhance reliability of therapy delivery and/or other functionality). Arrangement 12 can control duty cycle of power transfer between an external device 500 and an implantable device 200. Arrangement 12 can be performed by and/or can include one or more components positioned within external device 500, implantable device 200, and/or another component of apparatus 10. Arrangement 12 includes arrangement 11 as shown, such as arrangement 11 described hereabove in reference to FIG. 20A. Arrangement 12 comprises a block to calculate an error (also referred to as a "loop error") between a setpoint energy level and a measured energy level. The calculated error is provided to a Proportional Integrator (PI) controller (e.g. a PI controller that includes a derivate control) which determines a power transmission duty cycle based on the calculated error. A high proportional path gain allows the control loop of arrangement 12 to respond quickly to disturbances (e.g. power transfer disturbances), thereby providing reliability in implantable device 200 function (e.g. uninterrupted delivery of stimulation energy). Periodically updating the amplitude of power transfer to keep the average duty cycle low provides a large dynamic range in the duty cycle, such that the proportional path has the required dynamic range to quickly respond to disturbances. The integral path drives the steady state error to zero, thereby providing the optimized resilience to disturbance and optimized efficiency.

The setpoint can be determined dynamically. The error and/or gain can be asymmetric, and can be adjusted based on previous measurements. Applying the charge time can include allocation over multiple stimulation pulses, each with different amplitudes and/or timings (e.g. timings such as pulse width timing and/or burst duration timing). Power transfer from external device 500 to implantable device 200 can be periodically adjusted to maintain a duty cycle with the desired dynamic range.

Arrangement 12 manages significant disturbances by maintaining an energy setpoint that is close to the energy storage limit of energy storage assembly 270. The setpoint can be determined by periodically determining the energy storage limit itself, such as by increasing the duty cycle limit to the maximum for a short period. The energy storage limit can be measured, and the energy setpoint can be set to a value slightly below the measured maximum. If apparatus 10 is in a steady-state mode and power transfer efficiency suddenly increases, the available energy can rise and reach the limit. The measured error will therefore be limited to a value slightly above the setpoint, and, response could be slow causing power to be wasted. This undesired performance can be mitigated by raising the loop gain in response to consecutive negative errors, or with asymmetric gain based on the direction of the error. If power transfer is high and the therapy at a low level (e.g. a low energy delivery level), the minimum duty cycle required for the energy storage measurement can be greater than necessary, and power could be wasted. Conversely, if power transfer is too low, then the average duty cycle can be large, and apparatus 10 may not have the dynamic range to respond to a disturbance. Therefore, it can be desirable to keep the duty cycle within a controlled range, such as a range between approximately 20% and 40%, or between 25% and 33%. This range can be maintained by lowpass filtering the duty cycle with a first order digital filter, and sampling the output every several time-constants, such as every 4 time-constants. The time constant of the digital filter can be approximately the same as the stimulation period or longer than the stimulation period in order to behave as a lowpass filter. If the duty cycle is out of this range, power transfer amplitude can be adjusted accordingly.

Referring now to FIG. 21, a schematic view of a back-telemetry circuit of an implantable device 200 is illustrated, consistent with the present inventive concepts. Controller 250 of implantable device 200 can include back-telemetry module 251 as shown in FIG. 21. Back-telemetry module 251 can be configured to provide dynamic threshold and polarity. Back-telemetry module 251 can include redundant bit encoding.

In some embodiments, controller 250 comprises a dynamic receiver. The dynamic receiver can include a dynamic mechanism for threshold and polarity. The receiver can be configured to determine thresholds of width of pulses, and/or polarity of pulses, dynamically. Controller 250 can receive a series of pulses, and it can decode the pattern dynamically. The dynamic receiver can determine levels (e.g. 1's and 0's) based on known parameters, such as to calibrate the receiver.

In some embodiments, back-telemetry from implantable device 200 to external device 500 may comprise adjusting an impedance connected to antenna 240 of the implant. The external device 500 can detect these changes in impedance to recover (i.e. receive) information from implantable device 200. The impedance changes can be performed in short pulses, with information encoded in the length of the pulses. To maintain a balance in timing and in the average amplitude, a data bit can be comprised of both a short and a long pulse. For example, a "0" bit can be represented as a short pulse followed by a long pulse, and a "1" bit could be represented by a long pulse followed by a short pulse. In this way, both the "0" and the "1" bit have an equal length of time and the same average signal level, (i.e. both 0 and 1 have equal high periods and low periods). This combination also offers redundancy to improve error detection and recovery.

In some embodiments, the beginning of a response can be represented by a "sync" mark, which can comprise a combination of short and long pulses that would not be possible in a normal data stream. The data sequence can be a fixed length that is known a priori so that the expected number of pulses is known. Knowing the exact number of expected pulses can aid in detecting and recovering from errors, for example in case a pulse is missed (e.g. not properly detected by external device 500). Additionally, since each data bit is an equal length of time and the data length is known, the exact position of errors in the data can be determined if they occur. Since distortion is most likely at the beginning of a pulse sequence, a preamble (e.g. a sequence of dummy data) can precede the actual data and the sequence can be decoded in reverse order, from the final pulse towards the first. If the data length is known, the decoder can stop decoding once all the data is recovered, ignoring the possibly distorted pulses at the start of the sequence.

In some embodiments, external device 500 can recover these pulses and convert them to a digital signal using an analog filter with a comparator. If the encoding described above is used to maintain a constant average signal regardless of the content of the data, then the comparator can compare the average to the envelope of the recovered signal to perform this conversion. Since this signal is detected from an impedance change, it is possible that the pulses will be recovered as either increases in the signal level or decreases in the signal level depending on the characteristics of the link, such as transmitted power or coupling. External device 500 can dynamically determine the polarity of the pulses by reading a known value from the implantable device 200, decoding the response, and adjusting the polarity based on the result (e.g. calibrating external device 500 based on the result). Additionally, it is likely the signal will be distorted when recovered on external device 500, and this distortion may also change based on the transmitted power level and coupling. This can result in the durations of the pulses changing as the device operates normally. To correctly recover this data, the external device 500 can accumulate the durations of all the pulses in the response and divide by the number of pulses to determine the average pulse width. Then, external device 500 can use this average to differentiate between short and long pulses. By doing this, external device 500 will dynamically adjust the decoding threshold for the optimal recovery of the data.

In the illustrations described herebelow in reference to FIGS. 22A-F, the blue boxes represent the various stimulation elements 260. The orange boxes represent series impedance related to the associated stimulation element 260. The green boxes represent tissue impedance between the two adjacent stimulation elements 260.

Figure 22A:
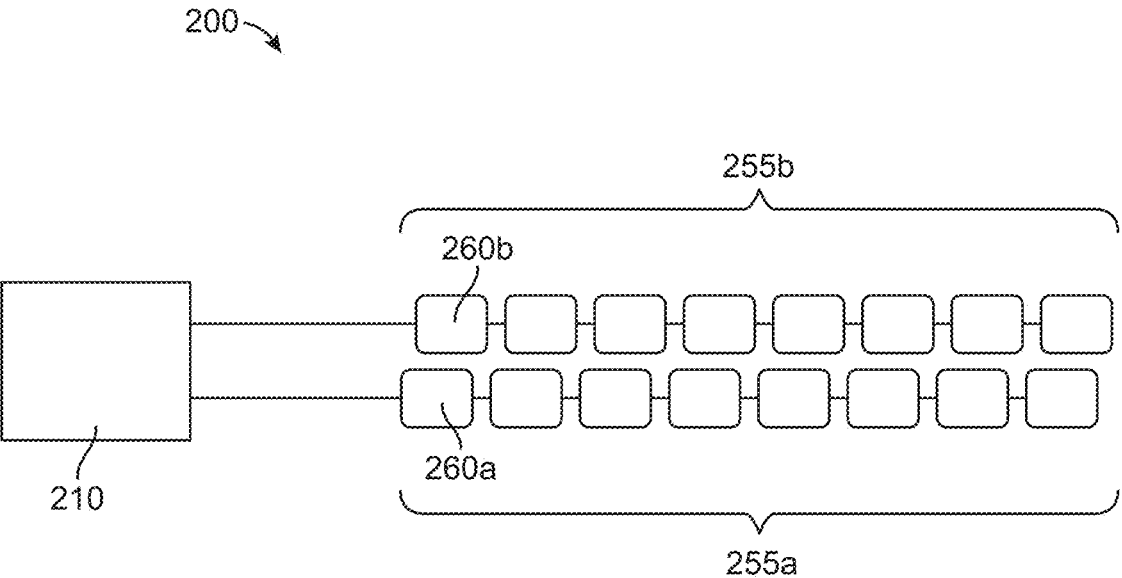

Referring now to FIG. 22A, a schematic view of an implantable device 200 comprising two leads 265 is illustrated, consistent with the present inventive concepts. Each lead 265 comprises multiple stimulation elements 260 (eight shown for each lead 265). In some embodiments, implantable system 20 is configured without a monopolar return path, such as when stimulation energy is delivered in a bipolar mode between pairs of stimulation elements 260 (e.g. without housing 210 of an implantable device 200 functioning as a current return path). During stimulation, certain stimulation elements 260 (e.g. electrodes) are configured as anodes, and certain stimulation elements 260 are configured as cathodes. Implantable device 200 comprises a current source that is connected to the cathodes while the anodes are connected to a system ground of implantable device 200 (e.g. to complete the electrical stimulation circuit). It is of interest to know the network of impedances between the various stimulation elements (e.g. between the cathodes and the anodes). These impedances can be found out if the impedance pertaining to each individual stimulation element 260 is known. In order to measure individual stimulation element 260 impedance (e.g. electrode impedance), a "pseudo-monopolar" connection can be made, as described herebelow in reference to FIG. 22B.

Figure 22B:
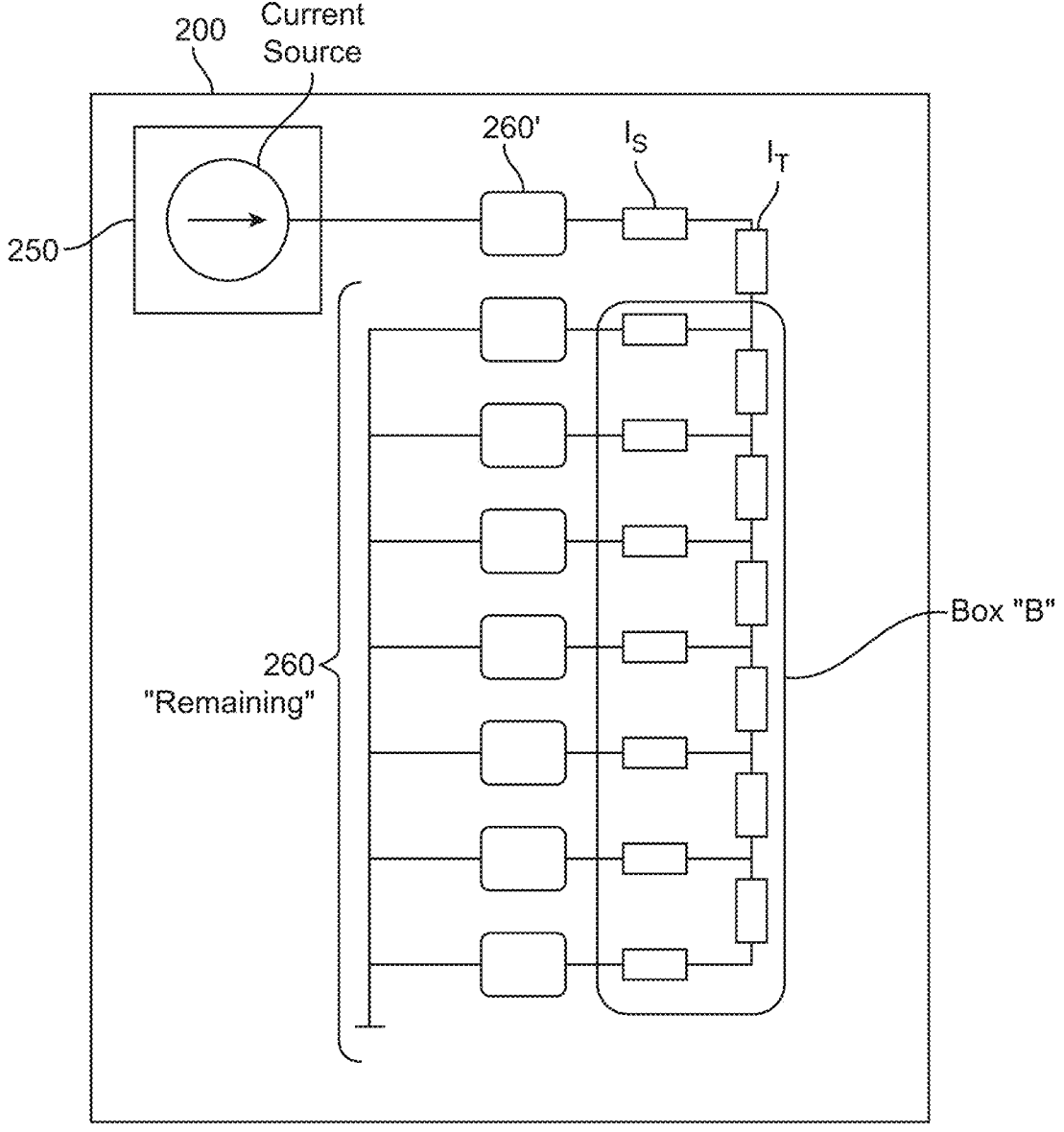

Referring now to FIG. 22B, a schematic view of an implantable device 200 including multiple stimulation elements 260 configured to perform an impedance measurement of a first stimulation element 260' is illustrated, consistent with the present inventive concepts. In a first step, stimulation element 260' is configured as a cathode, and all other "remaining" stimulation elements 260 (e.g. in the same lead 265) are assigned as anodes, where these remaining stimulation elements 260 are connected in parallel to the system ground. In doing so, the effect of individual remaining stimulation elements 260 shown including within the box "B" is minimized (e.g. allowing a "pseudo-monopolar" calculation to be made). A current source (e.g. of controller 250) drives a current pulse through this network and the resulting voltage pulse is measured at stimulation element 260' with respect to system ground. By sampling the voltage pulse close to the pulse rising edge and using ohm's law, an approximation of impedance pertaining to stimulation element 260' is obtained.

Similarly, impedance pertaining to all other stimulation elements 260 is measured. A similar process can be repeated for additional sets of stimulation elements 260 (e.g. additional stimulation elements 260 included on additional leads 265).

The stimulation element 260 impedance (e.g. electrode impedance) measured using this method is an "upper bound" on the actual impedance value. This bounded value is desirable for calculating current source compliance voltage requirements.

Figure 22C:
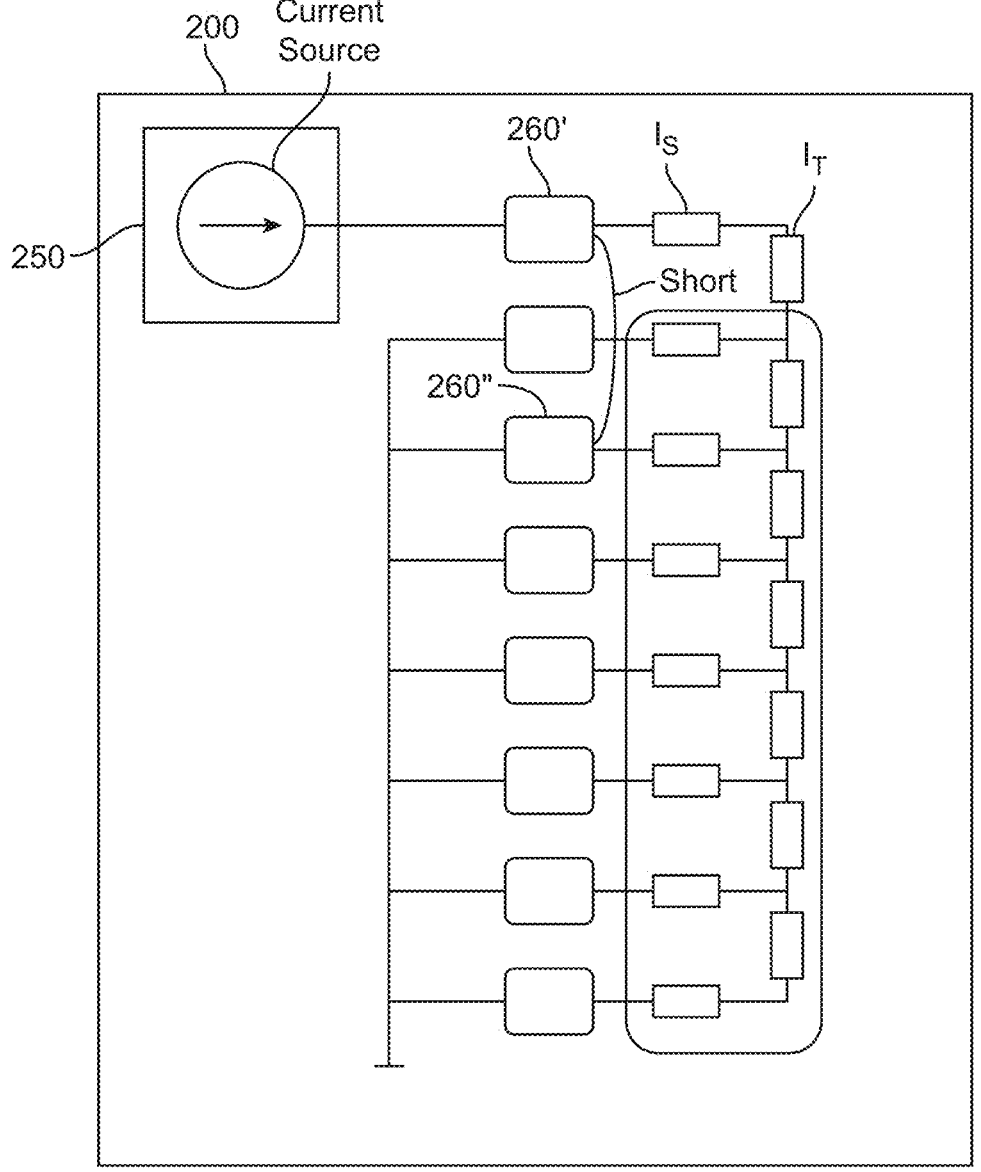

Referring now to FIG. 22C, a schematic view of an implantable device 200 including multiple stimulation elements 260 configured to perform a check for undesired shorts is illustrated, consistent with the present inventive concepts. In the embodiment of FIG. 22C, an undesired short exists between stimulation element 260' and stimulation element 260" as shown. When a current source (e.g. of controller 250) delivers a current pulse to element 260', the voltage developed at stimulation element 260' with respect to system ground is close to zero as the path of least resistance is from element 260' to element 260" to system ground. This current pulse results in a very small impedance measurement on stimulation element 260' (e.g. as described hereabove in reference to FIGS. 22A-B). Similarly, when measuring impedance pertaining to stimulation element 260", a very small impedance value is also measured. These two impedance measurements are indicative of a short between the two elements 260' and 260". In general, if such an impedance measurement results in a small value at any stimulation element 260, it is indicative that the stimulation element 260 is shorted to another stimulation element 260 (e.g. another element 260 of the same lead 265). Such a check for shorts can be performed during a manufacturing process, or at any time (e.g. just prior to and/or after implantable device 200 is implanted in the patient).

Figure 22D:
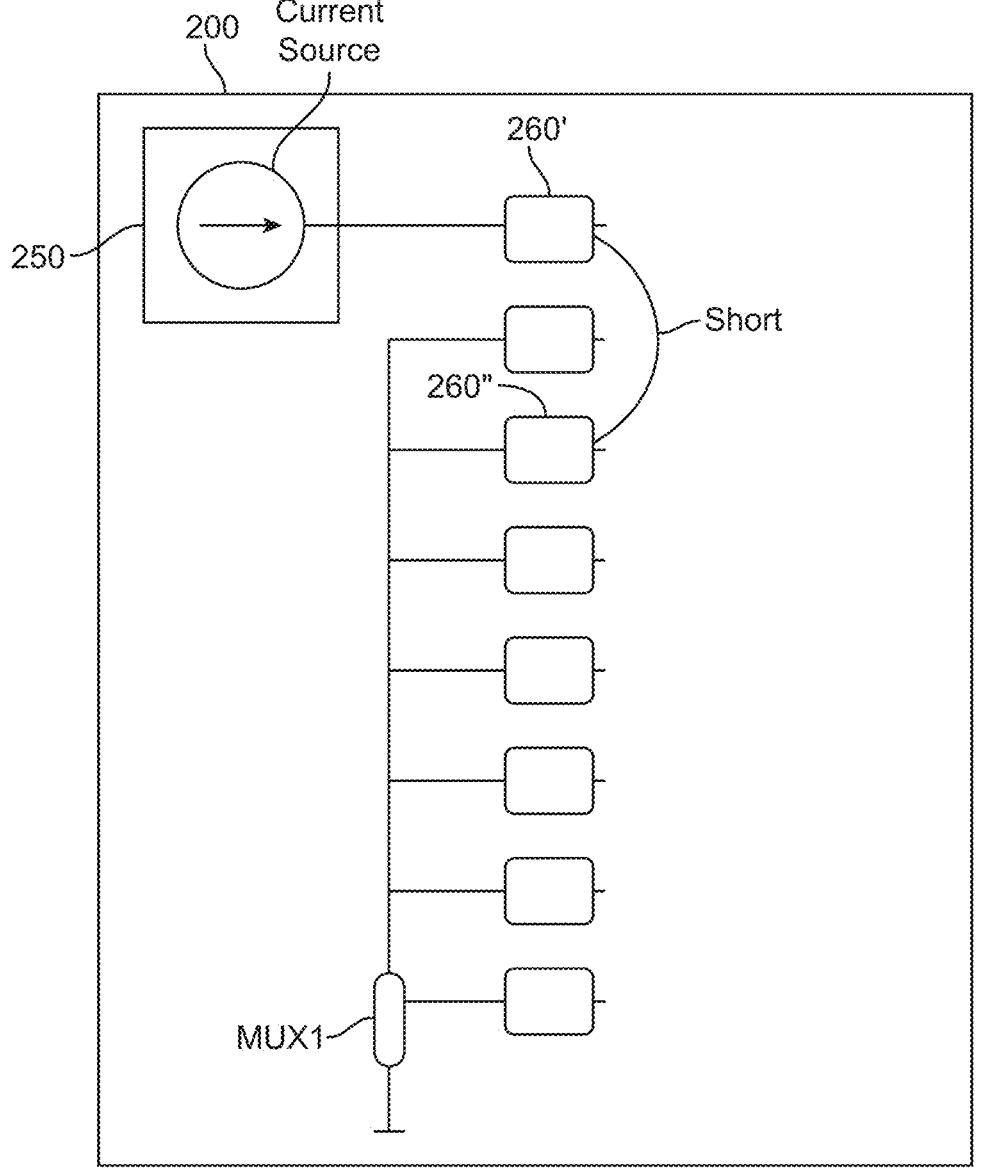

Referring now to FIG. 22D, a schematic view of an implantable device 200 including multiple stimulation elements 260 configured to perform a check for undesired shorts is illustrated, consistent with the present inventive concepts. In the embodiment of FIG. 22D, an undesired short exists between stimulation element 260' and stimulation element 260" as shown. To determine if a stimulation element 260 (e.g. stimulation element 260' shown) is shorted to any other stimulation element 260, a current source (e.g. of controller 250) is connected to stimulation element 260' and the resulting voltage is measured on all other stimulation elements 260. If there is no short (or other electrical connection path) between stimulation element 260' and all other elements 260, then no voltage shall be observed at those elements 260 (e.g. with respect to system ground). If a voltage is observed, then a short between element 260' and some other element 260 is determined by implantable device 200. In the illustration, a pulse generated by a current source connected to stimulation element 260' is observed on all other stimulation elements 260 (e.g. electrodes) due to a short between stimulation element 260' and 260". During use, such an observed pulse is indicative that stimulation element 260' is shorted to some other stimulation element 260.

Figure 22E:
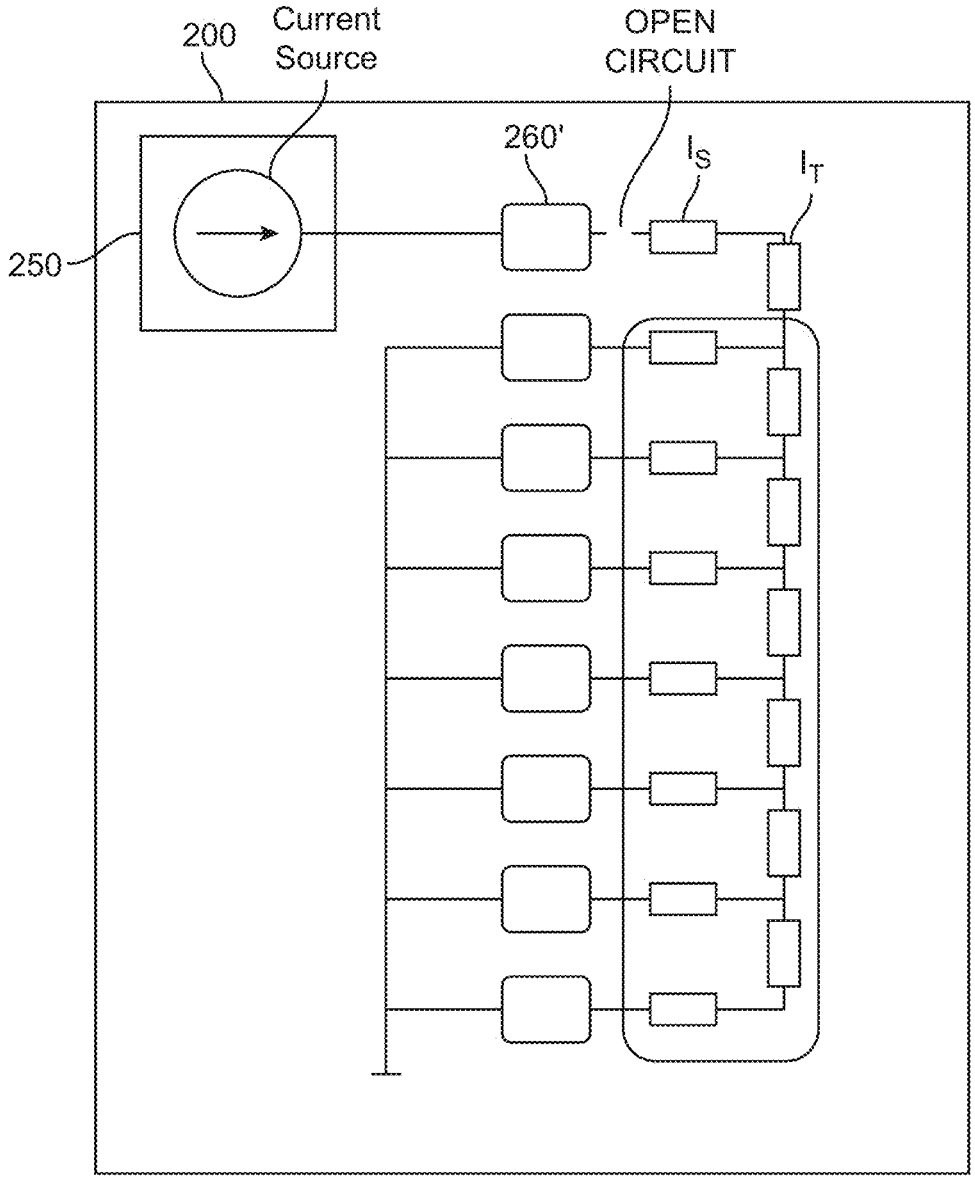

Referring now to FIG. 22E, a schematic view of an implantable device 200 including multiple stimulation elements 260 configured to perform a check for undesired open circuits is illustrated, consistent with the present inventive concepts. In the embodiment of FIG. 22E, an undesired open circuit exists at stimulation element 260' as shown. In a diagnostic test, a current source (e.g. of controller 250) attempts to deliver current through a stimulation element 260. If an open circuit is present, the voltage observed on that stimulation element 260 would be high. The high voltage is interpreted as a high impedance per the impedance measurement test described hereabove in reference to FIG. 22A-B.

Figure 22F:
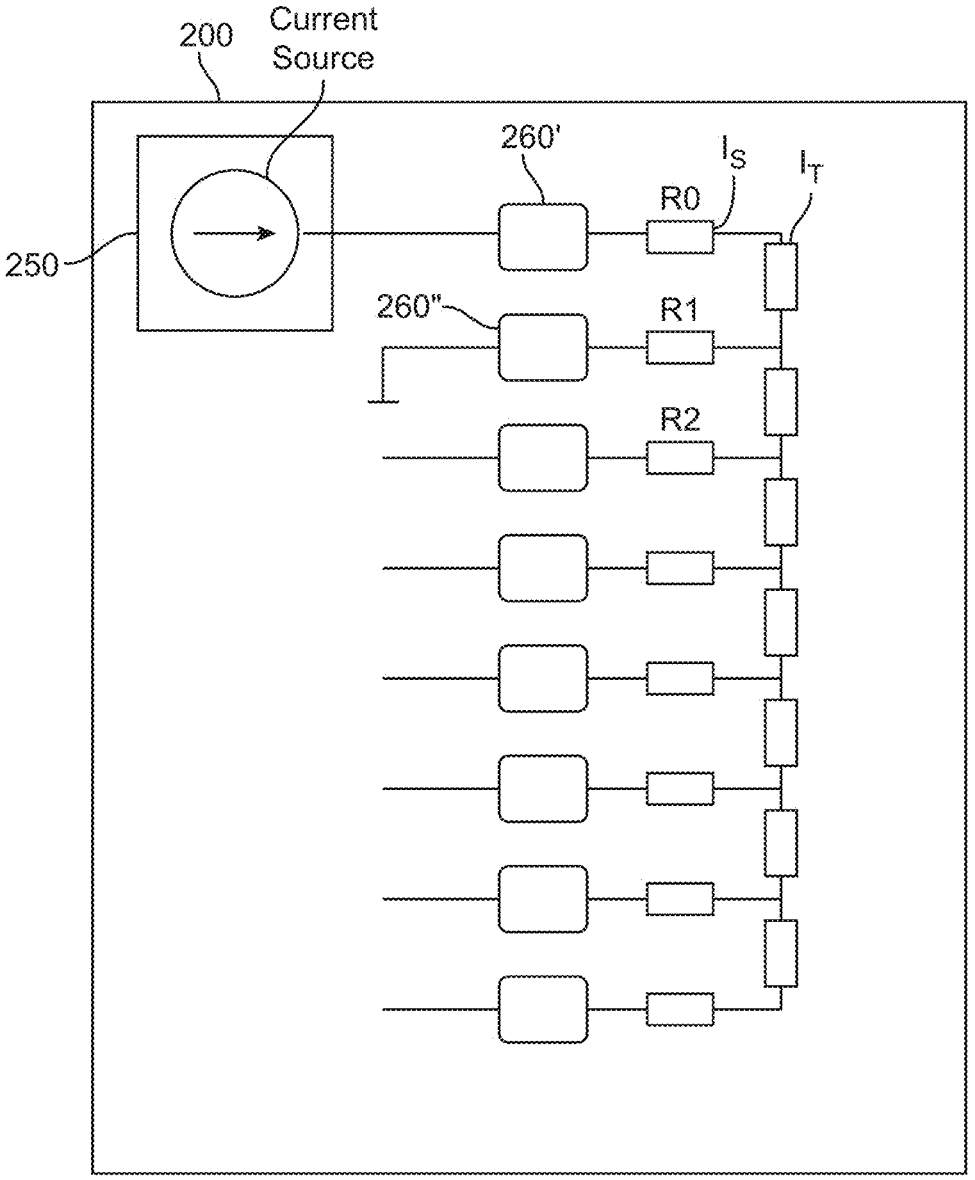

Referring now to FIG. 22F, a schematic view of an implantable device 200 including multiple stimulation elements 260 configured to measure individual stimulation element impedance is illustrated, consistent with the present inventive concepts. FIG. 22F illustrates an example electrical connection used to perform an impedance measurement method. In this configuration, a current source is connected to one stimulation element, stimulation element 260' shown, and the return path is completed using another stimulation element, stimulation element 260" shown. A voltage pulse resulting due to a current pulse generated by the current source is measured at stimulation element 260'. By sampling the voltage pulse close to the rising edge of the pulse, an estimate of the sum of individual impedances R0 and R1 is obtained. If R01 indicates the sum, then R01=R0+R1. Similarly, estimates for two other pairs can be obtained. For example, R12=R1+R2; and R02=R0+R2. These equations can be solved simultaneously to calculate the unknown impedance values: R0, R1 and R2. Similarly, all the remaining individual impedances can be calculated. Alternatively or additionally, the impedance measurement method described in FIG. 22A-B is used as a pre-processing step to find out if there are open electrodes (stimulation elements 260) in the lead 265, such that these elements can be omitted from the set of equations to be solved simultaneously. This method can limit inaccuracies that may result due to including open electrodes in the set of measurements. In some embodiments, estimates of several pairs can be analyzed together and the large set of equations solved using linear algebraic methods.

Referring now to FIG. 23, a graph of an amplitude modulation scheme is illustrated, consistent with the present inventive concepts. Transmissions between an external device 500 and one or more implantable devices 200 can comprise a modulated transmission signal, such as an amplitude modulated transmission signal as shown in FIG. 23. In some embodiments, the modulation depth is relatively "shallow" (e.g. a modulation depth less than 20%, or less than 5%). Such shallow modulation depths provide numerous advantages, such as reduced emissions (e.g. for regulatory compliance), improved efficiency, and/or reduced instantaneous power transfer. External device 500 can comprise an electronic potentiometer (e.g. controller 550 comprises the electronic potentiometer) that allows adjustment of the modulation depth (e.g. by adjusting the input voltage driving a gate of an amplifier providing the transmission signal, such as an amplifier which is operating at saturation). In some embodiments, the electronic potentiometer is adjusted in manufacturing of external device 500, such as using a set of values corresponding to a power amplifier setting. Alternatively or additionally, the electronic potentiometer can be adjusted in use (e.g. in the clinical setting). For example, controller 550 can include firmware that determines a desired modulation depth, such as to optimize efficiency of transmissions without sacrificing reliability of transmissions. Such adjustment in the clinical setting can minimize communication errors, such as when the associated implantable device 200 has been implanted relatively deep under the surface of the skin, such as when a component of an external device 500 (e.g. ferrite or other component) and/or implantable device 200 has been damaged or is otherwise compromised.

Referring now to FIGS. 24A-B, top views of an external device 500 positioned on a patient in a first orientation, and a second orientation, respectively, is illustrated, consistent with the present inventive concepts. In FIG. 24A, external device 500 is positioned in a first orientation, on a patient's skin above an implantable device 200 that has been implanted in the patient. In FIG. 24B, external device 500 is positioned in a second orientation, different than the first orientation (e.g. an orientation 180° offset from the first orientation). Apparatus 10 is configured to perform relatively equally in different orientations, such as when efficiency of transmissions from external device 500 to implantable device 200, from implantable device 200 to external device 500, and both, are relatively unaffected by the different orientations. Avoiding a particular orientation (e.g. particular placement of external device 500 on the patient's skin), greatly simplifies attachment of external device 500 to the patient's skin by a user (e.g. by the patient).

For example, antennas 240 and/or 540 can comprise a construction, and each can be oriented in implantable device 200 and/or external device 500, respectively, in a way that minimizes the impact of a particular orientation of external device 500 to an implanted implantable device 200. In some embodiments, antennas 240 and/or 540 comprise loop antennas, such as rectangular loop antennas. In some embodiments, the ratio of the size of external antenna 540 compared to the size of implantable antenna 240 is relatively high, such that the impact of orientation variations is minimized, such as a ratio of at least 2:1, 4:1, and/or 6:1.

Referring now to FIG. 25A, a schematic view of a reconfigurable stimulation block (RSB) portion 255b of electronic assembly 255 of implantable device 200 is illustrated, consistent with the present inventive concepts. RSB 255b can comprise one or more current sources, such as a high-side current source and a low-side current source. In the embodiment shown in FIG. 25A, there is only one (high-side) current source, and the current return path is to ground through the left-hand switch connected to VB (versus a return path through a low-side current source). In active charge recovery (bipolar stimulation), current direction is reversed by changing the MUXA and MUXB settings. For example, during a stimulation phase, E1 is connected to VA and E0 is connected to VB, whereas during a recovery phase, E1 is connected to VB and E0 is connected to VA. Current source and ground switch settings remain the same in both phases. As compared to an arrangement with both a high-side and a low-side current source, low-side current source and high-side supply switches have been eliminated.

Referring now to FIG. 25B, a diagram of a control input sequence is illustrated, consistent with the present inventive concepts. Use of the control signals in FIG. 25A are shown in FIG. 25B. Current flows through the dump switch when any bits of 'rsbx_isrc_sel<3:0>' is asserted and when 'rsbx_gate_reg' (sync signal) is not asserted. This time period needs to be small in order to minimize the power lost during the dump phase. The RSB 301 circuitry is designed to be operated with this time period as small as 1 μs. 'Rsbx_swselb' & 'rsbx_ss_sel' can be asserted at the same time as 'rsbx_isrc_sel' in order to shorten stimulation setup time. As show in FIG. 25B, these signals need not be de-asserted in the region between the two phases of stimulation.

In some embodiments, a DC blocking capacitor is included in RSB 301. In the embodiment shown in FIG. 25A, the DC-blocking capacitor CDC is not included, instead each stimulation element 260 (e.g. electrode) has a DC-blocking capacitor between each MUXA/B output terminal and the corresponding stimulation element 260 (tissue connection). There are 16 capacitors total (e.g. for spinal cord stimulation); and these capacitors are shared between all RSB 255bs. A single set of discharge switches is connected between the VA and VB nodes.

Referring additionally to FIG. 25C, a schematic view of another portion of electronic assembly 255 is illustrated, portion 255c, consistent with the present inventive concepts. Given that the stimulation current path contains switched capacitive elements, both in interface between stimulation elements 260 and tissue, and the DC-blocking capacitors, it is possible for chip nodes to go below the ground rail as follows. During the stimulation phase, one terminal of the series capacitor string is charged positively with respect to the other. During the recovery phase, that node is connected to ground and so the other terminal is charged negatively in respect, and so its voltage can go below ground. This can forward-bias ESD-protection and parasitic bulk diodes of the output circuits, and it can cause the recovery current to not be controlled. This, in turn, can cause charge-balance problems if the external DC-blocking capacitors aren't included, and/or inaccurate stimulation current. The solution is to add the option of series resistors between the ground switch and stimulation outputs during the recovery phase. As current flows through these resistors they create a voltage drop, which raises the otherwise-negative terminal to above ground potential. Typically the soft switches are enabled during the start of the recovery phase, and then switched out as the capacitor(s) discharge, to avoid loss in stimulation compliance. The architecture of the soft switch, and example resistance values, are listed below.

| rsbx_ss_sel | Resistance Value |
|---|---|
| 000000000000 | — |
| 000000000001 | 200 |
| 000000000010 | 200 |
| 000000000100 | 200 |
| 000000001000 | 200 |
| 000000010000 | 500 |
| 000000100000 | 800 |
| 000001000000 | 1.5k |
| 000010000000 | 2.7k |
| 000100000000 | 5.4k |
| 001000000000 | 8k |
| 010000000000 | 15k |
| 100000000000 | 50k |

Referring now to FIG. 26A-C, schematic views of a test fixture arrangement for testing electronic assembly 255 is illustrated, consistent with the present inventive concepts. Test fixture 97 is constructed and arranged to perform one or more tests on electronic assembly 255 of an implantable device 200. In a first embodiment, as described in reference to FIG. 26A, test fixture 97 is configured to perform a test on electronic assembly 255 when implantable device 200 is in a partially assembled state, when electrical access points on electronic assembly 255 are accessible to test fixture 97. In an alternative or additionally second embodiment, as described in reference to FIGS. 26B-C, test fixture 97 can be configured to perform a test on an electronic assembly 255 by connecting with one or more stimulation elements 260 (e.g. electrodes) and/or other stimulation energy-providing electrical access points outside of housing 210. In other words, test fixture 97 can be configured to perform a test on electronic assembly 255 when implantable device 200 is in a fully manufactured state (e.g. in a state ready for shipment to a customer and including a pre-attached lead 265 and/or an attachable lead 265). In the fully manufactured state, a ground pathway of electronic assembly 255 may not be available to perform a test in which electronic assembly 255 and test fixture 97 share a common ground.

Referring now to FIG. 26A, as described hereabove, test fixture 97 can be configured to test electronic assembly 255 while implantable device 200 is in a partially assembled state. Test fixture 97 includes connection point 9701a which is shown having been attached (e.g. by an employee of the manufacturer of electronic assembly 255) to electrical connection point 256a of electronic assembly 255, and connection point 9702 is shown similarly having been attached to electrical connection point 257 of electronic assembly 255 (e.g. creating a common ground between electronic assembly 255 and test fixture 97). Electrical connection point 256a is part of a first electrical signal pathway (e.g. wire or trace) that is configured to deliver stimulation energy to a first stimulation element 260a (not shown). Electrical connection point 256a can be positioned "downstream", as shown, of a capacitor in series with the first electrical signal pathway, capacitor C1, such that test fixture 97 can test the leakage current of capacitor C1. For example, during a test of the first signal pathway, an ASIC of electronic assembly 255 connects the upstream side of capacitor C1 to a switch, switch S1, by activating a multiplexor, MUX 1, to make the specific connection between C1 and S1. The ASIC also closes switch S1 such that the upstream side of capacitor C1 electrically connects to a ground pathway of electronic assembly 255, as shown. During this test of the first signal pathway, test fixture 97 electrically connects connection point 9701*a* to an ammeter, M1, which is attached to a voltage supply, DC voltage supply $V_{CC}$ shown. In this first connection configuration shown, ammeter M1 measures any leakage current of capacitor C1. Subsequent tests of all remaining capacitors C2 thru $C_N$ can be performed. Connection points 9701*b* thru 9701*n* of test fixture 97 are attached to corresponding connection points 256*b* thru 256*n* of electronic assembly 255 (e.g. connections which are made singly or collectively prior to each test). Sequential tests of each capacitor C2 thru $C_N$ can be performed when MUX 1 sequentially connects each capacitor C2 thru $C_N$, to switch S1 (e.g. which is closed and connected to the ground pathway of assembly 255), and a multiplexor of test fixture 97, MUX 2, simultaneously and respectively connects each connection point 9702*b* thru 9702*n* to voltage supply $V_{CC}$. In some embodiments, electronic assembly 255 is configured to provide stimulation energy to multiple stimulation elements 260 (e.g. electrodes), such as 4, 6, 8, 12, and/or 16 electrodes, such as when electronic assembly 255 comprises 4, 6, 8, 12, and/or 16 signal pathways, each including a capacitor as shown in FIG. 26A.

Referring now to FIG. 26B, as described hereabove, test fixture 97 can be configured to test electronic assembly 255 while implantable device 200 is in a fully assembled state (e.g. a state in which a ground pathway of electronic assembly 255 may not be available to connect to test fixture 97). Test fixture 97 includes connection point 9701*a* which is shown having been attached (e.g. by an employee of the manufacturer of implantable device 200 during a final test, or by a clinician or healthcare provider at a time proximate implantation of implantable device 200) to electrical connection point 256*a* of electronic assembly 255. Electrical connection point 256*a* is part (e.g. the end portion) of a first electrical signal pathway (e.g. wire or trace) that is configured to deliver stimulation energy to a first stimulation element 260*a* (not shown). In some embodiments, electrical connection point 256*a* comprises a portion of first stimulation element 260*a*. Electrical connection point 256*a* can be positioned "downstream", as shown, of a capacitor in series with the first electrical signal pathway, capacitor C1, such that test fixture 97 can test the leakage current of capacitor C1. For example, during a test of the first signal pathway, an ASIC of electronic assembly 255 connects the upstream side of capacitor C1 to a switch, switch S1, by activating a multiplexor, MUX 1, to make the specific connection between C1 and S1. The ASIC also closes switch S1, which is connected to an input of another multiplexor of electronic assembly 255, MUX 3 as shown. The ASIC activates MUX 3 such that the upstream side of all of the other capacitors, C2 through $C_N$, are connected to switch S1 as shown (e.g. shorted together). During this connection arrangement, MUX 2 of test fixture 97 connects connection point 9701*a* to ammeter M1. Test fixture 97 further includes another multiplexor, MUX 4 shown, which connects each of connection points 9701*b* thru 9701*n* to the ground of test fixture 97 (e.g. shorts each of connection points 9701*b* thru 9701*n* to test fixture 97 ground). In this connection scheme of electronic assembly 255 and test fixture 97, voltage provided by supply $V_{CC}$ is presented at the downstream side of capacitor C1. Any leakage current that passes through capacitor C1, subsequently leaks through all of the remaining capacitors C2 thru $C_N$, such that any leakage current measured by ammeter M1 is dominated by the leakage current through capacitor C1. The effective circuit and current path of testing a first stimulation pathway (including capacitor C1), is shown in FIG. 26C. Subsequent tests of all remaining capacitors C2 thru $C_N$ can be performed, such as in a similar fashion to that described hereabove in reference to FIG. 26A. For example, in a test of any capacitor $C_N$, MUX 1 connects switch 1 to the upstream side of capacitor $C_N$, and MUX 2 shorts each of the upstream sides of the remaining capacitors together. Test fixture 97 connects connection point 9701*b* to ammeter M1, and fixture 97 shorts the remaining connection points 9701 together and to the ground of test fixture 97. In some embodiments, electronic assembly 255 is configured to provide stimulation energy to multiple stimulation elements 260 (e.g. electrodes), such as 4, 6, 8, 12, and/or 16 electrodes, such as when electronic assembly 255 comprises 4, 6, 8, 12, and/or 16 signal pathways, each including a capacitor as shown in FIG. 26B.

Referring now to FIG. 27A-C, a series of views of stimulation waveforms are illustrated. In FIG. 27A, a tonic stimulation waveform for a single area (e.g. a single nerve or other tissue location) is illustrated. In FIG. 27B, a tonic stimulation waveform for multiple areas (e.g. two to five tissue locations capable of being stimulated by multiple stimulation elements 260 of a single lead 265 and/or multiple leads 265) is illustrated. In FIG. 27C, a tonic sequence stimulation waveform is illustrated.

When tonic stimulation is to be provided by apparatus 10 (e.g. to a single area), implantable device 200 can deliver a monophasic pulse as shown in FIG. 27A. When stimulation of a single area is provided, implantable device 200 can perform current steering (e.g. per electrode parameters).

When tonic stimulation of multiple areas is provided by apparatus 10, implantable device 200 can deliver evenly distributed pulses within the stimulation interval.

When tonic sequence stimulation is provided by apparatus 10, implantable device 200 can deliver a sequence of monophasic pulses, such as one pulse for each of multiple areas (e.g. 5 areas). For tonic sequence stimulation of multiple areas, implantable device 200 can sequence the pulses within the stimulation interval per the pulse width and inter-pulse gaps for each area.

In some embodiments, apparatus 10 includes available programs (e.g. created by apparatus 10 and/or a clinician user of apparatus 10) for stimulating different anatomical locations (e.g. back, leg, and the like, and/or multiple locations within the back, leg, and the like). In some embodiments, apparatus 10 is configured to operate in an "adjacent mode", in which apparatus 10 delivers a stimulation pulse in a first area, then a second area, and so on, and repeats. Individual cycles of stimulating a sequence of different areas can be separated by a delay. Alternatively or additionally, apparatus 10 can be configured to operate in an "evenly spaced mode"—where pulses are evenly spaced over a time period.

In some embodiments, apparatus 10 and implantable device 200 are configured to perform charge recovery within tissue in a passive arrangement. The charge recovery is performed to maintain a charge balance in the tissue. Implantable device 200 of FIG. 28A comprises a current source $CS_1$, a switch $S_1$, a DC blocking capacitor $C_{DCB}$, and two electrodes 260*a* and 260*b*, each connected as shown. Current source $CS_1$ is attached to a power supply 270 that provides voltage $V_{DD}$, also as shown. The tissue receiving stimulation energy from electrodes 260*a* and 260*b*, tissue $T_1$, can be electrically modeled as a resistor $R_2$ that is in series with a parallel connection of a capacitor $C_1$ and a resistor $R_1$, as shown.

In FIG. 28B, implantable device 200 is in a stimulation phase with current source $CS_1$ providing current, switch $S_1$ open, and current flowing in the direction shown, through capacitor $C_{DCB}$ and tissue $T_1$. During this stimulation phase, charge accumulates in tissue $T_1$. In FIG. 28C, implantable device 200 is in a passive charge recovery phase with current source $CS_1$ not providing current, and switch $S_1$ closed. During this charge recovery phase of FIG. 28C, electrodes 260a and 260b are shorted together, through capacitor $C_{DCB}$, and current flows in the direction shown, through switch $S_1$, removing the charge in tissue $T_1$ developed during the stimulation phase of FIG. 28B.

In FIG. 28D, a plot of current versus time is shown for the stimulation and passive charge recovery arrangement of FIGS. 28B-C. A series of stimulation pulses are delivered, each with a time period $TP_1$. In the time between stimulation pulses, time period $TP_2$, charge recovery occurs for a time period $TP_3$ that is based on a RC discharge curve, where an associated resistance $R_{TOT}$ and capacitance $C_{TOT}$ represents the total resistance and capacitance, respectively, in the discharge path. Time period $TP_3$ is typically on the order of a few milliseconds.

The passive charge recovery described in reference to FIGS. 28C-D provides energy efficiency since energy (current) is only applied by implantable device 200 (e.g. by energy storage assembly 270, typically a battery or capacitor) during the stimulation phase (e.g. versus active charge recovery in which energy is provided in both stimulation phases and charge recovery phases). In the embodiment shown in FIG. 28D, the stimulation rate is sufficiently low (e.g. less than 1 kHz) that the charge recovery period $TP_3$ is less than the time between stimulation pulses, time period $TP_2$. However in some embodiments, the stimulation rate is sufficiently high such that the charge recovery period $TP_3$ is greater than the time between pulses, time period $TP_2$, such as is shown in FIG. 28E.

In these high stimulation rate embodiments (e.g. at least 1 kHz up to hundreds of KHz), the duration of the stimulation pulse $TP_1$ and time between pulses $TP_2$ is much shorter than the RC time constant represented by time period $TP_3$, such as when each is on the order of one-tenth to one-five hundredth the duration of $TP_3$. In these embodiments, implantable device 200 is configured to allow charge due build up on the DC blocking capacitor $C_{DCB}$. This built-up charge translates to a bias voltage across capacitor $C_{DCB}$, which causes current to flow during the charge recovery period. An equilibrium is reached when the bias voltage across capacitor $C_{DCB}$ equals the total resistance in the stimulation ($R_{TOT}$) path times the stimulation current when time period $TP_1$ and $TP_2$ are equal.

FIGS. 28F and 28G show waveforms of current through electrodes 260a and 260b (e.g. the current through tissue $T_1$) and voltage developed across capacitor $C_{DCB}$ at low and high stimulation rates, respectively. As shown in FIG. 28G, a bias voltage is developed across capacitor $C_{DCB}$, which is approximately equal to the stimulation current during the stimulation phase times $R_{TOT}$ (the total series resistance in the stimulation path). An increased compliance voltage is required by current source $CS_1$ to overcome the bias voltage of capacitor $C_{DCB}$. In some embodiments, there is a fixed minimum compliance voltage (minimum setting for the power supply 270 that powers the current source $CS_1$) and the stimulation current amplitude times $R_{TOT}$ is less than or equal to 50% of the minimum compliance voltage. In these embodiments, energy can be recovered that would otherwise be wasted due to the minimum compliance voltage being greater than that required for active recovery. The long RC time constant requires a minimum amount of time (e.g. at least 2 milliseconds) for equilibrium to be reached. The asymmetry in the waveform can be mitigated by implantable device 200 ramping up and ramping down the stimulation current amplitude at the start and end of a time period in which stimulation energy is delivered.

The equilibrium bias voltage on capacitor $C_{DCB}$ is proportional to the ratio of the stimulation period $TP_1$ and the recovery time $TP_2$, such that increasing the recovery time $TP_2$ relative to the stimulation time $TP_1$ will proportionally reduce the bias voltage on capacitor $C_{DCB}$, which will reduce the required compliance voltage. In this arrangement, control is provided in shaping the charge recovery phase, as both the recovery time and the stimulation path resistance can be manipulated to change the characteristics of the recovery pulse. For example, implantable device 200 can be configured to manipulate the timing in which switch S1 is opened and/or closed, to control timing and/or duration of charge recovery. Alternatively or additionally, implantable device 200 can be configured to manipulate the impedance of the discharge path, such as when implantable device 200 includes one or more resistive components that can be included and/or excluded from the stimulation path.

While the embodiment of FIGS. 28A-G is shown with two electrodes as stimulation elements 260, four, six, eight, or more electrodes can be similarly configured to perform the passive charge recovery.

Referring now to FIG. 29, a stimulation waveform comprising multiple trains of monophasic pulses is illustrated, consistent with the present inventive concepts. In some embodiments, the stimulation apparatus of the present inventive concepts, apparatus 10 described herein, is configured to deliver one or more stimulation waveforms as described in reference to FIG. 29. The stimulation waveform shown in FIG. 29 comprises a series of narrow pulses (e.g. between 2 and 1000 pulses, eight monophasic pulses shown) for a train-on period $T_{ON}$ (e.g. a time period of between 1 μsec to 100 msec), after which no energy is delivered for a train-off period $T_{OFF}$ (e.g. a time period of between 1 μsec to 100 msec). The monophasic pulses can comprise an amplitude between 0.01 mA and 20 mA, such as an amplitude between 0.05 mA and 20 mA, or between 0.5 mA and 2.5 mA.

In some embodiments, apparatus 10 is configured to provide a stimulation waveform comprising a burst waveform (e.g. a compliance optimized burst waveform) by delivering one or more stimulation waveforms comprising a repeated cycle of "burst-on" periods $B_{ON}$ followed by "burst-off" periods $B_{OFF}$, as shown. Each burst-on period $B_{ON}$ can comprise one or more sets of $T_{ON}$ and $T_{OFF}$ periods. Each burst-on period $B_{ON}$ can comprise between 2 and 1000 $T_{ON}$ periods (e.g. between 2 and 1000 pairs of $T_{ON}$ and $T_{OFF}$ periods, or trains, five trains shown). The various train periods $T_{ON}$ can be similar or different (similar or different number of pulses, lengths of time, and the like). Each burst-off period $B_{OFF}$ can comprise a time period between 1 μsec and 10 seconds. Each burst-off period $B_{OFF}$ and/or train-off period $T_{OFF}$ can comprise a charge recovery slot, into which a charge recovery pulse in the opposite phase can be delivered. Alternatively or additionally, charge recovery can be achieved by passive means (e.g. one or more stimulation-delivering electrodes, stimulation elements 260, are allowed to simply discharge into tissue, such as by being electrically connected together such that the accumulated charge discharges in an opposite direction to the stimulation pulse), without actively delivering a pulse of opposite polarity.

The stimulation waveform shown in FIG. 29 can be constructed using key building blocks, such as one or more of, or all of: (1) narrow pulse widths; (2) high rate onset/offset; (3) low rate onset/offset; (4) low charge delivery/time; and/or (5) efficient charge recovery. As used herein, "onset" relates to the initial portion of a train of pulses, and "offset" relates to a final portion of a train of pulses, each of which are known to have specific stimulation effects (e.g. more neurons are stimulated during an onset portion vs subsequent portions). A "high rate onset/offset" relates to a stimulation waveform with relatively short pulse train periods as well as relatively short off times between pulse trains. A "low rate onset/offset" relates to a stimulation waveform with relatively long pulse train periods as well as relatively long off times between pulses trains.

A stimulation waveform comprising different pulse widths can be used by apparatus 10 and configured to selectively recruit nerve fibers that have different properties, such as diameters, myelinated vs unmyelinated, low vs high spontaneous rate, location (dorsal column vs dorsal horn vs dorsal root) and the like. When stimulation pulses are presented by apparatus 10 without charge recovery, the ensemble effect of these pulses may elicit responses that mimic wider pulses (e.g. pulses on the order of 10 ms in duration when the entire pulse train is considered and before any charge recovery occurs). Taken together, these two effects can affect nerve fibers more comprehensively than by just delivering pulses of a single width (e.g. with charge recovery).

A stimulation waveform of apparatus 10 comprising a high rate onset/offset can be configured to cause an increase in nerve fiber recruitment. The stimulation waveform can intentionally incorporate onset and offset at a relatively high rate (e.g. greater than or equal to 1 kHz) to harness this effect.

A stimulation waveform of apparatus 10 comprising a low rate onset/offset can be configured to disrupt accommodation and/or habituation, which represent common issues associated with spinal cord stimulation. Breaking up the stimulation waveform with a low rate (10's of Hz, such as at least 10 Hz) onset/offset can disrupt the accommodation.

A stimulation waveform of apparatus 10 comprising a low charge delivery/efficient charge recovery can be configured to provide a waveform flexibility that allows for charge recovery to occur in various time epochs. Based on first order modeling, the charge is recovered in the "burst off" epoch. With the narrow pulse width and high inter-pulse gaps, the charge delivered in the stimulation waveform is generally low. For example, in a single period (e.g. a time period of approximately 25 msec) charge is delivered for a duration between 1% and 15% of the time period, such as approximately 7% of the time period. Although charge delivery is relatively low (e.g. compared to a traditional burst waveform of approximately 20%) the thresholds measured with the stimulation waveform (during the human studies of Applicant described herein) are similar to a burst like stimulation (e.g. both within patient and in population averages). In effect, the stimulation waveform is highly power efficient when compared to stimulation waveforms used in commercial devices today.

In some embodiments, the structure of the stimulation waveform (e.g. narrow pulse width, high & low rate onset/offset) is configured to engage neurons in the Dorsal Horn (rather than the traditional Dorsal Column) with "Tonic" stimulation (although the ensemble charge delivery, such as approximately 10 msec before recovery, can activate Dorsal Column fibers). In addition, the narrow pulse width with low inter-pulse gap can be configured to cause glial cell activation.

In some embodiments, the stimulation waveform provided by apparatus 10 is combined with a Tonic-like stimulation paradigm to create a "hybrid waveform". Such a hybrid waveform can elicit Dorsal Column stimulation in addition to the mechanisms discussed hereabove.

Referring now to FIG. 29A, another stimulation waveform comprising multiple trains of monophasic pulses is illustrated, consistent with the present inventive concepts. In some embodiments, the stimulation apparatus of the present inventive concepts, apparatus 10 described herein, is configured to deliver one or more stimulation waveforms as described in reference to FIG. 29A. The stimulation waveform shown in FIG. 29A can be of similar timing and arrangement as the stimulation waveform shown in FIG. 29. The stimulation waveform shown in FIG. 29 includes a passive charge recovery that occurs during the $B_{OFF}$ period as shown. Alternatively or additionally, an active charge recovery can be performed.

Programmer 600 can allow an operator to set the rate of the stimulation waveform, such as to set a "train rate" that is defined by:

$$\text{Train Rate} = 1 / (\text{Train-On Period} + \text{Train-Off Period}),$$

as shown in FIG. 29A.

In some embodiments, apparatus 10 is configured to provide the stimulation waveform of FIG. 29A based on one or more provided (e.g. predetermined) sets of stimulation parameters (e.g. suggested sets of stimulation parameters selectable by an operator of apparatus 10 via programmer 600). For example, one or more sets of suggested stimulation parameters can comprise: a first set comprising a pulse width of 30 µsec, inter pulse interval of 60 µsec, train-on period of 1100 µsec, train-off period of 900 µsec, burst-on period of 9 msec, and burst-off period of 16 msec; a second set comprising a pulse width of 30 µsec, inter pulse interval of 60 µsec, train-on period of 1100 µsec, train-off period of 900 µsec, burst-on period of 10 msec, and burst-off period of 15 msec; and/or a third set comprising pulse width of 30 µsec, inter pulse interval of 60 µsec, train-on period of 1020 µsec, train-off period of 980 µsec, burst-on period of 9 msec, and burst-off period of 16 msec.

In some embodiments, apparatus 10 is configured to provide a stimulation waveform comprising low frequencies and "near DC" waveforms, and a set of stimulation parameters can comprise: a pulse width of 1000 µsec, inter pulse interval of 10 µsec, train-on period of 1000 µsec, train-off period of 10 µsec, burst-on period of 25 msec, and burst-off period of 15 msec.

In some embodiments, apparatus 10 is configured to provide a stimulation waveform comprising one, more than one, or all of the following stimulation parameters: a pulse width of at least 1 µsec and/or no more than 1 msec; an inter-pulse interval of at least 1 µsec and/or no more than 1 msec; a train-on period of at least 2 µsec and/or no more than 2 msec; a train-off period of at least 2 µsec and/or no more than 2 msec; a burst-on period of at least 2 msec and/or no more than 2 seconds; and/or a burst-off period of at least 2 msec and/or no more than 2 seconds.

In some embodiments, apparatus 10 is configured to provide a stimulation waveform comprising: a pulse width of 200 µsec; an inter-pulse interval of 500 µsec; a train-on period of 1 msec; a train-off period of 810 μsec; a burst-on period of 10 msec; and/or a burst-off period of 15 msec.

In some embodiments, apparatus 10 is configured to provide a stimulation waveform comprising: a pulse width of 480 μsec; an inter-pulse interval of 20 μsec; a train-on period of 1.1 msec; a train-off period of 900 μsec; a burst-on period of 9 msec; and/or a burst-off period of 16 msec.

Referring now to FIG. 29B, another stimulation waveform comprising multiple trains of monophasic pulses is illustrated, consistent with the present inventive concepts. In the embodiment shown in FIG. 29B, apparatus 10 can be configured to perform active charge recovery. Apparatus 10 can combine the stimulation waveform shown in FIG. 29B with a second, tonic-like waveform ("tonic waveform", "tonic stimulation", and the like herein), such as a second waveform that causes paresthesia to be generated. The paresthesia generated can be used to provide a reassurance to the patient that stimulation energy is being delivered, and if pain relief is not achieved quickly (e.g. as is often the case), the paresthesia can avoid the patient incorrectly assuming stimulation energy is not being delivered. The tonic waveform included in the stimulation provided by apparatus 10 can be provided initially at a relatively high amplitude, and subsequently decreased as pain relief is achieved (e.g. continually or intermittently decreased over hours, days, or weeks), such as a decrease of the tonic stimulation to a low amplitude, sub-threshold amplitude, or zero amplitude. Apparatus 10 can perform this decrease in the tonic stimulation in an adaptive manner, such as by including patient feedback on the pain relief achieved. Alternatively or additionally, the decrease in the tonic stimulation can be performed over a pre-defined duration. In some embodiments, a similar reduction in paresthesia-inducing tonic stimulation can be provided by apparatus 10 using a high frequency tonic stimulation waveform combined with a low frequency (paresthesia-inducing) tonic stimulation.

In some embodiments, apparatus 10 is configured to steer current delivered by one or more stimulation elements 260. In these embodiments, apparatus 10 can be configured with a set of amplitudes for the anodes and cathodes of a set of stimulation elements 260. The relative amplitudes of the anodes and cathodes can be set to deliver energy to a target anatomical location. The target anatomical location can be set using paresthesia mapping, such as by delivering a stimulation waveform that includes tonic stimulation configured to cause paresthesia, as described in reference to FIG. 29B and otherwise herein. As a patient changes their posture, the distance changes between the patient's spinal cord and stimulation elements 260 of one or more implanted leads 265. This changing posture will cause the electric fields generated by elements 260 to change, such as movement that causes the point of maximum field intensity, referred to as a "centroid", to no longer being present at the target anatomical location. In some embodiments, apparatus 10 is configured to cause the current steering amplitudes to change in either a deterministic or random manner. The configuration would result in a larger anatomical area receiving stimulation energy, such as to compensate for variations caused by patient movement (e.g. posture change), and/or to compensate for neural fatigue. In some embodiments, a user interface (e.g. a user interface of a programmer 600) can display an image of an anatomical area in which a user (e.g. the patient) can make a selection, and apparatus 10 is configured to traverse this area (e.g. either deterministically or randomly). In some embodiments, apparatus 10 is configured to collect and/or process posture data, such as to automatically readjust the centroid based on the patient's current posture.

Applicant has conducted non-human (e.g. rodent, such as rats) studies with apparatus 10 and the stimulation waveform as shown and described herein in reference to FIG. 29. Applicant collected recordings from wide-dynamic-range (WDR) cells in the dorsal horn of rats to compare the effects of the stimulation waveform of FIG. 29 (hereinafter "NTS1") to the effects of a wide pulse width burst-like waveform (hereinafter "Burst1"), specifically comparing their respective effects on cellular responses to painful stimuli. For this study, NTS1 comprised a pulse width of 30 us, an inter-pulse gap of 60 us, a train-on period of 1 msec, a train-off period of 900 us, a burst-on period of 9 msec, and a burst-off period of 16 msec. Additionally, for this study, Burst1 comprised a pulse width of 1 msec, an inter-pulse gap of 1 msec, a burst-on period of 10 msec, and a burst-off period of 15 msec. Applicant monitored both the spontaneous activity and evoked activity of the rat WDR cells before and after spinal cord stimulation (SCS) was delivered in the form of NTS1 and Burst1. The ratio between WDR responses before and after SCS was taken as a metric of neural inhibition in five WDR cells, such that a lower value corresponds to increased inhibition. In each of the five WDR cells, Applicant observed both spontaneous and evoked activity were inhibited more by NTS1 than by Burst1. The average inhibition (n=5) of spontaneous activity was 0.67 with NTS1, whereas the average inhibition (n=5) of spontaneous activity was 1.1 with Burst1. Similarly, the average inhibition (n=5) of evoked activity was 0.71 with NTS1, whereas the average inhibition (n=5) of evoked activity was 1.1 with Burst1. Additionally, Applicant compared the inhibition of activity with a biphasic 10 kHz stimulation waveform (hereinafter "10K1") to NTS1 in the same WDR neuron. The inhibition of evoked activity was 0.42 with NTS1 and 0.63 with 10K1. In addition, the duration of the inhibition lasted longer in the case of NTS1 as compared to 10K1, whereby inhibition with NTS1 comprised a duration of 25 minutes and inhibition with 10K1 comprised a duration of 10 minutes. Applicant proposes these Burst results are consistent with the findings of Crosby et al. 2015 (Burst and Tonic Spinal Cord Stimulation Differentially Activate GABAergic Mechanisms to Attenuate Pain in a Rat Model of Cervical Radiculopathy. *IEEE Transactions on Biomedical Engineering*, 62(6), 1604-1613. doi: 10.1109/tbme.2015.2399374), in which it was found that a spinal cord GABA-mediated mechanism is unlikely to be involved in the Burst1 mechanism of action.

Applicant has also conducted human clinical studies (a completed acute study and an in-process chronic study) with apparatus 10.

Acute Study

Under an acute protocol using apparatus 10 and the stimulation waveform NTS1, each as described herein, applicant conducted two multi-center, open label, prospective, feasibility studies across multiple sites in Australia and the United Kingdom to evaluate an apparatus 10 for the treatment of chronic pain via SCS. The apparatus 10 used comprised an external, proto-type device developed to provide stimulation and being capable of generating a number of waveforms, including NTS1 and a traditional low frequency Tonic stimulation pattern. Traditional Tonic stimulation can comprise a pulse width of approximately between 100 μsec and 600 μsec and can comprise a rate between approximately 20 Hz and 200 Hz. Tonic stimulation can also comprise higher rates, such as a stimulation waveform comprising a rate of approximately 1 kHz and a pulse width of less than 200 μsecs.

Patients with a diagnosis of chronic pain in the low back and/or legs (patients who indicated a 5 or above on the visual analog scale (VAS)) underwent trial implantation with commercially available spinal cord stimulation leads. Leads 265 were implanted in two different methods. In the "physiologic placement" group, leads 265 were placed based on a physiologic response to test stimulation energy being delivered (e.g. paresthesia felt in a pain area of the intended treatment). In the "anatomic placement" group, leads 265 were positioned via the patient's anatomy. Apparatus 10, such as using stimulation waveform NTS1 can provide pain relief by stimulating a particular segment of the patient's spinal cord, that can be unrelated to the pain location (e.g. where the patient might feel paresthesia). The implanting clinician places the leads 265 via anatomic markers (e.g. under fluoroscopic visualization) without stimulation testing intraoperatively.

Following lead 265 implantation, apparatus 10 was used for up to 15-days to provide spinal cord stimulation. Applicant tested both the paresthesia and paresthesia-independent stimulation patterns in each patient, for example, for 10 days with NTS1 stimulation followed by a "washout" period (e.g. a time period with no stimulation delivered in which effects of previous stimulation fade) and three days with Tonic stimulation. The washout periods in these studies varied by patient, and lasted up to 25 hours. In addition, during stimulation with NTS1 stimulation, the study randomized the activation of electrode (e.g. stimulation element 260) contacts (e.g. anatomic placement vs physiologic placement) in the first 20 patients. Responders were defined as those with an at least 50% reduction in the patient's pain from baseline, such as measured using the VAS.

Applicant observed seven of the ten patients in the anatomic placement group were back pain responders to the NTS1 stimulation, whereas four of the ten patients were back pain responders in the physiologic placement group. Applicant further observed that leg-pain was more responsive than back-pain to SCS of all types. Among responders to the NTS1 stimulation, the back pain reduction was 77% in the anatomic placement group and 59% in the physiologic placement group. Leg pain responders showed a reduction of 68% in the anatomic placement group and 67% in the physiologic placement group. Applicant observed anatomic placement group efficacy was statistically better than physiologic placement group efficacy in both the back and the leg at p<0.05.

In NTS1 stimulation responders, Applicant performed an analysis of cathode electrode locations (e.g. elements 260 of lead 265) to identify the optimal anatomic level for NTS1 stimulation efficacy. As shown in FIG. 30, seventy-four percent of the efficacious cathodes fell in the T9 vertebral body, 16% in T10, and 11% in T8. This data suggests that the T9 vertebral body, and specifically the top half of T9, can be an advantageous target for NTS1 stimulation.

Overall, Applicant observed that NTS1 stimulation therapy outcomes exceeded those derived from Tonic stimulation by 10-35%. In subsequent patients, anatomic placement was utilized due to the noted improved responder rates.

Thirty-one patients were evaluable for pain reduction in their lower backs, of which 22 of them were responders to NTS1 stimulation (p<0.001). When stimulated with conventional stimulation patterns (e.g. Tonic), 12 of these 31 patients were considered responders. Applicant observed a statistically significant higher responder rate in the back with NTS1 stimulation when compared to Tonic stimulation (p<0.001). Twenty-seven patients were evaluable for pain reduction in their legs/lower limbs. Twenty-two of these patients were responders when they received NTS1 stimulation and 13 patients were responders when they received Tonic stimulation. Applicant observed a stronger pain reduction in the leg/lower limbs with NTS1 stimulation when compared to Tonic stimulation (p<0.01).

The results from these human studies demonstrate NTS1 stimulation of apparatus 10 can provide paresthesia-independent pain relief when applied epidurally for a period of up to ten days. Applicant observed both back-pain and leg pain relief with NTS1 stimulation were superior to tonic stimulation, thus, demonstrating that NTS1 stimulation can provide improved outcomes to the patient.

Chronic Study

Applicant is conducting a multi-center, open label, study to confirm the safety and performance of apparatus 10 of the present inventive concepts. In addition, the study is capturing multiple standard outcome domains to confirm apparatus 10 performance and patient responses to the device and therapy.

The ongoing study will enroll up to 40 evaluable adult patients, suffering from chronic intractable pain in the legs and/or back, and implanted with implantable device 200, at up to 10 centers in Australia. The study includes three phases: Screening/Baseline, SCS Trial and Permanent Implant Phase. Patients are followed up for one year after implantable device 200 implantation.

Following confirmation of eligibility at the Screening/baseline, a "trial" period is performed to provide the patient an opportunity to experience the therapy for a short period of time before committing to a long-term implant. During such trials, leads 265 containing stimulation elements 260 are deployed into the epidural space using minimally invasive implantation techniques. Upon completion of a successful trial (e.g. at least a 50% reduction in their average NRS pain diary scores from baseline), patients move on to a phase in which implantable device 200 is implanted for a chronic period of time. Patients are then followed for 12 months with clinic visits at 2 weeks, 1 month, 3 months, 6 months, 9 months and 12 months. During each follow-up visit, programming of apparatus 10 may be performed, as needed; patient pain diaries are collected and reviewed, x-rays are taken if migration of a lead 265 is suspected, patients are asked to rate their pain using the VAS and NRS scales, several standardized and validated questionnaires are administered to patients including the EQ-5D for health-related QoL, Oswestry Disability Index to assess activities of daily living, pain and paresthesia maps to understand pain coverage, Brief Pain Inventory and the Beck Depression Inventory. In addition, medical and medication history and adverse events are collected and documented. Patients may return to the clinic for unscheduled visits for additional training on use of apparatus 10, reprogramming if stimulation coverage has changed, and trouble-shooting of device issues as well as reporting of adverse events.

Currently, six sites in Australia are actively screening and enrolling patients in the study. Sixty-three patients have been screened to-date; of these thirty patients have failed screening due to not meeting one or more eligibility criteria. Of the remaining thirty-three enrolled patients, thirty-one have received an implant and two patients are scheduled for surgery.

Six patients received a temporary "trial" where, leads 265 were percutaneously externalized and connected to a trialing system, as described herein. On successful completion of the trial, the leads 265 were removed and new leads 265 were chronically implanted with the remaining portions of implantable device 200. The remaining twenty-five patients received a different form of a trial, where both the leads 265 and the remaining portions of implantable device 200 were implanted during the trial. Two patients were considered trial failures and excluded from the study as they failed to achieve at least 50% pain relief from their baseline. Two patients did not complete the trial and were withdrawn from the study for non-compliance. Twenty-seven patients completed the trial phase successfully and entered the remaining chronic phase of the study. Of these, five patients have been excluded from analysis: three due to lead 265 migration; 1 due to connectivity issues with the external device 500, and 1 due to an infection leading to explantation of implantable device 200. One patient had only back pain and no leg pain at baseline. Two patients were programmed to provide tonic stimulation programs and the remaining nineteen patients were programmed with pulse stimulation pattern (PSP) as described herein (e.g. PSP1, PSP2, PSP3, and/or PSP4 described herein).

For the nineteen per protocol patients receiving PSP stimulation, the average NRS diary pain scores in the leg(s) at baseline was 6.79. Fourteen of these patients have completed a three-month follow up procedure. At this three-month point, the average NRS diary pain score associated with the patient's leg pain was 1.06, which correlated to an 84.42% reduction in leg pain from baseline. The average NRS diary score for pain in the patient's back at baseline was 6.89 (n=20). Fourteen patients have completed a three-month follow up procedure, and the average NRS diary pain score associated with the patient's back pain at the three-month point was 1.51, which correlates to a 78.14% reduction in back pain from baseline.

Referring now to FIGS. 31A-H, numerous graphs and circuit diagrams are illustrated, consistent with the present inventive concepts. Referring specifically to FIG. 31A, graphs of electrically-evoked compound action potential signals are illustrated. Referring specifically to FIG. 31B, a schematic of a stimulator and recording system is illustrated. Referring specifically to FIG. 31C, a schematic of an exemplary amplifier is illustrated. Referring specifically to FIGS. 31D-H, graphs of artifact recordings and electrically-evoked compound action potential signals are illustrated.

In the field of neurostimulation and neuromodulation, a recurring challenge is the measurement of electrically-evoked compound action potential (ECAP) signals. ECAPs are small voltage transients that are produced by neural tissue in response to electrical stimulation. These signals can be observed near the site of the applied stimulation, at roughly 200 μsec after the onset of the stimulation pulse. The magnitude of the ECAP, as well as the timing between peaks in the ECAP waveform, vary with the number of neurons recruited by the stimulation pulse. Thus, ECAP recordings can be an objective measure of the effectiveness of the stimulation. For example, ECAP recordings have been used to perform objective fitting in cochlear implant systems, and to adaptively control stimulation amplitude in response to anatomical movement in spinal cord stimulation (SCS) systems. FIG. 31A illustrate a series of typical ECAP signals, with ECAP magnitude varying with stimulation current level.

A principal challenge in ECAP recording is the relatively low amplitude of these signals, in the range of 1 μV to 2000 μV, compared to that of the preceding stimulation pulse, typically on the order of several volts. For this reason, an amplifier in an ECAP measurement system of implantable device 200 needs to recover quickly from input overload conditions so that it will operate in a linear region shortly after the end of the stimulation pulse. In addition, a signal tail follows the stimulation pulse, due to the RC discharge time of various capacitances in the stimulation signal path. This tail is called the artifact. It typically has similar spectral content to the ECAP signal, and the tail coincides with the ECAP in time. It has proven challenging to cancel the artifact (e.g. to extract the ECAP from the combined signal containing both ECAP and artifact components).

A number of solutions to the problem of artifact cancellation have been proposed and implemented over the course of the neurostimulation development. These techniques include forward masking (masker-probe), template subtraction, and alternating polarity. All of these approaches require that the amplification and recording system remains linear throughout the input signal range, in order to accurately perform the particular mathematical cancellation function between different recordings. Thus, in order to provide sufficient amplification of the ECAP signal without swamping the system with the artifact, the amplitude of the artifact needs to be of similar magnitude to that of the ECAP. To help keep the magnitude of the artifact within a manageable range, ECAP recording systems typically used balanced biphasic stimulation waveforms (active charge recovery). With a biphasic waveform, the stimulation charge is actively removed from the capacitances of the electrode-tissue interface and DC-blocking capacitors of implantable device 200, so the only charge remaining after the stimulation pulse is that due to parasitic capacitances in the system, non-linearities in the electrode 260—tissue interface, and current imbalance between the two stimulation phases. As a result, the RC discharge curve, and thus the artifact, are relatively short in time and low in magnitude.

However, if the goal is to measure ECAPs during the course of normal stimulation in SCS systems, the requirement to use biphasic stimulation can be a significant limitation. Since equal but opposite current is sourced to tissue during the stimulation and charge recovery phases, power consumption is typically about double in biphasic stimulation, as compared to monophasic stimulation (e.g. passive charge recovery). Since power consumption is crucial in most neurostimulation systems in order to minimize size and maximize battery life, many SCS paradigms involve monophasic stimulation. In monophasic stimulation, current is applied to tissue only during the stimulation phase. During charge recovery, the stimulating electrodes are shorted together to passively remove charge from the capacitances in the system. The recovery phase is an RC discharge, with a relatively large initial value and time constant. Thus, for monophasic stimulation, the magnitude of the artifact is much greater than for biphasic, and can swamp the ECAP recording system, making it difficult to apply any of the artifact cancellation methods discussed above.

Described herein is a means to maintain an ECAP recording system in a linear operating region even with the large artifacts found with monophasic (e.g. passive recovery) stimulation. FIG. 31B illustrates an overall block diagram showing both the implantable device 200 stimulator circuitry and a recording system 2100.

Implantable device 200 can be configured to implement monophasic stimulation, and can comprise a switchable current source $V_{DD}$ and a shorting switch S1. Current source $V_{DD}$ and shorting switch S1 can connect to one, two, or more stimulation electrodes 260 through DC-blocking capacitors $C_{DCB}$. Current source $V_{DD}$ can be switched on during a stimulation phase and turned off while shorting switch S1 is closed during a charge recovery phase.

Recording system 2100 can comprise a variable-gain amplifier, amplifier 2110, and an analog-to-digital convertor, ADC 2120. Amplifier 2110 can be configured to provide gain for a combined ECAP/artifact signal, and its output can be digitized by ADC 2120. Recording system 2100 can further comprise a digital-to-analog-convertor, DAC 2130, a random-access memory, RAM 2140, and a computing element 2150 (e.g. hardware and/or software) configured to perform inversion, scaling, and/or offset arithmetic of the combined ECAP/artifact signal. The output of DAC 2130 can drive an offset adjustment pin of amplifier 2110. RAM 2140 can be configured to provide the input of DAC 2130, and this input can contain digitized samples from ADC 2120 (e.g. samples that were previously inverted, scaled, and/or offset).

In these embodiments, a stimulation waveform is applied and the artifact is recorded with amplifier 2110 in a low gain setting, such that the artifact falls within an amplifier 2110 dynamic range. To record the artifact without the ECAP signal, one stimulation pulse can be followed by a second pulse within the refractory period of the neurons, such that there is minimal or no ECAP signal following the second pulse. The artifact from that second pulse is recorded. The low-gain artifact output from amplifier 2110 can be digitized by ADC 2120. The output from ADC 2120 can then be inverted (e.g. negated) such that the artifact and its inverse sum to zero. Computing element 2150 can also apply scale and offset factors to the inverted artifact, such as to provide adjustability.

Next, a recording of the ECAP signal can be performed, with amplifier 2110 at a high gain setting (e.g. a setting configured to provide sufficient resolution to the ECAP signal). While the ECAP signal is recorded, the previously-stored inverted artifact signal can be played back from RAM 2140, converted to an analog signal by DAC 2130, and applied to an offset pin of amplifier 2110. This playback can be synchronous with the sampling of the input signal. The offset pin can be positioned at a front end of amplifier 2110, where gain is low, and both input and offset are within a linear operating range. The previously recorded offset can be configured to negate the artifact component in the input signal. The result can comprise a reduction (e.g. significant reduction) in artifact amplitude, such that the result is within the linear range of amplifier 2110 at high gain setting. The ECAP signal, with a small residual artifact, can be accurately digitized by ADC 2120. Conventional artifact cancellation techniques, such as forward masking or template subtraction, can then be applied to fully extract the ECAP signal. Averaging of multiple ADC 2120 captures can be used to reduce noise, both in the low-gain artifact recording and the high-gain ECAP recording.

FIG. 31C illustrates an exemplary amplifier topology that supports the offset capability described herein. As shown, amplifier 2110 comprises an instrumentation amplifier front-end, followed by multiple cascaded gain stages. The gain setting of amplifier 2110 is determined by a multiplexor, which selects the output of one of the individual stages. Amplifier 2110 can comprise a front-end comprising a low gain (e.g. on the order of between 1 and 5), and can be configured to accommodate a large signal swing on its input and offset pins while remaining in the linear region. The subsequent gain stage(s) can comprise a higher gain, such that an overall system gain of 1000 or more can be achieved (depending on specifics of the design of amplifier 2110). The subtraction of the previously recorded artifact signal can be completed at the initial front-end stage. The resulting signal, comprising a much-reduced artifact, is then amplified by the subsequent high-gain stages and will remain linear.

Figure 31D:
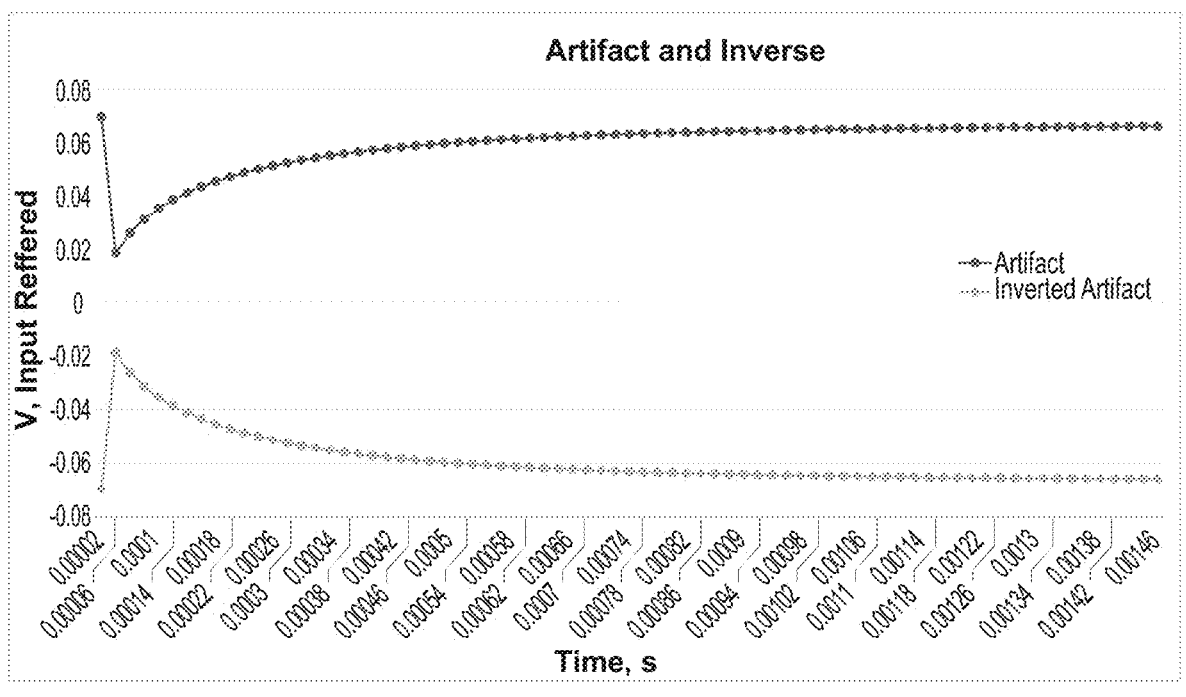

FIG. 31D illustrates an exemplary artifact recorded at a low gain setting, and its calculated inverse. As shown, the artifact includes a swing of around 40 mV, such that it would saturate the system at gains of 100 or greater (assuming a 3V operating range for amplifier 2110).

Figure 31E:
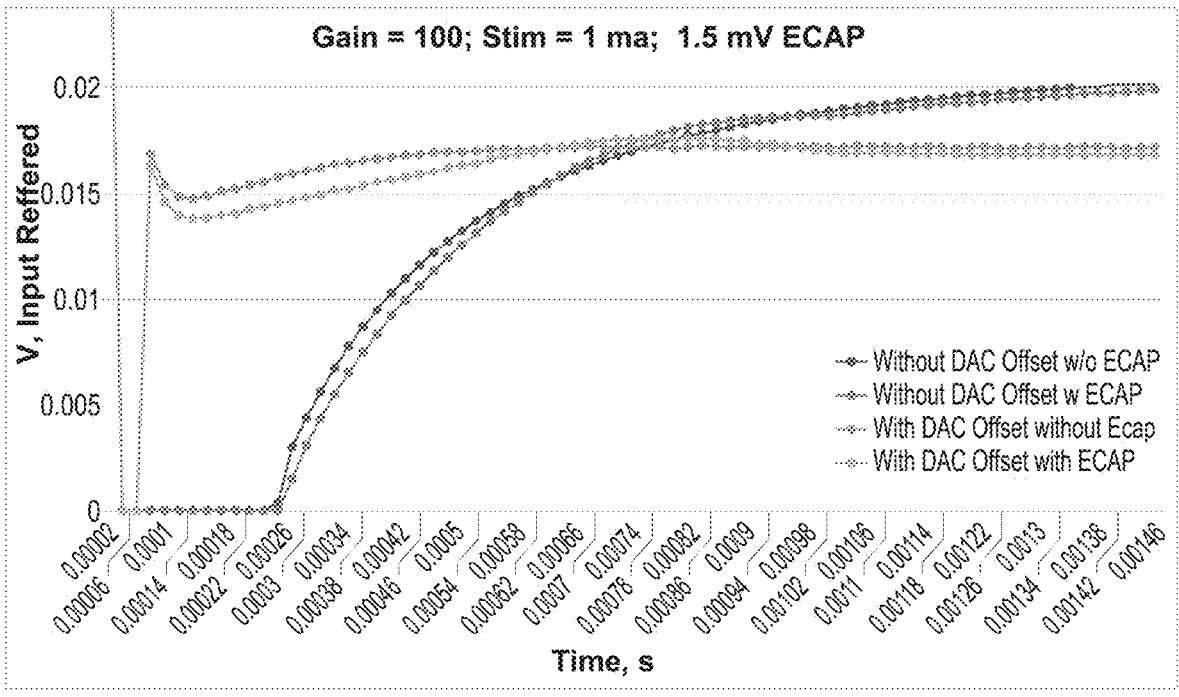

FIG. 31E illustrates a technique applied to recording an ECAP and comprising an artifact of similar magnitude to that shown in FIG. 31D. The ECAP signal is emulated by a single-cycle sine wave of 1 msec period, applied by a signal generator to the saline solution containing the stimulating and recording electrodes. Recordings both with and without ECAP are shown. Additionally, recordings using the conventional technique (e.g. without DAC offset) and the present inventive concepts (e.g. with DAC offset) are shown. The timescale starts at the end of a stimulation pulse. As shown in FIG. 31E, the recordings comprising DAC offset recover into the linear within about 60 µsec after the end of the stimulus, whereas the conventional recordings (e.g. without DAC offset) remain in saturation for approximately 250 µsec.

Figure 31F:
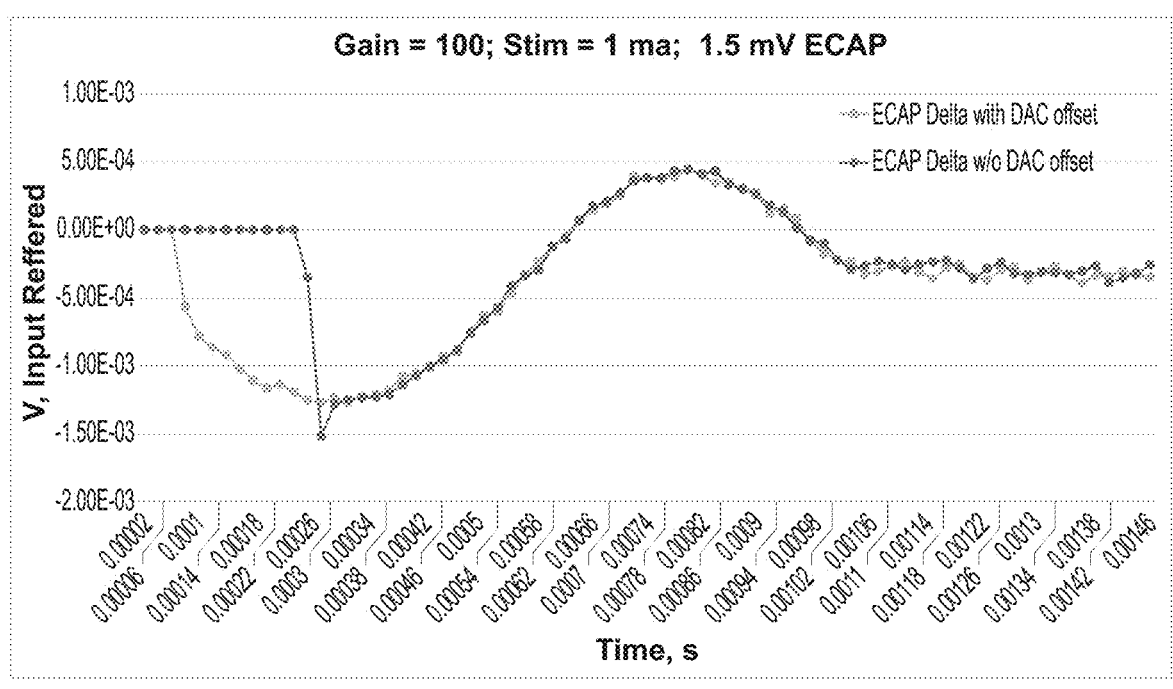

FIG. 31F illustrates the recordings as shown in FIG. 31E, comprising the signals without ECAP subtracted from the corresponding signals with ECAP. The result is the extracted ECAP represented by a single-cycle sine wave. As shown, the recording comprising DAC offset captures almost the full period of the sine wave, whereas the conventional recording (e.g. without DAC offset) loses about the first quarter of the period. Such a recording would correspond to roughly half of the N1 phase of an actual ECAP signal, as shown in FIG. 31A.

Figure 31G:
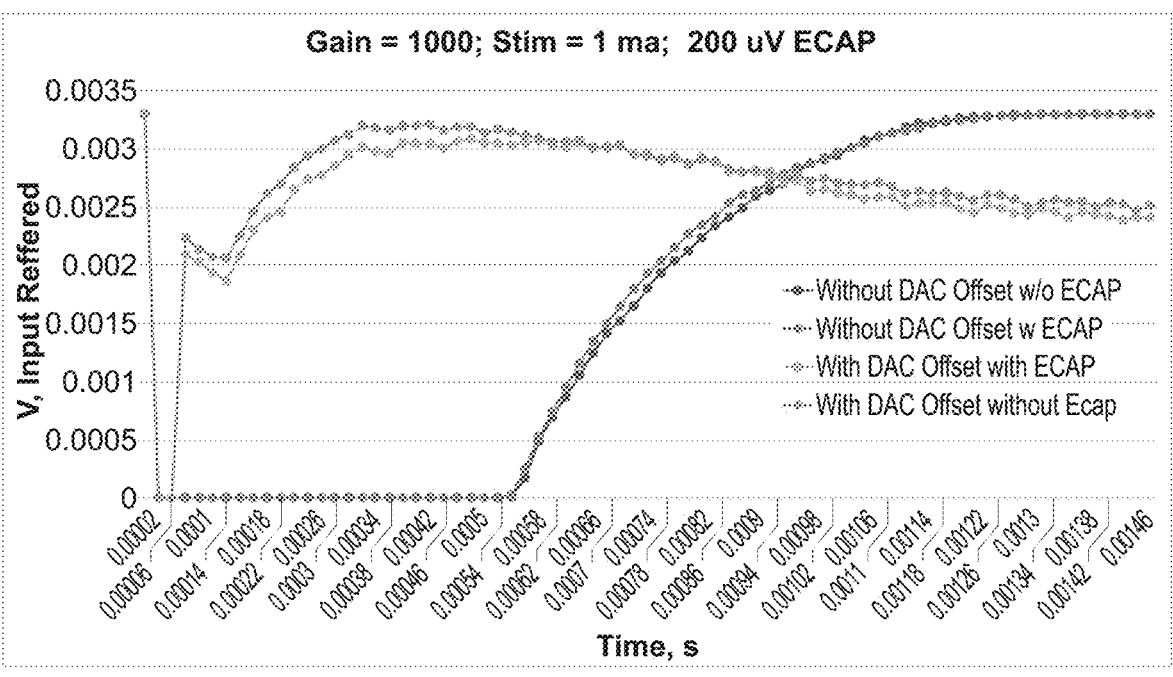

FIG. 31G illustrates similar recordings to those shown in FIG. 31E, but with an ECAP signal comprising a significantly lower magnitude, and an amplifier 2110 gain of 1000 (as opposed to 100). With the higher gain setting, it takes almost 700 µsec for the conventional recording (e.g. without DAC offset) to recover into the linear region of the amplifier 2110, whereas the recording comprising DAC offset recovers in approximately 100 µsec.

Figure 31H:
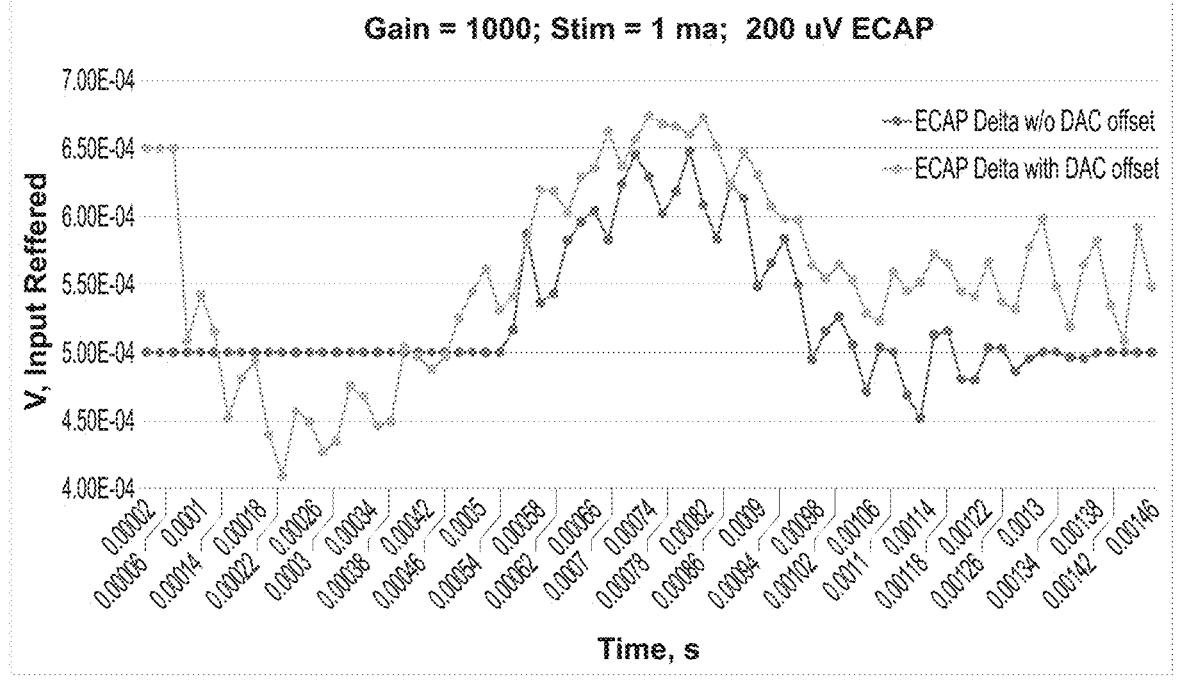

FIG. 31H illustrates the high-gain results after the artifact-only recordings are subtracted from their respective ECAP/artifact recordings. As shown, a majority of the sine period is preserved in the recording comprising DAC offset, whereas over half of the period is lost with the conventional recording (e.g. without DAC offset). This loss could correspond to loss of the entire N1 peak of an actual ECAP.

Referring now to FIG. 32, graphs showing two different types of stimulation waveforms that produce a similar physiologic effect are illustrated, consistent with the present inventive concepts. Tonic stimulation pulses that are separated by short periods of time (inter-pulse gaps of short duration) may be "recognized" by the patient's nervous system as if it were a single pulse, since the response rate (refractory period) of the associated nerve fibers is generally large (hundreds of microseconds to milliseconds). In some embodiments, implantable device 200 is configured to provide a set of relatively small duration pulses (e.g. a duration of no more than 300 us), separated by a relatively small inter-pulse gap (e.g. an off time of no more than 100 us), that creates a similar physiologic effect to a single pulse with a duration similar to the duration of the complete set of pulses. For example, as shown in FIG. 32, a stimulation waveform $SW_{32A}$ that comprises ten 40 µsec pulses, separated by nine 10 µsec inter-pulse gaps, can provide a similar physiologic effect as a stimulation waveform $SW_{32B}$ comprising a single 500 μsec pulse. The stimulation waveform $SW_{32A}$ can provide numerous advantages, such as power savings (e.g. 20% in the example shown in FIG. 32) without increasing stimulation threshold and/or without reducing efficacy. Numerous configurations of sets of multiple pulses can be delivered to provide a similar physiologic effect as a single pulse, such as a 500 μsec single pulse that is simulated with ten 30 μsec pulses separated by 20 μsec off times, or five 80 μsec pulses separated by 20 μsec off times, and the like.

In these embodiments, apparatus 10 includes a user interface (e.g. user interfaces 580 and/or 680 described herein) that allows a user (e.g. the patient or the patient's clinician) to enter a "pulse density percentage" which correlates to a relative "on time" of the charge within a set of multiple stimulation pulses (e.g. a set of multiple stimulation pulses that provide a similar physiologic effect as a single pulse). Based on the pulse density percentage entered, and a single pulse to simulate (e.g. a pulse width of a single pulse to simulate), apparatus 10 can calculate the pulse width and inter-pulse gap of a set of multiple pulses to be delivered in a stimulation waveform. Alternatively the user can specify, via the user interface, two or more parameters of: a pulse width; an inter-pulse gap; and/or a pulse density; to be used by apparatus 10 to create a stimulation waveform that simulates a particular single pulse (e.g. a single pulse with a particular pulse width known or entered into apparatus 10). In some embodiments, the user specifies, via the user interface, a single parameter of: a pulse width; an inter-pulse gap; and/or a pulse density; to be used by apparatus 10 to create a stimulation waveform that simulates a particular single pulse (e.g. a single pulse with a particular pulse width known or entered into apparatus 10), where apparatus 10 uses a default value for one or both of the non-specified parameters, and/or where apparatus 10 calculates one or both of the non-specified parameters (e.g. via a heuristic, machine learning, and/or other algorithmic approach).

Referring now to FIG. 33, graphs showing stimulation waveforms for stimulating multiple anatomical areas of a patient is illustrated, consistent with the present inventive concepts. In some embodiments, apparatus 10 is configured to stimulate multiple anatomical areas of a patient, such as to treat complex pain (e.g. a first stimulated area to treat back pain, and a second stimulated area to treat leg pain). In these embodiments, a first set of one or more stimulation elements 260 (e.g. electrodes) can deliver stimulation in a first area, and a second set of stimulation elements 260 can deliver stimulation in a second, different area. The first set of stimulation elements 260 can deliver energy with a first set of stimulation parameters, and the second set of stimulation elements 260 can deliver energy with a second set of stimulation parameters. The second set of stimulation parameters can be similar to and/or different from the first set of stimulation parameters.

Apparatus 10 can be configured to perform spinal cord stimulation using monophasic pulses with passive recovery, for example as opposed to biphasic pulses with active recovery, each as described herein. The monophasic pulses with passive recovery can be implemented to reduce power consumption. As the passive recovery relies on the natural decay of the accumulated charge, the time to dissipate the charge limits the maximum frequency of the stimulation, whereas biphasic pulses by their very nature are not limited in frequency.

In some embodiments, apparatus 10 is configured to provide multiple area stimulation, wherein a single set of stimulation elements 260 (e.g. electrodes) delivers stimulation energy to multiple anatomical areas. Apparatus 10 can be configured to stimulate at least two areas, at least four areas (as shown in FIG. 33), at least six areas, or at least eight areas. In these embodiments, stimulation energy can be delivered such that the anodes and cathodes of the stimulated areas are inverted to produce alternating polarities, thus mimicking the effect of biphasic pulses. This configuration can be implemented with passive recovery or without it (e.g. entirely without it). In alternative embodiments, the stimulation elements 260 could deliver multiple monophasic pulses with an intermittent pulse of opposite polarity (e.g. with or without passive recovery).

Stimulation waveforms $33_A$, $33_B$, and $33_C$ each stimulate four areas, Areas 1-4 shown, by delivering energy to a single set of stimulation elements 260 by varying which specific elements 260 receive energy and/or by varying the polarity of the energy delivered. The amount of current delivered, and the polarity of that current, can be selected to maintain charge balance. Various forms of multiple area stimulation including passive charge balancing can be performed by apparatus 10. For example, in stimulation waveform $33_A$, two pulses of a first (positive) polarity and equal amplitude and duration are delivered to stimulate Area 1 and Area 3, and two pulses of an opposite (negative) polarity with the same amplitude and duration are delivered to stimulate Area 2 and Area 4. In stimulation waveform $33_B$, three pulses of a first (positive) polarity with equal amplitude and duration are delivered to stimulate Area 1, Area 2, and Area 3, and a single pulse of an opposite (negative) polarity of the same duration but three times the amplitude is delivered to stimulate Area 4. In stimulation waveform $33_C$, three pulses of a first (positive) polarity with equal amplitude and duration are delivered to stimulate Area 1, Area 2, and Area 3, and a single pulse of an opposite (negative) polarity of the same amplitude but three times the duration is delivered to stimulate Area 4. It should be appreciated that other variations of adjusting polarity, amplitude, and pulse duration can be used, to stimulate the multiple areas, while passively maintaining charge balance.

Referring now to FIG. 34, a graph of a stimulation waveform is illustrated, consistent with the present inventive concepts. Apparatus 10 can be configured to deliver the stimulation waveform $SW_{34}$ shown in FIG. 34, such as via one or more stimulation elements 260 (e.g. electrode-based stimulation elements) that are positioned in one or more leads 265 of one or more implantable devices 200, each as described herein. The stimulation waveform $SW_{34}$ shown in FIG. 34 can include bursts of trains of pulses as shown. In some embodiments, apparatus 10 is configured to deliver a stimulation waveform (e.g. stimulation waveform $SW_{34}$ shown, delivered by one or more implantable devices 200) comprising one or more parameters selected from the group consisting of: pulses with a pulse width of at least 200 μsec and/or an inter-pulse gap of 500 μsec; pulses with a pulse width of at least 100 μsec and/or no more than 350 μsec; pulses with an inter-pulse gap of at least 200 μsec and/or no more than 600 μsec; trains with an on time of 900 μsec and/or an off time of 918 μsecs (e.g. a train of six pulses); trains with an on time of at least 300 μsec and/or an on time of no more than 1,100 μsec; trains with an off time of at least 350 μsec and/or an off time of no more than 1,000 μsec; bursts with an on time of 10 msec and/or an off time of 15 msec (e.g. a burst of five trains); and combinations of these. In some embodiments, apparatus 10 is configured to deliver a stimulation waveform (e.g. stimulation waveform $SW_{34}$ shown, delivered by one or more implantable devices 200) comprising one or more parameters selected from the group consisting of: pulses with a pulse width of at least 10 μsec and/or no more than 100 µsec; pulses with an inter-pulse gap of at least 400 µsec and/or no more than 1,000 µsec; trains with an on time of at least 500 µsec and/or an on time of no more than 2,000 µsec; trains with an off time of at least 500 µsec and/or an off time of no more than 2,000 µsec; bursts with an on time of at least 5 msec and/or no more than 50 msec; bursts with an off time of at least 5 msec and/or no more than 200 msec; and combinations of these.

Referring now to FIG. 35, a flow chart of a method of implanting a stimulator and programming a stimulation system is illustrated, consistent with the present inventive concepts. Method 3500 of FIG. 35 is described using apparatus 10 and its components.

In STEP 3510, one or more leads 265 of an implantable device 200 are implanted in the patient. A first lead 265*a* can be implanted by placing the tip of the first lead (e.g. with one or more stimulation elements 260 located on lead 265*a* proximate the tip) proximate the top of vertebra T8, at a location on or at least proximate the midline of the patient's spine. A second lead 265*b* can be implanted by placing the tip of the second lead (e.g. with one or more stimulation elements 260 located on lead 265*b* proximate the tip) proximate the top of vertebra T9, at a location proximate the side of the predominant pain. In some embodiments, the stimulation elements 260 of lead 265*a* and the stimulation elements 260 of lead 265*b* are implanted in a staggered arrangement. An image can be taken (e.g. at the end of the implantation procedure), such as an image taken at vertebra T10. The image can be a fluoroscopic and/or ultrasound image, such as an image of bone and/or other tissue, as well as markers of implantable device 200 (e.g. radiopaque markers and/or ultrasonically reflective markers, respectively). In some embodiments, such as when the patient is afflicted with severe scoliosis, the patient may be awakened (e.g. from anesthesia used during the implantation procedure), to confirm successful placement of leads 265*a* and/or 265*b* (e.g. confirm accuracy of midline placement) by delivery of paresthesia-inducing stimulation by implantable device 200.

In STEP 3520, stimulation programming of apparatus 10 is performed, for example soon after the implantation of the one or more leads 265. In some embodiments, the programming performed in STEP 3520 is performed at least one day following implantation of the one or more leads 265, such as to avoid the volatility associated with stimulation thresholds that occurs 24-48 hours after implantation. Stimulation thresholds are determined with the patient on their back (the supine position). Attempts to position the patient's back as flat as practical are performed (e.g. to achieve less than a 20° angle between the patient's back and the floor). An assessment of physiological midline is performed (e.g. using tonic and/or another stimulation waveform), at the middle of T9 on each lead 265. In some embodiments, stimulation waveform NTS1 described herein is used. The amplitude of the stimulation is increased (e.g. to well above a threshold) to check for left versus right paresthesia. The lead that is determined to be "most midline" is selected. In some embodiments, if one lead 265 provides only left paresthesia, and another lead 265 provides only right paresthesia, the lead 265 on the dominant pain side is selected. In some embodiments, to better determine which lead is more midline, amplitude of stimulation is increased to a high level to cause the side opposite that having paresthesia, to also have paresthesia, otherwise, if the lead is perfectly medial, increase to high level expecting bilateral. All stimulation can be provided as bipolar stimulation, such as with cathodes positioned rostrally, and anodes positioned caudally.

Referring additionally to FIG. 35A, an X-ray of a first lead 265*a* comprising eight stimulation elements 260, and a second lead 265*b* comprising eight stimulation elements 260 is illustrated, consistent with the present inventive concepts. Leads 265*a* and 265*b* can be positioned such that the stimulation elements 260 are implanted in the staggered arrangement shown in FIG. 35A. Designated on FIG. 35A are stimulation elements A3⁻, A4⁺, A5⁻, A6⁺, A7⁻, and A8⁺ of lead 265*a*, and stimulation elements B2− and B3+ of lead 265*b*. Apparatus 10 can include multiple sets of stimulation parameter settings (also referred to as "programs"), each comprising a particular pulse stimulation pattern (PSP) based on various stimulation parameters. Each program is provided by apparatus 10 for selection by the patient, clinician, and/or other user of apparatus 10. For example, a first program PSP1 can comprise stimulation via elements A7⁻ and A8⁺ at a level 70% of a paresthesia threshold, such as when bipolar stimulation is delivered via elements A7⁻ and A8⁺ that span the T9-T10 gap. A second program PSP2 can comprise stimulation via elements A5⁻ and A6⁺ at a level 70% of a paresthesia threshold (e.g. the next pair of elements, in a non-overlapping, caudal direction, in relation to program PSP1), such as when bipolar stimulation is delivered via elements A5⁻ and A6⁺. A third program PSP3 can comprise stimulation via elements A3⁻ and A4⁺ at a level 70% of a paresthesia threshold (e.g. the next pair of elements, in a non-overlapping, caudal direction, in relation to program PSP2), such as when bipolar stimulation is delivered via elements A3⁻ and A4⁺. A fourth program PSP4 can comprise stimulation via elements B2⁻ and B3⁺ at a level 70% of a paresthesia threshold (e.g. on the opposite lead 265*b* in the top half of T9), such as when bipolar stimulation is delivered via elements B2⁻ and B3⁺.

In STEP 3530, a paresthesia threshold is measured. With the patient lying on their back (e.g. as flat as practical as described herein), stimulation energy is delivered by implantable device 200 (e.g. via stimulation elements 260 of one or more leads 265) in a slow, amplitude-increasing manner (e.g. in 40 µA steps). Once the stimulation energy is delivered at a current above 1 mA, a step-level of amplitude increase can be made larger (e.g. a change to 120 µA steps). A "staircase" method to identify a paresthesia threshold can be used, where amplitudes are increased and/or decreased (e.g. in a step-wise fashion), and the patient is queried as to whether they are feeling paresthesia. In some embodiments, at least three thresholds of paresthesia are identified (e.g. the lowest amplitude in which paresthesia is felt by the patient), such as when apparatus 10 performs a check for consistency of these thresholds. A 70% level is calculated, correlating to 0.7 times the paresthesia threshold. In some embodiments, a patient may not provide feedback that correlates to a consistent paresthesia threshold. In these embodiments, amplitude of stimulation can be increased until a strong sensation of paresthesia is confirmed, after which the amplitude is decreased (e.g. slowly decreased) while monitoring just that particular location of paresthesia occurrence, and noting the threshold at which paresthesia is no longer present. This technique can avoid the illusory paresthesia sensations that can be felt by the patient at other body locations.

In STEP 3540, stimulation therapy is initiated using implantable device 200 and other components of apparatus 10 (e.g. programmer 600 and external device 500). In some embodiments, the patient utilizes multiple stimulation programs, such as for a period of 2 days each (e.g. in ascending order where PSP1 is used for two days, followed by PSP2 for 2 days, and so on). In this program-testing sequence, it may be desirable to have the patient not change the amplitude of stimulation (e.g. apparatus 10 can be configured to prevent the patient from changing stimulation amplitude in this sequence). If none of the various stimulation programs (e.g. PSP1, PSP2, PSP3, and/or PSP4 described herein) provide sufficient therapy (e.g. sufficient pain relief), additional programs can be provided by apparatus 10, and tested in a similar manner (e.g. in the same four spinal locations of the one or more leads 265). In some embodiments, an X-ray or other image can be taken to determine if a lead 265 has migrated.

An additional number of stimulation programs can be provided by apparatus 10, such as four stimulation programs, such as when each of the additional four stimulation programs comprise delivery of stimulation energy at 50% of the paresthesia threshold. For example, the additional four stimulation programs can be configured as bipolar stimulation as follows: A7$^-$ and A8$^+$ at 50%, A5$^-$ and A6$^+$ at 50%, A3$^-$ and A4$^+$ at 50%, and B2$^-$ and B3$^+$ at 50%.

In some embodiments, yet another set of stimulation programs, such as another four stimulation programs (e.g. totaling eight in addition to the original PSP1, PSP2, PSP3 and PSP4), can be provided by apparatus 10, such that the additional four stimulation programs comprise delivery of stimulation energy at 30% of the paresthesia threshold. For example, the additional four stimulation programs can be configured as bipolar stimulation as follows: A7$^-$ and A8$^+$ at 30%, A5$^-$ and A6$^+$ at 30%, A3$^-$ and A4$^+$ at 30%, and B2$^-$ and B3$^+$ at 30%.

Programmer 600 can be configured to automatically generate the multiple stimulation programs to be offered by apparatus 10. Apparatus 10 can be configured to automatically determine the location of the one or more leads 265 (e.g. using image processing of X-ray or other images). A clinician of the patient can measure paresthesia thresholds, as described herein, for one, more than one, or all of the stimulation programs available, as made available by user interface 680 of programmer 600. Apparatus 10 (via firmware, with or without data from patient programmer 600') can be configured to automatically sequence through one or more of the stimulation programs (e.g. using patient input regarding pain relief and/or presence of paresthesia).

Referring now to FIG. 36, a graph of a delivery of two stimulation programs in a combined arrangement is illustrated, consistent with the present inventive concepts. In some embodiments, apparatus 10 is configured to provide stimulation energy that represents a combination of multiple stimulation programs (also referred to as multiple stimulation waveforms), the stimulation energy delivered by an implantable device 200 in such a way that there is no overlap in stimulation pulses from different stimulation programs running at different pulse rates, and the total period of repetition of the programs is controlled. In these embodiments, apparatus 10 causes an implantable device 200 to deliver stimulation pulses for each stimulation program at equal time intervals and device 200 can "skip" pulses of either or both stimulation programs, as needed to maintain the desired pulse rate. Apparatus 10 can determine the time interval from the stimulation program with the highest rate, and/or from the desired accuracy of the specific pulse rates. Apparatus 10 can divide a time period into segments and at each segment either deliver or skip one or more pulses from each stimulation program. The length of the time period and the number of segments determine the maximum pulse rate and the accuracy at which other pulse rates can be delivered.

In an exemplary embodiment, two stimulation programs are be delivered. A first stimulation program has a pulse rate of 90 Hz, and the second stimulation program has a pulse rate of 100 Hz. The ratio between the rates of these two programs is 9:10, so total time period can be set by apparatus 10 to be the time needed to deliver 10 pulses of the higher rate program, in this example 100 msec, which is also the period of repetition. This period can be divided into 10 segments in order to deliver each of the 10 pulses of the higher rate program. In this example, the segment frequency is equal to the frequency of the highest stimulation rate and is 100 Hz. During stimulation energy delivery by implantable device 200, stimulation pulses from both stimulation programs be delivered during the first nine segments, and only the pulse from the higher rate program would be delivered during the final segment. In each individual time segment, the stimulation pulses can be delivered sequentially to prevent overlap. FIG. 36 illustrates this configuration including a first stimulation program with a pulse rate of 90 Hz, a second stimulation program with a pulse rate of 100 Hz, where none of the pulses overlap and the period of repetition is 100 msec. If the lower rate program required that additional pulses be skipped, these skipped pulses could be evenly distributed throughout the time period to better approximate the actual frequency of the pulse rate. Using this approach, pulse rates that are an integer multiple of the segment frequency can be delivered exactly (delivery of these pulses will be evenly spaced at the exact interval specified by their pulse rate).

When implantable device 200 receives stimulation waveform information that is provided by telemetry data received from external device 500, as described herein, there is an advantage of simplifying data transfer because communicating whether a pulse should occur in each segment is sufficient information to provide the desired programs simultaneously. For example, if two stimulation programs are to be delivered, there are three possible commands: activate the program one pulse only; activate the program two pulse only; or activate both pulses. If the segment frequency is chosen to be equal to the higher rate (meaning its pulse is always delivered), then there are only two possible commands: activate the program one pulse, or activate both pulses. With 3 programs, the number of possible commands increases to 4, and with 4 programs the number of possible commands increases to 8.

If the ratio between rates of multiple stimulation programs does not result in a desirable configuration, the pulse rate can be rounded to the nearest possible pulse rate (e.g. the nearest pulse rate of a set of pulse rates that are determined from the number of segments and the segment frequency). For example, in another exemplary embodiment, apparatus 10 can be configured to simultaneously deliver four programs with desired pulse rates of 24 Hz, 43 Hz, 86 Hz, and 99 Hz. To accurately deliver each pulse rate (e.g. and achieve a 1 Hz resolution), the segment frequency can be set to 100 Hz, but 100 segments would be required. This segmentation would make the total period 1 second instead of 100 ms. With this approach, the stimulation program with the 99 Hz rate would deliver pulses in 99 of the 100 segments, the stimulation program with the 86 Hz rate would deliver pulses in 86 of the 100 segments, and so on. Alternatively, if 20 segments were used at a segment frequency of 100 Hz, each rate could be rounded to the nearest 5 Hz. This rounding would result in rates of 25 Hz, 45 Hz, 85 Hz, and 100 Hz. The ratio would be 5:9:17:20, meaning the first program would deliver pulses in 5 of the 20 segments, the second program would deliver pulses in 9 of the 20 segments, and so on. The delivered and skipped pulses could again be evenly distributed throughout the 20 segments to better approximate the intended frequency. Using 20 segments results in a lower period and simplifies stimulation program delivery by apparatus 10.

Apparatus 10 can be configured to dynamically determine the segment frequency and segment period, such as a determination based on the desired pulse rates for multiple stimulation programs to be delivered. This configuration can accommodate arbitrary pulse rates with a desired amount of accuracy. The resolution of achievable pulse rates can be increased by increasing the number of segments, and the maximum pulse rate can be increased by increasing segment frequency. It may be desirable to keep the total repetition period of the program (the time to complete the total number of segments at the segment frequency) low so that the average pulse rate is accurate over short periods of time. Setting the segment frequency equal to the highest pulse rate of the various stimulation programs results in there being at most one pulse per segment, but it is also possible to execute multiple pulses per segment to achieve higher pulse rates than the segment frequency. The segments themselves are configured to be long enough to execute each pulse sequentially.

Apparatus 10 does not necessarily have to configure the segments to have equal lengths. It may be the case that one or more stimulation programs have long pulse widths that may require a longer segment to complete delivery of all the stimulation pulses. This longer segment may adversely affect another stimulation program running at a higher rate. The overall selection of segment lengths and the total period can be adjusted to mitigate adversely affecting pulse rates when these longer segments are present. Additionally, the stimulation programs with higher pulse rates can have multiple pulses delivered in some segments to maintain the appropriate overall pulse rate.

Referring now to FIGS. 37A-E, graphs of various stimulation waveforms modulated by an envelope signal are illustrated, consistent with the present inventive concepts. Apparatus 10 can be configured to provide a stimulation waveform that is modulated by an envelope signal, such as a sine wave as shown in FIGS. 37A-E. The stimulation waveforms can comprise one or more trains and/or bursts such as are described in reference to FIG. 29 and/or otherwise herein. A varied range of modulation frequencies can be utilized by apparatus 10. Modulation frequencies that are not whole integer ratios of the train and/or burst frequencies can be used. In some embodiments, apparatus 10 utilizes a modulation frequency that is between 0.01 and 100 times the train frequency.

Figure 37A:
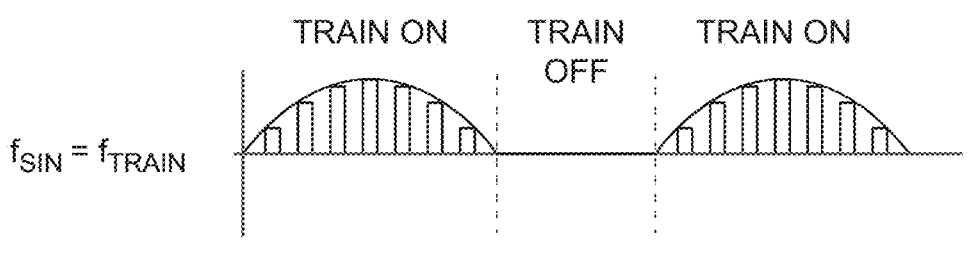

In FIG. 37A, the stimulation waveform shown and provided by apparatus 10 comprises a series of pulses in a train that is modulated by a sine wave, where the frequency of the sine wave equals the frequency of the train.

Figure 37B:
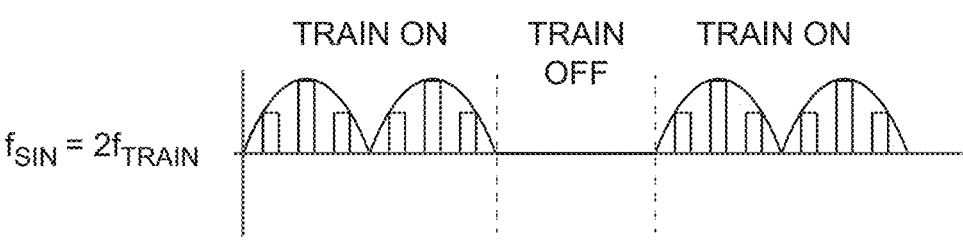

In FIG. 37B, the stimulation waveform shown and provided by apparatus 10 comprises a series of pulses in a train that is modulated by a sine wave, where the frequency of the sine wave equals two times the frequency of the train.

Figure 37C:
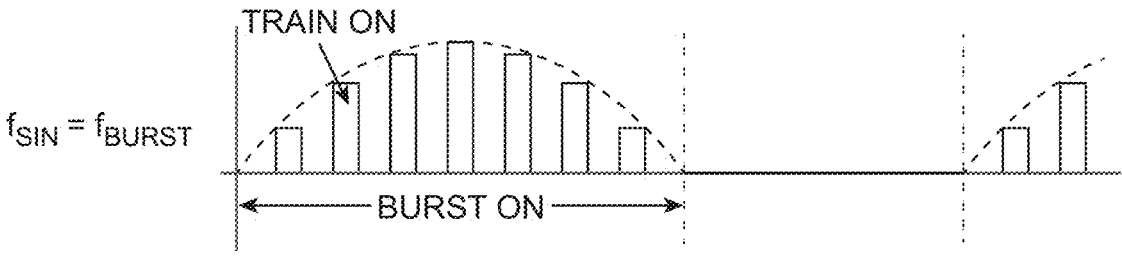

In FIG. 37C, the stimulation waveform shown and provided by apparatus 10 comprises a series of trains of a burst, where the burst is modulated by a sine wave, and where the frequency of the sine wave equals the frequency of the burst.

Figure 37D:
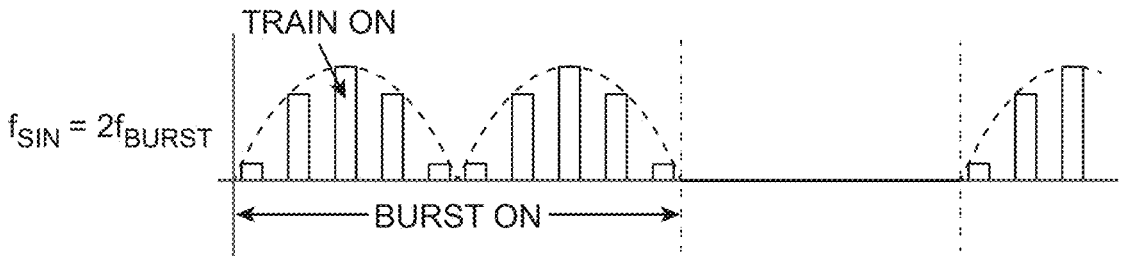

In FIG. 37D, the stimulation waveform shown and provided by apparatus 10 comprises a series of trains of a burst, where the burst is modulated by a sine wave, and where the frequency of the sine wave equals twice the frequency of the burst.

Figure 37E:
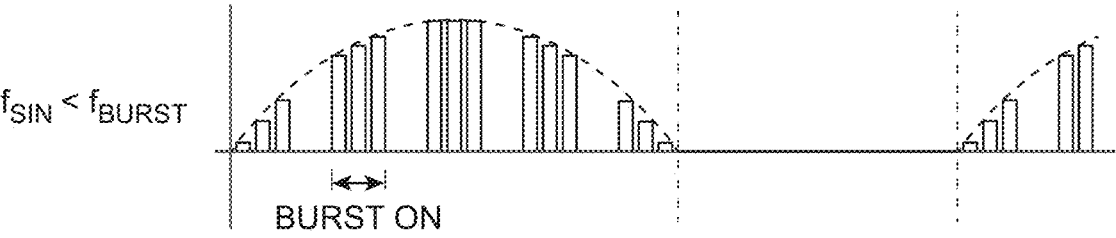

In FIG. 37E, the stimulation waveform shown and provided by apparatus 10 comprises a series of trains of a burst, where the burst is modulated by a sine wave, and where the frequency of the sine wave is less than the frequency of the burst.

While the stimulation waveforms of FIGS. 37A-E illustrate a waveform modulated by an envelope signal comprising a sine wave, apparatus 10 can be configured to utilize other envelope configurations (e.g. other envelope shapes), such as a triangle wave, square wave, trapezoidal wave, and the like.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A system for delivering stimulation energy to a patient, comprising:
   an implantable device comprising:
   at least one sensor for measuring electrically-evoked compound action potential (ECAP) signals; and
   at least one stimulation element configured to deliver the stimulation energy to tissue, wherein the system is configured to produce an artifact-compensated ECAP signal by:
   recording an artifact via an amplifier; and
   subsequently recording an ECAP signal via the amplifier while applying an inverse of the recorded artifact to an input of the amplifier.

2. The system of claim 1, wherein the amplifier is configured to record the ECAP signal with high gain.

3. The system of claim 1, wherein the amplifier is configured to record the artifact with low gain.

4. The system of claim 3, wherein the amplifier operates in a linear range.

5. The system of claim 1, wherein applying an inverse of the recorded artifact is a first artifact cancellation technique, and wherein the system is further configured to produce the artifact-compensated ECAP signal by applying a second artifact cancellation technique.

6. The system of claim 1 further comprising an analog to digital converter configured to perform a plurality of captures of one or both of the artifact and the ECAP signal, wherein the implantable device is configured to average the plurality of captures of one or both of the artifact and the ECAP signal to reduce noise.

7. The system of claim 1, wherein the stimulation energy delivered by the at least one implantable stimulation element comprises a tonic stimulation waveform that is provided at a high amplitude for a first time period, and wherein the tonic stimulation waveform is provided at a decreased amplitude during a subsequent second time period.

8. The system of claim 7, wherein the decreased amplitude comprises a sub-threshold amplitude or zero amplitude.

9. The system of claim 7, wherein the system is configured to deliver the decreased amplitude in an adaptive manner.

10. The system of claim 9, wherein the system is configured to deliver the decreased amplitude based on patient feedback regarding pain relief.

11. The system of claim 7, wherein the decreased amplitude is delivered over a pre-defined duration.

12. The system of claim 1, wherein the stimulation energy delivered by the at least one implantable stimulation element comprises a high frequency tonic stimulation waveform combined with a low frequency tonic stimulation waveform.

13. The system of claim 1, wherein the stimulation energy delivered by the at least one implantable stimulation element comprises a first plurality of pulses separated by an inter-pulse gap and configured to create a similar physiologic effect as a single pulse having a duration that is about equal to a duration of the first plurality of pulses.

14. The system of claim 13, wherein the system further comprises a user interface configured to allow an operator to enter a pulse density percentage, and wherein the stimulation energy is delivered based on the entered pulse density percentage.

15. The system of claim 14, wherein the system is configured to calculate a pulse width and the inter-pulse gap of the first plurality of pulses based on the pulse density percentage entered and a pulse width of a first pulse to stimulate.

16. The system of claim 1, wherein the at least one stimulation element comprises a set of stimulation elements that are configured to deliver the stimulation energy to a plurality of anatomical areas.

17. The system of claim 16, wherein the plurality of anatomical areas comprises at least four anatomical areas.

18. The system of claim 13, wherein a pulse width of each of the first plurality of pulses is more than 300 μs, and the inter-pulse gap is no more than 100 μs.

19. The system of claim 1, wherein the artifact comprises a signal tail of a first stimulation pulse, and wherein the signal tail results from an RC discharge time of capacitances in a path of the first stimulation pulse.

20. The system of claim 19, wherein the at least one stimulation element comprises an electrode, and wherein the path of the first stimulation pulse comprises an electrode-tissue interface.

21. The system of claim 1, wherein the recorded artifact and the inverse of the recorded artifact sum to zero.

22. The system of claim 1, wherein the system is configured to use the artifact-compensated ECAP signal to determine a stimulation paradigm for the patient, and to deliver the stimulation energy to the patient based on the determined stimulation paradigm.

23. The system of claim 1 further comprising an external device configured to transmit one or both of power and data to the implantable device.

24. The system of claim 1 further comprising a memory configured to store the recorded artifact, wherein the system is further configured to invert the stored artifact.

25. The system of claim 1 further comprising a digital-to-analog converter (DAC) configured to convert the inverse of the recorded artifact to an analog signal, wherein the analog signal is applied to the input of the amplifier while recording the ECAP signal.

26. The system of claim 1, wherein the amplifier comprises a variable-gain amplifier, and wherein the system is configured to record the artifact with the amplifier at a first gain setting and to record the ECAP signal with the amplifier at a second gain setting higher than the first gain setting.

27. The system of claim 1, wherein the input of the amplifier comprises an offset adjustment input.

* * * * *